US009926610B2

(12) United States Patent
Azzazy et al.

(10) Patent No.: US 9,926,610 B2
(45) Date of Patent: Mar. 27, 2018

(54) DETECTION OF NUCLEIC ACIDS USING UNMODIFIED GOLD NANOPARTICLES

(71) Applicant: AMERICAN UNIVERSITY IN CAIRO, New Cairo (EG)

(72) Inventors: Hassan Mohamed El-Said Azzazy, Alexandria (EG); Tamer Mohamed Samir, Cairo (EG); Sherif Mohamed Shawky, Cairo (EG)

(73) Assignee: AMERICAN UNIVERSITY IN CAIRO, New Cairo (EG)

( * ) Notice: Subject to any disclaimer, the term of this patent is extended or adjusted under 35 U.S.C. 154(b) by 255 days.

(21) Appl. No.: 14/294,011

(22) Filed: Jun. 2, 2014

(65) Prior Publication Data

US 2014/0356859 A1 Dec. 4, 2014

Related U.S. Application Data

(63) Continuation of application No. 14/110,639, filed as application No. PCT/US2012/032778 on Apr. 9, 2012, now abandoned.

(60) Provisional application No. 61/473,238, filed on Apr. 8, 2011, provisional application No. 61/473,242, filed on Apr. 8, 2011.

(51) Int. Cl.
*C12Q 1/04* (2006.01)
*C12Q 1/70* (2006.01)
*C12Q 1/68* (2018.01)

(52) U.S. Cl.
CPC .............. *C12Q 1/70* (2013.01); *C12Q 1/04* (2013.01); *C12Q 1/689* (2013.01); *C12Q 1/6813* (2013.01); *C12Q 1/6816* (2013.01); *C12Q 1/6818* (2013.01); *C12Q 2600/156* (2013.01)

(58) Field of Classification Search
None
See application file for complete search history.

(56) References Cited

U.S. PATENT DOCUMENTS 5,374,717 A * 12/1994 Rota .................... C07K 14/005
435/235.1
5,541,308 A * 7/1996 Hogan ................. C12Q 1/6811
435/6.12

(Continued)

OTHER PUBLICATIONS

Storhoff et al. Nature Biotechnology. 2004. 22(7): 883-887.*

(Continued)

*Primary Examiner* — Joseph G. Dauner
(74) *Attorney, Agent, or Firm* — Oblon, McClelland, Maier & Neustadt, L.L.P.

(57) ABSTRACT

A gold nanoparticle-based colorimetric assay kit for nucleic acids from viral, bacterial and other microorganisms that detects unamplified or amplified polynucleotides in clinical specimens using unmodified AuNPs and oligotargeter polynucleotides that bind to a pathogen's nucleic acids. A method for detecting a pathogen comprising contacting a sample suspected of containing microbes with a polynucleotide that binds to pathogen nucleic acid and with gold nanoparticles, detecting the aggregation of nanoparticles, and detecting pathogen polynucleotides in the sample when the nanoparticles aggregate (solution color becomes blue) in comparison with a control or a negative sample not containing the virus when nanoparticles do not aggregate (solution color remains red).

2 Claims, 25 Drawing Sheets

(56) References Cited

U.S. PATENT DOCUMENTS

| | | | | |
|---|---|---|---|---|
| 5,582,975 | A | * 12/1996 | Milliman | C12Q 1/689 435/6.12 |
| 7,427,674 | B2 | * 9/2008 | Aberham | C12Q 1/701 435/6.16 |
| 2009/0123916 | A1 | 5/2009 | La Scola et al. | |
| 2011/0008772 | A1 | 1/2011 | Lai et al. | |
| 2013/0236880 | A1 | 9/2013 | Shawky Abduo et al. | |
| 2015/0017258 | A1 | 1/2015 | Azzazy et al. | |

OTHER PUBLICATIONS

Nantachit et al. Transfusion. 2007. 47:1803-1808.*
Murakawa et al. DNA. 1988. 7(4):287-295.*
Ho et al. Journal of Clinical Microbiology. 1999. 37(8):2461-2465.*
Wagner et al. Applied and Environmental Microbiology. 1994 60(3):792-800.*
Communication pursuant to Rules 70(2) and 70a(2) EPC dated Mar. 27, 2015 in European Search Report No. 12768288.8.
U.S. Appl. No. 14/376,003, filed Jul. 31, 2014, Azzazy, et al.
U.S. Appl. No. 12/987,659, filed Jan. 10, 2011, Shawky Abduo, et al.
Partial European Search Report dated Nov. 11, 2014 in Patent Application No. 12768288.8.
Hosub Lee, et al., "Colorimetric genotyping of single nucleotide polymorphism based on selective aggregation of unmodified gold nanoparticles" Biosensors and Bioelectronics, vol. 26, No. 2, XP027320379, Oct. 2010, pp. 730-735.
Fan Xia, et al., "Colorimetric detection of DNA, small molecules, proteins, and ions using unmodified gold nanoparticles and conjugated polyelectrolytes" Center for Polymers and Organic Solids, Proceedings of the National Academy of Sciences, vol. 107, No. 24, XP055141430, Jun. 2010, pp. 10837-10841.
Ye Lim Jung, et al., "Direct colorimetric diagnosis of pathogen infections by utilizing thiol-labeled PCR primers and unmodified gold nanoparticles" Biosensors and Bioelectronics, vol. 25, No. 8, XP026941415, Apr. 2010, pp. 1941-1946.
Huixiang Li, et al., "Colorimetric detection of DNA sequences based on electrostatic interactions with unmodified gold nanoparticles" Proceedings of the National Academy of Sciences, vol. 101, No. 39, XP055141433, Sep. 2004, pp. 14036-14039.
Sherif M. Shawky, et al., "Direct detection of unamplified hepatitis C virus RNA using unmodified gold nanoparticles" Clinical Biochemistry, vol. 43, No. 13-14, XP027248991, Sep. 2010, pp. 1163-1168.
Marion Stoffels, et al., "rRNA probe-based cell fishing of bacteria" Environmental Microbiology, vol. 1, No. 3, XP002246085, Jun. 1999, pp. 259-271.
Michael Wagner, et al., "Development of an rRNA-Targeted Oligonucleotide Probe Specific for the Genus *Acinetobacter* and Its Application for In Situ Monitoring in Activated Sludge" Applied and Environmental Microbiology, American Society for Microbiology, vol. 60, No. 3, XP002097846, Mar. 1994, pp. 792-800.
Frick, W. Florian, et al., "Comparative Genomics of the IncA/C Multidrug Resistance Plasmid Family", Journal of Bacteriology, vol. 191, No. 15, pp. 4750-4757, Aug. 2009.
Kim, Eun-Young et al., "A real-time PCR-based method for determining the surface coverage of thiol-capped oligonucleotides bound onto gold nanoparticles", Nucleic Acids Research, vol. 34, No. 7, pp. e54 1-7, Apr. 2006.
Ullrich, P. et al, "Detection, Semiquantitation, and Genetic Variation in Hepatitis C Virus Sequences Amplified from the Plasma of Blood Donors with Elevated Alanine Aminotransferase", Journal of Clin. Invest. vol. 86, No. 5, pp. 1609-1614, Nov. 1990.
Huixiang Li, et al., "Label-Free Colorimetric Detection of Specific Sequences in Genomic DNA Amplified by the Polymerase Chain Reaction" Journal of the American Chemical Society, vol. 126, No. 35, XP055141425, Sep. 2004, pp. 10958-10961.
Fricke, W. Florian, et al., "Comparative Genomics of the IncA/C Multidrug Resistance Plasmid Family", Journal of Bacteriology, vol. 191, No. 15, pp. 4750-4757, Aug. 2009.
Ulrich, P. et al, "Detection, Semiquantitation, and Genetic Variation in Hepatitis C Virus Sequences Amplified from the Plasma of Blood Donors with Elevated Alanine Aminotransferase", The American Society for Clinical Investigations, Inc. vol. 86, No. 5, pp. 1609-1614, Nov. 1990.
International Search Report and Written Opinion dated Sep. 7, 2012 in PCT/US12/32778 Filed Apr. 9, 2012.
Office Action dated Sep. 20, 2016 in European Patent Application No. 12 768 288.8.
Form No. 18 with attached Search and Examination Report dated May 9, 2016 in African Regional Intellectual Property Organization (ARIPO) Patent Application No. AP/P/2013/007230.

* cited by examiner

FIG. 6
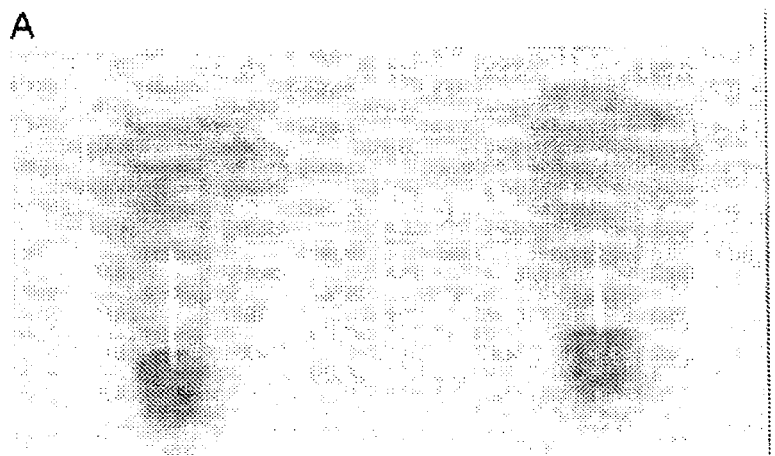
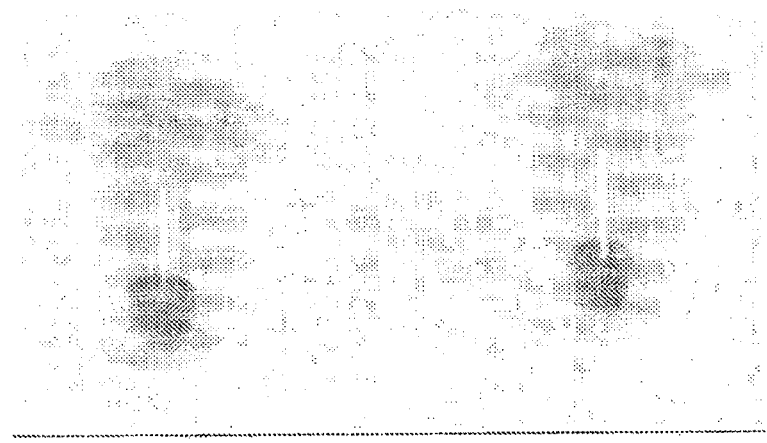

FIGURE 9

Example of oligotargeter alignment for WNV Oligotargeter
WNV-Targ 1: ACATAAGCGCGATAGTGCAGGGTGAAAGGATGG (SEQ ID NO: 549)
Probe hyberdizationpostion: 5093-5025

*SEQ# 25Oligotargeter alignment results (AlignX Vector NTI Advance® v.11.5)*

| | 5057 | 5060 5070 5080 5090 5100 5110 5120 |
|---|---|---|
| gi_21929232_gb_AF404753.1_ | 5057 | TTTATGGCAATGGAGTCATAATGCCCAACGGCTCATACATAAGCGCGATAGTGCAGGGTGAAAGGATGGA |
| i_374670371_gb_JN819315.1_ | 5023 | TTTATGGCAATGGAGTCATAATGCCCAACGGCTCATACATAAGCGCGATAGTGCAGGGTGAAAGGATGGA |
| gi_21929234_gb_AF404754.1_ | 5057 | TTTATGGCAATGGAGTCATAATGCCCAACGGCTCATACATAAGCGCGATAGTGCAGGGTGAAAGGATGGA |
| _315259427_gb_HQ596519.1_ | 5057 | TTTATGGCAATGGAGTCATAATGCCCAACGGCTCATACATAAGCGCGATAGTGCAGGGTGAAAGGATGGA |
| gi_21929238_gb_AF404756.1_ | 5057 | TTTATGGCAATGGAGTCATAATGCCCAACGGCTCATACATAAGCGCGATAGTGCAGGGTGAAAGGATGGA |
| i_374670375_gb_JN819317.1_ | 5034 | TTTATGGCAATGGAGTCATAATGCCCAACGGCTCATACATAAGCGCGATAGTGCAGGGTGAAAGGATGGA |
| [illegible] | 5057 | TTTATGGCAATGGAGTCATAATGCCCAACGGCTCAT[illegible]AGGATGGA |
| gi_21929240_gb_AF404757.1_ | 5057 | TCTATGGCAATGGAGTCATAATGCCCAACGGCTCCTACATAAGCGCGATAGTGCAGGGTGAAAGGATGGA |
| i_374670379_gb_JN819319.1_ | 5024 | TTTATGGCAATGGAGTCATAATGCCCAACGGCTCATACATAAGCGCGATAGTGCAGGGTGAAAGGATGGA |
| i_374670381_gb_JN819320.1_ | 5024 | TTTATGGCAATGGAGTCATAATGCCCAACGGCTCATACATAAGCGCGATAGTGCAGGGTGAAAGGATGGA |
| i_374670363_gb_JN819311.1_ | 5023 | TTTATGGCAATGGAGTCATAATGCCCAACGGCTCATACATAAGCGCGATAGTGCAGGGTGAAAGGATGGA |
| i_374670367_gb_JN819313.1_ | 5024 | TTTATGGCAATGGAGTCATAATGCCCAACGGCTCATACATAAGCGCGATAGTGCAGGGTGAAAGGATGGA |
| i_374670359_gb_JN819309.1_ | 5024 | TTTATGGCAATGGAGTCATAATGCCCAACGGCTCATACATAAGCGCGATAGTGCAGGGTGAAAGGATGGA |
| i_374670387_gb_JN819323.1_ | 5024 | TTTATGGCAATGGAGTCATAATGCCCAACGGCTCATACATAAGCGCGATAGTGCAGGGTGAAAGGATGGA |
| Consensus | 5057 | TTTATGGCAATGGAGTCATAATGCCCAACGGCTCATACATAAGCGCGATAGTGCAGGGTGAAAGGATGGA |

FIG. 10

| Genes | PCR primers sequences | amplicon Length (bp) |
|---|---|---|
| blaOXA-51-like | OXA-51-likeF: TAA TGC TTT GAT CGG CCT TG (SEQ ID NO: 602)<br>OXA-51-likeR: TGG ATT GCA CTT CAT CTT GG (SEQ ID NO: 603) | 353 bp |
| blaOXA-23-like | OXA-23-likeF: GAT CGG ATT GGA GAA CCA GA (SEQ ID NO: 604)<br>OXA-23-likeR: ATT TCT GAC CGC ATT TCC AT (SEQ ID NO: 605) | 501 bp |
| class I integrase gene | Int1F: CAG TGG ACA TAA GCC TGT TC (SEQ ID NO: 606)<br>Int1R: CCC GAG GCA TAG ACT GTA (SEQ ID NO: 607) | 160-167 bp |

FIG. 11

| Genes | PCR primers sequences | amplicon Length (bp) |
|---|---|---|
| ITS Region | 2F: TTGTACACACCGCCCGTC (SEQ ID NO: 608)<br>10R: TTCGCCCTTTCCCTCACGGTA (SEQ ID NO: 609) | 1230 bp |

FIG. 12

| Oligotargeter sequences | Best hits | Alignment identity |
|---|---|---|
| Oligotargeter 1:<br>AATTCATATATACCAAAACGCTCGATTC<br>(SEQ ID NO: 610) | 106 | 100% for different *Acinetobacter* species |
| Oligotargeter 2:<br>GACTGGTTGAAGTTATAGATAAAAGA<br>(SEQ ID NO: 611) | 177 | 100% for different *Acinetobacter* species |

FIG. 13

| Sample number | Gram reaction | capsule | Motility | catalase test | Citrate test | Glucose utilization | Citrate utilization | Citrate Growth at 37°C |
|---|---|---|---|---|---|---|---|---|
| 1 | negative | positive | Non motile | negative | positive | positive | positive | positive |
| 45 | negative | positive | Non motile | negative | positive | positive | positive | positive |
| 47 | negative | positive | Non motile | negative | positive | positive | positive | positive |
| 90 | negative | positive | Non motile | negative | positive | positive | positive | positive |
| 91 | negative | positive | Non motile | negative | positive | positive | positive | positive |
| 92 | negative | positive | Non motile | negative | positive | positive | positive | positive |
| 118 | negative | positive | Non motile | negative | positive | positive | positive | positive |
| 125 | negative | positive | Non motile | negative | positive | positive | positive | positive |
| 139 | negative | positive | Non motile | negative | positive | positive | positive | positive |
| 151 | negative | positive | Non motile | negative | positive | positive | positive | positive |
| 165 | negative | positive | Non motile | negative | positive | positive | positive | positive |
| 166 | negative | positive | Non motile | negative | positive | positive | positive | positive |
| 167 | negative | positive | Non motile | negative | positive | positive | positive | positive |
| 168 | negative | positive | Non motile | negative | positive | positive | positive | positive |
| 194 | negative | positive | Non motile | negative | positive | positive | positive | positive |
| 197 | negative | positive | Non motile | negative | positive | positive | positive | positive |
| 200 | negative | positive | Non motile | negative | positive | positive | positive | positive |
| 201 | negative | positive | Non motile | negative | positive | positive | positive | positive |
| 202 | negative | positive | Non motile | negative | positive | positive | positive | positive |
| 204 | negative | positive | Non motile | negative | positive | positive | positive | positive |
| 208 | negative | positive | Non motile | negative | positive | positive | positive | positive |
| 209 | negative | positive | Non motile | negative | positive | positive | positive | positive |

FIG. 17A

| Sample # | Sample | Biochemical identification | ITS amplification | Nested PCR | AuNPs assay |
|---|---|---|---|---|---|
| 92 | ETT | Acinetobacter baumannii | positive | positive | Confirmed |
| 202 | ETT | Acinetobacter baumannii | positive | positive | Confirmed |
| 168 | pus | Acinetobacter baumannii | positive | positive | Confirmed |
| 165 | pus | Acinetobacter baumannii | positive | positive | Confirmed |
| 166 | pus | Acinetobacter baumannii | positive | positive | Confirmed |
| 167 | pus | Acinetobacter baumannii | positive | positive | Confirmed |
| 197 | pus | Acinetobacter baumannii | positive | positive | Confirmed |
| 204AC | pus | Acinetobacter baumannii | positive | positive | Confirmed |
| 208 | pus | Acinetobacter baumannii | positive | positive | Confirmed |
| 209 | pus | Acinetobacter baumannii | positive | positive | Confirmed |
| 66 | pus | Acinetobacter baumannii | positive | positive | Confirmed |
| 91 | pus | Acinetobacter baumannii | positive | positive | Confirmed |
| 139 | sputum | Acinetobacter baumannii | positive | positive | Confirmed |
| 151 | sputum | Acinetobacter baumannii | positive | positive | Confirmed |
| 1 | sputum | Acinetobacter baumannii | positive | positive | Confirmed |
| 45 | sputum | Acinetobacter baumannii | positive | positive | Confirmed |

FIG. 17B

| Sample # | Sample | Biochemical identification | IS amplification | Nested PCR | AuNPassay |
|---|---|---|---|---|---|
| 47 | sputum | Acinetobacter baumannii | positive | positive | Confirmed |
| 84 | sputum | Acinetobacter baumannii | positive | positive | Confirmed |
| 90 | sputum | Acinetobacter baumannii | positive | positive | Confirmed |
| 94 | sputum | Acinetobacter baumannii | positive | positive | Confirmed |
| 118 | sputum | Acinetobacter baumannii | Positive | positive | Confirmed |
| 125 | sputum | Acinetobacter baumannii | Positive | positive | Confirmed |
| 194 | urine | Acinetobacter baumannii | Positive | positive | Confirmed |
| 200 | urine | Acinetobacter baumannii | Positive | positive | Confirmed |
| 201 | wound | Acinetobacter baumannii | Positive | positive | Confirmed |
| E. coli | ATCC | E. coli | Positive | negative | Confirmed |
| S. enteritidis | ATCC | S. enteritidis | Positive | negative | Confirmed |
| K. pneumonia | ATCC | K. pneumonia | Positive | negative | Confirmed |
| P. aeruginosa | ATCC | P. aeruginosa | Positive | negative | Confirmed |

FIG. 18

| Gene | PCR primer sequences | Tm (°C) | Amplicon Length (bp) |
|---|---|---|---|
| 16S rDNA | TBF: ACATGCAAGTCGAACGGAAAGG (SEQ ID NO: 612) | 51.5 | M. H37Ra: 650 bp |
| | TBR: CCTCCTGATATCTGCGCATTCCAC (SEQ ID NO: 613) | 54.4 | M. smegmatis: 638 bp |

FIG. 19

| Oligonucleotide sequences | Best hit | Alignment identity |
|---|---|---|
| TBG: TTGTCGCGTTGTTCGTGAAA (SEQ ID NO: 614) | 100 | 100% for different Mycobacteria species |
| TBS: ACCACAAGACATGCATCCCG (SEQ ID NO: 615) | 274 | 100% for Mycobacteria strains from M. tuberculosis complex |

FIG. 24

| DNA length (kb) | Concentration (ng/μL) | Molar Concentration (nM) | Detection Limit | DNA length (kb) |
|---|---|---|---|---|
| PCR product | 0.7 | 5.65 | 12440 | 1 ng |
| Genomic DNA | 4411 | 10 | 3.49 | 40 ng |

FIG. 25

| Step | Temp (C°) | Time (min) | No. of cycles |
|---|---|---|---|
| Initial denaturation | 95 | 2 | 1 |
| Denaturation | 95 | 0.5 | 30 |
| Annealing | 46 | 1 | 30 |
| Extension | 72 | 0.75 | 30 |
| Final extension | 72 | 2 | 1 |

FIG. 26

| Absorbance | M. smegmatis | M. H37Ra | M.Tb B | M.Tb D |
|---|---|---|---|---|
| 260 nm | 0.095 | 0.144 | 0.065 | 0.106 |
| 280 nm | 0.045 | 0.073 | 0.025 | 0.052 |
| 260/280 ratio | 2.11 | 1.97 | 2.6 | 2.04 |
| Concentration (µg/µl) | 0.0475 | 0.072 | 0.0325 | 0.053 |
| DNA yield (µg) | 2.375 | 3.6 | 1.625 | 2.65 |

FIG. 27

| Strain | H37Ra | | TB clinical strain | |
|---|---|---|---|---|
| OD 260 | 0.121 | | 0.160 | |
| Conc. (µg/µl) | 0.04 | | 0.03 | |
| Results | Conc. (ng/µl) | Results | Conc. (ng/µl) | Results |
| | 2.5 | +ve | 3.33 | +ve |
| | 1.25 | +ve | 1.67 | +ve |
| | 0.625 | +ve | 0.83 | +ve |
| | 0.3125 | -ve | 0.42 | -ve |

```
                              SEQUENCE LISTING

<160> NUMBER OF SEQ ID NOS: 632

<210> SEQ ID NO 1
<211> LENGTH: 23
<212> TYPE: DNA
<213> ORGANISM: Acinetobacter baumannii

<400> SEQUENCE: 1
agtcgagcgg gggaaggtag ctt                                              23

<210> SEQ ID NO 2
<211> LENGTH: 25
<212> TYPE: DNA
<213> ORGANISM: Acinetobacter baumannii

<400> SEQUENCE: 2
tttgatcatg gctcagattg aacgc                                            25

<210> SEQ ID NO 3
<211> LENGTH: 26
<212> TYPE: DNA
<213> ORGANISM: Acinetobacter baumannii

<400> SEQUENCE: 3
gatgctaata ccgcatacgt cctacg                                           26

<210> SEQ ID NO 4
<211> LENGTH: 25
<212> TYPE: DNA
<213> ORGANISM: Acinetobacter baumannii

<400> SEQUENCE: 4
gactgagaca cggcccagac tccta                                            25

<210> SEQ ID NO 5
<211> LENGTH: 26
<212> TYPE: DNA
<213> ORGANISM: Acinetobacter baumannii

<400> SEQUENCE: 5
cctagagata gtggacgtta ctcgca                                           26

<210> SEQ ID NO 6
<211> LENGTH: 25
<212> TYPE: DNA
<213> ORGANISM: Acinetobacter baumannii

<400> SEQUENCE: 6
aacttgggaa ttgcattcga tactg                                            25

<210> SEQ ID NO 7
<211> LENGTH: 25
<212> TYPE: DNA
<213> ORGANISM: Acinetobacter baumannii

<400> SEQUENCE: 7
cgaaagcatg gggagcaaac aggat                                            25

<210> SEQ ID NO 8
```

```
<211> LENGTH: 29
<212> TYPE: DNA
<213> ORGANISM: Acinetobacter baumannii

<400> SEQUENCE: 8
aaatgaattg acggggccc gcacaagcg                                      29

<210> SEQ ID NO 9
<211> LENGTH: 26
<212> TYPE: DNA
<213> ORGANISM: Acinetobacter baumannii

<400> SEQUENCE: 9
gtgtcgtgag atgttgggtt aagtcc                                        26

<210> SEQ ID NO 10
<211> LENGTH: 25
<212> TYPE: DNA
<213> ORGANISM: Acinetobacter baumannii

<400> SEQUENCE: 10
acacacgtgc tacaatggtc ggtac                                         25

<210> SEQ ID NO 11
<211> LENGTH: 25
<212> TYPE: DNA
<213> ORGANISM: Acinetobacter baumannii

<400> SEQUENCE: 11
atacgttccc gggccttgta cacac                                         25

<210> SEQ ID NO 12
<211> LENGTH: 21
<212> TYPE: DNA
<213> ORGANISM: Acinetobacter baumannii

<400> SEQUENCE: 12
tcaccccagt catcggccac a                                             21

<210> SEQ ID NO 13
<211> LENGTH: 30
<212> TYPE: DNA
<213> ORGANISM: Acinetobacter baumannii

<400> SEQUENCE: 13
tctaggtgat ccagccgcag gttcccctac                                    30

<210> SEQ ID NO 14
<211> LENGTH: 25
<212> TYPE: DNA
<213> ORGANISM: Acinetobacter baumannii

<400> SEQUENCE: 14
gaacgtattc accgcggcat tctga                                         25

<210> SEQ ID NO 15
<211> LENGTH: 25
<212> TYPE: DNA
<213> ORGANISM: Acinetobacter baumannii

<400> SEQUENCE: 15
ttgtagcacg tgtgtagccc tggcc                                         25
```

<210> SEQ ID NO 16
<211> LENGTH: 25
<212> TYPE: DNA
<213> ORGANISM: Acinetobacter baumannii

<400> SEQUENCE: 16
tctcacgaca cgagctgacg acagc                                         25

<210> SEQ ID NO 17
<211> LENGTH: 25
<212> TYPE: DNA
<213> ORGANISM: Acinetobacter baumannii

<400> SEQUENCE: 17
gtgcgggccc ccgtcaattc atttg                                         25

<210> SEQ ID NO 18
<211> LENGTH: 25
<212> TYPE: DNA
<213> ORGANISM: Acinetobacter baumannii

<400> SEQUENCE: 18
gctccccatg ctttcgtacc tcagc                                         25

<210> SEQ ID NO 19
<211> LENGTH: 26
<212> TYPE: DNA
<213> ORGANISM: Acinetobacter baumannii

<400> SEQUENCE: 19
gctcaccagt atcgaatgca attccc                                        26

<210> SEQ ID NO 20
<211> LENGTH: 26
<212> TYPE: DNA
<213> ORGANISM: Acinetobacter baumannii

<400> SEQUENCE: 20
gcgagtaacg tccactatct ctaggt                                        26

<210> SEQ ID NO 21
<211> LENGTH: 25
<212> TYPE: DNA
<213> ORGANISM: Acinetobacter baumannii

<400> SEQUENCE: 21
ctcagtccca gtgtggcgga tcatc                                         25

<210> SEQ ID NO 22
<211> LENGTH: 26
<212> TYPE: DNA
<213> ORGANISM: Acinetobacter baumannii

<400> SEQUENCE: 22
gcggtattag catcccttc gagatg                                         26

<210> SEQ ID NO 23
<211> LENGTH: 30
<212> TYPE: DNA
<213> ORGANISM: Acinetobacter baumannii

<400> SEQUENCE: 23
gcatacgtcc tacgggagaa agcaggggat                                    30

```
<210> SEQ ID NO 24
<211> LENGTH: 30
<212> TYPE: DNA
<213> ORGANISM: Acinetobacter baumannii

<400> SEQUENCE: 24 gcagggatc ttcggaccctt gcgctaatag                                    30

<210> SEQ ID NO 25
<211> LENGTH: 37
<212> TYPE: DNA
<213> ORGANISM: Acinetobacter baumannii

<400> SEQUENCE: 25
cctaccaagg cgacgatctg tagcgggtct gagagga                            37

<210> SEQ ID NO 26
<211> LENGTH: 32
<212> TYPE: DNA
<213> ORGANISM: Acinetobacter baumannii

<400> SEQUENCE: 26
gacgatctgt agcgggtctg agaggatgat cc                                 32

<210> SEQ ID NO 27
<211> LENGTH: 40
<212> TYPE: DNA
<213> ORGANISM: Acinetobacter baumannii

<400> SEQUENCE: 27
cgggtctgag aggatgatcc gccacactgg gactgagaca                         40

<210> SEQ ID NO 28
<211> LENGTH: 37
<212> TYPE: DNA
<213> ORGANISM: Acinetobacter baumannii

<400> SEQUENCE: 28
gggtctgaga ggatgatccg ccacactggg actgaga                            37

<210> SEQ ID NO 29
<211> LENGTH: 36
<212> TYPE: DNA
<213> ORGANISM: Acinetobacter baumannii

<400> SEQUENCE: 29
ggtctgagag gatgatccgc cacactggga ctgaga                             36

<210> SEQ ID NO 30
<211> LENGTH: 36
<212> TYPE: DNA
<213> ORGANISM: Acinetobacter baumannii

<400> SEQUENCE: 30
tgagaggatg atccgccaca ctgggactga gacacg                             36

<210> SEQ ID NO 31
<211> LENGTH: 36
<212> TYPE: DNA
<213> ORGANISM: Acinetobacter baumannii

<400> SEQUENCE: 31
ccagactcct acgggaggca gcagtgggga atattg                             36
```

<210> SEQ ID NO 32
<211> LENGTH: 38
<212> TYPE: DNA
<213> ORGANISM: Acinetobacter baumannii

<400> SEQUENCE: 32
tcctacggga ggcagcagtg gggaatattg gacaatgg           38

<210> SEQ ID NO 33
<211> LENGTH: 37
<212> TYPE: DNA
<213> ORGANISM: Acinetobacter baumannii

<400> SEQUENCE: 33
gggaaccctg atccagccat gccgcgtgtg tgaagaa            37

<210> SEQ ID NO 34
<211> LENGTH: 39
<212> TYPE: DNA
<213> ORGANISM: Acinetobacter baumannii

<400> SEQUENCE: 34
ccctgatcca gccatgccgc gtgtgtgaag aaggcctta          39

<210> SEQ ID NO 35
<211> LENGTH: 36
<212> TYPE: DNA
<213> ORGANISM: Acinetobacter baumannii

<400> SEQUENCE: 35
atccagccat gccgcgtgtg tgaagaaggc cttatg             36

<210> SEQ ID NO 36
<211> LENGTH: 36
<212> TYPE: DNA
<213> ORGANISM: Acinetobacter baumannii

<400> SEQUENCE: 36
gccatgccgc gtgtgtgaag aaggccttat ggttgt             36

<210> SEQ ID NO 37
<211> LENGTH: 30
<212> TYPE: DNA
<213> ORGANISM: Acinetobacter baumannii

<400> SEQUENCE: 37
gtggacgtta ctcgcagaat aagcaccggc                    30

<210> SEQ ID NO 38
<211> LENGTH: 30
<212> TYPE: DNA
<213> ORGANISM: Acinetobacter baumannii

<400> SEQUENCE: 38
ctaactctgt gccagcagcc gcggtaatac                    30

<210> SEQ ID NO 39
<211> LENGTH: 32
<212> TYPE: DNA
<213> ORGANISM: Acinetobacter baumannii

<400> SEQUENCE: 39
gggagaggat ggtagaattc caggtgtagc gg         32

<210> SEQ ID NO 40
<211> LENGTH: 36
<212> TYPE: DNA
<213> ORGANISM: Acinetobacter baumannii

<400> SEQUENCE: 40
ccaggtgtag cggtgaaatg cgtagagatc tggagg     36

<210> SEQ ID NO 41
<211> LENGTH: 40
<212> TYPE: DNA
<213> ORGANISM: Acinetobacter baumannii

<400> SEQUENCE: 41
gcggtgaaat gcgtagagat ctggaggaat accgatggcg     40

<210> SEQ ID NO 42
<211> LENGTH: 36
<212> TYPE: DNA
<213> ORGANISM: Acinetobacter baumannii

<400> SEQUENCE: 42
tgcgtagaga tctggaggaa taccgatggc gaaggc     36

<210> SEQ ID NO 43
<211> LENGTH: 30
<212> TYPE: DNA
<213> ORGANISM: Acinetobacter baumannii

<400> SEQUENCE: 43
gagatctgga ggaataccga tggcgaaggc     30

<210> SEQ ID NO 44
<211> LENGTH: 30
<212> TYPE: DNA
<213> ORGANISM: Acinetobacter baumannii

<400> SEQUENCE: 44
agagtttgat catggctcag attgaacgct     30

<210> SEQ ID NO 45
<211> LENGTH: 30
<212> TYPE: DNA
<213> ORGANISM: Acinetobacter baumannii

<400> SEQUENCE: 45
gcagccatct ggcctaatac tgacgctgag     30

<210> SEQ ID NO 46
<211> LENGTH: 30
<212> TYPE: DNA
<213> ORGANISM: Acinetobacter baumannii

<400> SEQUENCE: 46
actgacgctg aggtacgaaa gcatggggag     30

<210> SEQ ID NO 47
<211> LENGTH: 30
<212> TYPE: DNA
<213> ORGANISM: Acinetobacter baumannii

<400> SEQUENCE: 47
ggcctttgag gctttagtgg cgcagctaac                                     30

<210> SEQ ID NO 48
<211> LENGTH: 30
<212> TYPE: DNA
<213> ORGANISM: Acinetobacter baumannii

<400> SEQUENCE: 48
gcctggggag tacggtcgca agactaaaac                                     30

<210> SEQ ID NO 49
<211> LENGTH: 38
<212> TYPE: DNA
<213> ORGANISM: Acinetobacter baumannii

<400> SEQUENCE: 49
tggtgccttc gggaatctag atacaggtgc tgcatggc                             38

<210> SEQ ID NO 50
<211> LENGTH: 36
<212> TYPE: DNA
<213> ORGANISM: Acinetobacter baumannii

<400> SEQUENCE: 50
ggtgccttcg ggaatctaga tacaggtgct gcatgg                               36

<210> SEQ ID NO 51
<211> LENGTH: 38
<212> TYPE: DNA
<213> ORGANISM: Acinetobacter baumannii

<400> SEQUENCE: 51
ccttcgggaa tctagataca ggtgctgcat ggctgtcg                             38

<210> SEQ ID NO 52
<211> LENGTH: 36
<212> TYPE: DNA
<213> ORGANISM: Acinetobacter baumannii

<400> SEQUENCE: 52
ctgcatggct gtcgtcagct cgtgtcgtga gatgtt                               36

<210> SEQ ID NO 53
<211> LENGTH: 36
<212> TYPE: DNA
<213> ORGANISM: Acinetobacter baumannii

<400> SEQUENCE: 53
tgcatggctg tcgtcagctc gtgtcgtgag atgttg                               36

<210> SEQ ID NO 54
<211> LENGTH: 36
<212> TYPE: DNA
<213> ORGANISM: Acinetobacter baumannii

<400> SEQUENCE: 54
cagtgacaaa ctggaggaag gcggggacga cgtcaa                               36

<210> SEQ ID NO 55
<211> LENGTH: 40
<212> TYPE: DNA
<213> ORGANISM: Acinetobacter baumannii

<400> SEQUENCE: 55
tggaggaagg cggggacgac gtcaagtcat catggccctt                40

<210> SEQ ID NO 56
<211> LENGTH: 30
<212> TYPE: DNA
<213> ORGANISM: Acinetobacter baumannii

<400> SEQUENCE: 56
gggacgacgt caagtcatca tggcccttac                30

<210> SEQ ID NO 57
<211> LENGTH: 36
<212> TYPE: DNA
<213> ORGANISM: Acinetobacter baumannii

<400> SEQUENCE: 57
ccttacggcc agggctacac acgtgctaca atggtc                36

<210> SEQ ID NO 58
<211> LENGTH: 30
<212> TYPE: DNA
<213> ORGANISM: Acinetobacter baumannii

<400> SEQUENCE: 58
tacggccagg gctacacacg tgctacaatg                30

<210> SEQ ID NO 59
<211> LENGTH: 30
<212> TYPE: DNA
<213> ORGANISM: Acinetobacter baumannii

<400> SEQUENCE: 59
cgtagtccgg attggagtct gcaactcgac                30

<210> SEQ ID NO 60
<211> LENGTH: 30
<212> TYPE: DNA
<213> ORGANISM: Acinetobacter baumannii

<400> SEQUENCE: 60
ggtgaatacg ttcccgggcc ttgtacacac                30

<210> SEQ ID NO 61
<211> LENGTH: 30
<212> TYPE: DNA
<213> ORGANISM: Acinetobacter baumannii

<400> SEQUENCE: 61
cctaactgca aagagggcgg ttaccacggt                30

<210> SEQ ID NO 62
<211> LENGTH: 30
<212> TYPE: DNA
<213> ORGANISM: Acinetobacter baumannii

<400> SEQUENCE: 62
ctaactgcaa agagggcggt taccacggtg                30

<210> SEQ ID NO 63
<211> LENGTH: 36
<212> TYPE: DNA
<213> ORGANISM: Acinetobacter baumannii

<400> SEQUENCE: 63
ggtgtggccg atgactgggg tgaagtcgta acaagg                                    36

<210> SEQ ID NO 64
<211> LENGTH: 36
<212> TYPE: DNA
<213> ORGANISM: Acinetobacter baumannii

<400> SEQUENCE: 64
gtgtggccga tgactggggt gaagtcgtaa caaggt                                    36

<210> SEQ ID NO 65
<211> LENGTH: 36
<212> TYPE: DNA
<213> ORGANISM: Acinetobacter baumannii

<400> SEQUENCE: 65
gtggccgatg actggggtga agtcgtaaca aggtag                                    36

<210> SEQ ID NO 66
<211> LENGTH: 30
<212> TYPE: DNA
<213> ORGANISM: Acinetobacter baumannii

<400> SEQUENCE: 66
gccgatgact ggggtgaagt cgtaacaagg                                           30

<210> SEQ ID NO 67
<211> LENGTH: 25
<212> TYPE: DNA
<213> ORGANISM: Acinetobacter baumannii

<400> SEQUENCE: 67
ggctggatca cctccttaac gaaag                                                25

<210> SEQ ID NO 68
<211> LENGTH: 25
<212> TYPE: DNA
<213> ORGANISM: Acinetobacter baumannii

<400> SEQUENCE: 68
ggggtgaagt cgtaacaagg tagcc                                                25

<210> SEQ ID NO 69
<211> LENGTH: 25
<212> TYPE: DNA
<213> ORGANISM: Acinetobacter baumannii

<400> SEQUENCE: 69
tcacgtcttt catcgcctct gactg                                                25

<210> SEQ ID NO 70
<211> LENGTH: 25
<212> TYPE: DNA
<213> ORGANISM: Acinetobacter baumannii

<400> SEQUENCE: 70
gagatgtttc acttcccctc gttcg                                                25

<210> SEQ ID NO 71
<211> LENGTH: 30
<212> TYPE: DNA

-continued

<213> ORGANISM: Acinetobacter baumannii

<400> SEQUENCE: 71
gggacttagc ttagttggta gagcgcctgc                                    30

<210> SEQ ID NO 72
<211> LENGTH: 33
<212> TYPE: DNA
<213> ORGANISM: Acinetobacter baumannii

<400> SEQUENCE: 72
aacaagttgt tcttcataga tgtatctgag ggt                                33

<210> SEQ ID NO 73
<211> LENGTH: 31
<212> TYPE: DNA
<213> ORGANISM: Acinetobacter baumannii

<400> SEQUENCE: 73
ggtatgtgaa tttagattga agctgtacgg t                                  31

<210> SEQ ID NO 74
<211> LENGTH: 30
<212> TYPE: DNA
<213> ORGANISM: Acinetobacter baumannii

<400> SEQUENCE: 74
gcgttttggt atgtgaattt agattgaagc                                    30

<210> SEQ ID NO 75
<211> LENGTH: 30
<212> TYPE: DNA
<213> ORGANISM: Acinetobacter baumannii

<400> SEQUENCE: 75
actgaatcaa gcgttttggt atgtgaattt                                    30

<210> SEQ ID NO 76
<211> LENGTH: 30
<212> TYPE: DNA
<213> ORGANISM: Acinetobacter baumannii

<400> SEQUENCE: 76
tagcaaatta actgaatcaa gcgttttggt                                    30

<210> SEQ ID NO 77
<211> LENGTH: 33
<212> TYPE: DNA
<213> ORGANISM: Acinetobacter baumannii

<400> SEQUENCE: 77
aattgagaac tagcaaatta actgaatcaa gcg                                33

<210> SEQ ID NO 78
<211> LENGTH: 34
<212> TYPE: DNA
<213> ORGANISM: Acinetobacter baumannii

<400> SEQUENCE: 78
tgttcactca agagtttagg ttaagcaatt aatc                               34

<210> SEQ ID NO 79
<211> LENGTH: 35

-continued

<212> TYPE: DNA
<213> ORGANISM: Acinetobacter baumannii

<400> SEQUENCE: 79
aaataaattg ttcactcaag agtttaggtt aagca                               35

<210> SEQ ID NO 80
<211> LENGTH: 31
<212> TYPE: DNA
<213> ORGANISM: Acinetobacter baumannii

<400> SEQUENCE: 80
ttggcaaaat tgagtctgaa ataaattgtt c                                   31

<210> SEQ ID NO 81
<211> LENGTH: 30
<212> TYPE: DNA
<213> ORGANISM: Acinetobacter baumannii

<400> SEQUENCE: 81
ctcattaaca gattggcaaa attgagtctg                                     30

<210> SEQ ID NO 82
<211> LENGTH: 30
<212> TYPE: DNA
<213> ORGANISM: Acinetobacter baumannii

<400> SEQUENCE: 82
tcacggtaat tagtgtgatc tgacgaagac                                     30

<210> SEQ ID NO 83
<211> LENGTH: 30
<212> TYPE: DNA
<213> ORGANISM: Acinetobacter baumannii

<400> SEQUENCE: 83
tatagtcaag taattaagtg catgtggtgg                                     30

<210> SEQ ID NO 84
<211> LENGTH: 26
<212> TYPE: DNA
<213> ORGANISM: Acinetobacter baumannii

<400> SEQUENCE: 84
ggtagctatg ttcggaaggg ataacc                                         26

<210> SEQ ID NO 85
<211> LENGTH: 28
<212> TYPE: DNA
<213> ORGANISM: Acinetobacter baumannii

<400> SEQUENCE: 85
gccatcgctc aacggataaa aggtactc                                       28

<210> SEQ ID NO 86
<211> LENGTH: 25
<212> TYPE: DNA
<213> ORGANISM: Acinetobacter baumannii

<400> SEQUENCE: 86
aggtgggagg ctttgaagct ggaac                                          25

<210> SEQ ID NO 87

```
<211> LENGTH: 25
<212> TYPE: DNA
<213> ORGANISM: Acinetobacter baumannii

<400> SEQUENCE: 87
ggacgtatag ggtgtgatgc ctgcc                                              25

<210> SEQ ID NO 88
<211> LENGTH: 28
<212> TYPE: DNA
<213> ORGANISM: Acinetobacter baumannii

<400> SEQUENCE: 88
ggggtactct atgctgagat ctgatagc                                           28

<210> SEQ ID NO 89
<211> LENGTH: 26
<212> TYPE: DNA
<213> ORGANISM: Acinetobacter baumannii

<400> SEQUENCE: 89
gtgtgttgag aagcatgctg gaggta                                             26

<210> SEQ ID NO 90
<211> LENGTH: 26
<212> TYPE: DNA
<213> ORGANISM: Acinetobacter baumannii

<400> SEQUENCE: 90
ccaaaccgat gcaaactccg aatacc                                             26

<210> SEQ ID NO 91
<211> LENGTH: 25
<212> TYPE: DNA
<213> ORGANISM: Acinetobacter baumannii

<400> SEQUENCE: 91 gtataggga gccgtagaga aatcg                                               25

<210> SEQ ID NO 92
<211> LENGTH: 25
<212> TYPE: DNA
<213> ORGANISM: Acinetobacter baumannii

<400> SEQUENCE: 92
ggaagtgcga acgtagaggg tgata                                              25

<210> SEQ ID NO 93
<211> LENGTH: 25
<212> TYPE: DNA
<213> ORGANISM: Acinetobacter baumannii

<400> SEQUENCE: 93
gtcaagtaat taagtgcatg tggtg                                              25

<210> SEQ ID NO 94
<211> LENGTH: 26
<212> TYPE: DNA
<213> ORGANISM: Acinetobacter baumannii

<400> SEQUENCE: 94
ttgggtgttg tatagtcaag cctcac                                             26
```

```
<210> SEQ ID NO 95
<211> LENGTH: 25
<212> TYPE: DNA
<213> ORGANISM: Acinetobacter baumannii

<400> SEQUENCE: 95
ttgggtgttg tatagtcaag cctca                                          25

<210> SEQ ID NO 96
<211> LENGTH: 28
<212> TYPE: DNA
<213> ORGANISM: Acinetobacter baumannii

<400> SEQUENCE: 96
ccctcgttcg ccttgcaaca ctatgtat                                       28

<210> SEQ ID NO 97
<211> LENGTH: 25
<212> TYPE: DNA
<213> ORGANISM: Acinetobacter baumannii

<400> SEQUENCE: 97
tcacaggggt tcttttcgcc tttcc                                          25

<210> SEQ ID NO 98
<211> LENGTH: 26
<212> TYPE: DNA
<213> ORGANISM: Acinetobacter baumannii

<400> SEQUENCE: 98
ggcttgatta gcctttcacc cctatc                                         26

<210> SEQ ID NO 99
<211> LENGTH: 30
<212> TYPE: DNA
<213> ORGANISM: Acinetobacter baumannii

<400> SEQUENCE: 99
ccgactcgac tagtgagcta ttacgctttc                                     30

<210> SEQ ID NO 100
<211> LENGTH: 26
<212> TYPE: DNA
<213> ORGANISM: Acinetobacter baumannii

<400> SEQUENCE: 100
acacagaagt aatggaatat taacca                                         26

<210> SEQ ID NO 101
<211> LENGTH: 25
<212> TYPE: DNA
<213> ORGANISM: Acinetobacter baumannii

<400> SEQUENCE: 101
cccgaagtta cggtaccatt ttgcc                                          25

<210> SEQ ID NO 102
<211> LENGTH: 25
<212> TYPE: DNA
<213> ORGANISM: Acinetobacter baumannii

<400> SEQUENCE: 102
tcactgagcc tctgctggag acagc                                          25
```

<210> SEQ ID NO 103
<211> LENGTH: 25
<212> TYPE: DNA
<213> ORGANISM: Acinetobacter baumannii

<400> SEQUENCE: 103
acgctgagcg caccttcgta ctcct                                          25

<210> SEQ ID NO 104
<211> LENGTH: 25
<212> TYPE: DNA
<213> ORGANISM: Acinetobacter baumannii

<400> SEQUENCE: 104
tgtctcacga cgttctaaac ccagc                                          25

<210> SEQ ID NO 105
<211> LENGTH: 28
<212> TYPE: DNA
<213> ORGANISM: Acinetobacter baumannii

<400> SEQUENCE: 105
ggtgttgtat agtcaagcct cacgagca                                       28

<210> SEQ ID NO 106
<211> LENGTH: 27
<212> TYPE: DNA
<213> ORGANISM: Acinetobacter baumannii

<400> SEQUENCE: 106
ttaggttaag caattaatct agatgaa                                        27

<210> SEQ ID NO 107
<211> LENGTH: 30
<212> TYPE: DNA
<213> ORGANISM: Acinetobacter baumannii

<400> SEQUENCE: 107
ggattacaga aattagtaaa taaagattga                                     30

<210> SEQ ID NO 108
<211> LENGTH: 30
<212> TYPE: DNA
<213> ORGANISM: Acinetobacter baumannii

<400> SEQUENCE: 108
cagtagcgag gttaaccgta tagggagcc                                      30

<210> SEQ ID NO 109
<211> LENGTH: 38
<212> TYPE: DNA
<213> ORGANISM: Acinetobacter baumannii

<400> SEQUENCE: 109
gatcctgaaa ccgcatgcat acaagcagtg ggagcacc                            38

<210> SEQ ID NO 110
<211> LENGTH: 30
<212> TYPE: DNA
<213> ORGANISM: Acinetobacter baumannii

<400> SEQUENCE: 110
ctgaccgata gtgaaccagt accgtgaggg                                     30

<210> SEQ ID NO 111
<211> LENGTH: 38
<212> TYPE: DNA
<213> ORGANISM: Acinetobacter baumannii

<400> SEQUENCE: 111
ggggaccatc ctccaaggct aaatactcct gactgacc                    38

<210> SEQ ID NO 112
<211> LENGTH: 40
<212> TYPE: DNA
<213> ORGANISM: Acinetobacter baumannii

<400> SEQUENCE: 112
cacgaaaggg cacacataat gatgacgagt agggcgaggc                  40

<210> SEQ ID NO 113
<211> LENGTH: 30
<212> TYPE: DNA
<213> ORGANISM: Acinetobacter baumannii

<400> SEQUENCE: 113
gctctgggaa gtgcgaacgt agagggtgat                             30

<210> SEQ ID NO 114
<211> LENGTH: 38
<212> TYPE: DNA
<213> ORGANISM: Acinetobacter baumannii

<400> SEQUENCE: 114
gcaaggcgaa cgaggggaag tgaaacatct cagtaccc                    38

<210> SEQ ID NO 115
<211> LENGTH: 36
<212> TYPE: DNA
<213> ORGANISM: Acinetobacter baumannii

<400> SEQUENCE: 115
ggcgatgaaa gacgtgatag cctgcgaaaa gctccg                      36

<210> SEQ ID NO 116
<211> LENGTH: 40
<212> TYPE: DNA
<213> ORGANISM: Acinetobacter baumannii

<400> SEQUENCE: 116
tacacaggaa tcgtacccga aaccgacaca ggtggtcagg                  40

<210> SEQ ID NO 117
<211> LENGTH: 39
<212> TYPE: DNA
<213> ORGANISM: Acinetobacter baumannii

<400> SEQUENCE: 117
cccctaaggc gaggccgaaa ggcgtagtcg atgggaaaa                   39

<210> SEQ ID NO 118
<211> LENGTH: 37
<212> TYPE: DNA
<213> ORGANISM: Acinetobacter baumannii

<400> SEQUENCE: 118

```
cccgttcgcc gaaagaccaa gggttccagt ccaacgt                                    37

<210> SEQ ID NO 119
<211> LENGTH: 32
<212> TYPE: DNA
<213> ORGANISM: Acinetobacter baumannii

<400> SEQUENCE: 119
gtatacgtgg taggggagcg ttctgtaagc cg                                         32

<210> SEQ ID NO 120
<211> LENGTH: 30
<212> TYPE: DNA
<213> ORGANISM: Acinetobacter baumannii

<400> SEQUENCE: 120
gcgtaatagc tcactagtcg agtcggcctg                                            30

<210> SEQ ID NO 121
<211> LENGTH: 30
<212> TYPE: DNA
<213> ORGANISM: Acinetobacter baumannii

<400> SEQUENCE: 121
cgatgtggga aggcatagac agctaggagg                                            30

<210> SEQ ID NO 122
<211> LENGTH: 39
<212> TYPE: DNA
<213> ORGANISM: Acinetobacter baumannii

<400> SEQUENCE: 122
gtgtctggtg ggtagtttga ctggggcggt ctcctccta                                  39

<210> SEQ ID NO 123
<211> LENGTH: 36
<212> TYPE: DNA
<213> ORGANISM: Acinetobacter baumannii

<400> SEQUENCE: 123
gttccagtgg agccgtcctt gaaataccac cctggt                                     36

<210> SEQ ID NO 124
<211> LENGTH: 36
<212> TYPE: DNA
<213> ORGANISM: Acinetobacter baumannii

<400> SEQUENCE: 124
gtgtaggata ggtgggaggc tttgaagctg gaacgc                                     36

<210> SEQ ID NO 125
<211> LENGTH: 30
<212> TYPE: DNA
<213> ORGANISM: Acinetobacter baumannii

<400> SEQUENCE: 125
cgctgtctcc agcagaggct cagtgaaatc                                            30

<210> SEQ ID NO 126
<211> LENGTH: 37
<212> TYPE: DNA
<213> ORGANISM: Acinetobacter baumannii

<400> SEQUENCE: 126
```
tggcataatg atggcggcgc tgtctccagc agaggct    37

<210> SEQ ID NO 127
<211> LENGTH: 25
<212> TYPE: DNA
<213> ORGANISM: Acinetobacter baumannii

<400> SEQUENCE: 127
cgtgaggctt gactatacaa caccc    25

<210> SEQ ID NO 128
<211> LENGTH: 25
<212> TYPE: DNA
<213> ORGANISM: Acinetobacter baumannii

<400> SEQUENCE: 128
gcagttgtat ataaagcatc aatcg    25

<210> SEQ ID NO 129
<211> LENGTH: 26
<212> TYPE: DNA
<213> ORGANISM: Acinetobacter baumannii

<400> SEQUENCE: 129
tgagctggcg atgacttact ctcaca    26

<210> SEQ ID NO 130
<211> LENGTH: 26
<212> TYPE: DNA
<213> ORGANISM: Acinetobacter baumannii

<400> SEQUENCE: 130
gagctggcga tgacttactc tcacat    26

<210> SEQ ID NO 131
<211> LENGTH: 30
<212> TYPE: DNA
<213> ORGANISM: Acinetobacter baumannii

<400> SEQUENCE: 131
gtgaaccacc tgatcccttc ccgaactcag    30

<210> SEQ ID NO 132
<211> LENGTH: 30
<212> TYPE: DNA
<213> ORGANISM: Acinetobacter baumannii

<400> SEQUENCE: 132
gctggcgacc atagcaagag tgaaccacct    30

<210> SEQ ID NO 133
<211> LENGTH: 25
<212> TYPE: DNA
<213> ORGANISM: Acinetobacter baumannii

<400> SEQUENCE: 133
ctctgtacac gacaaatttc acaga    25

<210> SEQ ID NO 134
<211> LENGTH: 26
<212> TYPE: DNA
<213> ORGANISM: Acinetobacter baumannii

<400> SEQUENCE: 134
ctctgtacac gacaaatttc acagaa    26

<210> SEQ ID NO 135
<211> LENGTH: 25
<212> TYPE: DNA
<213> ORGANISM: Acinetobacter baumannii

<400> SEQUENCE: 135
ccatttagtg aaaaagtgca ggcta    25

<210> SEQ ID NO 136
<211> LENGTH: 26
<212> TYPE: DNA
<213> ORGANISM: Acinetobacter baumannii

<400> SEQUENCE: 136
gatcggattg gagaaccaga aaacgg    26

<210> SEQ ID NO 137
<211> LENGTH: 27
<212> TYPE: DNA
<213> ORGANISM: Acinetobacter baumannii

<400> SEQUENCE: 137
agagctcttt tttattttct attgatc    27

<210> SEQ ID NO 138
<211> LENGTH: 25
<212> TYPE: DNA
<213> ORGANISM: Acinetobacter baumannii

<400> SEQUENCE: 138
caactgagaa atttgacgat aatca    25

<210> SEQ ID NO 139
<211> LENGTH: 25
<212> TYPE: DNA
<213> ORGANISM: Acinetobacter baumannii

<400> SEQUENCE: 139
aatgcagaag ttgatgtctt gttca    25

<210> SEQ ID NO 140
<211> LENGTH: 25
<212> TYPE: DNA
<213> ORGANISM: Acinetobacter baumannii

<400> SEQUENCE: 140
agggtctgtc aagcgcgtat ttcca    25

<210> SEQ ID NO 141
<211> LENGTH: 25
<212> TYPE: DNA
<213> ORGANISM: Acinetobacter baumannii

<400> SEQUENCE: 141
acaatggttc tccaatattc gcggg    25

<210> SEQ ID NO 142
<211> LENGTH: 26
<212> TYPE: DNA
<213> ORGANISM: Acinetobacter baumannii

```
<400> SEQUENCE: 142
tcaagctctt aaataatatt cagctg                                          26

<210> SEQ ID NO 143
<211> LENGTH: 28
<212> TYPE: DNA
<213> ORGANISM: Acinetobacter baumannii

<400> SEQUENCE: 143
caagctctta aataatattc agctgttt                                        28

<210> SEQ ID NO 144
<211> LENGTH: 25
<212> TYPE: DNA
<213> ORGANISM: Acinetobacter baumannii

<400> SEQUENCE: 144
gcggtgttag ctataagctt ctgtt                                           25

<210> SEQ ID NO 145
<211> LENGTH: 25
<212> TYPE: DNA
<213> ORGANISM: Acinetobacter baumannii

<400> SEQUENCE: 145
tgtcaccaat catttaggaa agaat                                           25

<210> SEQ ID NO 146
<211> LENGTH: 25
<212> TYPE: DNA
<213> ORGANISM: Acinetobacter baumannii

<400> SEQUENCE: 146
gaccaagtgc aactgacttt agata                                           25

<210> SEQ ID NO 147
<211> LENGTH: 30
<212> TYPE: DNA
<213> ORGANISM: Acinetobacter baumannii

<400> SEQUENCE: 147
aatagataac tcattgaaat aatgtcataa                                      30

<210> SEQ ID NO 148
<211> LENGTH: 25
<212> TYPE: DNA
<213> ORGANISM: Acinetobacter baumannii

<400> SEQUENCE: 148
ttaaatgtag aggctggcac atatt                                           25

<210> SEQ ID NO 149
<211> LENGTH: 25
<212> TYPE: DNA
<213> ORGANISM: Acinetobacter baumannii

<400> SEQUENCE: 149
ggaaacaaac tctacctctt gaata                                           25

<210> SEQ ID NO 150
<211> LENGTH: 28
<212> TYPE: DNA
```

<213> ORGANISM: Acinetobacter baumannii

<400> SEQUENCE: 150
tttataaaat tagagtttct gtcaagct 28

<210> SEQ ID NO 151
<211> LENGTH: 30
<212> TYPE: DNA
<213> ORGANISM: Acinetobacter baumannii

<400> SEQUENCE: 151
ccaattaaac gctgaatcgc catttgaaca 30

<210> SEQ ID NO 152
<211> LENGTH: 30
<212> TYPE: DNA
<213> ORGANISM: Acinetobacter baumannii

<400> SEQUENCE: 152
aaaaccaatt aaacgctgaa tcgccatttg 30

<210> SEQ ID NO 153
<211> LENGTH: 30
<212> TYPE: DNA
<213> ORGANISM: Acinetobacter baumannii

<400> SEQUENCE: 153
cccttatcct atcaggattc tgccttctta 30

<210> SEQ ID NO 154
<211> LENGTH: 30
<212> TYPE: DNA
<213> ORGANISM: Acinetobacter baumannii

<400> SEQUENCE: 154
ctctgtacac gacaaatttc acagaaccct 30

<210> SEQ ID NO 155
<211> LENGTH: 30
<212> TYPE: DNA
<213> ORGANISM: Acinetobacter baumannii

<400> SEQUENCE: 155
ttccacgata aacgattgcg agcatcagga 30

<210> SEQ ID NO 156
<211> LENGTH: 30
<212> TYPE: DNA
<213> ORGANISM: Acinetobacter baumannii

<400> SEQUENCE: 156
caatgtccaa aggataggta tcgctattcc 30

<210> SEQ ID NO 157
<211> LENGTH: 30
<212> TYPE: DNA
<213> ORGANISM: Acinetobacter baumannii

<400> SEQUENCE: 157
ctgaatttcc acgttttatta agcaatgtcc 30

<210> SEQ ID NO 158
<211> LENGTH: 30

```
<212> TYPE: DNA
<213> ORGANISM: Acinetobacter baumannii

<400> SEQUENCE: 158
aaaatggcta taaagcgttg aatcaaagca                                    30

<210> SEQ ID NO 159
<211> LENGTH: 30
<212> TYPE: DNA
<213> ORGANISM: Acinetobacter baumannii

<400> SEQUENCE: 159
ctgcgaacac attcacaata cggtctttac                                    30

<210> SEQ ID NO 160
<211> LENGTH: 30
<212> TYPE: DNA
<213> ORGANISM: Acinetobacter baumannii

<400> SEQUENCE: 160
tcaccgataa actctctgtc tgcgaacaca                                    30

<210> SEQ ID NO 161
<211> LENGTH: 30
<212> TYPE: DNA
<213> ORGANISM: Acinetobacter baumannii

<400> SEQUENCE: 161
acacgaatgc agaagttgat gtcttgttca                                    30

<210> SEQ ID NO 162
<211> LENGTH: 30
<212> TYPE: DNA
<213> ORGANISM: Acinetobacter baumannii

<400> SEQUENCE: 162
cgcaaagcac tttaaatgtg acttgttcca                                    30

<210> SEQ ID NO 163
<211> LENGTH: 30
<212> TYPE: DNA
<213> ORGANISM: Acinetobacter baumannii

<400> SEQUENCE: 163
gagcgcaaag cactttaaat gtgacttgtt                                    30

<210> SEQ ID NO 164
<211> LENGTH: 30
<212> TYPE: DNA
<213> ORGANISM: Acinetobacter baumannii

<400> SEQUENCE: 164
gatgagcgca aagcacttta aatgtgactt                                    30

<210> SEQ ID NO 165
<211> LENGTH: 30
<212> TYPE: DNA
<213> ORGANISM: Acinetobacter baumannii

<400> SEQUENCE: 165
atgatgagcg caaagcactt taaatgtgac                                    30

<210> SEQ ID NO 166
```

```
<211> LENGTH: 30
<212> TYPE: DNA
<213> ORGANISM: Acinetobacter baumannii

<400> SEQUENCE: 166
ataatcacaa gcatgatgag cgcaaagcac                                        30

<210> SEQ ID NO 167
<211> LENGTH: 30
<212> TYPE: DNA
<213> ORGANISM: Acinetobacter baumannii

<400> SEQUENCE: 167
tttaaaataa tcacaagcat gatgagcgca                                        30

<210> SEQ ID NO 168
<211> LENGTH: 36
<212> TYPE: DNA
<213> ORGANISM: Acinetobacter baumannii

<400> SEQUENCE: 168
tcccagtcta tcaggaactt gcgcgacgta tcggtc                                 36

<210> SEQ ID NO 169
<211> LENGTH: 40
<212> TYPE: DNA
<213> ORGANISM: Acinetobacter baumannii

<400> SEQUENCE: 169
agctttctgc agtcccagtc tatcaggaac ttgcgcgacg                             40

<210> SEQ ID NO 170
<211> LENGTH: 27
<212> TYPE: DNA
<213> ORGANISM: Mycobacterium tuberculosis

<400> SEQUENCE: 170
gggaaactgg gtctaatacc ggatagg                                           27

<210> SEQ ID NO 171
<211> LENGTH: 28
<212> TYPE: DNA
<213> ORGANISM: Mycobacterium tuberculosis

<400> SEQUENCE: 171
aaactgggtc taataccgga taggacca                                          28

<210> SEQ ID NO 172
<211> LENGTH: 25
<212> TYPE: DNA
<213> ORGANISM: Mycobacterium tuberculosis

<400> SEQUENCE: 172
gcgtggccgt ttgttttgtc aggat                                             25

<210> SEQ ID NO 173
<211> LENGTH: 25
<212> TYPE: DNA
<213> ORGANISM: Mycobacterium tuberculosis

<400> SEQUENCE: 173 ccctttttcca aagggagtgt ttggg                                            25
```

<210> SEQ ID NO 174
<211> LENGTH: 25
<212> TYPE: DNA
<213> ORGANISM: Mycobacterium tuberculosis

<400> SEQUENCE: 174
gacgacgggt agccggcctg agagg                                             25

<210> SEQ ID NO 175
<211> LENGTH: 25
<212> TYPE: DNA
<213> ORGANISM: Mycobacterium tuberculosis

<400> SEQUENCE: 175
taggtggttt gtcgcgttgt tcgtg                                             25

<210> SEQ ID NO 176
<211> LENGTH: 25
<212> TYPE: DNA
<213> ORGANISM: Mycobacterium tuberculosis

<400> SEQUENCE: 176
ctaacgcatt aagtaccccg cctgg                                             25

<210> SEQ ID NO 177
<211> LENGTH: 25
<212> TYPE: DNA
<213> ORGANISM: Mycobacterium tuberculosis

<400> SEQUENCE: 177
ggaaggtggg gatgacgtca agtca                                             25

<210> SEQ ID NO 178
<211> LENGTH: 25
<212> TYPE: DNA
<213> ORGANISM: Mycobacterium tuberculosis

<400> SEQUENCE: 178
gacgaagtcg taacaaggta gccgt                                             25

<210> SEQ ID NO 179
<211> LENGTH: 25
<212> TYPE: DNA
<213> ORGANISM: Mycobacterium tuberculosis

<400> SEQUENCE: 179
tttacgccca gtaattccgg acaac                                             25

<210> SEQ ID NO 180
<211> LENGTH: 20
<212> TYPE: DNA
<213> ORGANISM: Mycobacterium tuberculosis

<400> SEQUENCE: 180
aattccggac aacgctcgca                                                   20

<210> SEQ ID NO 181
<211> LENGTH: 23
<212> TYPE: DNA
<213> ORGANISM: Mycobacterium tuberculosis

<400> SEQUENCE: 181
ccagtaattc cggacaacgc tcg                                               23

<210> SEQ ID NO 182
<211> LENGTH: 28
<212> TYPE: DNA
<213> ORGANISM: Mycobacterium tuberculosis

<400> SEQUENCE: 182
ttccagtctc ccctgcagta ctctagtc                                    28

<210> SEQ ID NO 183
<211> LENGTH: 27
<212> TYPE: DNA
<213> ORGANISM: Mycobacterium tuberculosis

<400> SEQUENCE: 183
gaattccagt ctcccctgca gtactct                                     27

<210> SEQ ID NO 184
<211> LENGTH: 28
<212> TYPE: DNA
<213> ORGANISM: Mycobacterium tuberculosis

<400> SEQUENCE: 184
ttccagtctc ccctgcagta ctctagtc                                    28

<210> SEQ ID NO 185
<211> LENGTH: 27
<212> TYPE: DNA
<213> ORGANISM: Mycobacterium tuberculosis

<400> SEQUENCE: 185
cttagaaagg aggtgatcca gccgcac                                     27

<210> SEQ ID NO 186
<211> LENGTH: 25
<212> TYPE: DNA
<213> ORGANISM: Mycobacterium tuberculosis

<400> SEQUENCE: 186
ttggggcgtt ttcgtggtgc tcctt                                       25

<210> SEQ ID NO 187
<211> LENGTH: 27
<212> TYPE: DNA
<213> ORGANISM: Mycobacterium tuberculosis

<400> SEQUENCE: 187
attcgcttaa cctcgcggca tcgcagc                                     27

<210> SEQ ID NO 188
<211> LENGTH: 25
<212> TYPE: DNA
<213> ORGANISM: Mycobacterium tuberculosis

<400> SEQUENCE: 188
aggtaaggtt cttcgcgttg catcg                                       25

<210> SEQ ID NO 189
<211> LENGTH: 25
<212> TYPE: DNA
<213> ORGANISM: Mycobacterium tuberculosis

<400> SEQUENCE: 189
gtctcccctg cagtactcta gtctg                                       25

<210> SEQ ID NO 190
<211> LENGTH: 25
<212> TYPE: DNA
<213> ORGANISM: Mycobacterium tuberculosis

<400> SEQUENCE: 190
tattccccac tgctgcctcc cgtag                                  25

<210> SEQ ID NO 191
<211> LENGTH: 25
<212> TYPE: DNA
<213> ORGANISM: Mycobacterium tuberculosis

<400> SEQUENCE: 191
tcgacttgca tgtgttaagc acgcc                                  25

<210> SEQ ID NO 192
<211> LENGTH: 34
<212> TYPE: DNA
<213> ORGANISM: Mycobacterium tuberculosis

<400> SEQUENCE: 192
caccatcgac gaaggtccgg gttctctcgg attg                        34

<210> SEQ ID NO 193
<211> LENGTH: 25
<212> TYPE: DNA
<213> ORGANISM: Mycobacterium tuberculosis

<400> SEQUENCE: 193
tgttcgtgaa atctcacggc ttaac                                  25

<210> SEQ ID NO 194
<211> LENGTH: 32
<212> TYPE: DNA
<213> ORGANISM: Mycobacterium tuberculosis

<400> SEQUENCE: 194
gcgtgcgggc gatacgggca gactagagta ct                          32

<210> SEQ ID NO 195
<211> LENGTH: 35
<212> TYPE: DNA
<213> ORGANISM: Mycobacterium tuberculosis

<400> SEQUENCE: 195
ctaataccgg ataggaccac gggatgcatg tcttg                       35

<210> SEQ ID NO 196
<211> LENGTH: 29
<212> TYPE: DNA
<213> ORGANISM: Mycobacterium tuberculosis

<400> SEQUENCE: 196
ggccacactg ggactgagat acggcccag                              29

<210> SEQ ID NO 197
<211> LENGTH: 29
<212> TYPE: DNA
<213> ORGANISM: Mycobacterium tuberculosis

<400> SEQUENCE: 197
ccatcgacga aggtccgggt tctctcgga                                    29

<210> SEQ ID NO 198
<211> LENGTH: 24
<212> TYPE: DNA
<213> ORGANISM: Mycobacterium tuberculosis

<400> SEQUENCE: 198
cgcgtctaga gataggcgtt ccct                                         24

<210> SEQ ID NO 199
<211> LENGTH: 31
<212> TYPE: DNA
<213> ORGANISM: Mycobacterium tuberculosis

<400> SEQUENCE: 199
gggggcccgc acaagcggcg gagcatgtgg a                                 31

<210> SEQ ID NO 200
<211> LENGTH: 25
<212> TYPE: DNA
<213> ORGANISM: Mycobacterium tuberculosis

<400> SEQUENCE: 200
tgatcctggc tcaggacgaa cgctg                                        25

<210> SEQ ID NO 201
<211> LENGTH: 25
<212> TYPE: DNA
<213> ORGANISM: Mycobacterium tuberculosis

<400> SEQUENCE: 201
gctggcggcg tgcttaacac atgca                                        25

<210> SEQ ID NO 202
<211> LENGTH: 25
<212> TYPE: DNA
<213> ORGANISM: Mycobacterium tuberculosis

<400> SEQUENCE: 202
ggaccacggg atgcatgtct tgtgg                                        25

<210> SEQ ID NO 203
<211> LENGTH: 25
<212> TYPE: DNA
<213> ORGANISM: Mycobacterium tuberculosis

<400> SEQUENCE: 203
cctgagaggg tgtccggcca cactg                                        25

<210> SEQ ID NO 204
<211> LENGTH: 25
<212> TYPE: DNA
<213> ORGANISM: Mycobacterium tuberculosis

<400> SEQUENCE: 204
ggggatgacg gccttcgggt tgtaa                                        25

<210> SEQ ID NO 205
<211> LENGTH: 25
<212> TYPE: DNA
<213> ORGANISM: Mycobacterium tuberculosis

<400> SEQUENCE: 205
aactacgtgc cagcagccgc ggtaa                                          25

<210> SEQ ID NO 206
<211> LENGTH: 30
<212> TYPE: DNA
<213> ORGANISM: Mycobacterium tuberculosis

<400> SEQUENCE: 206
gggtctctgg gcagtaactg acgctgagga                                     30

<210> SEQ ID NO 207
<211> LENGTH: 30
<212> TYPE: DNA
<213> ORGANISM: Mycobacterium tuberculosis

<400> SEQUENCE: 207
gcgtggggag cgaacaggat tagataccct                                     30

<210> SEQ ID NO 208
<211> LENGTH: 30
<212> TYPE: DNA
<213> ORGANISM: Mycobacterium tuberculosis

<400> SEQUENCE: 208
ctggggagta cggccgcaag gctaaaactc                                     30

<210> SEQ ID NO 209
<211> LENGTH: 25
<212> TYPE: DNA
<213> ORGANISM: Mycobacterium tuberculosis

<400> SEQUENCE: 209
agcaccacga aaacgcccca actgg                                          25

<210> SEQ ID NO 210
<211> LENGTH: 25
<212> TYPE: DNA
<213> ORGANISM: Mycobacterium tuberculosis

<400> SEQUENCE: 210
aaggagcacc acgaaaacgc cccaa                                          25

<210> SEQ ID NO 211
<211> LENGTH: 25
<212> TYPE: DNA
<213> ORGANISM: Mycobacterium tuberculosis

<400> SEQUENCE: 211
ccggcagcgt atccattgat gctcg                                          25

<210> SEQ ID NO 212
<211> LENGTH: 25
<212> TYPE: DNA
<213> ORGANISM: Mycobacterium tuberculosis

<400> SEQUENCE: 212
gccggcagcg tatccattga tgctc                                          25

<210> SEQ ID NO 213
<211> LENGTH: 25
<212> TYPE: DNA
<213> ORGANISM: Mycobacterium tuberculosis

<400> SEQUENCE: 213
agccggcagc gtatccattg atgct                                         25

<210> SEQ ID NO 214
<211> LENGTH: 30
<212> TYPE: DNA
<213> ORGANISM: Mycobacterium tuberculosis

<400> SEQUENCE: 214
ccaccatgcg cccttagaca cttacaaaca                                    30

<210> SEQ ID NO 215
<211> LENGTH: 31
<212> TYPE: DNA
<213> ORGANISM: Mycobacterium tuberculosis

<400> SEQUENCE: 215
acttgttcca ggtgttgtcc caccgccttg g                                  31

<210> SEQ ID NO 216
<211> LENGTH: 31
<212> TYPE: DNA
<213> ORGANISM: Mycobacterium tuberculosis
<220> FEATURE:
<221> NAME/KEY: misc_feature
<222> LOCATION: (27)..(27)
<223> OTHER INFORMATION: n is a, c, g, or t

<400> SEQUENCE: 216
acacactgtt gggtcctgag gcaacanctc g                                  31

<210> SEQ ID NO 217
<211> LENGTH: 36
<212> TYPE: DNA
<213> ORGANISM: Mycobacterium tuberculosis

<400> SEQUENCE: 217
aggggttctt gtctgtagtg ggcgagagcc gggtgc                             36

<210> SEQ ID NO 218
<211> LENGTH: 26
<212> TYPE: DNA
<213> ORGANISM: Mycobacterium tuberculosis

<400> SEQUENCE: 218
acacactgtt gggtcctgag gcaaca                                        26

<210> SEQ ID NO 219
<211> LENGTH: 25
<212> TYPE: DNA
<213> ORGANISM: Mycobacterium tuberculosis

<400> SEQUENCE: 219
gaactggata gtggttgcga gcatc                                         25

<210> SEQ ID NO 220
<211> LENGTH: 30
<212> TYPE: DNA
<213> ORGANISM: Mycobacterium tuberculosis

<400> SEQUENCE: 220
gcgtaggccg tgagggggttc ttgtctgtag                                   30

```
<210> SEQ ID NO 221
<211> LENGTH: 30
<212> TYPE: DNA
<213> ORGANISM: Mycobacterium tuberculosis

<400> SEQUENCE: 221
tggggcgtag gccgtgaggg gttcttgtct                                      30

<210> SEQ ID NO 222
<211> LENGTH: 30
<212> TYPE: DNA
<213> ORGANISM: Mycobacterium tuberculosis

<400> SEQUENCE: 222
cactcggact tgttccaggt gttgtcccac                                      30

<210> SEQ ID NO 223
<211> LENGTH: 30
<212> TYPE: DNA
<213> ORGANISM: Mycobacterium tuberculosis

<400> SEQUENCE: 223
cgagcatcaa tggatacgct gccggctagc                                      30

<210> SEQ ID NO 224
<211> LENGTH: 26
<212> TYPE: DNA
<213> ORGANISM: Mycobacterium tuberculosis

<400> SEQUENCE: 224
gagccgggtg catgacaaca aagttg                                          26

<210> SEQ ID NO 225
<211> LENGTH: 27
<212> TYPE: DNA
<213> ORGANISM: Mycobacterium tuberculosis

<400> SEQUENCE: 225
cactcggact tgttccaggt gttgtcc                                         27

<210> SEQ ID NO 226
<211> LENGTH: 29
<212> TYPE: DNA
<213> ORGANISM: Mycobacterium tuberculosis

<400> SEQUENCE: 226
ctggcgttga gcgtagtagg cagcctcga                                       29

<210> SEQ ID NO 227
<211> LENGTH: 25
<212> TYPE: DNA
<213> ORGANISM: Mycobacterium tuberculosis

<400> SEQUENCE: 227
agtcgaccca gcgcgcggtg gccaa                                           25

<210> SEQ ID NO 228
<211> LENGTH: 23
<212> TYPE: DNA
<213> ORGANISM: Mycobacterium tuberculosis

<400> SEQUENCE: 228
tcgctgatcc ggccacagcc cgt                                             23
```

<210> SEQ ID NO 229
<211> LENGTH: 29
<212> TYPE: DNA
<213> ORGANISM: Mycobacterium tuberculosis

<400> SEQUENCE: 229
ttgcggtggg gtgtcgagtc gatctgcac                                29

<210> SEQ ID NO 230
<211> LENGTH: 30
<212> TYPE: DNA
<213> ORGANISM: Mycobacterium tuberculosis

<400> SEQUENCE: 230
tggatgcctg cctcggcgag ccgctcgctg                               30

<210> SEQ ID NO 231
<211> LENGTH: 30
<212> TYPE: DNA
<213> ORGANISM: Mycobacterium tuberculosis

<400> SEQUENCE: 231
tcgacatcct cgatggaccg ccagggcttg                               30

<210> SEQ ID NO 232
<211> LENGTH: 30
<212> TYPE: DNA
<213> ORGANISM: Mycobacterium tuberculosis

<400> SEQUENCE: 232
ccgccagccc aggatcctgc gagcgtaggc                               30

<210> SEQ ID NO 233
<211> LENGTH: 30
<212> TYPE: DNA
<213> ORGANISM: Mycobacterium tuberculosis

<400> SEQUENCE: 233
gaaccctgcc caggtcgaca cataggtgag                               30

<210> SEQ ID NO 234
<211> LENGTH: 30
<212> TYPE: DNA
<213> ORGANISM: Mycobacterium tuberculosis

<400> SEQUENCE: 234
agtcgaccca gcgcgcggtg gccaactcga                               30

<210> SEQ ID NO 235
<211> LENGTH: 30
<212> TYPE: DNA
<213> ORGANISM: Mycobacterium tuberculosis

<400> SEQUENCE: 235
cgccagggct tgccgggttt gatcagctcg                               30

<210> SEQ ID NO 236
<211> LENGTH: 30
<212> TYPE: DNA
<213> ORGANISM: Mycobacterium tuberculosis

<400> SEQUENCE: 236
gctcgctgaa ccggatcgat gtgtactgag                               30

<210> SEQ ID NO 237
<211> LENGTH: 30
<212> TYPE: DNA
<213> ORGANISM: Mycobacterium tuberculosis

<400> SEQUENCE: 237
aggatcctgc gagcgtaggc gtcggtgaca                                    30

<210> SEQ ID NO 238
<211> LENGTH: 24
<212> TYPE: DNA
<213> ORGANISM: Staphylococcus aureus

<400> SEQUENCE: 238
agagtttgat cctggctcag gatg                                          24

<210> SEQ ID NO 239
<211> LENGTH: 29
<212> TYPE: DNA
<213> ORGANISM: Staphylococcus aureus

<400> SEQUENCE: 239
ttagtattta tgagctaatc aaacatcat                                     29

<210> SEQ ID NO 240
<211> LENGTH: 25
<212> TYPE: DNA
<213> ORGANISM: Staphylococcus aureus

<400> SEQUENCE: 240
gcttaccaag gcaacgatgc atagc                                         25

<210> SEQ ID NO 241
<211> LENGTH: 26
<212> TYPE: DNA
<213> ORGANISM: Staphylococcus aureus

<400> SEQUENCE: 241
gcaagcgtta tccggaatta ttgggc                                        26

<210> SEQ ID NO 242
<211> LENGTH: 25
<212> TYPE: DNA
<213> ORGANISM: Staphylococcus aureus

<400> SEQUENCE: 242
ctaacgcatt aagcactccg cctgg                                         25

<210> SEQ ID NO 243
<211> LENGTH: 25
<212> TYPE: DNA
<213> ORGANISM: Staphylococcus aureus

<400> SEQUENCE: 243
ctaagttgac tgccggtgac aaacc                                         25

<210> SEQ ID NO 244
<211> LENGTH: 25
<212> TYPE: DNA
<213> ORGANISM: Staphylococcus aureus

<400> SEQUENCE: 244

-continued ggtgggacaa atgattgggg tgaag       25

<210> SEQ ID NO 245
<211> LENGTH: 20
<212> TYPE: DNA
<213> ORGANISM: Staphylococcus aureus

<400> SEQUENCE: 245
aggtgatcca gccgcacctt       20

<210> SEQ ID NO 246
<211> LENGTH: 25
<212> TYPE: DNA
<213> ORGANISM: Staphylococcus aureus

<400> SEQUENCE: 246
aagaagatgt tccgaatata tcctt       25

<210> SEQ ID NO 247
<211> LENGTH: 26
<212> TYPE: DNA
<213> ORGANISM: Staphylococcus aureus

<400> SEQUENCE: 247
ctttatggga tttgcttgac ctcgcg       26

<210> SEQ ID NO 248
<211> LENGTH: 25
<212> TYPE: DNA
<213> ORGANISM: Staphylococcus aureus

<400> SEQUENCE: 248
tggtaaggtt cttcgcgttg cttcg       25

<210> SEQ ID NO 249
<211> LENGTH: 25
<212> TYPE: DNA
<213> ORGANISM: Staphylococcus aureus

<400> SEQUENCE: 249
ttcctcttct gcactcaagt tttcc       25

<210> SEQ ID NO 250
<211> LENGTH: 25
<212> TYPE: DNA
<213> ORGANISM: Staphylococcus aureus

<400> SEQUENCE: 250
aagattccct actgctgcct cccgt       25

<210> SEQ ID NO 251
<211> LENGTH: 25
<212> TYPE: DNA
<213> ORGANISM: Staphylococcus aureus

<400> SEQUENCE: 251
gtccgttcgc tcgacttgca tgtat       25

<210> SEQ ID NO 252
<211> LENGTH: 30
<212> TYPE: DNA
<213> ORGANISM: Staphylococcus aureus

<400> SEQUENCE: 252
gtcccacctt cgacggctag ctcctaaaag                                           30

<210> SEQ ID NO 253
<211> LENGTH: 30
<212> TYPE: DNA
<213> ORGANISM: Staphylococcus aureus

<400> SEQUENCE: 253
gtgttacaaa ctctcgtggt gtgacgggcg                                           30

<210> SEQ ID NO 254
<211> LENGTH: 30
<212> TYPE: DNA
<213> ORGANISM: Staphylococcus aureus

<400> SEQUENCE: 254
acccaacatc tcacgacacg agctgacgac                                           30

<210> SEQ ID NO 255
<211> LENGTH: 30
<212> TYPE: DNA
<213> ORGANISM: Staphylococcus aureus

<400> SEQUENCE: 255
gagtttcaac cttgcggtcg tactccccag                                           30

<210> SEQ ID NO 256
<211> LENGTH: 30
<212> TYPE: DNA
<213> ORGANISM: Staphylococcus aureus

<400> SEQUENCE: 256
ctcatcgttt acggcgtgga ctaccagggt                                           30

<210> SEQ ID NO 257
<211> LENGTH: 30
<212> TYPE: DNA
<213> ORGANISM: Staphylococcus aureus

<400> SEQUENCE: 257
tattaccgcg gctgctggca cgtagttagc                                           30

<210> SEQ ID NO 258
<211> LENGTH: 30
<212> TYPE: DNA
<213> ORGANISM: Staphylococcus aureus

<400> SEQUENCE: 258
gatcaccctc tcaggtcggc tatgcatcgt                                           30

<210> SEQ ID NO 259
<211> LENGTH: 30
<212> TYPE: DNA
<213> ORGANISM: Staphylococcus aureus

<400> SEQUENCE: 259
aggttatcca cgtgttactc acccgtccgc                                           30

<210> SEQ ID NO 260
<211> LENGTH: 21
<212> TYPE: DNA
<213> ORGANISM: Staphylococcus aureus

<400> SEQUENCE: 260
ttaagttatt aagggcgcac g                                           21

<210> SEQ ID NO 261
<211> LENGTH: 25
<212> TYPE: DNA
<213> ORGANISM: Staphylococcus aureus

<400> SEQUENCE: 261
cgagaggacc gggatggaca tacct                                       25

<210> SEQ ID NO 262
<211> LENGTH: 25
<212> TYPE: DNA
<213> ORGANISM: Staphylococcus aureus

<400> SEQUENCE: 262
gagacctaca agtcgagcag ggtcg                                       25

<210> SEQ ID NO 263
<211> LENGTH: 25
<212> TYPE: DNA
<213> ORGANISM: Staphylococcus aureus

<400> SEQUENCE: 263
ggaaagaccc cgtggagctt tactg                                       25

<210> SEQ ID NO 264
<211> LENGTH: 25
<212> TYPE: DNA
<213> ORGANISM: Staphylococcus aureus

<400> SEQUENCE: 264
cagtgaatag gcccaagcga ctgtt                                       25

<210> SEQ ID NO 265
<211> LENGTH: 25
<212> TYPE: DNA
<213> ORGANISM: Staphylococcus aureus

<400> SEQUENCE: 265
gataggcgaa gcgtgcgatt ggatt                                       25

<210> SEQ ID NO 266
<211> LENGTH: 25
<212> TYPE: DNA
<213> ORGANISM: Staphylococcus aureus

<400> SEQUENCE: 266
agtgacactg cgccgaaaat gtacc                                       25

<210> SEQ ID NO 267
<211> LENGTH: 26
<212> TYPE: DNA
<213> ORGANISM: Staphylococcus aureus

<400> SEQUENCE: 267
gctttagggc tagcctcaag tgatga                                      26

<210> SEQ ID NO 268
<211> LENGTH: 30
<212> TYPE: DNA
<213> ORGANISM: Staphylococcus aureus

```
<400> SEQUENCE: 268
cgtgtgctta caagtagtca gagcccgtta                                    30

<210> SEQ ID NO 269
<211> LENGTH: 26
<212> TYPE: DNA
<213> ORGANISM: Staphylococcus aureus

<400> SEQUENCE: 269
gagcccaaac caacaagctt gcttgt                                        26

<210> SEQ ID NO 270
<211> LENGTH: 25
<212> TYPE: DNA
<213> ORGANISM: Staphylococcus aureus

<400> SEQUENCE: 270
aataacgcgt ttcctgtagg atgga                                         25

<210> SEQ ID NO 271
<211> LENGTH: 23
<212> TYPE: DNA
<213> ORGANISM: Staphylococcus aureus

<400> SEQUENCE: 271
gatcttataa ccgaagttgg gaa                                           23

<210> SEQ ID NO 272
<211> LENGTH: 26
<212> TYPE: DNA
<213> ORGANISM: Staphylococcus aureus

<400> SEQUENCE: 272
ctcgccgcta ctaagggaat cgaatt                                        26

<210> SEQ ID NO 273
<211> LENGTH: 25
<212> TYPE: DNA
<213> ORGANISM: Staphylococcus aureus

<400> SEQUENCE: 273
aggttctatt tcactcccct tccgg                                         25

<210> SEQ ID NO 274
<211> LENGTH: 26
<212> TYPE: DNA
<213> ORGANISM: Staphylococcus aureus

<400> SEQUENCE: 274
ccaggttcga ttggaatttc tccgct                                        26

<210> SEQ ID NO 275
<211> LENGTH: 26
<212> TYPE: DNA
<213> ORGANISM: Staphylococcus aureus

<400> SEQUENCE: 275
ctcgactagt gagctattac gcactc                                        26

<210> SEQ ID NO 276
<211> LENGTH: 25
<212> TYPE: DNA
```

<213> ORGANISM: Staphylococcus aureus

<400> SEQUENCE: 276
ataggtggta caggaatatc aacct          25

<210> SEQ ID NO 277
<211> LENGTH: 25
<212> TYPE: DNA
<213> ORGANISM: Staphylococcus aureus

<400> SEQUENCE: 277
gagcacccct tctcccgaag ttacg          25

<210> SEQ ID NO 278
<211> LENGTH: 25
<212> TYPE: DNA
<213> ORGANISM: Staphylococcus aureus

<400> SEQUENCE: 278
tgatttcacc gagtctctcg ttgag          25

<210> SEQ ID NO 279
<211> LENGTH: 25
<212> TYPE: DNA
<213> ORGANISM: Staphylococcus aureus

<400> SEQUENCE: 279
cactctatga atgatttcca accat          25

<210> SEQ ID NO 280
<211> LENGTH: 25
<212> TYPE: DNA
<213> ORGANISM: Staphylococcus aureus

<400> SEQUENCE: 280
gacggatagg gaccgaactg tctca          25

<210> SEQ ID NO 281
<211> LENGTH: 25
<212> TYPE: DNA
<213> ORGANISM: Staphylococcus aureus

<400> SEQUENCE: 281
aagtaaaagt gattttgctt cgcaa          25

<210> SEQ ID NO 282
<211> LENGTH: 34
<212> TYPE: DNA
<213> ORGANISM: Staphylococcus aureus

<400> SEQUENCE: 282
gtctctcttg agtggatcct gagtacgacg gagc          34

<210> SEQ ID NO 283
<211> LENGTH: 30
<212> TYPE: DNA
<213> ORGANISM: Staphylococcus aureus

<400> SEQUENCE: 283
ggagccgtag cgaaagcgag tctgaatagg          30

<210> SEQ ID NO 284
<211> LENGTH: 30

```
<212> TYPE: DNA
<213> ORGANISM: Staphylococcus aureus

<400> SEQUENCE: 284
agtgagcgga tgaactgagg gtagcggaga                                30

<210> SEQ ID NO 285
<211> LENGTH: 30
<212> TYPE: DNA
<213> ORGANISM: Staphylococcus aureus

<400> SEQUENCE: 285
ggacaatggt aggagagcgt tctaagggcg                                30

<210> SEQ ID NO 286
<211> LENGTH: 30
<212> TYPE: DNA
<213> ORGANISM: Staphylococcus aureus

<400> SEQUENCE: 286
cgggagaagg ggtgctcttt agggttaacg                                30

<210> SEQ ID NO 287
<211> LENGTH: 30
<212> TYPE: DNA
<213> ORGANISM: Staphylococcus aureus

<400> SEQUENCE: 287
cgtaaggtga tgtataggg ctgacgcctg                                 30

<210> SEQ ID NO 288
<211> LENGTH: 32
<212> TYPE: DNA
<213> ORGANISM: Staphylococcus aureus

<400> SEQUENCE: 288
tcggcacagc ttgtacagga taggtaggag cc                             32

<210> SEQ ID NO 289
<211> LENGTH: 30
<212> TYPE: DNA
<213> ORGANISM: Staphylococcus aureus

<400> SEQUENCE: 289
ggcataaggg agcttgactg cgagacctac                                30

<210> SEQ ID NO 290
<211> LENGTH: 30
<212> TYPE: DNA
<213> ORGANISM: Staphylococcus aureus

<400> SEQUENCE: 290
gactgcgaga cctacaagtc gagcagggtc                                30

<210> SEQ ID NO 291
<211> LENGTH: 30
<212> TYPE: DNA
<213> ORGANISM: Staphylococcus aureus

<400> SEQUENCE: 291
ctgggttcag aacgtcgtga gacagttcgg                                30

<210> SEQ ID NO 292
```

```
<211> LENGTH: 25
<212> TYPE: DNA
<213> ORGANISM: Staphylococcus aureus

<400> SEQUENCE: 292
aaggatatat tcggaacatc ttctt                                          25

<210> SEQ ID NO 293
<211> LENGTH: 28
<212> TYPE: DNA
<213> ORGANISM: Staphylococcus aureus

<400> SEQUENCE: 293
ttgtacattg aaaactagat aagtaagt                                       28

<210> SEQ ID NO 294
<211> LENGTH: 23
<212> TYPE: DNA
<213> ORGANISM: Staphylococcus aureus

<400> SEQUENCE: 294
aaacgcgtta ttaatcttgt gag                                            23

<210> SEQ ID NO 295
<211> LENGTH: 23
<212> TYPE: DNA
<213> ORGANISM: Staphylococcus aureus

<400> SEQUENCE: 295
aaacgcgtta ttaatcttgt gag                                            23

<210> SEQ ID NO 296
<211> LENGTH: 32
<212> TYPE: DNA
<213> ORGANISM: Staphylococcus aureus

<400> SEQUENCE: 296
ttgaattcat aagaaataat cgctagtgtt cg                                  32

<210> SEQ ID NO 297
<211> LENGTH: 35
<212> TYPE: DNA
<213> ORGANISM: Staphylococcus aureus

<400> SEQUENCE: 297
taagcttgaa ttcataagaa ataatcgcta gtgtt                               35

<210> SEQ ID NO 298
<211> LENGTH: 35
<212> TYPE: DNA
<213> ORGANISM: Staphylococcus aureus

<400> SEQUENCE: 298
ttttaaataa gcttgaattc ataagaaata atcgc                               35

<210> SEQ ID NO 299
<211> LENGTH: 34
<212> TYPE: DNA
<213> ORGANISM: Staphylococcus aureus

<400> SEQUENCE: 299
aaaccgagtg aataaagagt tttaaataag cttg                                34
```

-continued

<210> SEQ ID NO 300
<211> LENGTH: 30
<212> TYPE: DNA
<213> ORGANISM: Staphylococcus aureus

<400> SEQUENCE: 300
tttaccaagc aaaaccgagt gaataaagag                               30

<210> SEQ ID NO 301
<211> LENGTH: 30
<212> TYPE: DNA
<213> ORGANISM: Staphylococcus aureus

<400> SEQUENCE: 301
aggatatatt cggaacatct tcttcagaag                               30

<210> SEQ ID NO 302
<211> LENGTH: 28
<212> TYPE: DNA
<213> ORGANISM: Staphylococcus aureus

<400> SEQUENCE: 302
gaataacgtg acatattgta ttcagttt                                 28

<210> SEQ ID NO 303
<211> LENGTH: 29
<212> TYPE: DNA
<213> ORGANISM: Staphylococcus aureus

<400> SEQUENCE: 303
tgttttgtta ttcatctata tcgtattt                                 29

<210> SEQ ID NO 304
<211> LENGTH: 25
<212> TYPE: DNA
<213> ORGANISM: Staphylococcus aureus

<400> SEQUENCE: 304
cgttacggat tgcttcactg ttttg                                    25

<210> SEQ ID NO 305
<211> LENGTH: 25
<212> TYPE: DNA
<213> ORGANISM: Staphylococcus aureus

<400> SEQUENCE: 305
ttgttgcata ccatcagtta ataga                                    25

<210> SEQ ID NO 306
<211> LENGTH: 25
<212> TYPE: DNA
<213> ORGANISM: Staphylococcus aureus

<400> SEQUENCE: 306
ttactgccta attcgagtgc tactc                                    25

<210> SEQ ID NO 307
<211> LENGTH: 25
<212> TYPE: DNA
<213> ORGANISM: Staphylococcus aureus

<400> SEQUENCE: 307
tcgttactca tgccatacat aaatg                                    25

<210> SEQ ID NO 308
<211> LENGTH: 26
<212> TYPE: DNA
<213> ORGANISM: Staphylococcus aureus

<400> SEQUENCE: 308
actgcatcat ctttatagcc tttata                                    26

<210> SEQ ID NO 309
<211> LENGTH: 25
<212> TYPE: DNA
<213> ORGANISM: Staphylococcus aureus

<400> SEQUENCE: 309
tttggaacga tgcctatctc atatg                                     25

<210> SEQ ID NO 310
<211> LENGTH: 30
<212> TYPE: DNA
<213> ORGANISM: Staphylococcus aureus

<400> SEQUENCE: 310
tgtttatatc tttaacgcct aaactattat                                30

<210> SEQ ID NO 311
<211> LENGTH: 26
<212> TYPE: DNA
<213> ORGANISM: Staphylococcus aureus

<400> SEQUENCE: 311 atgaaaaga taaaaattgt tccact                                     26

<210> SEQ ID NO 312
<211> LENGTH: 25
<212> TYPE: DNA
<213> ORGANISM: Staphylococcus aureus

<400> SEQUENCE: 312
gtagtcttat ataaggagga tattg                                     25

<210> SEQ ID NO 313
<211> LENGTH: 26
<212> TYPE: DNA
<213> ORGANISM: Staphylococcus aureus

<400> SEQUENCE: 313
aaaaacgagt agatgctcaa tataaa                                    26

<210> SEQ ID NO 314
<211> LENGTH: 27
<212> TYPE: DNA
<213> ORGANISM: Staphylococcus aureus

<400> SEQUENCE: 314
tttctgaaga ctatatcaaa caacaaa                                   27

<210> SEQ ID NO 315
<211> LENGTH: 28
<212> TYPE: DNA
<213> ORGANISM: Staphylococcus aureus

<400> SEQUENCE: 315
gctccaacat gaagatggct atcgtgtc                                  28

<210> SEQ ID NO 316
<211> LENGTH: 25
<212> TYPE: DNA
<213> ORGANISM: Staphylococcus aureus

<400> SEQUENCE: 316
gctcaacaag ttccagatta caact                                              25

<210> SEQ ID NO 317
<211> LENGTH: 29
<212> TYPE: DNA
<213> ORGANISM: Staphylococcus aureus

<400> SEQUENCE: 317
gatataccaa gtgattatcc attttataa                                          29

<210> SEQ ID NO 318
<211> LENGTH: 25
<212> TYPE: DNA
<213> ORGANISM: Staphylococcus aureus

<400> SEQUENCE: 318
aattggcaaa tccggtactg cagaa                                              25

<210> SEQ ID NO 319
<211> LENGTH: 25
<212> TYPE: DNA
<213> ORGANISM: Staphylococcus aureus

<400> SEQUENCE: 319
gtagtcttat ataaggagga tattg                                              25

<210> SEQ ID NO 320
<211> LENGTH: 30
<212> TYPE: DNA
<213> ORGANISM: Staphylococcus aureus

<400> SEQUENCE: 320
ttggaacgat gcctatctca tatgctgttc                                         30

<210> SEQ ID NO 321
<211> LENGTH: 30
<212> TYPE: DNA
<213> ORGANISM: Staphylococcus aureus

<400> SEQUENCE: 321
taacggtttt aagtggaacg aaggtatcat                                         30

<210> SEQ ID NO 322
<211> LENGTH: 30
<212> TYPE: DNA
<213> ORGANISM: Staphylococcus aureus

<400> SEQUENCE: 322
ttcttcagag ttaatgggac caacataacc                                         30

<210> SEQ ID NO 323
<211> LENGTH: 30
<212> TYPE: DNA
<213> ORGANISM: Staphylococcus aureus

<400> SEQUENCE: 323
ttttcgtgtc ttttaataag tgaggtgcgt                                30

<210> SEQ ID NO 324
<211> LENGTH: 30
<212> TYPE: DNA
<213> ORGANISM: Staphylococcus aureus

<400> SEQUENCE: 324
ccggatttgc caattaagtt tgcataagat                                30

<210> SEQ ID NO 325
<211> LENGTH: 30
<212> TYPE: DNA
<213> ORGANISM: Staphylococcus aureus

<400> SEQUENCE: 325
gccatcatca tgtttggatt atctttatca                                30

<210> SEQ ID NO 326
<211> LENGTH: 30
<212> TYPE: DNA
<213> ORGANISM: Staphylococcus aureus

<400> SEQUENCE: 326
tcatcataca ctttacctga gattttggca                                30

<210> SEQ ID NO 327
<211> LENGTH: 32
<212> TYPE: DNA
<213> ORGANISM: Staphylococcus aureus

<400> SEQUENCE: 327
cctgtttgag ggtggatagc agtacctgag cc                             32

<210> SEQ ID NO 328
<211> LENGTH: 25
<212> TYPE: DNA
<213> ORGANISM: Staphylococcus aureus

<400> SEQUENCE: 328
aattggcaaa tccggtactg cagaa                                     25

<210> SEQ ID NO 329
<211> LENGTH: 29
<212> TYPE: DNA
<213> ORGANISM: Staphylococcus aureus

<400> SEQUENCE: 329
gatataccaa gtgattatcc attttataa                                 29

<210> SEQ ID NO 330
<211> LENGTH: 25
<212> TYPE: DNA
<213> ORGANISM: Staphylococcus aureus

<400> SEQUENCE: 330
gctcaacaag ttccagatta caact                                     25

<210> SEQ ID NO 331
<211> LENGTH: 27
<212> TYPE: DNA
<213> ORGANISM: Staphylococcus aureus

<400> SEQUENCE: 331
tttctgaaga ctatatcaaa caacaaa                                   27

<210> SEQ ID NO 332
<211> LENGTH: 26
<212> TYPE: DNA
<213> ORGANISM: Staphylococcus aureus

<400> SEQUENCE: 332
aaaaacgagt agatgctcaa tataaa                                    26

<210> SEQ ID NO 333
<211> LENGTH: 30
<212> TYPE: DNA
<213> ORGANISM: Staphylococcus aureus

<400> SEQUENCE: 333
cgagagacaa ataggagtaa tgataatgaa                                30

<210> SEQ ID NO 334
<211> LENGTH: 27
<212> TYPE: DNA
<213> ORGANISM: Staphylococcus aureus

<400> SEQUENCE: 334
tgaatatgtt ggtgacttta ttaaacc                                   27

<210> SEQ ID NO 335
<211> LENGTH: 25
<212> TYPE: DNA
<213> ORGANISM: Staphylococcus aureus

<400> SEQUENCE: 335
tgagcaaaag attgaagaag gtaaa                                     25

<210> SEQ ID NO 336
<211> LENGTH: 30
<212> TYPE: DNA
<213> ORGANISM: Staphylococcus aureus

<400> SEQUENCE: 336
tgttaaagta agatatttat ctgaagaaga                                30

<210> SEQ ID NO 337
<211> LENGTH: 30
<212> TYPE: DNA
<213> ORGANISM: Staphylococcus aureus

<400> SEQUENCE: 337
tctttaatga attatcaaaa tatgttaaaa                                30

<210> SEQ ID NO 338
<211> LENGTH: 26
<212> TYPE: DNA
<213> ORGANISM: Staphylococcus aureus

<400> SEQUENCE: 338
aacgagagac aaataggagt aatgat                                    26

<210> SEQ ID NO 339
<211> LENGTH: 28
<212> TYPE: DNA
<213> ORGANISM: Staphylococcus aureus

```
<400> SEQUENCE: 339
tcccttccta aaaattctg tctttaac                                          28

<210> SEQ ID NO 340
<211> LENGTH: 26
<212> TYPE: DNA
<213> ORGANISM: Staphylococcus aureus

<400> SEQUENCE: 340
gtggccaaca gtttgcgtga aatgac                                           26

<210> SEQ ID NO 341
<211> LENGTH: 25
<212> TYPE: DNA
<213> ORGANISM: Staphylococcus aureus

<400> SEQUENCE: 341
caatcattac cagcattacc tgtaa                                            25

<210> SEQ ID NO 342
<211> LENGTH: 25
<212> TYPE: DNA
<213> ORGANISM: Staphylococcus aureus

<400> SEQUENCE: 342
aagcgattgt aataaaactt gtcat                                            25

<210> SEQ ID NO 343
<211> LENGTH: 26
<212> TYPE: DNA
<213> ORGANISM: Staphylococcus aureus

<400> SEQUENCE: 343
cggaatgcat ttgatgtacc accagc                                           26

<210> SEQ ID NO 344
<211> LENGTH: 25
<212> TYPE: DNA
<213> ORGANISM: Staphylococcus aureus

<400> SEQUENCE: 344
atttcatgtt ttgataattc ccttc                                            25

<210> SEQ ID NO 345
<211> LENGTH: 36
<212> TYPE: DNA
<213> ORGANISM: Staphylococcus aureus

<400> SEQUENCE: 345
ttgaccgtta taatttctat ggtgttagtg gtaaat                                36

<210> SEQ ID NO 346
<211> LENGTH: 30
<212> TYPE: DNA
<213> ORGANISM: Staphylococcus aureus

<400> SEQUENCE: 346
gatgcaaatg agcaaaagat tgaagaaggt                                       30

<210> SEQ ID NO 347
<211> LENGTH: 36
<212> TYPE: DNA
<213> ORGANISM: Staphylococcus aureus
```

<400> SEQUENCE: 347
ttgaccgtta taatttctat ggtgttagtg gtaaat                                36

<210> SEQ ID NO 348
<211> LENGTH: 35
<212> TYPE: DNA
<213> ORGANISM: Staphylococcus aureus

<400> SEQUENCE: 348
cgttgtctat acctacatat cgatccatat ttacc                                35

<210> SEQ ID NO 349
<211> LENGTH: 30
<212> TYPE: DNA
<213> ORGANISM: Staphylococcus aureus

<400> SEQUENCE: 349
gcggtccagt gatcgattat gaaaatcaag                                      30

<210> SEQ ID NO 350
<211> LENGTH: 30
<212> TYPE: DNA
<213> ORGANISM: Staphylococcus aureus

<400> SEQUENCE: 350
cagtcatttc acgcaaactg ttggccacta                                      30

<210> SEQ ID NO 351
<211> LENGTH: 30
<212> TYPE: DNA
<213> ORGANISM: Staphylococcus aureus

<400> SEQUENCE: 351
gagtttggtg cctttacaga tagcatgcca                                      30

<210> SEQ ID NO 352
<211> LENGTH: 30
<212> TYPE: DNA
<213> ORGANISM: Staphylococcus aureus

<400> SEQUENCE: 352
acaaatttaa cagctaaaga gtttggtgcc                                      30

<210> SEQ ID NO 353
<211> LENGTH: 25
<212> TYPE: DNA
<213> ORGANISM: Staphylococcus aureus

<400> SEQUENCE: 353
atggctgaat tacctcaatc aagaa                                           25

<210> SEQ ID NO 354
<211> LENGTH: 26
<212> TYPE: DNA
<213> ORGANISM: Staphylococcus aureus

<400> SEQUENCE: 354
cagcacaagg tgttcgctta attcgc                                          26

<210> SEQ ID NO 355
<211> LENGTH: 25
<212> TYPE: DNA

<213> ORGANISM: Staphylococcus aureus

<400> SEQUENCE: 355
ggtattacac ttcgtgaagg tgacg                                    25

<210> SEQ ID NO 356
<211> LENGTH: 25
<212> TYPE: DNA
<213> ORGANISM: Staphylococcus aureus

<400> SEQUENCE: 356
ttgaacttga aaatgatgaa atcat                                    25

<210> SEQ ID NO 357
<211> LENGTH: 30
<212> TYPE: DNA
<213> ORGANISM: Staphylococcus aureus

<400> SEQUENCE: 357
ggtggatttg aagacttaga ggacgaggac                               30

<210> SEQ ID NO 358
<211> LENGTH: 25
<212> TYPE: DNA
<213> ORGANISM: Staphylococcus aureus

<400> SEQUENCE: 358
atgaaattat ttcaacgatt cgtga                                    25

<210> SEQ ID NO 359
<211> LENGTH: 25
<212> TYPE: DNA
<213> ORGANISM: Staphylococcus aureus

<400> SEQUENCE: 359
tgatgaaaca agtttacgta ctggt                                    25

<210> SEQ ID NO 360
<211> LENGTH: 27
<212> TYPE: DNA
<213> ORGANISM: Staphylococcus aureus

<400> SEQUENCE: 360
tcaatggtgt acttagctta agtaaga                                  27

<210> SEQ ID NO 361
<211> LENGTH: 25
<212> TYPE: DNA
<213> ORGANISM: Staphylococcus aureus

<400> SEQUENCE: 361
atggctcaag atttcagtta tcgtt                                    25

<210> SEQ ID NO 362
<211> LENGTH: 28
<212> TYPE: DNA
<213> ORGANISM: Staphylococcus aureus

<400> SEQUENCE: 362
gcgctgtgaa ctgaactttt gaaggagg                                 28

<210> SEQ ID NO 363
<211> LENGTH: 27

```
<212> TYPE: DNA
<213> ORGANISM: Staphylococcus aureus

<400> SEQUENCE: 363 cccctacat atagggaagt cttattt                                        27

<210> SEQ ID NO 364
<211> LENGTH: 25
<212> TYPE: DNA
<213> ORGANISM: Staphylococcus aureus

<400> SEQUENCE: 364
catacgtacc attgcttcat agata                                         25

<210> SEQ ID NO 365
<211> LENGTH: 26
<212> TYPE: DNA
<213> ORGANISM: Staphylococcus aureus

<400> SEQUENCE: 365
ccattgatca attctgttaa gttatg                                        26

<210> SEQ ID NO 366
<211> LENGTH: 25
<212> TYPE: DNA
<213> ORGANISM: Staphylococcus aureus

<400> SEQUENCE: 366
cacgtaaatc agtaataccg tcaat                                         25

<210> SEQ ID NO 367
<211> LENGTH: 25
<212> TYPE: DNA
<213> ORGANISM: Staphylococcus aureus

<400> SEQUENCE: 367
atttcatcga tatgatctaa cgcaa                                         25

<210> SEQ ID NO 368
<211> LENGTH: 28
<212> TYPE: DNA
<213> ORGANISM: Staphylococcus aureus

<400> SEQUENCE: 368
cctcgtcctc taagtcttca aatccacc                                      28

<210> SEQ ID NO 369
<211> LENGTH: 25
<212> TYPE: DNA
<213> ORGANISM: Staphylococcus aureus

<400> SEQUENCE: 369
ttttcaagtt caatagcatt cacta                                         25

<210> SEQ ID NO 370
<211> LENGTH: 25
<212> TYPE: DNA
<213> ORGANISM: Staphylococcus aureus

<400> SEQUENCE: 370
agtgtaatac ctttcacacc cgttg                                         25

<210> SEQ ID NO 371
```

<211> LENGTH: 25
<212> TYPE: DNA
<213> ORGANISM: Staphylococcus aureus

<400> SEQUENCE: 371
taagcgaaca ccttgtgctg cacga                                              25

<210> SEQ ID NO 372
<211> LENGTH: 26
<212> TYPE: DNA
<213> ORGANISM: Staphylococcus aureus

<400> SEQUENCE: 372
ccctacatat agggaagtct tatttt                                             26

<210> SEQ ID NO 373
<211> LENGTH: 30
<212> TYPE: DNA
<213> ORGANISM: Staphylococcus aureus

<400> SEQUENCE: 373
tagggcttga tgtagctcat gcaaacagtg                                         30

<210> SEQ ID NO 374
<211> LENGTH: 30
<212> TYPE: DNA
<213> ORGANISM: Staphylococcus aureus

<400> SEQUENCE: 374
gcaacgggtg tgaaaggtat tacacttcgt                                         30

<210> SEQ ID NO 375
<211> LENGTH: 35
<212> TYPE: DNA
<213> ORGANISM: Staphylococcus aureus

<400> SEQUENCE: 375
atcaagacag tctaaaggta ttcctgtagt gaatg                                   35

<210> SEQ ID NO 376
<211> LENGTH: 30
<212> TYPE: DNA
<213> ORGANISM: Staphylococcus aureus

<400> SEQUENCE: 376
ccaagtgaat aaggctcgta tgattgaaaa                                         30

<210> SEQ ID NO 377
<211> LENGTH: 30
<212> TYPE: DNA
<213> ORGANISM: Staphylococcus aureus

<400> SEQUENCE: 377
tcctgatatt tcaattgctg agttaatgga                                         30

<210> SEQ ID NO 378
<211> LENGTH: 32
<212> TYPE: DNA
<213> ORGANISM: Staphylococcus aureus

<400> SEQUENCE: 378
accctcatgg tgacttatct atctatgaag ca                                      32

```
<210> SEQ ID NO 379
<211> LENGTH: 30
<212> TYPE: DNA
<213> ORGANISM: Staphylococcus aureus

<400> SEQUENCE: 379
tgccagatgt tcgtgacggt ttaaaaccag                              30

<210> SEQ ID NO 380
<211> LENGTH: 30
<212> TYPE: DNA
<213> ORGANISM: Staphylococcus aureus

<400> SEQUENCE: 380
aaatgaacga aatattacca gtgaaatgcg                              30

<210> SEQ ID NO 381
<211> LENGTH: 32
<212> TYPE: DNA
<213> ORGANISM: Staphylococcus aureus

<400> SEQUENCE: 381
agagagccgt cagtcttacc tgctcgattc cc                           32

<210> SEQ ID NO 382
<211> LENGTH: 23
<212> TYPE: DNA
<213> ORGANISM: Staphylococcus aureus

<400> SEQUENCE: 382
tttttatagt tcgcgacgac gtc                                     23

<210> SEQ ID NO 383
<211> LENGTH: 27
<212> TYPE: DNA
<213> ORGANISM: Staphylococcus aureus

<400> SEQUENCE: 383
gatatctatc gttgtgtatt gtttgtt                                 27

<210> SEQ ID NO 384
<211> LENGTH: 26
<212> TYPE: DNA
<213> ORGANISM: Staphylococcus aureus

<400> SEQUENCE: 384
caccaggttt aacgacatgt actccg                                  26

<210> SEQ ID NO 385
<211> LENGTH: 26
<212> TYPE: DNA
<213> ORGANISM: Staphylococcus aureus

<400> SEQUENCE: 385
cttcctcttt tggtgcttga gcatcg                                  26

<210> SEQ ID NO 386
<211> LENGTH: 25
<212> TYPE: DNA
<213> ORGANISM: Staphylococcus aureus

<400> SEQUENCE: 386
agaaagcatt ttgttgttct ttgtt                                   25
```

```
<210> SEQ ID NO 387
<211> LENGTH: 29
<212> TYPE: DNA
<213> ORGANISM: Staphylococcus aureus

<400> SEQUENCE: 387
tatgatgact ttacaaatac atacagggg                                29

<210> SEQ ID NO 388
<211> LENGTH: 25
<212> TYPE: DNA
<213> ORGANISM: Staphylococcus aureus

<400> SEQUENCE: 388
agaacaacgt aacggcttca tccaa                                    25

<210> SEQ ID NO 389
<211> LENGTH: 25
<212> TYPE: DNA
<213> ORGANISM: Staphylococcus aureus

<400> SEQUENCE: 389
tgacccaagt caaagtgcta acctt                                    25

<210> SEQ ID NO 390
<211> LENGTH: 25
<212> TYPE: DNA
<213> ORGANISM: Staphylococcus aureus

<400> SEQUENCE: 390
caagctccaa aagctgatgc gcaac                                    25

<210> SEQ ID NO 391
<211> LENGTH: 25
<212> TYPE: DNA
<213> ORGANISM: Staphylococcus aureus

<400> SEQUENCE: 391
atgactttac aaatacatac agggg                                    25

<210> SEQ ID NO 392
<211> LENGTH: 30
<212> TYPE: DNA
<213> ORGANISM: Staphylococcus aureus

<400> SEQUENCE: 392
ttacagatgc aatacctaca cctagtttac                               30

<210> SEQ ID NO 393
<211> LENGTH: 30
<212> TYPE: DNA
<213> ORGANISM: Staphylococcus aureus

<400> SEQUENCE: 393
gatcagcgtt taagttaggc atatttaaca                               30

<210> SEQ ID NO 394
<211> LENGTH: 30
<212> TYPE: DNA
<213> ORGANISM: Staphylococcus aureus

<400> SEQUENCE: 394
aatgaaacca ttgcgttgct cttcgtttaa                               30
```

<210> SEQ ID NO 395
<211> LENGTH: 30
<212> TYPE: DNA
<213> ORGANISM: Staphylococcus aureus

<400> SEQUENCE: 395
gttgccgtct tctttaccag gtttgttgcc                                      30

<210> SEQ ID NO 396
<211> LENGTH: 32
<212> TYPE: DNA
<213> ORGANISM: Staphylococcus aureus

<400> SEQUENCE: 396
acgacatgta ctccgttgcc gtcttcttta cc                                   32

<210> SEQ ID NO 397
<211> LENGTH: 30
<212> TYPE: DNA
<213> ORGANISM: Staphylococcus aureus

<400> SEQUENCE: 397
atagttcgcg acgacgtcca gctaataacg                                      30

<210> SEQ ID NO 398
<211> LENGTH: 25
<212> TYPE: DNA
<213> ORGANISM: Hepatitis B virus

<400> SEQUENCE: 398
gggacgtcct ttgtctacgt cccgt                                           25

<210> SEQ ID NO 399
<211> LENGTH: 28
<212> TYPE: DNA
<213> ORGANISM: Hepatitis B virus

<400> SEQUENCE: 399
acagcttgga ggcttgaaca gtaggaca                                        28

<210> SEQ ID NO 400
<211> LENGTH: 21
<212> TYPE: DNA
<213> ORGANISM: Hepatitis B virus

<400> SEQUENCE: 400
atggagagca caacatcagg a                                               21

<210> SEQ ID NO 401
<211> LENGTH: 22
<212> TYPE: DNA
<213> ORGANISM: Hepatitis B virus

<400> SEQUENCE: 401
ccaacgtttg gttttattag gg                                              22

<210> SEQ ID NO 402
<211> LENGTH: 20
<212> TYPE: DNA
<213> ORGANISM: Hepatitis B virus

<400> SEQUENCE: 402

```
tggggtactt taccgcagga                                              20

<210> SEQ ID NO 403
<211> LENGTH: 20
<212> TYPE: DNA
<213> ORGANISM: Hepatitis B virus

<400> SEQUENCE: 403
gtttcgctcc agaccggctg                                              20

<210> SEQ ID NO 404
<211> LENGTH: 20
<212> TYPE: DNA
<213> ORGANISM: Hepatitis B virus

<400> SEQUENCE: 404
tcctttgtct acgtcccgtc                                              20

<210> SEQ ID NO 405
<211> LENGTH: 20
<212> TYPE: DNA
<213> ORGANISM: Hepatitis B virus

<400> SEQUENCE: 405
catggtgctg gtgaacagac                                              20

<210> SEQ ID NO 406
<211> LENGTH: 24
<212> TYPE: DNA
<213> ORGANISM: Hepatitis B virus

<400> SEQUENCE: 406
ggcctctacc gtcccttct tcat                                          24

<210> SEQ ID NO 407
<211> LENGTH: 20
<212> TYPE: DNA
<213> ORGANISM: Hepatitis B virus

<400> SEQUENCE: 407
ccatgcccca aagccaccca                                              20

<210> SEQ ID NO 408
<211> LENGTH: 22
<212> TYPE: DNA
<213> ORGANISM: Hepatitis B virus

<400> SEQUENCE: 408
atgtcctact gttcaagcct cc                                           22

<210> SEQ ID NO 409
<211> LENGTH: 22
<212> TYPE: DNA
<213> ORGANISM: Hepatitis B virus

<400> SEQUENCE: 409
ctcaaggaca gtttctcttc ca                                           22

<210> SEQ ID NO 410
<211> LENGTH: 22
<212> TYPE: DNA
<213> ORGANISM: Hepatitis B virus

<400> SEQUENCE: 410
```

```
atggacattg acccgtataa ag                                              22

<210> SEQ ID NO 411
<211> LENGTH: 23
<212> TYPE: DNA
<213> ORGANISM: Hepatitis B virus

<400> SEQUENCE: 411
ctaacattga gattcccgag att                                             23

<210> SEQ ID NO 412
<211> LENGTH: 26
<212> TYPE: DNA
<213> ORGANISM: Hepatitis B virus

<400> SEQUENCE: 412
cttatagacc accaaatgcc cctatc                                          26

<210> SEQ ID NO 413
<211> LENGTH: 25
<212> TYPE: DNA
<213> ORGANISM: Hepatitis B virus

<400> SEQUENCE: 413
tgtgtaagac cttgggcaag acctg                                           25

<210> SEQ ID NO 414
<211> LENGTH: 32
<212> TYPE: DNA
<213> ORGANISM: Hepatitis B virus

<400> SEQUENCE: 414
cgcacctctc tttacgcgga ctccccgtct gt                                   32

<210> SEQ ID NO 415
<211> LENGTH: 36
<212> TYPE: DNA
<213> ORGANISM: Hepatitis B virus

<400> SEQUENCE: 415 acttttccc ctctgcctaa tcatctcatg ttcatg                                36

<210> SEQ ID NO 416
<211> LENGTH: 35
<212> TYPE: DNA
<213> ORGANISM: Hepatitis B virus

<400> SEQUENCE: 416
ttcaagcctc caagctgtgc cttgggtggc tttgg                                35

<210> SEQ ID NO 417
<211> LENGTH: 26
<212> TYPE: DNA
<213> ORGANISM: Hepatitis B virus

<400> SEQUENCE: 417
tataaagaat ttggagcttc tgtgga                                          26

<210> SEQ ID NO 418
<211> LENGTH: 32
<212> TYPE: DNA
<213> ORGANISM: Hepatitis B virus
```

<400> SEQUENCE: 418
ggagtgtgga ttcgcactcc tcccgcttac ag                                  32

<210> SEQ ID NO 419
<211> LENGTH: 31
<212> TYPE: DNA
<213> ORGANISM: Hepatitis B virus

<400> SEQUENCE: 419
caaatgcccc tatcttatca acacttccgg a                                   31

<210> SEQ ID NO 420
<211> LENGTH: 31
<212> TYPE: DNA
<213> ORGANISM: Hepatitis B virus

<400> SEQUENCE: 420
caggtcccct agaagaagaa ctccctcgcc t                                   31

<210> SEQ ID NO 421
<211> LENGTH: 30
<212> TYPE: DNA
<213> ORGANISM: Hepatitis B virus

<400> SEQUENCE: 421
ggattcctag gacccctgct cgtgttacag                                     30

<210> SEQ ID NO 422
<211> LENGTH: 30
<212> TYPE: DNA
<213> ORGANISM: Hepatitis B virus

<400> SEQUENCE: 422
gcagtcccca acctccaatc actcaccaac                                     30

<210> SEQ ID NO 423
<211> LENGTH: 30
<212> TYPE: DNA
<213> ORGANISM: Hepatitis B virus

<400> SEQUENCE: 423
tcctatggga gtgggcctca gtccgtttct                                     30

<210> SEQ ID NO 424
<211> LENGTH: 30
<212> TYPE: DNA
<213> ORGANISM: Hepatitis B virus

<400> SEQUENCE: 424
cggtcaggtc tctgccaagt gtttgctgac                                     30

<210> SEQ ID NO 425
<211> LENGTH: 30
<212> TYPE: DNA
<213> ORGANISM: Hepatitis B virus

<400> SEQUENCE: 425
ctttgctgcc cctttacac aatgtggcta                                      30

<210> SEQ ID NO 426
<211> LENGTH: 33
<212> TYPE: DNA
<213> ORGANISM: Hepatitis B virus

```
<400> SEQUENCE: 426
gcctttatat gcatgtatac aatctaagca ggc                                   33

<210> SEQ ID NO 427
<211> LENGTH: 34
<212> TYPE: DNA
<213> ORGANISM: Hepatitis B virus

<400> SEQUENCE: 427
ctgtgccttc tcatctgccg gaccgtgtgc actt                                  34

<210> SEQ ID NO 428
<211> LENGTH: 30
<212> TYPE: DNA
<213> ORGANISM: Hepatitis B virus

<400> SEQUENCE: 428
cttcgcttca cctctgcacg tagcatggag                                       30

<210> SEQ ID NO 429
<211> LENGTH: 30
<212> TYPE: DNA
<213> ORGANISM: Hepatitis B virus

<400> SEQUENCE: 429
gaggactctt ggactctcag caatgtcaac                                       30

<210> SEQ ID NO 430
<211> LENGTH: 31
<212> TYPE: DNA
<213> ORGANISM: Hepatitis B virus

<400> SEQUENCE: 430
aaagactgtt tgtttaaaga ctgggaggag t                                     31

<210> SEQ ID NO 431
<211> LENGTH: 30
<212> TYPE: DNA
<213> ORGANISM: Hepatitis B virus

<400> SEQUENCE: 431
gagatctcct cgacaccgcc tctgctctgt                                       30

<210> SEQ ID NO 432
<211> LENGTH: 30
<212> TYPE: DNA
<213> ORGANISM: Hepatitis B virus

<400> SEQUENCE: 432
gcctctgctc tgtatcggga ggccttagag                                       30

<210> SEQ ID NO 433
<211> LENGTH: 20
<212> TYPE: DNA
<213> ORGANISM: Human immunodeficiency virus type 1

<400> SEQUENCE: 433
atgggtgcga gagcgtcagt                                                  20

<210> SEQ ID NO 434
<211> LENGTH: 22
<212> TYPE: DNA
```

```
<213> ORGANISM: Human immunodeficiency virus type 1

<400> SEQUENCE: 434
ttattgtgac gagggtcgt tg                                               22

<210> SEQ ID NO 435
<211> LENGTH: 24
<212> TYPE: DNA
<213> ORGANISM: Human immunodeficiency virus type 1

<400> SEQUENCE: 435
cccttcagac aggatcagaa gaac                                            24

<210> SEQ ID NO 436
<211> LENGTH: 22
<212> TYPE: DNA
<213> ORGANISM: Human immunodeficiency virus type 1

<400> SEQUENCE: 436
gtgcccttct ttgccacaat tg                                              22

<210> SEQ ID NO 437
<211> LENGTH: 30
<212> TYPE: DNA
<213> ORGANISM: Human immunodeficiency virus type 1

<400> SEQUENCE: 437
ctgacacagg acacagcaat caggtcagcc                                      30

<210> SEQ ID NO 438
<211> LENGTH: 30
<212> TYPE: DNA
<213> ORGANISM: Human immunodeficiency virus type 1

<400> SEQUENCE: 438
tagtgcagaa catccagggg caaatggtac                                      30

<210> SEQ ID NO 439
<211> LENGTH: 30
<212> TYPE: DNA
<213> ORGANISM: Human immunodeficiency virus type 1

<400> SEQUENCE: 439
gtagaagaga aggctttcag cccagaagtg                                      30

<210> SEQ ID NO 440
<211> LENGTH: 30
<212> TYPE: DNA
<213> ORGANISM: Human immunodeficiency virus type 1

<400> SEQUENCE: 440
aaactctaag agccgagcaa gcttcacagg                                      30

<210> SEQ ID NO 441
<211> LENGTH: 30
<212> TYPE: DNA
<213> ORGANISM: Human immunodeficiency virus type 1

<400> SEQUENCE: 441
agcattggga ccagcggcta cactagaaga                                      30

<210> SEQ ID NO 442
<211> LENGTH: 30
```

```
<212> TYPE: DNA
<213> ORGANISM: Human immunodeficiency virus type 1

<400> SEQUENCE: 442
aatgatgaca gcatgtcagg gagtaggagg                                           30

<210> SEQ ID NO 443
<211> LENGTH: 20
<212> TYPE: DNA
<213> ORGANISM: Human immunodeficiency virus type 2

<400> SEQUENCE: 443
ttgtgtgggc agcgaatgaa                                                      20

<210> SEQ ID NO 444
<211> LENGTH: 26
<212> TYPE: DNA
<213> ORGANISM: Human immunodeficiency virus type 2

<400> SEQUENCE: 444
acctctttgt atggtctctc cctctg                                               26

<210> SEQ ID NO 445
<211> LENGTH: 22
<212> TYPE: DNA
<213> ORGANISM: Human immunodeficiency virus type 2

<400> SEQUENCE: 445
gcttgcacgc agaagagaaa gt                                                   22

<210> SEQ ID NO 446
<211> LENGTH: 23
<212> TYPE: DNA
<213> ORGANISM: Human immunodeficiency virus type 2

<400> SEQUENCE: 446
agtgtccctc ctttccacag ttc                                                  23

<210> SEQ ID NO 447
<211> LENGTH: 32
<212> TYPE: DNA
<213> ORGANISM: Human immunodeficiency virus type 2

<400> SEQUENCE: 447
atgaatccca ccctagaaga gatgctaacc gc                                        32

<210> SEQ ID NO 448
<211> LENGTH: 30
<212> TYPE: DNA
<213> ORGANISM: Human immunodeficiency virus type 2

<400> SEQUENCE: 448
tgagggcaga acaaacagac ccagcagtaa                                           30

<210> SEQ ID NO 449
<211> LENGTH: 30
<212> TYPE: DNA
<213> ORGANISM: Human immunodeficiency virus type 2

<400> SEQUENCE: 449
ggatgtatag gccacaaaat cccgtaccgg                                           30

<210> SEQ ID NO 450
```

<211> LENGTH: 30
<212> TYPE: DNA
<213> ORGANISM: Human immunodeficiency virus type 2

<400> SEQUENCE: 450
cttaccagca ggacagctca gagacccaag 30

<210> SEQ ID NO 451
<211> LENGTH: 30
<212> TYPE: DNA
<213> ORGANISM: Human immunodeficiency virus type 2

<400> SEQUENCE: 451
caggatttca ggcactctca gaaggctgca 30

<210> SEQ ID NO 452
<211> LENGTH: 30
<212> TYPE: DNA
<213> ORGANISM: Human immunodeficiency virus type 2

<400> SEQUENCE: 452
agtggaggaa aagaagttcg gggcagaagt 30

<210> SEQ ID NO 453
<211> LENGTH: 30
<212> TYPE: DNA
<213> ORGANISM: Human immunodeficiency virus type 2

<400> SEQUENCE: 453
acagcaccac ctagtgggaa aagaggaaac 30

<210> SEQ ID NO 454
<211> LENGTH: 30
<212> TYPE: DNA
<213> ORGANISM: Human immunodeficiency virus type 2

<400> SEQUENCE: 454
tacaagtaga ccaacagcac cacctagtgg 30

<210> SEQ ID NO 455
<211> LENGTH: 25
<212> TYPE: DNA
<213> ORGANISM: Influenza A virus (H5N1)

<400> SEQUENCE: 455
attggaatat ggtaactgca acacc 25

<210> SEQ ID NO 456
<211> LENGTH: 25
<212> TYPE: DNA
<213> ORGANISM: Influenza A virus (H5N1)

<400> SEQUENCE: 456
gcttcttctt gcaatagtca gtctt 25

<210> SEQ ID NO 457
<211> LENGTH: 28
<212> TYPE: DNA
<213> ORGANISM: Influenza A virus (H5N1)

<400> SEQUENCE: 457
gccaatgacc tctgttaccc agggaatt 28

```
<210> SEQ ID NO 458
<211> LENGTH: 26
<212> TYPE: DNA
<213> ORGANISM: Influenza A virus (H5N1)

<400> SEQUENCE: 458
gagcagacaa ggctctatca aaaccc                                    26

<210> SEQ ID NO 459
<211> LENGTH: 25
<212> TYPE: DNA
<213> ORGANISM: Influenza A virus (H5N1)

<400> SEQUENCE: 459
attccacaac atccaccctc tcacc                                     25

<210> SEQ ID NO 460
<211> LENGTH: 25
<212> TYPE: DNA
<213> ORGANISM: Influenza A virus (H5N1)

<400> SEQUENCE: 460
actcagtttg aggctgttgg aaggg                                     25

<210> SEQ ID NO 461
<211> LENGTH: 26
<212> TYPE: DNA
<213> ORGANISM: Influenza A virus (H5N1)

<400> SEQUENCE: 461
gactacccgc agtattcaga agaagc                                    26

<210> SEQ ID NO 462
<211> LENGTH: 25
<212> TYPE: DNA
<213> ORGANISM: Influenza A virus (H5N1)

<400> SEQUENCE: 462
gttattaaat tcccttccaa cagcc                                     25

<210> SEQ ID NO 463
<211> LENGTH: 25
<212> TYPE: DNA
<213> ORGANISM: Influenza A virus (H5N1)

<400> SEQUENCE: 463
tgtaacgatc cattggagca catcc                                     25

<210> SEQ ID NO 464
<211> LENGTH: 27
<212> TYPE: DNA
<213> ORGANISM: Influenza A virus (H5N1)

<400> SEQUENCE: 464
tgagtcatga aagtctagag ttctctc                                   27

<210> SEQ ID NO 465
<211> LENGTH: 30
<212> TYPE: DNA
<213> ORGANISM: Influenza A virus (H5N1)

<400> SEQUENCE: 465
cctgccatcc tccctctata aaacctgcta                                30
```

<210> SEQ ID NO 466
<211> LENGTH: 25
<212> TYPE: DNA
<213> ORGANISM: Influenza A virus (H5N1)

<400> SEQUENCE: 466
caaagtttat tgcatcattc gattt                                    25

<210> SEQ ID NO 467
<211> LENGTH: 25
<212> TYPE: DNA
<213> ORGANISM: Influenza A virus (H5N1)

<400> SEQUENCE: 467
gggtcctccc tggtatggac atgct                                    25

<210> SEQ ID NO 468
<211> LENGTH: 28
<212> TYPE: DNA
<213> ORGANISM: Influenza A virus (H5N1)

<400> SEQUENCE: 468
gcagagtttc ccgttgtgtg tcttttcc                                 28

<210> SEQ ID NO 469
<211> LENGTH: 30
<212> TYPE: DNA
<213> ORGANISM: Influenza A virus (H5N1)

<400> SEQUENCE: 469
gcaacaccaa gtgtcaaact ccaatagggg                               30

<210> SEQ ID NO 470
<211> LENGTH: 25
<212> TYPE: DNA
<213> ORGANISM: Influenza A virus (H5N1)

<400> SEQUENCE: 470
ggctgttgga agggaattta ataac                                    25

<210> SEQ ID NO 471
<211> LENGTH: 30
<212> TYPE: DNA
<213> ORGANISM: Influenza A virus (H5N1)

<400> SEQUENCE: 471 tagggggcgat aaactccagt atgccattcc                              30

<210> SEQ ID NO 472
<211> LENGTH: 34
<212> TYPE: DNA
<213> ORGANISM: Influenza A virus (H5N1)

<400> SEQUENCE: 472
gctatagcag gttttataga gggaggatgg cagg                          34

<210> SEQ ID NO 473
<211> LENGTH: 30
<212> TYPE: DNA
<213> ORGANISM: Influenza A virus (H5N1)

<400> SEQUENCE: 473
gagtgggtac gctgcagaca aagaatccac                               30

<210> SEQ ID NO 474
<211> LENGTH: 30
<212> TYPE: DNA
<213> ORGANISM: Influenza A virus (H5N1)

<400> SEQUENCE: 474
agttccctag cactggcaat catggtggct                                    30

<210> SEQ ID NO 475
<211> LENGTH: 32
<212> TYPE: DNA
<213> ORGANISM: Influenza A virus (H5N1)

<400> SEQUENCE: 475
gcgactacag cttaggata atgcaaagga gc                                  32

<210> SEQ ID NO 476
<211> LENGTH: 30
<212> TYPE: DNA
<213> ORGANISM: Influenza A virus (H5N1)

<400> SEQUENCE: 476
ctttacgaca aggtgcgact acagcttagg                                    30

<210> SEQ ID NO 477
<211> LENGTH: 30
<212> TYPE: DNA
<213> ORGANISM: Influenza A virus (H5N1)

<400> SEQUENCE: 477
ggaatgcccc aaatatgtga aatcaaacag                                    30

<210> SEQ ID NO 478
<211> LENGTH: 30
<212> TYPE: DNA
<213> ORGANISM: Influenza A virus (H5N1)

<400> SEQUENCE: 478
gctcagaaat agccctcaag gagagagaag                                    30

<210> SEQ ID NO 479
<211> LENGTH: 30
<212> TYPE: DNA
<213> ORGANISM: Influenza A virus (H5N1)

<400> SEQUENCE: 479
gcaaagtgga agggtggagt tcttttggac                                    30

<210> SEQ ID NO 480
<211> LENGTH: 30
<212> TYPE: DNA
<213> ORGANISM: Influenza A virus (H5N1)

<400> SEQUENCE: 480
gatctaaggt aaacgggcaa agtggaaggg                                    30

<210> SEQ ID NO 481
<211> LENGTH: 30
<212> TYPE: DNA
<213> ORGANISM: Influenza A virus (H5N1)

<400> SEQUENCE: 481
ctatgaagaa ctgaaacacc tattgagcag                             30

<210> SEQ ID NO 482
<211> LENGTH: 30
<212> TYPE: DNA
<213> ORGANISM: Influenza A virus (H5N1)

<400> SEQUENCE: 482
ctgttaccca gggaatttca acaactatga                             30

<210> SEQ ID NO 483
<211> LENGTH: 24
<212> TYPE: DNA
<213> ORGANISM: Influenza A virus (H5N1)

<400> SEQUENCE: 483
gtcaaagaca gaagccctca caga                                   24

<210> SEQ ID NO 484
<211> LENGTH: 26
<212> TYPE: DNA
<213> ORGANISM: Influenza A virus (H5N1)

<400> SEQUENCE: 484
ttggaatagt tagcttaatg ttacag                                 26

<210> SEQ ID NO 485
<211> LENGTH: 22
<212> TYPE: DNA
<213> ORGANISM: Influenza A virus (H5N1)

<400> SEQUENCE: 485
agccttgctg aatgacaagc ac                                     22

<210> SEQ ID NO 486
<211> LENGTH: 27
<212> TYPE: DNA
<213> ORGANISM: Influenza A virus (H5N1)

<400> SEQUENCE: 486
ttgctttact gtaatgactg atggacc                                27

<210> SEQ ID NO 487
<211> LENGTH: 22
<212> TYPE: DNA
<213> ORGANISM: Influenza A virus (H5N1)

<400> SEQUENCE: 487
ggtgtcccct aacggggcat at                                     22

<210> SEQ ID NO 488
<211> LENGTH: 22
<212> TYPE: DNA
<213> ORGANISM: Influenza A virus (H5N1)

<400> SEQUENCE: 488
ggatgctgga caaaactccc ac                                     22

<210> SEQ ID NO 489
<211> LENGTH: 23
<212> TYPE: DNA
<213> ORGANISM: Influenza A virus (H5N1)

<400> SEQUENCE: 489

-continued

```
ccctgagtca aaagaaagt tct                                         23

<210> SEQ ID NO 490
<211> LENGTH: 24
<212> TYPE: DNA
<213> ORGANISM: Influenza A virus (H5N1)

<400> SEQUENCE: 490
gagccattta cacatgcaca ttca                                       24

<210> SEQ ID NO 491
<211> LENGTH: 24
<212> TYPE: DNA
<213> ORGANISM: Influenza A virus (H5N1)

<400> SEQUENCE: 491
ggaccacaac tacctgttcc atca                                       24

<210> SEQ ID NO 492
<211> LENGTH: 24
<212> TYPE: DNA
<213> ORGANISM: Influenza A virus (H5N1)

<400> SEQUENCE: 492
caaattgtgc tctctttagg ccgc                                       24

<210> SEQ ID NO 493
<211> LENGTH: 30
<212> TYPE: DNA
<213> ORGANISM: Influenza A virus (H5N1)

<400> SEQUENCE: 493
agacagggaa tcaatgccaa gctgaaccga                                 30

<210> SEQ ID NO 494
<211> LENGTH: 30
<212> TYPE: DNA
<213> ORGANISM: Influenza A virus (H5N1)

<400> SEQUENCE: 494
tagcggatgg gcggtataca gtaaggacaa                                 30

<210> SEQ ID NO 495
<211> LENGTH: 30
<212> TYPE: DNA
<213> ORGANISM: Influenza A virus (H5N1)

<400> SEQUENCE: 495
ggggctgtgg ctgtattgaa atacaatggc                                 30

<210> SEQ ID NO 496
<211> LENGTH: 30
<212> TYPE: DNA
<213> ORGANISM: Influenza A virus (H5N1)

<400> SEQUENCE: 496
ggaatttctg gtccagacaa tggggctgtg                                 30

<210> SEQ ID NO 497
<211> LENGTH: 30
<212> TYPE: DNA
<213> ORGANISM: Influenza A virus (H5N1)
```

<400> SEQUENCE: 497
tgttgcttgg tcagctagtg cttgccatga                                    30

<210> SEQ ID NO 498
<211> LENGTH: 30
<212> TYPE: DNA
<213> ORGANISM: Influenza A virus (H5N1)

<400> SEQUENCE: 498
gctgaatgac aagcactcca atgggactgt                                    30

<210> SEQ ID NO 499
<211> LENGTH: 30
<212> TYPE: DNA
<213> ORGANISM: Influenza A virus (H5N1)

<400> SEQUENCE: 499
atgcagtgga gttttcggag acaatccacg                                    30

<210> SEQ ID NO 500
<211> LENGTH: 30
<212> TYPE: DNA
<213> ORGANISM: Influenza A virus (H5N1)

<400> SEQUENCE: 500
atcaaaatct ggagtatcaa ataggatata                                    30

<210> SEQ ID NO 501
<211> LENGTH: 30
<212> TYPE: DNA
<213> ORGANISM: Influenza A virus (H5N1)

<400> SEQUENCE: 501
aaatcacatg tgtgtgtagg gataattggc                                    30

<210> SEQ ID NO 502
<211> LENGTH: 30
<212> TYPE: DNA
<213> ORGANISM: Influenza A virus (H5N1)

<400> SEQUENCE: 502
ccggcgaaat cacatgtgtg tgtagggata                                    30

<210> SEQ ID NO 503
<211> LENGTH: 30
<212> TYPE: DNA
<213> ORGANISM: Influenza A virus (H5N1)

<400> SEQUENCE: 503
cctgttatcc tgatgccggc gaaatcacat                                    30

<210> SEQ ID NO 504
<211> LENGTH: 30
<212> TYPE: DNA
<213> ORGANISM: Influenza A virus (H5N1)

<400> SEQUENCE: 504
ctgtaatgac tgatggacca agtagtgggc                                    30

<210> SEQ ID NO 505
<211> LENGTH: 30
<212> TYPE: DNA
<213> ORGANISM: Influenza A virus (H5N1)

```
<400> SEQUENCE: 505
gagttttgtc cagcatccag aactgacagg                                    30

<210> SEQ ID NO 506
<211> LENGTH: 30
<212> TYPE: DNA
<213> ORGANISM: Influenza A virus (H5N1)

<400> SEQUENCE: 506
cctaacgggg catatggggt aaaagggttt                                    30

<210> SEQ ID NO 507
<211> LENGTH: 24
<212> TYPE: DNA
<213> ORGANISM: Influenza A virus (H5N1)

<400> SEQUENCE: 507
acgttctctc tatcatcccg tcag                                          24

<210> SEQ ID NO 508
<211> LENGTH: 28
<212> TYPE: DNA
<213> ORGANISM: Influenza A virus (H5N1)

<400> SEQUENCE: 508
taagctatat aagaagctga aaagagaa                                      28

<210> SEQ ID NO 509
<211> LENGTH: 26
<212> TYPE: DNA
<213> ORGANISM: Influenza A virus (H5N1)

<400> SEQUENCE: 509
gcaggcagcg gaagccatgg aggtcg                                        26

<210> SEQ ID NO 510
<211> LENGTH: 27
<212> TYPE: DNA
<213> ORGANISM: Influenza A virus (H5N1)

<400> SEQUENCE: 510
actgccctat ccatattatt tggatct                                       27

<210> SEQ ID NO 511
<211> LENGTH: 20
<212> TYPE: DNA
<213> ORGANISM: Influenza A virus (H5N1)

<400> SEQUENCE: 511
tcacttgatc ccgccatctg                                               20

<210> SEQ ID NO 512
<211> LENGTH: 29
<212> TYPE: DNA
<213> ORGANISM: Influenza A virus (H5N1)

<400> SEQUENCE: 512
tcacttgaat cgctgcatct gcactccca                                     29

<210> SEQ ID NO 513
<211> LENGTH: 30
<212> TYPE: DNA
```

<213> ORGANISM: Influenza A virus (H5N1)

<400> SEQUENCE: 513
cgctttgtcc agaatgccct aaatggaaat                30

<210> SEQ ID NO 514
<211> LENGTH: 30
<212> TYPE: DNA
<213> ORGANISM: Influenza A virus (H5N1)

<400> SEQUENCE: 514
gcgtagacgc tttgtccaga atgccctaaa                30

<210> SEQ ID NO 515
<211> LENGTH: 30
<212> TYPE: DNA
<213> ORGANISM: Influenza A virus (H5N1)

<400> SEQUENCE: 515
gggatgttgg gatttgtatt cacgctcacc                30

<210> SEQ ID NO 516
<211> LENGTH: 30
<212> TYPE: DNA
<213> ORGANISM: Influenza A virus (H5N1)

<400> SEQUENCE: 516
gaccaatcct gtcacctctg actaaaggga                30

<210> SEQ ID NO 517
<211> LENGTH: 30
<212> TYPE: DNA
<213> ORGANISM: Influenza A virus (H5N1)

<400> SEQUENCE: 517
ccgatctcga ggctctcatg gagtggctaa                30

<210> SEQ ID NO 518
<211> LENGTH: 30
<212> TYPE: DNA
<213> ORGANISM: Influenza A virus (H5N1)

<400> SEQUENCE: 518
aagccgagat cgcgcagaaa cttgaagatg                30

<210> SEQ ID NO 519
<211> LENGTH: 30
<212> TYPE: DNA
<213> ORGANISM: Influenza A virus (H5N1)

<400> SEQUENCE: 519
tggcaactat caccaaccca ctaatcaggc                30

<210> SEQ ID NO 520
<211> LENGTH: 30
<212> TYPE: DNA
<213> ORGANISM: Influenza A virus (H5N1)

<400> SEQUENCE: 520
acaacagaat gggcacagtg accacggaag                30

<210> SEQ ID NO 521
<211> LENGTH: 30

<212> TYPE: DNA
<213> ORGANISM: Influenza A virus (H5N1)

<400> SEQUENCE: 521
aataacattc catggggcta aggaggtcgc                                         30

<210> SEQ ID NO 522
<211> LENGTH: 30
<212> TYPE: DNA
<213> ORGANISM: Influenza A virus (H5N1)

<400> SEQUENCE: 522
ttgaaaattt gcaggcctac cagaaacgaa                                         30

<210> SEQ ID NO 523
<211> LENGTH: 30
<212> TYPE: DNA
<213> ORGANISM: Influenza A virus (H5N1)

<400> SEQUENCE: 523
actcatccca actctagtgc tggtctgaga                                         30

<210> SEQ ID NO 524
<211> LENGTH: 30
<212> TYPE: DNA
<213> ORGANISM: Influenza A virus (H5N1)

<400> SEQUENCE: 524
ccatggaggt cgctaatcag gctaggcaga                                         30

<210> SEQ ID NO 525
<211> LENGTH: 25
<212> TYPE: DNA
<213> ORGANISM: West Nile virus

<400> SEQUENCE: 525
ggcaatcttg ccctcagtag ttgga                                              25

<210> SEQ ID NO 526
<211> LENGTH: 25
<212> TYPE: DNA
<213> ORGANISM: West Nile virus

<400> SEQUENCE: 526
ctctcagtgc ttcagccatc tcagc                                              25

<210> SEQ ID NO 527
<211> LENGTH: 21
<212> TYPE: DNA
<213> ORGANISM: West Nile virus

<400> SEQUENCE: 527
agtagttcgc ctgtgtgagc t                                                  21

<210> SEQ ID NO 528
<211> LENGTH: 20
<212> TYPE: DNA
<213> ORGANISM: West Nile virus

<400> SEQUENCE: 528
gttttgagct ccgccgattg                                                    20

<210> SEQ ID NO 529

```
<211> LENGTH: 20
<212> TYPE: DNA
<213> ORGANISM: West Nile virus

<400> SEQUENCE: 529
aattaacaca gtgcgagctg                                           20

<210> SEQ ID NO 530
<211> LENGTH: 20
<212> TYPE: DNA
<213> ORGANISM: West Nile virus

<400> SEQUENCE: 530
ctggcgatca ggccaatcat                                           20

<210> SEQ ID NO 531
<211> LENGTH: 20
<212> TYPE: DNA
<213> ORGANISM: West Nile virus

<400> SEQUENCE: 531
acatcgactg ttggtgcaca                                           20

<210> SEQ ID NO 532
<211> LENGTH: 20
<212> TYPE: DNA
<213> ORGANISM: West Nile virus

<400> SEQUENCE: 532
cagctgtcgc cttcgagaac                                           20

<210> SEQ ID NO 533
<211> LENGTH: 20
<212> TYPE: DNA
<213> ORGANISM: West Nile virus

<400> SEQUENCE: 533
ttcaactgcc ttggaatgag                                           20

<210> SEQ ID NO 534
<211> LENGTH: 20
<212> TYPE: DNA
<213> ORGANISM: West Nile virus

<400> SEQUENCE: 534
agcgtgcacg ttcacggaga                                           20

<210> SEQ ID NO 535
<211> LENGTH: 20
<212> TYPE: DNA
<213> ORGANISM: West Nile virus

<400> SEQUENCE: 535
gacactgggt gtgccataga                                           20

<210> SEQ ID NO 536
<211> LENGTH: 21
<212> TYPE: DNA
<213> ORGANISM: West Nile virus

<400> SEQUENCE: 536
agcattcact tgtgactgca c                                         21
```

```
<210> SEQ ID NO 537
<211> LENGTH: 34
<212> TYPE: DNA
<213> ORGANISM: West Nile virus

<400> SEQUENCE: 537
tataatgctg atatgattga ccctttcag ttgg                        34

<210> SEQ ID NO 538
<211> LENGTH: 25
<212> TYPE: DNA
<213> ORGANISM: West Nile virus

<400> SEQUENCE: 538
gcgtttacgg ttgggatcac atgca                                 25

<210> SEQ ID NO 539
<211> LENGTH: 25
<212> TYPE: DNA
<213> ORGANISM: West Nile virus

<400> SEQUENCE: 539
gcggatggcc cgcaactgaa gtgat                                 25

<210> SEQ ID NO 540
<211> LENGTH: 22
<212> TYPE: DNA
<213> ORGANISM: West Nile virus

<400> SEQUENCE: 540
cctcctctct ttgtgtattg ga                                    22

<210> SEQ ID NO 541
<211> LENGTH: 20
<212> TYPE: DNA
<213> ORGANISM: West Nile virus

<400> SEQUENCE: 541
aggaggcgtg ttgtgggaca                                       20

<210> SEQ ID NO 542
<211> LENGTH: 20
<212> TYPE: DNA
<213> ORGANISM: West Nile virus

<400> SEQUENCE: 542
acgttttccc gaggcgaagt                                       20

<210> SEQ ID NO 543
<211> LENGTH: 20
<212> TYPE: DNA
<213> ORGANISM: West Nile virus

<400> SEQUENCE: 543
cgcctcggga aaacgttctc                                       20

<210> SEQ ID NO 544
<211> LENGTH: 20
<212> TYPE: DNA
<213> ORGANISM: West Nile virus

<400> SEQUENCE: 544
ctgcgaacgt tgcttctctg                                       20
```

<210> SEQ ID NO 545
<211> LENGTH: 29
<212> TYPE: DNA
<213> ORGANISM: West Nile virus

<400> SEQUENCE: 545
aacgagatgg gttggctaga taagaccaa                                    29

<210> SEQ ID NO 546
<211> LENGTH: 31
<212> TYPE: DNA
<213> ORGANISM: West Nile virus

<400> SEQUENCE: 546 ctcttttag tcctggtttt tccatgttct t                                  31

<210> SEQ ID NO 547
<211> LENGTH: 34
<212> TYPE: DNA
<213> ORGANISM: West Nile virus

<400> SEQUENCE: 547
atatttaatc aattgtaaat agacaatata agta                              34

<210> SEQ ID NO 548
<211> LENGTH: 20
<212> TYPE: DNA
<213> ORGANISM: West Nile virus

<400> SEQUENCE: 548
agatcctgtg ttctcgcacc                                              20

<210> SEQ ID NO 549
<211> LENGTH: 33
<212> TYPE: DNA
<213> ORGANISM: West Nile virus

<400> SEQUENCE: 549
acataagcgc gatagtgcag ggtgaaagga tgg                               33

<210> SEQ ID NO 550
<211> LENGTH: 30
<212> TYPE: DNA
<213> ORGANISM: West Nile virus

<400> SEQUENCE: 550
tcgcctgtgt gagctgacaa acttagtagt                                   30

<210> SEQ ID NO 551
<211> LENGTH: 30
<212> TYPE: DNA
<213> ORGANISM: West Nile virus

<400> SEQUENCE: 551
ggctctcttg gcgttcttca ggttcacagc                                   30

<210> SEQ ID NO 552
<211> LENGTH: 30
<212> TYPE: DNA
<213> ORGANISM: West Nile virus

<400> SEQUENCE: 552
gcagtgctgg atcgatggag aggtgtgaac                                   30

<210> SEQ ID NO 553
<211> LENGTH: 30
<212> TYPE: DNA
<213> ORGANISM: West Nile virus

<400> SEQUENCE: 553
aggattaaca acaattaaca cagtgcgagc                30

<210> SEQ ID NO 554
<211> LENGTH: 30
<212> TYPE: DNA
<213> ORGANISM: West Nile virus

<400> SEQUENCE: 554
ggctctcttg gcgttcttca ggttcacagc                30

<210> SEQ ID NO 555
<211> LENGTH: 30
<212> TYPE: DNA
<213> ORGANISM: West Nile virus

<400> SEQUENCE: 555
gcaagagccg ggctgtcaat atgctaaaac                30

<210> SEQ ID NO 556
<211> LENGTH: 30
<212> TYPE: DNA
<213> ORGANISM: West Nile virus

<400> SEQUENCE: 556
ggatcttgag gaaccctgga tatgccctgg                30

<210> SEQ ID NO 557
<211> LENGTH: 30
<212> TYPE: DNA
<213> ORGANISM: West Nile virus

<400> SEQUENCE: 557
ccactcaaga cgcagtcgga ggtcactgac                30

<210> SEQ ID NO 558
<211> LENGTH: 30
<212> TYPE: DNA
<213> ORGANISM: West Nile virus

<400> SEQUENCE: 558
gttcatggac ctcaacctcc cttggagcag                30

<210> SEQ ID NO 559
<211> LENGTH: 30
<212> TYPE: DNA
<213> ORGANISM: West Nile virus

<400> SEQUENCE: 559
gactgtgaac cacggtcagg gattgacacc                30

<210> SEQ ID NO 560
<211> LENGTH: 30
<212> TYPE: DNA
<213> ORGANISM: West Nile virus

<400> SEQUENCE: 560

```
gtcgcacgga aactactcca cacaggttgg                                    30

<210> SEQ ID NO 561
<211> LENGTH: 30
<212> TYPE: DNA
<213> ORGANISM: West Nile virus

<400> SEQUENCE: 561
ggaccaacta ctgtggagtc gcacggaaac                                    30

<210> SEQ ID NO 562
<211> LENGTH: 30
<212> TYPE: DNA
<213> ORGANISM: West Nile virus

<400> SEQUENCE: 562
gctaccgtca gcgatctctc caccaaagct                                    30

<210> SEQ ID NO 563
<211> LENGTH: 30
<212> TYPE: DNA
<213> ORGANISM: West Nile virus

<400> SEQUENCE: 563
ggttctcgaa ggcgacagct gcgtgactat                                    30

<210> SEQ ID NO 564
<211> LENGTH: 30
<212> TYPE: DNA
<213> ORGANISM: West Nile virus

<400> SEQUENCE: 564
gacactgggt gtgccataga catcagccgg                                    30

<210> SEQ ID NO 565
<211> LENGTH: 30
<212> TYPE: DNA
<213> ORGANISM: West Nile virus

<400> SEQUENCE: 565
ggaactacgg tcaccctgag tgagagctgc                                    30

<210> SEQ ID NO 566
<211> LENGTH: 30
<212> TYPE: DNA
<213> ORGANISM: West Nile virus

<400> SEQUENCE: 566
gataatacca gtcacactgg cgggaccacg                                    30

<210> SEQ ID NO 567
<211> LENGTH: 30
<212> TYPE: DNA
<213> ORGANISM: West Nile virus

<400> SEQUENCE: 567
ggtctcacca gcactcggat gttcctgaag                                    30

<210> SEQ ID NO 568
<211> LENGTH: 30
<212> TYPE: DNA
<213> ORGANISM: West Nile virus

<400> SEQUENCE: 568
```
gggaagcagt gaaggacgag ctgaacactc                                       30

<210> SEQ ID NO 569
<211> LENGTH: 30
<212> TYPE: DNA
<213> ORGANISM: West Nile virus

<400> SEQUENCE: 569
ccggcaagag ctgagatgtg gaagtggagt                                       30

<210> SEQ ID NO 570
<211> LENGTH: 30
<212> TYPE: DNA
<213> ORGANISM: West Nile virus

<400> SEQUENCE: 570
aggcagcttg atcagggaga agaggagtgc                                       30

<210> SEQ ID NO 571
<211> LENGTH: 32
<212> TYPE: DNA
<213> ORGANISM: West Nile virus

<400> SEQUENCE: 571
cactggcggt agcttggatg atactgagag cc                                    32

<210> SEQ ID NO 572
<211> LENGTH: 30
<212> TYPE: DNA
<213> ORGANISM: West Nile virus

<400> SEQUENCE: 572
atttctggga aatcaacaga tatgtggatt                                       30

<210> SEQ ID NO 573
<211> LENGTH: 30
<212> TYPE: DNA
<213> ORGANISM: West Nile virus

<400> SEQUENCE: 573
gctcatgttt gctgctttcg tgatttctgg                                       30

<210> SEQ ID NO 574
<211> LENGTH: 30
<212> TYPE: DNA
<213> ORGANISM: West Nile virus

<400> SEQUENCE: 574
cgtctacagg atcatgactc gtgggctgct                                       30

<210> SEQ ID NO 575
<211> LENGTH: 30
<212> TYPE: DNA
<213> ORGANISM: West Nile virus

<400> SEQUENCE: 575
catactgggg cagtgtcaag gaggatcgac                                       30

<210> SEQ ID NO 576
<211> LENGTH: 30
<212> TYPE: DNA
<213> ORGANISM: West Nile virus

```
<400> SEQUENCE: 576
acagaagact gagaacagcc gtgctagcgc                                    30

<210> SEQ ID NO 577
<211> LENGTH: 30
<212> TYPE: DNA
<213> ORGANISM: West Nile virus

<400> SEQUENCE: 577
ctaccctcac ccacaggctg atgtctcctc                                    30

<210> SEQ ID NO 578
<211> LENGTH: 30
<212> TYPE: DNA
<213> ORGANISM: West Nile virus

<400> SEQUENCE: 578
cagactgaga tcccggatcg agcttggaac                                    30

<210> SEQ ID NO 579
<211> LENGTH: 30
<212> TYPE: DNA
<213> ORGANISM: West Nile virus

<400> SEQUENCE: 579
gagcagggtg attgacagcc ggaagagtgt                                    30

<210> SEQ ID NO 580
<211> LENGTH: 30
<212> TYPE: DNA
<213> ORGANISM: West Nile virus

<400> SEQUENCE: 580
agggagagtg atcctgggag aaccatctgc                                    30

<210> SEQ ID NO 581
<211> LENGTH: 30
<212> TYPE: DNA
<213> ORGANISM: West Nile virus

<400> SEQUENCE: 581
ggatggggaa taccggctca gaggagaaga                                    30

<210> SEQ ID NO 582
<211> LENGTH: 30
<212> TYPE: DNA
<213> ORGANISM: West Nile virus

<400> SEQUENCE: 582
agataggttt gggaggcgct gtcttgggag                                    30

<210> SEQ ID NO 583
<211> LENGTH: 30
<212> TYPE: DNA
<213> ORGANISM: West Nile virus

<400> SEQUENCE: 583
gacaccatgt acgttgtggc cactgcagag                                    30

<210> SEQ ID NO 584
<211> LENGTH: 30
<212> TYPE: DNA
<213> ORGANISM: West Nile virus
```

```
<400> SEQUENCE: 584
ccgtctgtga agacagtacg agaagccgga                                    30

<210> SEQ ID NO 585
<211> LENGTH: 30
<212> TYPE: DNA
<213> ORGANISM: West Nile virus

<400> SEQUENCE: 585
gtcccagaat tagagcgcac cacacccatc                                    30

<210> SEQ ID NO 586
<211> LENGTH: 32
<212> TYPE: DNA
<213> ORGANISM: West Nile virus

<400> SEQUENCE: 586
ggacaagtca ccctcaccgt tacggtaaca gc                                 32

<210> SEQ ID NO 587
<211> LENGTH: 30
<212> TYPE: DNA
<213> ORGANISM: West Nile virus

<400> SEQUENCE: 587
gtgacaacag cggtcctcac tccactgcta                                    30

<210> SEQ ID NO 588
<211> LENGTH: 30
<212> TYPE: DNA
<213> ORGANISM: West Nile virus

<400> SEQUENCE: 588
ctggtgagga tgatggaagg ggaaggagtg                                    30

<210> SEQ ID NO 589
<211> LENGTH: 30
<212> TYPE: DNA
<213> ORGANISM: West Nile virus

<400> SEQUENCE: 589
agaaagaact caggaggagg tgtcgagggc                                    30

<210> SEQ ID NO 590
<211> LENGTH: 30
<212> TYPE: DNA
<213> ORGANISM: West Nile virus

<400> SEQUENCE: 590
gaggagcgcc agagaagcag ttgaagatcc                                    30

<210> SEQ ID NO 591
<211> LENGTH: 30
<212> TYPE: DNA
<213> ORGANISM: West Nile virus

<400> SEQUENCE: 591
gagtggtcag gctcctctca aaaccatggg                                    30

<210> SEQ ID NO 592
<211> LENGTH: 30
<212> TYPE: DNA
```

<213> ORGANISM: West Nile virus

<400> SEQUENCE: 592
acgactcagg cgtgagtaca gttcgacgtg 30

<210> SEQ ID NO 593
<211> LENGTH: 30
<212> TYPE: DNA
<213> ORGANISM: West Nile virus

<400> SEQUENCE: 593
gggtgagtcg agcttcaggc aatgtggtac 30

<210> SEQ ID NO 594
<211> LENGTH: 30
<212> TYPE: DNA
<213> ORGANISM: West Nile virus

<400> SEQUENCE: 594
gtgacatcgg agagtcctcg tcaagtgctg 30

<210> SEQ ID NO 595
<211> LENGTH: 30
<212> TYPE: DNA
<213> ORGANISM: West Nile virus

<400> SEQUENCE: 595
ccaagaagtc agagggtaca caaagggcgg 30

<210> SEQ ID NO 596
<211> LENGTH: 30
<212> TYPE: DNA
<213> ORGANISM: West Nile virus

<400> SEQUENCE: 596
ggcatccagt ctctaggggc acagcaaaac 30

<210> SEQ ID NO 597
<211> LENGTH: 30
<212> TYPE: DNA
<213> ORGANISM: West Nile virus

<400> SEQUENCE: 597
gaagttgagt agacggtgct gcctgcgact 30

<210> SEQ ID NO 598
<211> LENGTH: 30
<212> TYPE: DNA
<213> ORGANISM: West Nile virus

<400> SEQUENCE: 598
catgtaagcc ctcagaaccg tctcggaagg 30

<210> SEQ ID NO 599
<211> LENGTH: 34
<212> TYPE: DNA
<213> ORGANISM: West Nile virus

<400> SEQUENCE: 599
accagggcga aaggactaga ggttagagga gacc 34

<210> SEQ ID NO 600
<211> LENGTH: 30

<212> TYPE: DNA
<213> ORGANISM: West Nile virus

<400> SEQUENCE: 600
ggtcagggga aggactagag gttagtggag 30

<210> SEQ ID NO 601
<211> LENGTH: 30
<212> TYPE: DNA
<213> ORGANISM: West Nile virus

<400> SEQUENCE: 601
ggagatcttc tgctctgcac aaccagccac 30

<210> SEQ ID NO 602
<211> LENGTH: 20
<212> TYPE: DNA
<213> ORGANISM: Artificial Sequence
<220> FEATURE:
<223> OTHER INFORMATION: Synthetic DNA, blaOXA-51 like forward primer

<400> SEQUENCE: 602
taatgctttg atcggccttg 20

<210> SEQ ID NO 603
<211> LENGTH: 20
<212> TYPE: DNA
<213> ORGANISM: Artificial Sequence
<220> FEATURE:
<223> OTHER INFORMATION: Synthetic DNA; blaOXA-51-like reverse primer

<400> SEQUENCE: 603
tggattgcac ttcatcttgg 20

<210> SEQ ID NO 604
<211> LENGTH: 20
<212> TYPE: DNA
<213> ORGANISM: Artificial Sequence
<220> FEATURE:
<223> OTHER INFORMATION: Synthetic DNA; blaOXA-23-like forward primer

<400> SEQUENCE: 604
gatcggattg gagaaccaga 20

<210> SEQ ID NO 605
<211> LENGTH: 20
<212> TYPE: DNA
<213> ORGANISM: Artificial Sequence
<220> FEATURE:
<223> OTHER INFORMATION: Synthetic DNA; blaOXA-23-like reverse primer

<400> SEQUENCE: 605
atttctgacc gcatttccat 20

<210> SEQ ID NO 606
<211> LENGTH: 20
<212> TYPE: DNA
<213> ORGANISM: Artificial Sequence
<220> FEATURE:
<223> OTHER INFORMATION: Synthetic DNA; class I integrase gene forward primer

<400> SEQUENCE: 606
cagtggacat aagcctgttc 20

```
<210> SEQ ID NO 607
<211> LENGTH: 18
<212> TYPE: DNA
<213> ORGANISM: Artificial Sequence
<220> FEATURE:
<223> OTHER INFORMATION: Synthetic DNA; reverse primer class I integrase
      gene

<400> SEQUENCE: 607
cccgaggcat agactgta                                                  18

<210> SEQ ID NO 608
<211> LENGTH: 18
<212> TYPE: DNA
<213> ORGANISM: Artificial Sequence
<220> FEATURE:
<223> OTHER INFORMATION: Synthetic DNA; forward primer ITS region

<400> SEQUENCE: 608
ttgtacacac cgcccgtc                                                  18

<210> SEQ ID NO 609
<211> LENGTH: 20
<212> TYPE: DNA
<213> ORGANISM: Artificial Sequence
<220> FEATURE:
<223> OTHER INFORMATION: Synthetic DNA; reverse primer ITS region

<400> SEQUENCE: 609
ttcgcctttc cctcacggta                                                20

<210> SEQ ID NO 610
<211> LENGTH: 26
<212> TYPE: DNA
<213> ORGANISM: Artificial Sequence
<220> FEATURE:
<223> OTHER INFORMATION: Synthetic DNA; oligotargeter 1 for
      Acinetobacter

<400> SEQUENCE: 610
aattcatata ccaaaacgct cgattc                                         26

<210> SEQ ID NO 611
<211> LENGTH: 26
<212> TYPE: DNA
<213> ORGANISM: Artificial Sequence
<220> FEATURE:
<223> OTHER INFORMATION: Synthetic DNA; Oligotargeter 2 for
      Acinetobacter

<400> SEQUENCE: 611
gactggttga agttatagat aaaaga                                         26

<210> SEQ ID NO 612
<211> LENGTH: 22
<212> TYPE: DNA
<213> ORGANISM: Artificial Sequence
<220> FEATURE:
<223> OTHER INFORMATION: Synthetic DNA; TB forward primer

<400> SEQUENCE: 612
acatgcaagt cgaacggaaa gg                                             22

<210> SEQ ID NO 613
<211> LENGTH: 24
<212> TYPE: DNA
<213> ORGANISM: Artificial Sequence
```

<220> FEATURE:
<223> OTHER INFORMATION: Synthetic DNA; TB reverse primer

<400> SEQUENCE: 613
cctcctgata tctgcgcatt ccac 24

<210> SEQ ID NO 614
<211> LENGTH: 20
<212> TYPE: DNA
<213> ORGANISM: Artificial Sequence
<220> FEATURE:
<223> OTHER INFORMATION: Synthetic DNA; oligotargeter for mycobacteria

<400> SEQUENCE: 614
ttgtcgcgtt gttcgtgaaa 20

<210> SEQ ID NO 615
<211> LENGTH: 20
<212> TYPE: DNA
<213> ORGANISM: Artificial Sequence
<220> FEATURE:
<223> OTHER INFORMATION: Synthetic DNA; oligotargeter for
M. tuberculosis complex

<400> SEQUENCE: 615
accacaagac atgcatcccg 20

<210> SEQ ID NO 616
<211> LENGTH: 72
<212> TYPE: DNA
<213> ORGANISM: West Nile virus

<400> SEQUENCE: 616
tttatggcaa tggagtcata atgcccaacg gctccataca taagaggaga tagtgcaggg 60
tgaaaggatg ga 72

<210> SEQ ID NO 617
<211> LENGTH: 72
<212> TYPE: DNA
<213> ORGANISM: West Nile virus

<400> SEQUENCE: 617
tttatggcaa tggagtcata atgcccaacg gctctataca taagcgacga tagtgcaggg 60
tgaaaggatg ga 72

<210> SEQ ID NO 618
<211> LENGTH: 72
<212> TYPE: DNA
<213> ORGANISM: West Nile virus

<400> SEQUENCE: 618
tttatggcaa tggagtcata atgcccaacg tgctcataca taagatagag tagtgcaggg 60
tgaaaggatg ga 72

<210> SEQ ID NO 619
<211> LENGTH: 72
<212> TYPE: DNA
<213> ORGANISM: West Nile virus

<400> SEQUENCE: 619
tttatggcaa tggagtcata atgcccaacg gcttatacat aagcggaata tagtgcaggg 60
tgaaaggatg ga 72

-continued

<210> SEQ ID NO 620
<211> LENGTH: 72
<212> TYPE: DNA
<213> ORGANISM: West Nile virus

<400> SEQUENCE: 620
tttatggcaa tggagtcata atgcccaacg gctccataca taagaggaga tagtgcaggg    60
tgaaaggatg ga                                                       72

<210> SEQ ID NO 621
<211> LENGTH: 72
<212> TYPE: DNA
<213> ORGANISM: West Nile virus

<400> SEQUENCE: 621
tttatggcaa tggagtcata atgcccaacg ctcatacata agcgcgagga tagtgcaggg    60
tgaaaggatg ga                                                       72

<210> SEQ ID NO 622
<211> LENGTH: 72
<212> TYPE: DNA
<213> ORGANISM: West Nile virus

<400> SEQUENCE: 622
tttatggcaa tggagtcata atgcccaacg gctatacata agcggataga tagtgcaggg    60
tgaaaggatg ga                                                       72

<210> SEQ ID NO 623
<211> LENGTH: 72
<212> TYPE: DNA
<213> ORGANISM: West Nile virus

<400> SEQUENCE: 623
tttatggcaa tggagtcata atgcccaacg gcttatacat aagcggaata tagtgcaggg    60
tgaaaggatg ga                                                       72

<210> SEQ ID NO 624
<211> LENGTH: 72
<212> TYPE: DNA
<213> ORGANISM: West Nile virus

<400> SEQUENCE: 624
tttatggcaa tggagtcata atgcccaacg gctcatacat aagcgcgaga tagtgcaggg    60
tgaaaggatg ga                                                       72

<210> SEQ ID NO 625
<211> LENGTH: 72
<212> TYPE: DNA
<213> ORGANISM: West Nile virus

<400> SEQUENCE: 625
tttatggcaa tggagtcata atgcccaacg gctcatacat agaggccgga tagtgcaggg    60
tgaaaggatg ga                                                       72

<210> SEQ ID NO 626
<211> LENGTH: 72
<212> TYPE: DNA
<213> ORGANISM: West Nile virus

```
<400> SEQUENCE: 626
tttatggcaa tggagtcata atgcccaacg gctctataca taagcgacga tagtgcaggg    60
tgaaaggatg ga                                                        72

<210> SEQ ID NO 627
<211> LENGTH: 72
<212> TYPE: DNA
<213> ORGANISM: West Nile virus

<400> SEQUENCE: 627
tttatggcaa tggagtcata atgcccaacg gctccataca taagaggaga tagtgcaggg    60
tgaaaggatg ga                                                        72

<210> SEQ ID NO 628
<211> LENGTH: 72
<212> TYPE: DNA
<213> ORGANISM: West Nile virus

<400> SEQUENCE: 628
tttatggcaa tggagtcata atgcccaacg gctccataca taagaggaga tagtgcaggg    60
tgaaaggatg ga                                                        72

<210> SEQ ID NO 629
<211> LENGTH: 72
<212> TYPE: DNA
<213> ORGANISM: West Nile virus

<400> SEQUENCE: 629
tttatggcaa tggagtcata atgcccaacg gctccataca taagaggaga tagtgcaggg    60
tgaaaggatg ga                                                        72

<210> SEQ ID NO 630
<211> LENGTH: 72
<212> TYPE: DNA
<213> ORGANISM: West Nile virus

<400> SEQUENCE: 630
tttatggcaa tggagtcata atgcccaacg gctccataca taagaggaga tagtgcaggg    60
tgaaaggatg ga                                                        72

<210> SEQ ID NO 631
<211> LENGTH: 70
<212> TYPE: DNA
<213> ORGANISM: West Nile virus

<400> SEQUENCE: 631
tttatggcaa tggagtcata atgcccaacg gctcatacat aagcgcgata gtgcagggtg    60
aaaggatgga                                                           70

<210> SEQ ID NO 632
<211> LENGTH: 70
<212> TYPE: DNA
<213> ORGANISM: West Nile virus

<400> SEQUENCE: 632
tctatggcaa tggagtcata atgcccaacg gctcctacat aagcgcgata gtgcagggtg    60
aaaggatgga                                                           70
```

DETECTION OF NUCLEIC ACIDS USING UNMODIFIED GOLD NANOPARTICLES

CROSS-REFERENCE TO RELATED APPLICATIONS

This application claims priority to U.S. Provisional Application No. 61/473,238, filed Apr. 8, 2011 and to U.S. Provisional Application No. 61/473,242, filed Apr. 8, 2011, which are both incorporated by reference in their entireties.

BACKGROUND OF THE INVENTION

Field of the Invention

Gold nanoparticle-based colorimetric and fluorimetric assays for detection of amplified and unamplified nucleic acids in clinical specimens from *Acinetobacter,* mycobacteria, *staphylococcus*, hepatitis B virus, human immunodeficiency virus, influenza virus, and West Nile Virus.

Description of the Related Art

Gold nanoparticles or AuNPs exhibit a unique phenomenon known as Surface Plasmon Resonance, which is responsible for their intense red color in suspension. This color changes to blue upon aggregation of AuNPs. Several molecular assays are available for detection of microbial DNA, including DNA from bacteria like Acinetobacteria, staphylococci, and mycobacteria, and from viruses such as Hepatitis B Virus, Human Immunodeficiency Virus (HIV), Influenza A Virus, and West Nile Virus. Despite the high sensitivity and specificity of these methods, they are time-consuming, labor intensive, expensive, and require specialized equipment and thus are not suitable for use in many developing countries or for use in the field. Therefore, there is a great need to develop a low-tech assay for the direct detection of unamplified nucleic acids from microbial with acceptable sensitivity and specificity, short turn around time, and cost-effectiveness. Such an assay would have great utility in quickly and inexpensively characterizing microbes and controlling microbial pathogens in developing countries with limited resources and high infection rates, such as Egypt.

Nanoparticles have been recently proposed as promising tools to develop the next generation of diagnostic assays. Because of their unique properties and ability to interact with biomolecules on one-to-one basis, various nanoparticles show great promise to meet the rigorous demands of the clinical laboratory for sensitivity and cost-effectiveness, and can be used in the future in point-of-care diagnosis.

Gold nanoparticles ("AuNPs") are spheres with a typical diameter of approximately 2-50 nm. They exhibit a unique phenomenon known as Surface Plasmon Resonance (SPR), which is responsible for their intense red color, and which changes to blue upon aggregation of AuNPs.

The addition of salt shields the surface charge on the AuNPs, which are typically negatively charged owing to adsorbed negatively charged citrate ions on their surfaces, leading to aggregation of AuNPs and a red-to-blue color shift. SPR is also responsible for the large absorption and scattering cross-sections of AuNPs which are 4-5 orders of magnitude larger than those of conventional dyes. These unique optical properties have allowed the use of AuNPs in simple and rapid colorimetric assays for clinical diagnosis offering higher sensitivity and specificity than current detection techniques. Suitable components and procedures for making gold nanoparticles are known in the art and are incorporated by reference to the articles cited herein.

Li et al. developed a colorimetric assay using unmodified citrate-coated AuNPs. This method is based on the property of single-stranded DNA (ssDNA) which adsorbs on citrate-coated AuNPs. This adsorption increases the negative charge on the AuNPs leading to increased repulsion between the particles, thus preventing aggregation. The adsorption of ssDNA on AuNPs occurs due to the fact that ssDNA can uncoil and expose its nitrogenous bases. The attractive electrostatic forces between the bases and the AuNPs allow adsorption of the ssDNA. On the other hand, double-stranded DNA (dsDNA) does not adsorb on AuNPs due to the repulsion between its negatively-charged phosphate backbone and the negatively-charged coating of citrate ions on the surfaces of the AuNPs. Therefore, when AuNPs are added to a saline solution containing the target DNA and its complementary unlabeled single-stranded polynucleotide, AuNPs aggregate (since the single-stranded polynucleotides are not free to stabilize the AuNPs) and the solution color changes to blue. However, in the absence of the target or the presence of a non-complementary target, the complementary single-stranded polynucleotides are free to stabilize the AuNPs thus preventing their aggregation and the solution color remains red. This method has been used to detect single nucleotide polymorphisms in PCR-amplified genomic DNA extracted from clinical samples. Moreover, based on the same principle, AuNPs are capable of quenching fluorescent dyes and this property has been used for detection of synthetic nucleic sequences with high sensitivity and selectivity. Shawky, et al., Clin. Biochem. 43:1163-1168 (2010) disclosed direct detection of unamplified hepatitis C virus RNA using unmodified gold nanoparticles. However, this method has not been proven or evaluated for microbes which contain more extensive and complex genomes or for clinical samples containing such microbes.

Bacteria

Mycobacteria

*Mycobacterium tuberculosis*

Tuberculosis (TB) is a contagious disease caused by the airborne pathogen *Mycobacterium tuberculosis*. The disease currently infects about one third of the world's population, with 8-9 million new infections annually; it claims a victim every 10 seconds. With an estimated death toll of 1.3 million victims in 2008 alone, TB claims more human lives every year than any other single pathogen. In Africa, HIV is the single most important factor contributing to the increase the incidence of TB since 1990 and TB became generally the leading cause of HIV-related deaths. The *M. tuberculosis* complex includes other TB-causing mycobacteria: *M. tuberculosis, M. bovis, M. bovis* BCG, *M. africanum, M. canetti, M. caprae, M. microti* and *M. pinnipedii. Mycobacterium bovis* and *Mycobacterium microti* are also the causative agents of TB in animals but can be transmitted to humans, such as immunocompromised patients.

*Mycobacterium tuberculosis* is an acid fast beaded *bacillus*. It is non-motile non-spore forming rod which appears either straight or slightly curved under microscopic examination. Its genomic DNA has 70% GC content and its cell wall has high lipid content. It is able to survive in harsh environmental conditions and divides inside of host cells every 12-24 h. Once the TB bacilli are inhaled, they enter the alveoli to the alveolar space which is the first to have a role in eliminating the bacteria recruiting macrophages and pathogenesis in the lung starts. The first contact of the bacilli is with macrophage where they have the ability to reside in the macrophage bypassing phagocytosis and multiply but develop to dormant stage with low replication rate and metabolic activity.

The disease can develop to be extra-pulmonary, the infection proceed in other organs such as bones and brains. The bacilli cause high inflammatory host responses which may be fatal. The clinical manifestation starts with non specific symptoms including cough, fever, malaise, and weight loss. At late stages, bloody reproductive cough develop with pulmonary symptoms.

Nontuberculous Mycobacteria (NTM)

Nontuberculous mycobacteria (NTM) include the mycobacterial species other than those comprising the *Mycobacterium tuberculosis* complex. They are opportunistic environmental bacterial pathogens that commonly inhabit different water bodies and soil and have the ability to attach to surfaces and form biofilms. This accounts for their survival in areas with direct human contact such as water plumbing and pose a threat of nosocomial infection in case of adherence to areas such catheter surfaces. Nevertheless, there are no known instances of human-to-human transmission and environmental exposure is believed to be the path to infection. NTM are not obligate pathogens and their main threat is in the case of immunocompromised patients, e.g., in subjects having AIDS and cystic fibrosis, which accounts for their increased importance with the HIV pandemic. NTM members include slow-growing bacteria (colony appearance on solid media takes more than 7 days) such as *M. ulcerans, M. kansasii*, and *M. scrofulaceum*, and rapid-growing bacteria (colonies appear on solid media in ≤7 day) such as *M. fortuitum, M. abscessus*, and *M. mucogenicum*. Another notable NTM member is noncultivatable *M. leprae*, the causative agent of leprosy. NTM can cause various diseases including pulmonary infections with TB-like presentations e.g. *M. avium* and *M. malmoense*, skin and soft-tissue infections and post-operative wound infections, e.g. *M. fortuitum* and *M. mucogenicum*, in addition to gastrointestinal diseases, lymphadenitis, and disseminated disease in immunocompromised patients. Treatment of NTM is challenging as many members are resistant to most common anti-mycobacterial drugs and the treatment must be customized depending on the infecting species and the clinical manifestation. This makes their prompt diagnosis essential for effective patient management.

*Acinetobacter*

*Acinetobacter* is a genus of gram-negative bacteria associated with a variety of hospital-acquired infection. Their ability for long-term survival in hospital environment and extreme ability to develop resistance to all the known conventional antibiotics raised serious concerns throughout the past decades. Under microscopical examination, they are short, plump, gram negative rods that are difficult to destain and may therefore be misidentified as either gram negative or gram positive cocci.

*Acinetobacters* are strictly aerobic, non-fermenting and non-motile short gram-negative rods in the logarithmic phase becoming more coccoid at the stationary phase. *Acinetobacters* grow readily on common laboratory media and are usually isolated on blood agar.

*Acinetobacter* genus is classified into 33 species based on genetic relatedness. Species 2 (*Acinetobacter baumannii*) is the most important clinically, where about 90% of the clinical isolates are found to be infected with *Acinetobacter baumannii*.

*A. baumannii* is an opportunistic pathogen that infects immune-compromised patients. It is a causative agent of nosocomial pneumonia, bacteremia, meningitis, and urinary tract infection, resulting in attributable mortalities of up to 23% for hospitalized patients and 43% for patients under intensive care. More recently *Acinetobacter* has caused serious infections among American military personnel serving in Iraq and Afghanistan.

The reason why *Acinetobacter* infections pose such a serious problem is due to the bacteria's minimal nutritional requirements and their ability to survive under harsh conditions of pH & temperature. These properties facilitate *Acinetobacter*'s ability to colonize inert surfaces such as hospital surfaces and tools for prolonged periods. Additionally, the bacterium has the ability to develop and express resistance to nearly all available antibiotics.

*A. baumannii*, along with *Aspergillus* spp., extended-spectrum β-lactamase-producing Enterobacteriaceae, vancomycin-resistant *Enterococcus faecium*, *Pseudomonas aeruginosa*, and methicillin-resistant *Staphylococcus aureus*, have been identified by the Antimicrobial Availability Task Force of the Infectious Diseases Society of America as pathogens for which there is an immediate need for new drug development.

Methicillin-Resistant *Staphylococcus Aureus* (MRSA)

*Staphylococcus aureus* is a ubiquitous gram-positive bacterium that causes severe morbidity and mortality worldwide. *S. aureus* rapidly develops resistance to antibiotics. In the 1960s, the methicillin group of antibiotics (including cloxacillin) was introduced allowing the control of infections caused by *S. aureus*. However, in 1961, resistance to methicillin soon evolved by hospital-acquired methicillin resistant *Staphylococcus aureus* (HA-MRSA). Resistance to methicillin occurred due to the acquisition of a MecA gene carried on a mobile genetic element (Staphylococcal Cassette Chromosome mec; SCCmec).

Although, MRSA was mostly confined to hospital-acquired infections for a long period of time, in 1993, a new form of MRSA known as community-acquired MRSA (CA-MRSA) appeared in Western Australia. The incidence of community-associated infections was thought to emerge due to the development of hypervirulent and/or highly transmissible MRSA strains. CA-MRSA is currently a global health problem and is epidemic in the U.S.

In 2004, MRSA was reported as the most frequent cause of infection that was presented to emergency departments in the US. In 2005, in Egypt, it was reported that the percentage of MRSA from *S. aureus* isolates was 63% (n=243). CA-MRSA is mostly transmitted via skin-to-skin contact. Predisposing risk factors to CA-MRSA infection include skin trauma, injection drug use, and poor personal hygiene. Risk groups for CA-MRSA infection include professional athletes (contact sports), military personnel, children, and incarcerated individuals. Disease severity ranges from minor skin and soft tissue infections to severe life threatening complications; including fatal sepsis, necrotizing fasciitis and pneumonia. CA-MRSA is treated using oral antimicrobial agents including cotrimoxazole, clinamycin, tetracyclines (doxycycline and minocycline), rifampicin and fusidic acid. It is important to note that no clinically approved vaccine for the prevention of *S. aureus* infections is available.

The DNA genome of *S. aureus* is 2.8-2.9 Mb in size; composed of core and accessory genes. Most of the core genes are associated with metabolism and other housekeeping functions. However, some core genes were found not be linked to growth/survival but instead associated with *S. aureus*-specific virulence genes. Accessory genome usually consists of mobile genetic elements (MGEs) including bacteriophages, pathogenicity islands, chromosomal cassettes, genomic islands, and transposons. These are mostly responsible for virulence, drug and metal resistance, substrate utilization and miscellaneous metabolism. *S. aureus* isolates also often carry one or more free or integrated plasmids. These plasmids carry genes responsible for resistance to antibiotics, heavy metals, or antiseptics. Two main differences exist between CA-MRSA and HA-MRSA. The first is the presence of SCCmec (mobile genetic elements) types IV & V in CA-MRSA while HA-MRSA mainly harbor SCCmec types I, II, and III. Panton-Valentine leukocidin (PVL) exotoxin is found in severe skin infections and necrotizing pneumonia associated with CA-MRSA.

Viruses

Hepatitis B Virus (HBV)

Hepatitis B virus (HBV) currently infects about two billion patients worldwide leading to 600,000 deaths yearly. Disease chronicity rates differ according to the age group, where it is ≤5% in generally healthy infected adults and 80-90% in perinatally infected children. About 350 million patients suffer from chronic HBV worldwide. In 15-40% of Chronic HBV patients, cirrhosis with or without HCC develops. HBV accounts for 30% of cirrhotic and 50% of HCC cases, worldwide. In Egypt, the cumulative seroprevalence of HBV infection was reported to be 1.3% as determined by measuring hepatitis B surface antigen (HBsAg) using ELISA.

HBV can be transmitted through perinatal (vertical transmission), percutaneous or sexual routes. In countries with high seroprevalence of HBV (more than 8%), the disease is mostly acquired during childhood through perinatal or horizontal transmission. In countries with an intermediate seroprevalence (2-7%), the disease may be acquired during childhood or even at a later age (through sexual transmission, drug abuse or unsafe health practices). In low prevalence countries (seroprevalence less than 2%), the disease is usually acquired through sexual transmission or drug abuse. The U.S. Food and Drug Administration (FDA) has approved six drugs for HBV treatment, namely interferon-alpha, PEGylated IFN-a, lamivudine (cytidine analog), adefovir dipivoxil (dATP analog that function as chain terminator), entecavir (20-deoxyguanosine analog), and telbivudine (dTTP analog).

The HBV viral genome is a 3.2 kb circular partially duplex DNA molecule with the circularity maintained by 5' cohesive ends. The negative DNA strand is responsible for mRNA transcription. The genome is composed of condensed coding regions having four overlapping open reading frames (ORFs). ORF P codes for a terminal protein on the minus strand as well as viral polymerase, ORF C codes for nucleocapsid structural protein as well as HBV e antigen (HBeAg), ORF S/pre-S codes for viral surface glycoproteins and ORF X codes for a transcriptional transactivator that is involved in HCC development. Mis-incorporations of nucleotides occur during viral replication due to lack of proofreading activity of DNA- and RNA-dependent DNA polymerase. This leads to the emergence of different HBV genotypes and subgenotypes. At least eight different genotypes (A-H) have been identified so far.

Human Immunodeficiency Virus (HIV)

Human immunodeficiency virus (HIV) is the causative agent of acquired immunodeficiency syndrome (AIDS) and infects more than 33.3 million individuals worldwide, with 2.6 million new infections in 2009. HIV is regarded as a global epidemic and strikes the resource-poor regions of sub-Saharan Africa. In 2009, about 1.8 million) lives were lost due to AIDS of which 72% were in sub-Saharan Africa.

HIV infection causes destruction of CD4 T cells, and as the virus continues to replicate, it continues to cause a state of immune activation which overwhelms the homeostasis of the patient's immune system. This gravely compromises the body's immunity, and AIDS typically develops within 8-10 years. In the course of infection, various opportunistic infections take over such as those caused by *M. tuberculosis, S. pneumonia*, esophageal Candidiasis, and cytomegalovirus. This can occur as early as within one month of infection. HIV is transmitted through contact with infected bodily fluid such as blood, semen, and breast milk, and the infection can spread via syringe sharing, blood transfusion, sexual intercourse, and from pregnant mothers to their babies. Interestingly, it is estimated that 20-80% of HIV-infected individuals are unaware of their infection and would go on about their life with no protective measures for controlling infection spread.

The HIV virus is a spherical lentivirus belonging to the retroviruses family and ranges in diameter between 100 and 120 nm. It is composed of a lipid bilayer envelope enclosing a nucleocapsid which contains the viral genome; two copies of a 9.2 kb single-stranded positive-sense RNA molecule. Other proteins, e.g., integrase, a viral protease, and reverse transcriptase are also enclosed within the nucleocapsid including those vital for virus replication. There are two HIV types; HIV-1 and HIV-2, but the geographical spread of HIV-2 is rather limited. There is no vaccine for HIV. Costly and complex highly active antiretroviral therapy (HAART) is the currently available treatment. Early diagnosis of AIDS is an important factor in determining HAART efficacy.

Influenza A (H1N1 and H5N1)

Influenza is an infectious disease that is caused by the influenza viruses; RNA viruses of family Orthomyxoviridae. Influenza viruses infect both birds and mammals. Influenza is an air born infection transmitted through droplets or by direct contact with birds or animal droppings. Through the past few years major pandemic outbreaks of two influenza A viruses caused the world millions of deaths and loss of billions of dollars. These influenza A viruses were the swine flu (H1N1) influenza A virus and the avian flu (H5N1) influenza A virus.

The 2009 (H1N1) influenza pandemic more commonly, albeit inaccurately, known as the swine flu pandemic, bore a heavy global economic and societal burden. The pandemic infected about 50 million people, claimed over 18,449 lives, and spread to more than 214 countries between April 2009 and August 2010.

The influenza A (H5N1) virus known as avian flu, is an epizootic disease that infects both man and birds. There have been several outbreaks caused by H5N1 influenza A virus through the past years in Asia, Europe, the Near East, and Africa. Incidence is not expected to decrease in the next years.

The symptoms of H1N1 and H5N1 infections are similar to the seasonal influenza, e.g., fever, cough, sore throat, and myalgia. However, children, young adults, and individuals with cardiac or pulmonary problems, as well as pregnant women are quite susceptible to complications including pneumonia, encephalopathy, and secondary bacterial infections, which were among the causes of fatalities.

Subtypes H1N1 (swine flu) or H5N1 (avian flu), each of which are causative agents for pandemic influenza, belongs to the Orthomyxoviridae family. The virus consists of a negative-sense single stranded RNA genome enclosed within a lipid envelope. The influenza A virus 13.5 kb genome consists of 8 segments encoding 11 viral proteins.

These proteins are: PA, PB1, and PB2 which are involved in the RNA-dependent RNA polymerase complex; nucleoprotein (NP); nonstructural proteins (NS1 and NEP), matrix proteins (M1 and M2), and the glycoproteins, hemagglutinin (HA) and neuraminidase (NA). HA and NA are the antigenic determinants upon which the subtypes of influenza A are classified. This airborne virus has a typical incubation period ranging from 1.5 to 3 days, but can reach up to 7 days, and spreads from human to human. It can be transmitted via exposure to aerosol droplets, e.g., through sneezing, or through contact with secretion containing the pathogen. The name "swine flu" is misleading, as the H1N1 virus that caused the 2009 pandemic is not the same as the one endemic in pigs, but is actually a new virus. The new virus was termed 2009 H1N1 influenza for clear discrimination. There was no evidence of pig to human transmission of the 2009 virus and the swift spread of the infection was due to human to human transmission. The avian flu (H5N1) is transmitted from birds to humans with little evidences of human to human transmission.

West Nile Virus (WNV)

WNV is a mosquito-transmitted virus, mainly by the species *Culex*, and infects different species including birds, horses, and humans. Humans and horses are considered dead-end hosts for the virus, but it is maintained in nature via bird-mosquito transmission. WNV cannot be transmitted between humans via casual contacts but can be through contaminated blood products, and vertically from mother to offspring intrauterinely or via breastfeeding. There is no vaccine currently available for humans against WNV. The virus was discovered in Uganda in 1937, but spread to United States and Canada in the late 1990s. Its epidemiology is variable, but is has subsequently become a considerable threat particularly in transfusion centers.

The incubation period of WNV ranges from 2 to 15 days and most infection—about 80% of cases—are asymptomatic. In symptomatic patients, the disease manifests usually as a mild self-limiting febrile condition, which can be associated with nausea, myalgia, headache, chills, and vomiting. However, about 5% of symptomatic patients develop neurological manifestations of the disease including encephalitis, meningitis, and acute flaccid paralysis. Individuals most susceptible to WNV infection and complications are those with compromised immunity such as those infected with human immunodeficiency virus, as well as older adults.

WNV belongs to the family Flaviviridae, the same family which encompasses hepatitis C virus, Japanese encephalitis viruses, and human immunodeficiency virus. It is a 50 nm enveloped positive strand RNA virus with a genome of about 11 kb. The genome is contained in an icosahedral nucleocapsid within a lipid envelope. The genome has a single open reading frame, flanked by untranslated regions on both terminals, and encodes a single polyprotein which is then cleaved by viral and cellular proteases to yield 10 proteins—3 structural proteins and 7 non-structural proteins.

Current Diagnostic Strategies

*Acinetobacter*

Current protocols for isolation and identification of *Acinetobacter* include the isolation on selective differential media (such as Herellea agar or Chromagar), biochemical testing and molecular approaches. Molecular diagnostic approaches are considered more reliable tests for genus and species identification than conventional methods. Detection of *Acinetobacter* resistant strains is achieved by agar diffusion methods and molecular assays. Agar diffusion methods involve the determination of the susceptibility pattern of the isolated strains by standard agar diffusion approach using sets of antibiotic discs representing different antibiotic classes. Advanced molecular methods such as PCR and Real-Time PCR are also used for detection of specific genes associated with *Acinetobacter* resistance.

*Mycobacterium tuberculosis*

The main strategies for TB diagnosis have not changed much for decades, and the primary detection methods of active infection rely on finding the TB bacilli in patient sputum smears, an approach that misses about 30-35% of positive cases and the detection rates are highly variable ranging from 20-80%. Detection rates below 20% are observed in HIV patients. Smear microscopy remains the primary identification tool especially in the developing countries. However, its accuracy depends on the bacterial load and the quality of the sputum specimen and the training of the laboratory technicians. Isolation and culturing of *Mycobacterium* on liquid or solid media is more sensitive method and allows for testing antibacterial sensitivity. However, culturing *Mycobacterium* requires biosafety facilities that are expensive to set up and maintain and require highly trained laboratory technicians. Some developing countries do not have a TB culturing facility at all, while in other countries TB culture is performed in national reference laboratories or in hospitals in large cities. Only few developing countries have the access to high quality sensitivity testing of first-line drugs and even fewer for testing second line drugs. Even when capacity exists TB diagnosis by culture still can take weeks because of the slow growth rate of mycobacteria. In most countries, TB culturing takes place in central laboratories. Therefore, clinical specimens often have to be sent to distant laboratories increasing processing time thus affecting the results.

Molecular detection lines based on PCR, Real-time PCR and microarray are used for the identification of *mycobacterium* and the detection of resistant strains Molecular methods might prove advantages regarding sensitivity and processing time, however performing these methods need highly equipped laboratories with highly trained staff. This will limit the benefits of the low income countries which represent the majority of HBCs which in turn will limit the impact of these new methods on the global TB control efforts.

The current facts regarding TB incidence and prevalence, together with socioeconomic status of the high burden countries, raise the need of developing new diagnostic tools. Optimum new diagnostic tools should be highly specific, highly sensitive, require low cost/low tech laboratory and minimal skilled labor, thus it can be widely used in low income countries and positively impact the global TB control efforts.

Nontuberculous Mycobacteria

Diagnosis of NTM requires clinical suspicion and exclusion of TB and lung malignancy in case of pulmonary manifestation as well chest radiograph. Laboratory tests available for diagnosis of NTM include culturing and smear microscopy, biochemical tests such as nitrate reduction, as well as molecular methods such as PCR and loop-mediated isothermal amplification (LAMP). Traditional culturing and phenotypic examination methods, albeit being cheap, are slow, tedious, and are of limited reproducibility and sensitivity. Additionally, *M. Leprae* cannot be cultured and the laboratory diagnosis of leprosy is based on histological examination of skin biopsies. PCR-based molecular assays are available gaining popularity due to their specificity and rapid turnaround time but their use is hindered by cost in developing countries.

Methicillin-Resistant *Staphylococcus Aureus* (MRSA)

Diagnostic assays for MRSA detection can be divided into culture-based methods as well as molecular assays. Culture-based methods can be further divided into conventional and rapid-culture based methods. Conventional culture-based methods depend on selective culturing in liquid and/or on solid media. These methods are time-consuming where the result is given to the patient after about 2-3 days, resulting in the development of severe complications as well as significant disease spread. Also it may give false-positive or false-negative results with sensitivity and specificity of 78-80% and 99%, respectively. More rapid culture-based methods utilizing chromogenic agars have been developed that produce results within 1.35-2.31 days. These culture agars incorporate a colorless chromogenic substrate that mimics a metabolic substrate. When the colorless chromogenic substrate is cleaved by a specific target bacterial enzyme, it becomes insoluble and colored. When the cleaved chromogen accumulates within the bacterial cell, the color builds up and the colony possessing the enzyme can be easily differentiated.

Currently available chromogenic media for MRSA diagnosis include ChromID (bioMérieux, Marcy l'Etoile, France), CHROMagar MRSA (CHROMagar Microbiology, France; BD Diagnostics, Belgium), MRSA Select (BioRad Laboratories, Belgium), Chromogenic MRSA/Denim Blue agar (Oxoid, Basingstoke, UK), MRSA Ident agar (Heipha Gmbh, Eppelheim, Germany), Chromogen oxacillin *S. aureus* medium (Axon Labs AG, Stuttgart, Germany), and Oxacillin resistance screening agar base (ORSAB, Oxoid). Although chromogenic media are about 2 to 13 times more expensive than conventional media, it spares a number of subcultures, additional tests/reagents and technologist's time that are needed to confirm diagnosis in case of conventional culture-based MRSA detection. Sensitivity and specificity differ according to the media used, ranging from 40-100% and 44-100%, respectively.

A culture-based assay for MRSA detection has been developed (Baclite Rapid MRSA test; 3M Healthcare, Berkshire, UK). This assay detects ciprofloxacin-resistant MRSA strains by the measurement of adenylate kinase (AK) activity using bioluminescence. The total assay time is 5 hrs with assay sensitivity and specificity of 90.4% and 95.7%, respectively. However, the material cost of the assay is $9.5-12/test, which is higher than conventional culture-based methods. Another drawback is that cases of either CA-MRSA or HA-MRSA that are not resistant to ciprofloxacin will be missed.

Molecular methods provide many advantages over culture methods including higher sensitivity (lower detection limits), higher-throughput screening and faster detection (as low as 75 min), thus reducing risk of disease spread and progression. Available PCR methods for MRSA include the IDI-MRSA (GenOhm, San Diego, Calif.; BD Diagnostics), GeneXpert MRSA assay (Cepheid, Sunnyvale, Calif.), the GenoType MRSA Direct (Hain Lifescience, Nehren, Germany), the Hyplex StaphyloResist® PCR (BAG, Lich, Germany) and Lightcycler *Staphylococcus* and MRSA detection kit (LC assay, Roche Diagnostics, Mannheim, Germany). Sensitivity of PCR was found to be superior to cultural methods where a sensitivity of 93% has been reported. Specificity reported for PCR was 96%. However, the major drawback in molecular methods is their cost. For example, IDI-MRSA is a FDA cleared kit for the direct detection of MRSA from nasal specimens with high sensitivity and specificity. However, it is significantly more expensive than culture-based detection methods ($36.70/test).

Thus novel molecular methods that are cost-effective are highly needed to allow for the inexpensive as well as rapid detection of MRSA allowing control over disease spread and progression. The developed gold nanoparticle (AuNP)-based assay benefits from the unique physical properties of the AuNPs allowing for the sensitive, rapid and inexpensive detection of such deadly bacteria. It is important to note that the assay of the present invention uses unmodified AuNPs which makes the assay much simpler compared to other published assays utilizing probe-modified AuNPs.

Hepatitis B Virus (HBV)

Many markers are available for HBV diagnosis. Alanine aminotransferases (ALT) are significantly elevated in case of HBV acute infection and declines when viremia is cleared. In case of inactive carriers, ALT levels decline and normalize. Regarding anti-HBV antibodies, after exposure, anti-HBc IgM infection rises then declines, while, anti-HBc IgG rises and persists even after resolving of acute infection. In case of inactive carriers, anti-HBc IgM levels decline and normalize. Other markers for HBV detection include HBV antigens. HBsAg is a marker used for confirmation of acute infection that can be detected using enzyme immunoassays (EIA) around 6 weeks after exposure. If HBsAg persists for more than 6 months, this indicates chronic infection. HBeAg is a marker that indicates active viral replication. Recently, there is interest in the development of immunoassays that quantify (not only determine presence) HBeAg and HBsAg levels in patient blood. These assays may be used for therapeutic monitoring.

The final marker for infection is HBV DNA that is detected using molecular diagnostic assays. The presence of HBV DNA is an indication of active replication and can be detected at less than 6 weeks after exposure. In case of inactive carrier state, HBV DNA levels drop to less than $10^5$ copies/mL.

Four main types of molecular assays have been developed for the diagnosis and management of HBV; namely quantitative viral load, genotyping, drug resistance mutation, and core promoter/precore mutation assays. Detection and quantitation of HBV DNA in plasma and serum has many advantages including; early detection of infection, allows for drug monitoring; helps assess disease activity in chronic patients, gold standard for the determination of HBV viral replication, confirms spontaneous remission or co-infection and finally detects occult infections (detectable HBV DNA in the absence of HBsAg). However, these tests are not well standardized, cut-off levels for inactive disease are still unclear and assays are relatively expensive.

Available viral load detection assays include signal amplification as well as target amplification assays. Signal amplification assays are less sensitive than target amplification assays, however, they are less prone to contamination. Examples of signal amplification assays include Digene Hybrid Capture assay (Digene Diagnostics; Corporation, Gaithersburg, Md.) and VERSANT HBV DNA 3.0 Assay (bDNA). Digene Hybrid Capture assay depends on the hybridization between HBV DNA and an RNA probe followed by their capture to an immobilized anti-RNA:DNA antibody. A chemiluminesence signal proportional to the HBV DNA level is then achieved by the addition of enzyme-linked antibodies. The quantification range is $1.4 \times 10^5$-$1.7 \times 10^9$ copies/mL. The second signal amplification method is bDNA (HBV DNA 3.0 Assay; Siemens Medical Solutions Diagnostics; Tarrytown, N.Y.). Signal amplification in this case depends on a series of sequential DNA hybridizations. The dynamic range of the assay is $2 \times 10^3$ to $1 \times 10^8$ copies/mL.

Regarding target amplification assays, one of the first commercial HBV DNA PCR assays developed was the AMPLICOR HBV MONITOR test (Roche Diagnostics; Basel, Switzerland). This was followed later by a semi-automated test known as COBAS AMPLICOR HBV MONITOR test (Roche Diagnostics; Basel, Switzerland). The lower and upper limits of detection were $2 \times 10^2$ and $2 \times 10^5$ copies/mL, respectively. Recently, Real-time PCR assays have been developed. These assays have a broader dynamic range, are less prone to contamination and are faster than conventional PCR assays.

Commercially available Real-time PCR assays include the COBAS TaqMan HBV test (Roche Molecular Diagnostics; Pleasonton, Calif.; quantitative range: $1.7 \times 10^2$ to $8.5 \times 10^8$ copies/ml), the Abbott Real-Time HBV assay (Abbott Laboratories; Abbott Park, Ill.; Taqman probe; quantitative range: 34 to $3.4 \times 10^9$ copies/ml), The Real Art kit for the Rotor-Gene m instrument (Corbett Research; Sydney, Australia; molecular beacons; quantitative range: $\sim 10^2$ to $6 \times 10^8$ copies/ml). Although Real-time PCR assays are highly sensitive, rapid and less prone to contamination, they are relatively expensive.

Many HBV genotyping assays have been developed including sequencing, INNO-LiPA, restriction fragment polymorphism (RFLP), multiplex PCR, oligonucleotide microarray chips, reverse dot blot, restriction fragment mass polymorphism (RFMP), invader assay, and Real-time PCR. Most of these assays are time consuming, expensive and/or require facilities and resources only available in a developed infrastructure.

Direct sequencing can identify known as well as new resistance mutations; this method can't detect mutants present in low concentrations. Thus hybridization-based methods have been developed and were found to be more sensitive (detect mutants present in low concentrations) and less labor intensive. However, they can't detect new mutations and require individual probes for each mutation to be detected. The second generation hybridization-based assay (INNO-LiPA DR, version 2.0) can detect mutations in reverse transcriptase enzyme at codons 80, 173, 180, and 204 (linked to lamivudine resistance) and at codons 181 and 236 (linked to adefovir resistance). The concordance with direct sequencing was ~95%. However, this assay is still expensive and results are sometimes non-conclusive (faint bands).

Assays that detect Core Promoter/Precore Mutations that are linked to antiviral resistance include Affigene HBV Mutant VL19 [Sangtec Molecular Diagnostics AB] (hybridization/direct sequencing) and INNO-LiPA HBV PreCore (PCR plus hybridization). The INNO-LiPA HBV PreCore assay detects three mutations; namely basal core promoter nucleotides (1762 and 1764) and precore codon 28. INNO-LiPA HBV PreCore assays has high concordance with direct sequencing (~90%) and is more efficient than direct sequencing in detecting mixed populations.

Novel molecular methods that are cost-effective are highly needed to allow for the inexpensive as well as rapid detection of active infection by detecting HBV DNA in serum. Also inexpensive and rapid assays are still needed for HBV genotyping and the detection of mutations linked to antiviral resistance. The developed AuNP-based assay benefits from the unique physical properties of AuNPs allowing for the sensitive, rapid and inexpensive detection of HBV DNA in serum, HBV genotyping and the detection of mutations linked to antiviral resistance. It is important to note that our assay uses unmodified AuNPs which makes the assay much simpler compared to other published assays utilizing probe-modified AuNPs.

Human Immunodeficiency Virus (HIV)

A variety of serological and molecular assays are employed for HIV detection in clinical specimens. The primary screening method for HIV diagnosis is the detection of its specific antibodies in patient serum or plasma using enzyme immunoassays (EIAs). HIV specific antibodies can be detected typically 3-6 weeks post-infection and within 12 weeks of infection it is detected in about 99% of cases. Another important serological test is the detection of HIV p24 antigen (viral capsid protein) whose levels begin to rise within the first 3 weeks of infection, making it an earlier marker than antibodies. Fourth-generation immunoassays allow its simultaneous detection with HIV antibodies. A positive serology result requires performance of a confirmatory test, the most common of which is the costly and time consuming Western blotting. Line immunoassays can also be used for confirmation. Rapid tests for antibody detection in saliva are also available and their sensitivity and specificity exceed 99% (OraQuick® Advance Rapid HIV-1/2). EIAs typically cost 0.5-1 USD per test, while rapid tests cost 1-3 USD.

Molecular testing has gained favor in HIV diagnosis on account of its sensitivity and significant reduction of window period. The utilization of molecular testing for donated blood screening in the US decreased the window period to 12-15 days. However, the main utility of molecular testing is viral load quantitation, and has special utility in determination of HIV status of infants born to infected mothers. This is due to the fact that maternal antibodies may be detected in infants for up to 15 months. The main limitation of molecular testing is being quite expensive and demanding in terms of equipment infrastructure and personnel training. Reverse transcription PCR is the basic molecular technology for HIV detection, but different technologies have been developed and commercialized including Real-time PCR and branched DNA detection.

Influenza A (H1N1 and H5N1)

Initially there was no diagnostic test with suitable clinical performance to detect the novel H1N1 virus, which may have allowed the virus to spread for possibly months in the population undetected, prior to the outbreak. In order to establish a diagnosis of H1N1 infection for a patient presenting with flu-like symptoms, a positive result by reverse transcription polymerase chain reaction (RT-PCR) or viral culture is required by the Centers for Disease Control (CDC). Both tests are costly, time-consuming, where PCR takes several hours while the gold standard; the viral culture requires 2-7 days. Viral culture is highly labor intensive and requires downstream characterization of the cultured virus by hemagglutination inhibition (HI) and NA inhibition tests, or PCR. It also falls short of the desired 100% sensitivity. The R-Mix viral culture (Diagnostic Hybrids, Athens, Ohio) has a sensitivity of 88.9% and a specificity of 100%, while RT-PCR (Luminex RVP; Luminex, Austin, Tex.) demonstrates sensitivity of 97.8% and a specificity of 100%. Both PCR and viral culture require highly equipped laboratories and trained personnel. Real-time RT-PCR is becoming a favored method for molecular diagnosis of 2009 H1N1 influenza, where the CDC has published a recommended protocol for Real-time RT-PCR that utilizes TaqMan® probes. Identification of 2009 H1N1 and its differentiation from seasonal influenza A requires the targeting of two genomic regions of the virus; the matrix gene (to determine it is influenza A) and different regions of the HA gene (to differentiate the 2009 H1N1 subtype).

Rapid influenza antigen detection assays are available and yield results within 30 minutes and are specific to 2009 H1N1 virus. These are mainly enzymatic activity optical assays or direct fluorescent antibody tests. However, their sensitivities are quite low and variable (10-70%) and cannot distinguish influenza A subtypes. This makes them unsuitable for excluding H1N1 infection in patients with influenza-like symptoms. The WHO recommended detection of influenza A H5N1 virus using reverse transcriptase (RT)-PCR employing specific primers for H5 gene (HA gene). However the RT-PCR is a time consuming and prone to cross contamination especially in high-throughput laboratories during outbreaks. Recently new methods based on reverse transcriptase loop-mediated isothermal amplification (RT-LAMP) has been reported.

West Nile Virus (WNV): Current Diagnostic Strategies

Challenges preventing effective detection of WNV include the very low levels of viremia in human blood and tissues at time of symptoms onset, and the potential cross reaction from other flaviviruses. The gold standard for WNV detection is Plaque Reduction Neutralization Test (PNRT), and serological tests are the primary methods used in clinical diagnosis of the infection. Detection of anti-WNV IgM using the IgM antibody-capture ELISA (MAC-ELISA) are recommended immunoassays along with indirect IgG ELISA. MAC-ELISA can allow detection of acute infection in human serum or CSF (sampling 8-45 days after infection), and there are 4 commercial ELISA kits IgM for WNV IgM detection approved by the FDA. More specific immunofluorescence assays were also developed for detection of anti-WNV IgM. The sensitivities of different ELISA based assays for anti-WNV IgG and IgM range from 90 to 95% while the specificities range from 96%-100%. An important issue is the fact that sera positive by MAC-ELISA require PNRT confirmation due to potential cross-reactivity with antibodies against other flaviviruses. Unfortunately, PNRT requires 6 days and biosafety level 3 facilities due to use of live viruses, which diminishes the advantages of rapidity and low cost gained by using ELISA. Nevertheless, detection of anti-WNV IgM in CSF is direct evidence of the infection. The turnaround around time of ELISA, albeit fast compared to PNRT, is still inconvenient, as it takes 2 days to yield results due to overnight incubation. The more complex epitope blocking ELISA is also sometimes used due to being species independent. Another issue with use of MAC-ELISAs is the fact that IgM can persist for in serum for about a year, which would prevent discrimination between early and late stage infections. Also, if the serum sampled too early neither specific IgM or IgG would have been generated against WNV, thus yielding false negative results. This would mean the need for the more complex and expensive nucleic acid testing for the virus.

Various molecular assays are available for detection of WNV RNA including conventional RT-PCR, real-time RT-PCR with different chemistries, loop-mediated isothermal amplification (LAMP), and nucleic acid sequence-based amplification (NASBA). For almost a decade real-time RT-PCR has been used for screening human samples for WNV, and there are currently two FDA-approved commercial assays; TaqScreen West Nile Virus Test (Roche Molecular Systems, Pleasanton, Calif., USA), and Procleix® West Nile Virus Assay (Gen-Probe Inc., San Diego, Calif./Chiron Corporation, Emeryville, Calif., USA). Real-time RT-PCR assays based on TaqMan chemistry can detect WNV down to 0.1 PFU of viral RNA. SYBR Green-based assays are also available but are less sensitive. A major issue with molecular tests, in addition to cost, is the fact the used primers and probes may fail to detect new strains with new mutations, and may detect just one of the two WNV lineages. This has warranted efforts for targeting regions conserved in both lineages. Despite the analytical advantages offered by molecular assays their cost and complexity are still a hindrance to their use in limited-resource settings. Also, the turnaround time and susceptibility to interference continue to loom over the more common immunological assays.

BRIEF DESCRIPTION OF THE INVENTION

The inventors have discovered that an unmodified gold nanoparticle-based (AuNP-based) colorimetric method can be used to directly detect unamplified or amplified microbial nucleic acids extracted from clinical specimens and have invented a simple, rapid, and sensitive colorimetric assay that can sensitively detect different pathogens in clinical samples even under field conditions. The invention provides a highly sensitive and specific way to detect unamplified target nucleic acids from samples containing nucleic acids from *Acinetobacter, Mycobacterium, Staphylococcus*, Hepatitis B Virus, Human Immunodeficiency Virus, Influenza virus, or West Nile Virus. The invention provides a way to avoid the cost, delay and risks of conventional method that require polynucleotide labeling and modification of gold nanoparticles. Thus, providing a simple, rapid and inexpensive way to detect these pathogens compared to conventional methods.

One embodiment of the invention is a method for detecting a nucleic acid of a microorganism selected from the group consisting of Acinetobacteria, mycobacteria, staphylococci, hepatitis B viruses, human immunodeficiency viruses, influenza viruses, and West Nile viruses comprising: contacting a sample suspected of containing the nucleic acids of one of these pathogens with an oligotargeter that binds specifically to nucleic acids from the pathogen and with gold nanoparticles, detecting the aggregation of nanoparticles, and detecting Acinetobacteria, mycobacteria, staphylococci, hepatitis B viruses, human immunodeficiency viruses, influenza viruses, or West Nile viruses in the sample when the nanoparticles aggregate in comparison with a control or a negative sample not containing the pathogen where the nanoparticles do not aggregate.

In this method a nucleic acid, a sample to be assayed for the presence Acinetobacteria, mycobacteria, staphylococci, hepatitis B viruses, human immunodeficiency viruses, influenza viruses, or West Nile viruses is obtained. The nature of the sample will vary depending on the organism or pathogen being tested for. Examples of biological samples include blood, plasma, serum, CSF, urine, sputum, and mucosal secretions. Other biological samples suspected of containing nucleic acids from the microorganism of interest may also be used.

Nucleic acids in the sample may be tested directed in the method or may be further isolated or purified from the sample. In some embodiments, the nucleic acids in the sample are amplified using methods such as the polymerase chain reaction (PCR).

The sample is then contacted with an oligotargeter sequence. The oligotargeter sequence is selected to be a complement of a nucleic acid sequence of Acinetobacteria, mycobacteria, staphylococci, hepatitis B viruses, human immunodeficiency viruses, influenza viruses, or West Nile viruses. An oligotargeter will be of a length sufficient to recognize and bind the target nucleic acid in a sample. Preferably, an oligotargeter will contain about 15 to 40 contiguous nucleotides that correspond to a genomic or non-genomic nucleic acid sequence of a target nucleic acid from one of the pathogens named above. All intermediate values within this range are contemplated as well as longer or shorter contiguous nucleotide sequences that function as oligotargeters within this method.

In some embodiments the oligotargeter may be modified to improve its stability or other functional properties. For example, the oligotargeter may be made from a modified nucleic acid that contains inosine, a modified base, or that has a chemically-modified phosphate backbone.

In other embodiments, the oligotargeter may be tagged. For example, its 5' end can be conjugated to a FAM dye, fluorescent dye, or fluorophore whose emission can be quenched by gold nanoparticles. In such an embodiment, the presence of the target nucleic acid from the pathogen is detected by the emission of fluorescence. FIG. 2 illustrates an embodiment that employs quenching.

The sample is contacted with a selected oligotargeter polynucleotide sequence under conditions that permit it to anneal to nucleic acids present in the tested sample. Double-stranded portions of nucleic acids in the sample are denatured or unfolded, generally by heating, to form single strands. Contact conditions are standardized or controlled to permit recognition and annealing between the oligotargeter sequence and a single-stranded portion of nucleic acid from the pathogen in the sample. Appropriate selections of salt concentration, buffer/pH selection, oligotargeter concentration, target concentration, and denaturation and annealing temperatures are made to enable recognition and annealing of the oligotargeter sequence to target nucleic acids in the sample. The conditions above are preferably selected to optimize the ability of the oligotargeter to bind to target nucleic acid in the sample. This annealing (hybridization) takes place before the addition or simultaneously in the presence of gold nanoparticles (AuNPs) under conditions which do not affect the stability and dispersity of the colloidal gold nanoparticles.

After sufficient time has passed to permit annealing (hybridization) between the target nucleic acids in the sample and the oligotargeter, gold nanoparticles are introduced. Unmodified colloidal gold nanoparticles that have not been conjugated to antibodies or other protein or carbohydrate ligands are generally employed in this step. Gold nanoparticles are spheroidal or spherical in shape and generally range in size from 2 nm to 80 nm. Subranges and intermediate values falling within this range are also contemplated for the gold nanoparticles used in the invention, including subranges of 2-12 nm, 12 to 20 nm, 20-40 nm, and 40-80 nm.

The concentration of gold nanoparticles is selected to permit interaction between the gold nanoparticles and free oligotargeter sequences that have not annealed to target nucleic acids may be used. Similarly, a buffer that permits the interaction of gold nanoparticles and free oligotargeters, such as a citrate buffer is used for this step. Preferably, the concentrations of ingredients for both the oligotargeter/target annealing step and the interaction of unbound or free oligotargeter with the gold nanoparticles are selected to optimize sensitivity and specificity of the detection of the target nucleic acid in a particular kind of sample.

After a sufficient time has passed for free oligotargeters and gold nanoparticles to interact, the color of the sample, oligotargeter and gold nanoparticle mixture is determined. Samples where the gold nanoparticles have not aggregated remain red, while samples where the gold nanoparticles have aggregated turn blue. When a threshold amount of free oligotargeters remains available to bind to the gold nanoparticles, they prevent gold nanoparticle aggregation by creating a repulsive electrostatic charge between the gold nanoparticles that prevents their aggregation. However, when this threshold amount of free oligotargeters is reduced by the annealing (hybridization) of the oligotargeters to complementary target nucleic acid in the sample, then there are insufficient free oligotargeters present to prevent aggregation of the gold nanoparticles. Thus, a blue color indicates the presence of the target nucleic acid sequence that is complementary to the oligotargeter sequence and has bound to it, thus preventing the oligotargeter from effective binding to the nanoparticles and inhibiting their aggregation. A colorimetric determination may be made visually (by eye) or by qualitative or quantitative mechanical or electronic means. Positive or negative control samples may be used to help make a colorimetric determination. FIG. 1 generally illustrates one embodiment of this method.

As an optional preliminary step, any nucleic acids present in a fresh or stored sample may be extracted, enriched, or concentrated by a conventional chemical or biochemical method, for example, by using a commercial nucleic acid purification kit. A sample may be diluted, serially diluted or titrated prior to its use in this method. Thus, a target nucleic acid from *Acinetobacter*, mycobacteria, *staphylococcus*, hepatitis B virus, human immunodeficiency virus, influenza virus, or West Nile Virus can be purified or isolated from other components of a biological sample prior to its contact with the oligotargeter and gold nanoparticles.

In some embodiments of this method, no amplification will be performed on any nucleic acids in the test sample. In other embodiments, nucleic acids in a sample may be amplified using PCR and selected primers, such as primers that amplify a particular polynucleotide sequence or gene of interest in the pathogen.

A specific embodiment of the invention is a method for detecting the presence of *Acinetobacter* in a sample, for example, detecting *Acinetobacter baumannii*. Exemplary biological samples that may be collected for this embodiment include those from the skin, oral cavity or respiratory tract of a subject.

Oligotargeters that selectively detect *Acinetobacter* are described by SEQ ID NOS: 23-66 (16s region), 71-82 (ITS region), 105-126 (23s region), 131-132 (5s region), and 151-169 (ISAba1-OXA-23).

For embodiments of this method that amplify an Acinetobacteria target nucleic acid, a sense primer selected the group consisting of SEQ ID NOS: 1-11 (16s region), 67-68 (ITS region), 83-93 (23 s region), 127-128 (5s region), and 133-141 (ISAba1-OXA-23) and an antisense primer selected from the group consisting of SEQ ID NOS: 12-22 (16s region), 69-70 (ITS region), 94-104 (23s region), 129-130 (5s region), and 142-150 (ISAba1-OXA-23) can be used to amplify nucleic acids in the sample which can then be identified using an AuNP-based method using an oligotargeter that binds to the amplified nucleic acid, such as those described by SEQ ID NOS: 23-66 (16s region), 71-82 (ITS region), 105-126 (23s region), 131-132 (5s region), and 151-169 (ISAba1-OXA-23).

A mycobacteria oligotargeter may be selected to bind to a conserved mycobacterial nucleic acid sequence found in at least two of *M. tuberculosis, M. africanum, M. bovis, M. canetti* and *M. microti*. Alternatively, mycobacteria oligotargeters may selectively bind target nucleic acids in *M. tuberculosis* but not in *M. africanum, M. bovis, M. canetti* and *M. microti*; may selectively bind to target nucleic acids in *M. leprae, M. marinum,* or other tuberculous mycobacteria, but not in *M. tuberculosis, M. africanum, M. bovis, M.*

*canetti* and *M. microti*; or may selectively bind target nucleic acids of *M. avium, M. kansasii*, or another non-tuberculous *mycobacterium*, but not to nucleic acids of *M. tuberculosis, M. africanum, M. bovis, M. canetti* and *M. microti*.

A mycobacteria oligotargeter may be taken from a conserved region of the mycobacterial genomic sequences 16S (two regions), ITS region, IS6110 or the X-Conserved region.

Oligotargeters that selectively detect mycobacteria are described by SEQ ID NOS: 192-208 (16s region) and 215-225 (ITS region).

For embodiments of this method that amplify a target nucleic acid from mycobacteria, a sense primer selected the group consisting of SEQ ID NOS: 170-178 (16s region) and 209-210 (ITS region) and an antisense primer selected from the group consisting of SEQ ID NOS: 179-191 (16s region) and 211-214 (ITS region) can be used to amplify nucleic acids in the sample which can then be identified by an AuNP-based methods using at least one oligotargeter that binds to the amplified nucleic acid, such as those described by SEQ ID NOS: 192-208 (16s region) and 215-225 (ITS region).

A specific embodiment of the invention is a method for detecting the presence of Methicillin-Resistant *Staphylococcus Aureus* (MRSA) in a sample. Exemplary biological samples that may be collected for this embodiment include those from the anterior nares, throat, urinary tract, perineum, rectum, wounds, or sputum; or is obtained from a medical device.

Oligotargeters that selectively detect Methicillin Resistant *Staphylococcus Aureus* (MRSA) are described by SEQ ID NOS: 252-259 (16s region), 282-291 (23s region), 296-302 (ITS region), 319-332 (mecA), 345-352 (femA), 373-381 (gyrA), and 392-397 (spa).

For embodiments of this method that amplify a target nucleic acid from Methicillin-Resistant *Staphylococcus Aureus* (MRSA), a sense primer selected the group consisting of SEQ ID NOS: 238-244 (16s region), 260-270 (23s region), 292-293 (ITS region), 303-310 (mecA), 333-338 (femA), 353-362 (gyrA), and 382-386 (spa) and an antisense primer selected from the group consisting of SEQ ID NOS: 245-251 (16s region), 271-281 (23s region), 294 (ITS region), 311-318 (mecA), 339-344 (femA), 363-372 (gyrA), and 387-391 (spa) may be used to amplify nucleic acids in the sample which can then be detected by an AuNP-based method using at least one oligotargeter that recognizes the amplified nucleic acids.

A specific embodiment of the invention is a method for detecting the presence of HBV in a sample. Exemplary biological samples that may be collected for this embodiment include those from the blood, plasma or serum.

Oligotargeters that selectively detect HBV are described by SEQ ID NOS: 414 (target 1411-1880), 415-420 (CDC Polymerase [P]), 421-423 (HbsAg), 424-428 (RNA pre-alpha region), 429-430 (DNA enhancer 2), and 431-432 (CDS CO peptide).

For embodiments of this method that amplify a target nucleic acid from HBV, a sense primer selected the group consisting of SEQ ID NOS: 398 (target 1411-1880), 400 (HbsAg), 402 (RNA pre-alpha region), 404 (RNA pre-beta region), 406 (RNA epsilon element), 408 (CDS CO peptide), 410 (HbcAg) and 412 (CDC Polymerase [P]) and an antisense primer selected from the group consisting of SEQ ID NOS: 399 (target 1411-1880), 401 (HbsAg), 403 (RNA pre-alpha region), 405 (RNA pre-beta region), 407 (RNA epsilon element), and 409 (CDS CO peptide), 411 (HbcAg) and 413 (CDC Polymerase [P]) may be used to amplify nucleic acids in the sample which can then be detected by an AuNP-based method using at least one oligotargeter that recognizes the nucleic acid amplified by the sense and antisense primers, such as one selected from the group consisting of SEQ ID NOS: 414 (target 1411-1880), 415-420 (CDC Polymerase [P]), 421-423 (HbsAg), 424-428 (RNA pre-alpha region), 429-430 (DNA enhancer 2), and 431-432 (CDS CO peptide).

A specific embodiment of the invention is a method for detecting the presence of HIV-1 or HIV-2 in a sample. Exemplary biological samples that may be collected for this embodiment include those from the blood, plasma or serum.

Oligotargeters that selectively detect HIV-1 are described by SEQ ID NOS: 437-442 (gag) and those that identify HIV-2 by SEQ ID NOS: 447-454 (gag-pol).

For embodiments of this method that amplify a target nucleic acid from HIV-1 a sense primer selected the group consisting of SEQ ID NOS: 433 and 435 (gag) and an antisense primer selected from the group consisting of SEQ ID NOS: 434 and 436 (gag) may be used to amplify nucleic acid in the sample which may then be identified by an AuNP-based method using at least one oligotargeter that binds to the amplified nucleic acid, such as one described by SEQ ID NOS: 437-442 (gag).

For embodiments of this method that amplify a target nucleic acid from HIV-2 a sense primer selected the group consisting of SEQ ID NOS: 443 and 445 (gag-pol); and an antisense primer selected from the group consisting of SEQ ID NOS: 444 and 446 (gag-pol) may be used to amplify nucleic acid in the sample which may then be identified using an AuNP-based method using at least one oligotargeter that binds to the amplified nucleic acid, such as one selected from the group consisting of SEQ ID NOS: 447-454 (gag-pol).

A specific embodiment of the invention is a method for detecting the presence of Influenza in a sample, such as Influenza A (H1N1 & H5N1). Exemplary biological samples that may be collected for this embodiment include those from the respiratory tract.

Oligotargeters that selectively detect Influenza are described by SEQ ID NOS: 469-482 (HA gene), 493-506 (NA gene) and 513-524 (M1 gene).

For embodiments of this method that amplify a target nucleic acid from Influenza, a sense primer selected the group consisting of SEQ ID NOS: 455-461 (HA gene), 483-487 (NA gene) and 507-509 (M1 gene); and an antisense primer selected from the group consisting of SEQ ID NOS: 462-468 (HA gene), 488-492 (NA gene) and 510-512 (M1 gene) may be used to amplify nucleic acid in the sample. The amplified nucleic acid may be identified by an AuNP-based method using at least one oligotargeter that binds to the amplified nucleic acid, such as those described by SEQ ID NOS: 469-482 (HA gene), 493-506 (NA gene) and 513-524 (M1 gene).

A specific embodiment of the invention is a method for detecting the presence of West Nile Virus in a sample. Exemplary biological samples that may be collected for this embodiment include those from the blood, plasma, serum, or CSF. Oligotargeters that selectively detect West Nile virus are described by SEQ ID NOS: 539 (4603-5131 target), 550 (5'UTR), 551-553 (Mat_Peptide_2), 554-555 (Mat_Peptide_1), 556-557 (Mat_Peptide_3), 558-563 ((Mat_Peptide_5), 564-569 (Mat_Peptide_6), 570-571 (Mat_Peptide_7), 572-573 (Mat_Peptide_8), 574-581 (Mat_Peptide_9), 582-583 (Mat_Peptide_10), 584-587 (Mat_Peptide_12), 588-596 (Mat_Peptide_13) and 597-601 (3'UTR).

For embodiments of this method that amplify a target nucleic acid from West Nile virus using at least a pair of sense and antisense primers selected the group consisting of SEQ ID NOS: 525 (4603-5131 target), 527 (5'UTR), 529 (Mat_Peptide), 531 (Mat_Peptide), 533 (Mat_Peptide), 535 (Mat_Peptide), 537 (Mat_Peptide), 539 (Mat_Peptide), 541 (Mat_Peptide_9), 543 (Mat_Peptide_10), 545 (Mat_Peptide_12), and 547 (3'UTR) and an antisense primer selected from the group consisting of SEQ ID NOS: 526 (4603-5131 target), 528 (5'UTR), 530 (Mat_Peptide), 532 (Mat_Peptide), 534 (Mat_Peptide), 535 (Mat_Peptide), 536 (Mat_Peptide), 540 (Mat_Peptide_8), 542 (Mat_Peptide_9), 544 (Mat_Peptide_10), 546 (Mat_Peptide_12), and 548 (3'UTR), may be used to amplify nucleic acid in the sample which can then be detected by an AuNP-based method using at least one oligotargeter that binds to the nucleic acid amplified by the sense and antisense primers, such as those described by SEQ ID NOS: 539 (4603-5131 target), 550 (5'UTR), 551-553 (Mat_Peptide_2), 554-555 (Mat_Peptide_1), 556-557 (Mat_Peptide_3), 558-563 ((Mat_Peptide_5), 564-569 (Mat_Peptide_6), 570-571 (Mat_Peptide_7), 572-573 (Mat_Peptide_8), 574-581 (Mat_Peptide_9), 582-583 (Mat_Peptide_10), 584-587 (Mat_Peptide_12), 588-596 (Mat_Peptide_13) and 597-601 (3'UTR).

For the specific embodiments above, samples can be isolated or obtained from various kinds of patients or subjects. For example, they may be obtained from a subject under treatment for an infection or exposure to said microorganism; a sample may represent one or more longitudinal acquired samples from a subject undergoing treatment for an infection or exposure to said microorganism; or a sample can be obtained from a subject suspected of having an asymptomatic or latent infection by the microorganism.

The detection methods as disclosed herein may be practiced in a manner that helps determine the general or specific identity of one of the pathogens, such as its genus, species, sub-species, serotype, subtype, or strain. This may be accomplished by the selection of an oligotargeter or, for embodiments using amplification, a combination of primers and oligotargeters, that identifies unique genetic features of particular subtype of a pathogen or that identifies one or more single nucleotide polymorphisms in an amplified or unamplified nucleic acid of the microorganism. Similarly, one may determine the pathogenicity or drug resistance of a particular subtype or strain microorganism by contacting the sample with an oligotargeter that binds to a polynucleotide sequence of the microorganism that is associated with its pathogenicity or drug-resistance.

Another aspect of the invention pertains to kits for detecting *Acinetobacter*, mycobacteria, *staphylococcus*, hepatitis B virus, human immunodeficiency virus, influenza virus, or West Nile Virus. These embodiments include the following:

A kit for detecting Acinetobacteria comprising:

gold nanoparticles, at least one oligotargeter that binds to nucleic acid of an *Acinetobacterium*, and optionally, at least one: biological sample preservative or additive, buffer for extracting Acinetobacteria nucleic acid, modified silica nanoparticles, column or other device for purifying Acinetobacteria nucleic acids, reaction buffer, negative control sample, positive control sample, Acinetobacteria primer, Acinetobacteria probe, container, a colorimetric chart, packaging material, or instruction for use in detecting Acinetobacteria.

A kit that comprises at least one Acinetobacteria oligotargeter selected from the group consisting of SEQ ID NOS: 23-66 (16s region), 71-82 (ITS region), 105-126 (23s region), 131-132 (5s region), and 151-169 (ISAba1-OXA-23).

A kit that comprises a sense primer selected the group consisting of SEQ ID NOS: 1-11 (16s region), 67-68 (ITS region), 83-93 (23 s region), 127-128 (5s region), and 133-141 (ISAba1-OXA-23); an antisense primer selected from the group consisting of SEQ ID NOS: 12-22 (16s region), 69-70 (ITS region), 94-104 (23s region), 129-130 (5s region), and 142-150 (ISAba1-OXA-23); and at least one oligotargeter that binds to the nucleic acids amplified by the sense and antisense primers; this oligotargeter may be selected from the group consisting of SEQ ID NOS: 23-66 (16s region), 71-82 (ITS region), 105-126 (23s region), 131-132 (5s region), and 151-169 (ISAba1-OXA-23).

A kit for detecting mycobacteria comprising:

gold nanoparticles, at least one oligotargeter that binds to nucleic acid of a *mycobacterium*, and optionally, at least one: biological sample preservative or additive, buffer for extracting mycobacteria nucleic acid, modified silica nanoparticles, column or other device for purifying mycobacteria nucleic acids, reaction buffer, negative control sample, positive control sample, mycobacteria primer, mycobacteria probe, container, a colorimetric chart, packaging material, or instruction for use in detecting mycobacteria. A kit that comprises a mycobacteria oligotargeter selected from the group consisting of SEQ ID NOS: 192-208 (16s region) and 215-225 (ITS region).

A kit that comprises a sense primer for mycobacteria selected from the group consisting of SEQ ID NOS: 170-178 (16s region) and 209-210 (ITS region); an antisense primer for mycobacteria selected from the group consisting of SEQ ID NOS: 179-191 (16s region) and 211-214 (ITS region); and at least one oligotargeter that binds to the amplified nucleic acid which may be selected from the group consisting of SEQ ID NOS:192-208 (16s region) and 215-225 (ITS region).

A kit for detecting *staphylococcus* comprising:

gold nanoparticles, at least one oligotargeter that binds to nucleic acid of a *staphylococcus*, such as MRSA, and optionally, at least one: biological sample preservative or additive, buffer for extracting *staphylococcus* nucleic acid, modified silica nanoparticles, column or other device for purifying *staphylococcus* nucleic acids, reaction buffer, negative control sample, positive control sample, *staphylococcus* primer, *staphylococcus* probe, container, a colorimetric chart, packaging material, or instruction for use in detecting *staphylococcus*. A kit that comprises an *staphylococcus* oligotargeter selected from the group consisting of SEQ ID NOS: 252-259 (16s region), 282-291 (23s region), 296-302 (ITS region), 319-332 (mecA), 345-352 (femA), 373-381 (gyrA), and 392-397 (spa).

A kit that comprises a sense primer selected the group consisting of SEQ ID NOS: 238-244 (16s region), 260-270 (23s region), 292-293 (ITS region), 303-310 (mecA), 333-338 (femA), 353-362 (gyrA), and 382-386 (spa); an antisense primer selected from the group consisting of SEQ ID NOS: 245-251 (16s region), 271-281 (23s region), 294 (ITS region), 311-318 (mecA), 339-344 (femA), 363-372 (gyrA), and 387-391 (spa); and at least one oligotargeter that binds to the nucleic acids amplified by the sense and anti sense primers. This oligotargeter may be selected from the group consisting of SEQ ID NOS: 252-259 (16s region), 282-291 (23s region), 296-302 (ITS region), 319-332 (mecA), 345-352 (femA), 373-381 (gyrA), and 392-397 (spa).

A kit for detecting HBV (Hepatitis V virus) comprising:
gold nanoparticles,
at least one oligotargeter that binds to nucleic acid of HBV, and optionally,
at least one: biological sample preservative or additive, buffer for extracting HBV nucleic acid, modified silica nanoparticles, column or other device for purifying HBV nucleic acids, reaction buffer, negative control sample, positive control sample, HBV primer, HBV probe, container, a colorimetric chart, packaging material, or instruction for use in detecting HBV.

A kit that comprises at least one HBV oligotargeter selected from the group consisting of SEQ ID NOS: 414 (target 1411-1880), 415-420 (CDC Polymerase [P]), 421-423 (HbsAg), 424-428 (RNA pre-alpha region), 429-430 (DNA enhancer 2), and 431-432 (CDS CO peptide).

A kit that comprises a sense primer selected the group consisting of SEQ ID NOS: 398 (target 1411-1880), 400 (HbsAg), 402 (RNA pre-alpha region), 404 (RNA pre-beta region), 406 (RNA epsilon element), 408 (CDS CO peptide), 410 (HbcAg) and 412 (CDC Polymerase [P]); an antisense primer selected from the group consisting of SEQ ID NOS: 399 (target 1411-1880), 401 (HbsAg), 403 (RNA pre-alpha region), 405 (RNA pre-beta region), 407 (RNA epsilon element), and 409 (CDS CO peptide), 411 (HbcAg) and 413 (CDC Polymerase [P]); and at least one HBV oligotargeter that binds to the amplified nucleic acid. This oligotargeter may be selected from the group consisting of SEQ ID NOS: 414 (target 1411-1880), 415-420 (CDC Polymerase [P]), 421-423 (HbsAg), 424-428 (RNA pre-alpha region), 429-430 (DNA enhancer 2), and 431-432 (CDS CO peptide).

A kit for detecting HIV (Human Immunodeficiency virus) comprising:
gold nanoparticles,
at least one oligotargeter that binds to nucleic acid of HIV, and optionally,
at least one: biological sample preservative or additive, buffer for extracting HIV nucleic acid, modified silica nanoparticles, column or other device for purifying HIV nucleic acids, reaction buffer, negative control sample, positive control sample, HIV primer, HIV probe, container, a colorimetric chart, packaging material, or instruction for use in detecting HIV.

A kit that comprises at least one HIV-1 oligotargeter selected from the group consisting of SEQ ID NOS: 437-442 (gag).

A kit that comprises at least one HIV-2 oligotargeter selected from the group consisting of SEQ ID NOS: 447-454 (gag-pol).

A kit that comprises a sense primer for HIV-1 selected the group consisting of SEQ ID NOS: 433 and 435 (gag); an antisense primer for HIV-1 selected from the group consisting of SEQ ID NOS: 434 and 436 (gag); and at least one HIV-1 oligotargeter that binds to the amplified nucleic acid. This oligotargeter may be selected from the group consisting of SEQ ID NOS: 437-442 (gag).

A kit that comprises a sense primer for HIV-2 selected the group consisting of SEQ ID NOS: 443 and 445 (gag-pol); an antisense primer for HIV-2 selected from the group consisting of SEQ ID NOS: 444 and 446; and at least one HIV-2 oligotargeter that binds to nucleic acid amplified by the sense and antisense primers. This HIV-2 oligotargeter may be selected from the group consisting of SEQ ID NOS: 447-454 (gag-pol).

A kit for detecting Influenza virus, such as Influenza A (H1N1) comprising:
gold nanoparticles,
at least one oligotargeter that binds to nucleic acid of Influenza virus, and optionally, at least one: biological sample preservative or additive, buffer for extracting Influenza virus nucleic acid, modified silica nanoparticles, column or other device for purifying Influenza virus nucleic acids, reaction buffer, negative control sample, positive control sample, Influenza virus primer, Influenza virus probe, container, a colorimetric chart, packaging material, or instruction for use in detecting Influenza virus.

A kit that comprises at least one Influenza virus oligotargeter selected from the group consisting of SEQ ID NOS: 469-482 (HA gene), 493-506 (NA gene) and 513-524 (M1 gene).

A kit that comprises a sense primer selected the group consisting of SEQ ID NOS: 455-461 (HA gene), 483-487 (NA gene) and 507-509 (M1 gene); an antisense primer selected from the group consisting of SEQ ID NOS: 462-468 (HA gene), 488-492 (NA gene) and 510-512 (M1 gene), and at least one Influenza virus oligotargeter that binds to the nucleic acid amplified by the sense and antisense primers, such as one selected from the group consisting of SEQ ID NOS: 469-482 (HA gene), 493-506 (NA gene) and 513-524 (M1 gene).

A kit for detecting West Nile virus comprising:
gold nanoparticles,
at least one oligotargeter that binds to nucleic acid of West Nile virus, and optionally, at least one: biological sample preservative or additive, buffer for extracting West Nile virus nucleic acid, modified silica nanoparticles, column or other device for purifying West Nile virus nucleic acids, reaction buffer, negative control sample, positive control sample, West Nile virus primer, West Nile virus probe, container, a colorimetric chart, packaging material, or instruction for use in detecting West Nile virus.

A kit that comprises a West Nile virus oligotargeter selected from the group consisting of SEQ ID NOS: 539 (4603-5131 target), 550 (5'UTR), 551-553 (Mat_Peptide_2), 554-555 (Mat_Peptide_1), 556-557 (Mat_Peptide_3), 558-563 ((Mat_Peptide_5), 564-569 (Mat_Peptide_6), 570-571 (Mat_Peptide_7), 572-573 (Mat_Peptide_8), 574-581 (Mat_Peptide_9), 582-583 (Mat_Peptide_10), 584-587 (Mat_Peptide_12), 588-596 (Mat_Peptide_13) and 597-601 (3'UTR).

A kit that comprises a sense primer for West Nile virus selected from the group consisting of SEQ ID NOS: 525 (4603-5131 target), 527 (5'UTR), 529 (Mat_Peptide), 531 (Mat_Peptide), 533 (Mat_Peptide), 535 (Mat_Peptide), 537 (Mat_Peptide), 539 (Mat_Peptide), 541 (Mat_Peptide_9), 543 (Mat_Peptide_10), 545 (Mat_Peptide_12), and 547 (3'UTR); and an antisense primer selected from the group consisting of SEQ ID NOS: 526 (4603-5131 target), 528 (5'UTR), 530 (Mat_Peptide), 532 (Mat_Peptide), 534 (Mat_Peptide), 535 (Mat_Peptide), 536 (Mat_Peptide), 540 (Mat_Peptide_8), 542 (Mat_Peptide_9), 544 (Mat_Peptide_10), 546 (Mat_Peptide_12), and 548 (3'UTR); and one or more West Nile virus oligotargeters that bind to the nucleic acid amplified by the sense and antisense primers, such as one selected from the group consisting of SEQ ID NOS: 539 (4603-5131 target), 550 (5'UTR), 551-553 (Mat_Peptide_2), 554-555 (Mat_Peptide_1), 556-557 (Mat_Peptide_3), 558-563 ((Mat_Peptide_5), 564-569 (Mat_Peptide_6), 570-571 (Mat_Peptide_7), 572-573 (Mat_Peptide_8), 574-581 (Mat_Peptide_9), 582-583 (Mat_

Peptide_10), 584-587 (Mat_Peptide_12), 588-596 (Mat_Peptide_13) and 597-601 (3'UTR).

BRIEF DESCRIPTION OF THE DRAWINGS

FIG. 6. Colorimetric detection of RNA or DNA using unmodified AuNPs. Each tube contains extracted RNA or DNA, 1 µM oligotargeter and 0.08 M NaCl. The samples are denatured at 95° C. for 30 s and annealed at 59° C. for 30 s and then 10 µL of 15 nm AuNPs was added after cooling the mixture at room temperature for 10 min. The photographs were taken after 1 min from the addition of the AuNPs. (a) Negative samples containing target RNA or DNA and (b) positive samples. Note the change in color from red to blue in the positive samples.

FIG. 9. Example of oligotargeter alignment for WNV Oligotargeter.

FIG. 10. Genes, PCR primers and amplicon lengths for PCR amplification of *Acinetobacter baumannii* sequences.

FIG. 11. Genes, PCR primers and amplicon lengths for PCR amplification of ITS regions.

FIG. 12. Oligotargeter sequences, Blast hits and alignment identity for *Acinetobacter* species.

FIG. 13. Isolate identifications.

FIGS. 17A and 17B. AuNP assay results.

FIG. 18 shows genes, PCR primers, Tm and amplicon lengths for *mycobacterium*.

FIG. 19 shows Oligotargeter sequences, Blast hits and Alignment identity for mycobacteria species.

FIG. 24. Evaluation of assay detection limits.

FIG. 25. Conditions for detection of Mycobacteria tuberculosis DNA.

FIG. 26. Nested PCR for detection of Mycobacteria tuberculosis DNA.

FIG. 27. Results for detection of M. t. DNA from Example 2C.

DETAILED DESCRIPTION OF THE INVENTION

Figure 1:
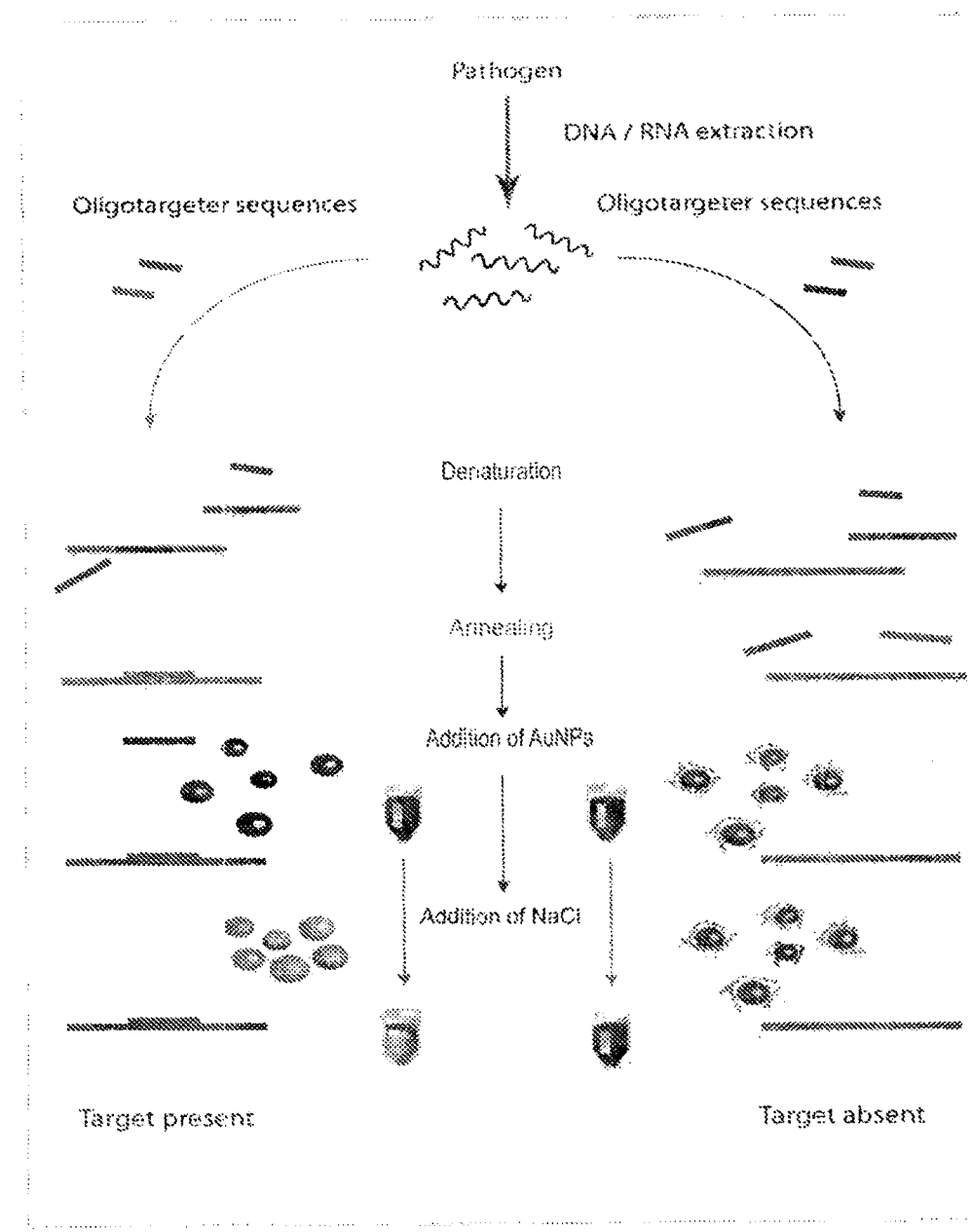
FIG. 1. Principle of AuNPs-based assay for detection of unamplified pathogenic nucleic acid. In case of positive specimens, the target nucleic acid is present and hybridizes to the oligotargeter, making it unavailable to stabilize the AuNPs. They thus aggregate and the color shifts to blue. On the contrary, in negative samples, the target is absent and the oligotargeter stabilizes the AuNPs and the color remains red.
Figure 2:
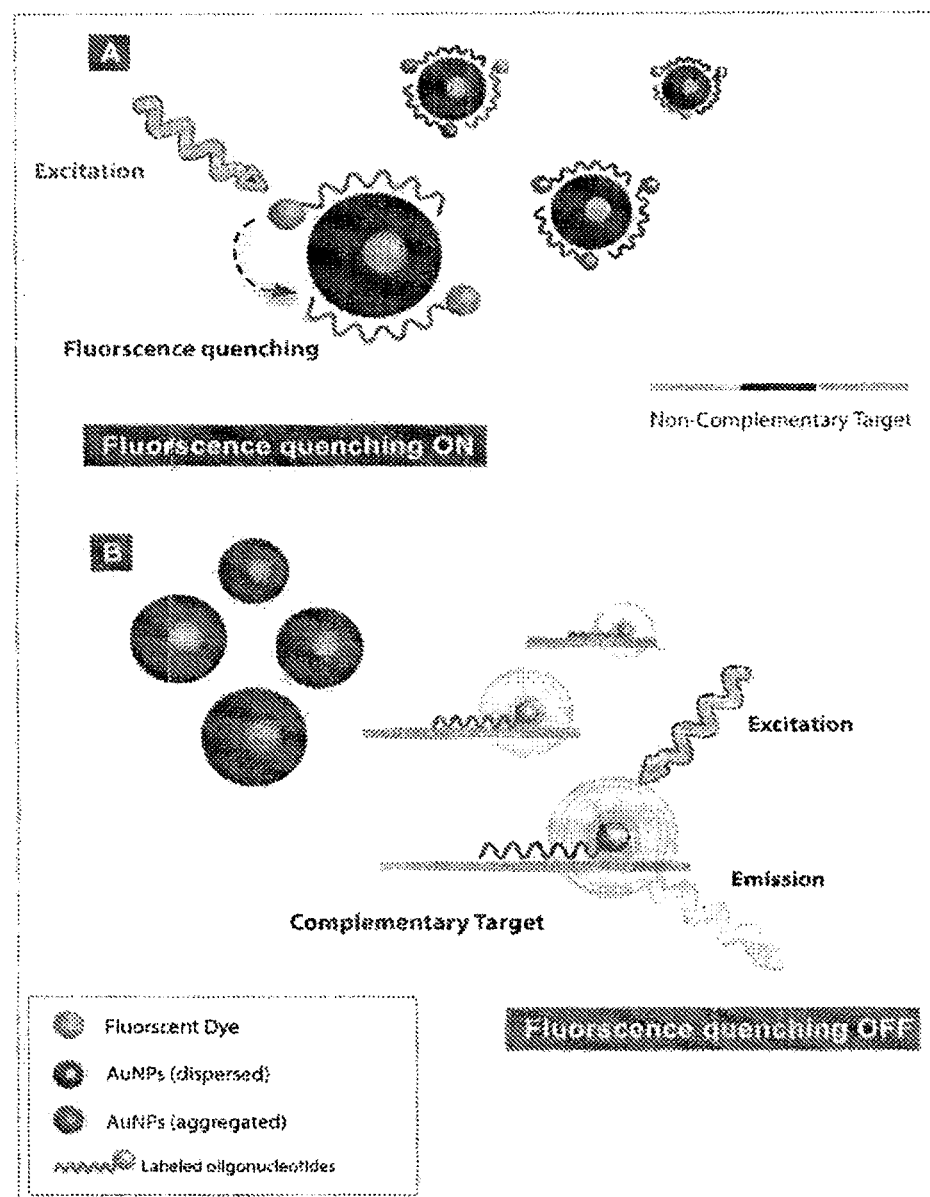
FIG. 2. Principle of nucleic acid detection assay based on fluorescence quenching by unmodified AuNPs. A) In absence of complementary target sequence, the fluorescent dye-labeled oligonucleotides remain adsorbed onto the AuNPs and the fluorescence is quenched, and the AuNPs remain dispersed (red). B) Upon hybridization with the complementary target, the labeled oligonucleotide move away from the AuNPs, thereby restoring the dye's fluorescence and allowing aggregation of AuNPs (blue).

A colorimetric assay has been developed using unmodified AuNPs for the direct detection of unamplified DNA or RNA in biological fluids containing different kinds of microbes. In some embodiments the DNA or RNA may be amplified and it others it is not necessary. The assay has a detection limit of 0.6-0.8 ng (0.0028-0.00373 pM/uL) in samples including sputum, pleural fluid, blood, cerebrospinal fluid, tissue biopsy samples, feces, bacterial isolates, and pus from a wound. The highly sensitive assay of the invention can be applied for tracking microbial titers. Method sensitivity can be controlled by changing buffers and or the kind or concentration of oligotargeter as well as the concentration of gold nanoparticles. The lower the concentration of the probes used the higher the sensitivity. It is logical that using oligotargeters to target repeats should increase the sensitivity but might affect the specificity on strain level. However, oligotargeters have been identified that target a repeat region in microbes that, according to BLAST similarity check, would be highly specific only to particular microbes.

The invention has several other advantages in addition to its high sensitivity including excellent specificity, short turnaround time, and cost effectiveness. The assay is economical, for example, 1 gram of gold is sufficient to prepare 1 liter of 15 nm gold nanoparticles and only about 10 µL of gold nanoparticles are required per assay. Thus, based on a cost of 1 gram of gold chloride of about 200 euros, the assay is highly cost effective. While the cost of DNA or RNA extract kits used to extract microbial nucleic acid from clinical samples may vary, this cost generally ranges between 100-200 euros for 50 extractions and thus the overall cost of this assay is low, especially compared to more complicated prior art assays. Moreover, the use of AuNPs eliminates the need for expensive detection instrumentation and does not require functionalization of the AuNPs, the oligotargeter, or the target.

Moreover, this assay may be adapted into a quantitative test by spectrophotometric quantification of the resulting blue color against a standard curve or developing a fluorometric version of the test by utilization of the size and distance nanoparticle surface energy transfer (NSET) properties of AuNPs.

The assay of the invention may be further modified to detect SNPs of sequences of a microorganism, for example to discriminate between genotypes, variants or even quasispecies by manipulating the annealing temperature of the oligotargeters. This has great implications for microbiological genotyping, subtyping, and monitoring of factors correlated to treatment of a condition, disorder or disease.

The invention permits use of unmodified AuNPs for direct detection of unamplified microbe nucleic acids in clinical specimens and may be competitively used in place of other commercial immunoassays and RT-PCR methods as routine tests for management of patients infected with particular microorganisms.

The following abbreviations and terms appear herein.

AuNPs: Gold Nanoparticles. These are generally spheroidal or spherical and range in diameter from 2 to 80 nm. Unmodified AuNPs have not been bound to protein or carbohydrate ligands such as antibodies, lectins, or nucleic acids. The term "gold nanoparticle" refers to spherical gold nanoparticles. Generally, the gold nanoparticles are produced by citrate reduction method and have an average diameter ranging from 2.0 nm to 100 nm, preferably, an average diameter ranging from 10 to 25 nm, and more preferably from 15 to 20 nm. When the size of the gold nanoparticle is too small, then performance is reduced because surface-plasmon resonance would be reduced and completely abolished for particles <2 nm and the color change will not be observed and when it is too large, then performance is reduced because the aggregation affinity of the nanoparticles would be higher leading to false positive results.

The gold nanoparticles used in the invention may be produced or synthesized by methods known in the art, such as those described above in the background section. Alternatively, exemplary methods include (a) by reduction of chloroauric acid with sodium borohydride; (b) By reduction of chloroauric acid with hydrogen peroxide; or (c) by a single phase microemulsion method. These methods of producing gold nanoparticles are hereby incorporated by reference to the articles cited above.

Sample describes a material suspected to contain a microorganism to be assayed for detection. Generally, a biological sample is obtained from a subject suspected of having been exposed to or having a microbial infection. Biological samples include whole blood, plasma or serum, or other bodily fluids that may contain the microorganism. These may include, for example, plasma, serum, spinal fluid, lymph fluid, secretions from the respiratory, gastrointestinal, or genitourinary systems including bronchial lavage, tears, saliva, milk, urine, semen, skin swabs, tissue biopsies, and red or white blood cells or platelets. Samples may also be obtained from tissue cell culture, such as cultured leukocytes, and constitute cells, including recombinant cells, or medium in which a microorganism may be detected. In some cases a tissue sample may be used in the assay or processed for use in the assay, for example, by a conventional method used to extract the microbial nucleic acids from the sample.

A sample may also be processed to remove non-nucleic acid components or to isolated or further purify nucleic acids it contains by a capture method that captures at least one biological material of interest. This method comprises contacting a sample suspected of containing the nucleic acid to be purified or isolated with a substrate containing iron oxide, gold, or silver nanoparticles, quantum dots or silica nanoparticles for a time and under conditions sufficient for the material to bind to these materials and optionally eluting the captured nucleic acid or other component from the substrate. For example, a sample suspected to contain *Acinetobacter* or mycobacteria nucleic acids is contacted with silica nanoparticles for a time and under conditions sufficient for the material to bind to the silica nanoparticles. The captured nucleic acid on the silica nanoparticles can then be washed or processed, and the eluted from the silica nanoparticles for further purification or characterization of the captured and released material. In this method, silica nanoparticles can be conjugated to a ligand that is a nucleic acid complementary to a nucleic acid to be detected or that is an aptamer that binds to the nucleic acid to be detected. For example, the silica nanoparticles can be conjugated to a ligand that binds to material containing or associated with the nucleic acid to be detected and the method can further involve isolating or purifying the nucleic acid from the material bound to the silica nanoparticles. Those of skill in the art may select various ligands for use in this capture method. Examples of such ligands include antibodies or fragments of antibodies containing binding sites such as those of IgA, IgD, IgE, IgG, IgM and the various subtypes of these kinds of antibodies. This capture method may be employ a ligand that is an aptamer that binds to a protein, carbohydrate, lipid or other material associated with the nucleic acid to be captured or detected. It also may employ ligands that bind directed to a material, such as DNA or RNA or a complex or aggregate of a nucleic acid with a peptide, polypeptide or protein, to be captured or detected. The ligand in this capture method may comprise various lectins, such as one or more mannose binding lectin(s), one or more N-acetyl glucosamine(s) with or without sialic acid binding lectin(s); one or more galactose/N-acetylgalactosamine binding lectin(s); one or more N-acetylneuraminic acid binding lectin(s); or one or more fucose binding lectin(s).

The ligand used in this method may be a specific probe for the nucleic acid to be detected that is conjugated to at least one member selected from the group consisting of iron oxide, gold, silver, quantum dots and silica nanoparticles of different sizes. The method may further involve extracting the nucleic acid from the material containing it or from the material from which it is associated which has been bound to said ligand. It also may comprise contacting the sample with nanoparticles selected from the group consisting of iron oxide, gold, silver, quantum dots and silica nanoparticles, which have been conjugated to a probe comprising an oligotargeter sequence. For example, the sample may be contacted with at least one oligotargeter as disclosed herein.

Alternatively, a material containing the nucleic acids, such as an aggregate containing nucleic acid, may be captured by the substrates described above. Similarly, a non-nucleic acid component of a biological sample or undesired nucleic acid can be separated and removed from a nucleic acid of interest in a biological sample may be captured thus removing it from the rest of the sample containing the nucleic acid of interest.

Isolated or purified microorganism describes one that has been removed from its original environment, such as from the skin, blood or respiratory system of a host. It also encompasses a biological sample that has been processed to remove some or all of the contaminants or substances associated with the microorganism. Contaminants include host components or components of other kinds of microorganisms, such as nucleic acids from the host other microorganisms in a biological sample. A microorganism may also be isolated or purified from tissue culture or from a microbial culture.

Preservative or additive for a sample includes additives such as heparin or EDTA. The term also includes other agents which prevent degradation of microbial DNA or RNA or permit microbial DNA or RNA to be easily recognized in the method of the invention. These include normal saline or commercially available preservatives such as the one found in PAX gene tubes. The term "extraction buffer" refers to agents and materials useful for extracting, purifying or isolating microbial DNA or RNA from a biological sample.

Denaturation refers to a process of unfolding microbial nucleic acids or separating the strands of a duplex nucleic acid. For example, a nucleic acid may be denatured by heating it to a temperature of 65, 75, 85, 90, and 95-100° C. Denaturation may also be facilitated by addition of other ingredients such as salts, formamide, or sodium hydroxide.

Hybridization buffer refers to a buffer that permits hybridization to occur between an oligotargeter sequence and a target nucleic acid, for example, 10 mM phosphate buffered saline (PBS), pH 7.0. Samples are admixed with the oligotargeter in hybridization buffer and subsequently denatured and annealed prior to admixture with gold nanoparticles. A preferred buffer is phosphate-buffered saline ("PBS"), pH 7.0-7.4. Monovalent cation (e.g., sodium or potassium) salt concentration can range from 50 mM to 300 mM. Suitable hybridization buffers and protocols are well-known in the art and are incorporated by reference to Maniatis, et al., *Molecular Cloning: A Laboratory Manual*, $2^{nd}$ edition or *Current Protocols in Molecular Biology*, vol. 1 (updated October, 2010). Salt concentration is selected based on the volume and concentration of the gold nanoparticles.

Oligotargeter describes a polynucleotide that binds to a microbial nucleic acid. An oligotargeter forms binds via nucleic acid complementarity to a nucleic acid sequence in a target region of the microbial genomic nucleic acid. The oligotargeter will be long enough to bind to microbial nucleic acid in a sample. Preferably, it will comprise 15, 16, 17, 18, 19, 20, 21, 22, 23, 24, 25, 26, 27, 28, 29, 30, 31, 32, 33, 34, 35, 36, 37, 38, 39 or 40 bp. If the sequence is less than 19 bp, then performance will be reduced because shorter sequence will bind to non-specific sequences which would result in false positive results or if it exceeds 40 bp, then performance may be reduced because of dimerization and hairpin formation in the oligotargeter sequence risking an increase in false positive results. The oligotargeter may correspond to any portion of genomic RNA or DNA or its cellular nucleic acid components. However, it preferably will be selected to bind to a highly conserved portion and can be used to differentiate between different genera, species, subtypes, strains or variants of a microorganism. For detection of infection by a particular microorganism, preferably the oligotargeter will bind to a genomic sequence shared different pathogenic variants or subtypes of the microorganism causing human infection. For example, an oligotargeter may be selected to bind to a nucleic acid sequence conserved in the genomic DNA of mycobacteria.

Alternatively, an oligotargeter can be selected to distinguish among strains of an organism by making it complementary to subtype, species or strain-specific nucleic acids or designing it to bind to target nucleic acids containing one or more SNPs characteristic of a subtype of a pathogen. Genomic sequences can retrieved from GenBank or other nucleic acid databases and alignments of sequences from different subtypes of a pathogen performed using BLAST or other alignment software.

Modified oligotargeter is one that may contain one or more modified bases or contain a modification to or replacement of the phosphate backbone structure of a conventional oligonucleotide but otherwise substantially maintain its ability to hybridize to a target sequence, such as sequences derived from target genomic DNA or cellular RNA. For example, a modification to oligotargeter sequence that increases stability or resistance to degradation or improves binding specificity or sensitivity may be made. Examples of modifications to increase nuclease resistance of the oligotargeter include the following: (a) phosphorothioate modified sequence (where one of the oxygen on the phosphate of phosphodiester bond is replaced with a sulphur atom); (b) 3'-propryl group (C3 spacer, adding a propyl group at the 3' end); and (c) Inverted end (3'-3' linkage), though other modifications known to those in the art may also be employed.

For some applications an oligotargeter or modified oligotargeter may contain one, two, three, four or more degenerate bases, which can base pair with A, T, G, C and/or U. Degenerate bases may be incorporated into an oligotargeter to increase its affinity for the mycobacteria target sequence. For example, an oligotargeter containing one, two, three, four or more degenerate bases (e.g., inosine) in its oligonucleotide sequence can be used to overcome or compensate for a mutation that may occur within the same genotype and subtype (quasi species). Inosine resembles guanine, but without the 2-amino group, and can form stable (wobble) base pairs with adenine, cytosine and uracil that are similar in terms of interaction strength. Therefore, inosine in a probe can bind to perfectly complementary polynucleotide or ones that have mismatches at the location of the inosine to form duplex structures of comparable stability.

Variants of the oligotargeters disclosed herein having at least 80, 85, 90, 95% sequence identity or similarity or having one, two, three, four, five, six, seven, eight, nine or ten deletions, substitutions, insertions to the oligotargeter sequences described herein may be employed so long as they competently bind to the target sequence. For example, an oligotargeter variant may have 1, 2, 3, 4, 5, 6, 7, 8, 9 or 10 terminal nucleotides added to its 5' and/or 3' termini so long as these additions do not substantially affect its ability to bind to the target sequence.

With regard to the nucleic acid sequences described herein, the terms "percentage identity" and "percentage similarity" refer to a measure of the degree of identity or similarity of two sequences based upon an alignment of the sequences which maximizes identity or similarity between aligned nucleotides, and which is a function of the number of identical or similar nucleotides, the number of total nucleotides, and the presence and length of gaps in the sequence alignment. A variety of algorithms and computer programs are available for determining sequence similarity using standard parameters. Sequence similarity can be determined by the BLASTn program for nucleic acid sequences, which is available through the National Center for Biotechnology Information (http://_www.ncbi.nlm.nih.gov/blast/Blast.cgi?PAGE=Nucleotides)(last accessed Apr. 9, 2012). The percent identity of two nucleotide sequences may be made using the BLASTn preset "search for short and near exact matches" using a word size of 7 with the filter off, an expect value of 1,000 and match/mismatch of 2/−3, gap costs existence 5, extension 2; or standard nucleotide BLAST using a word size of 11, filter setting "on" (dust) and expect value of 10.

An oligotargeter may also be modified by conjugation to a detectable moiety, such as a fluorophore. For example, the 5' end of a oligotargeter polynucleotide sequence may be conjugated to an FAM dye whose fluorescence can be quenched by gold nanoparticles.

Different oligotargeter sequences and primers (when an amplification step is used) are employed to detect different organisms.

*Acinetobacter*: Oligotargeters that specifically target genus and species conserved regions in 16s, 23s, ITS, OXA gene, gyrA gene, rpoB gene, aminoglycoside acetyltransferases (AAC), phosphotransferases (APH), and nucleotidyltransferases (ANT) regions will be designed and tested in the AuNPs-based assay. In case of the PCR AuNP based assay, appropriate primers will be designed to amplify each of the above mentioned regions.

Methicillin-resistant *staphylococcus aureus* (MRSA): Six primers are designed so that the right-junction sequences of SCCmec (types I, II, III, IV and V; one primer for each type) and the conserved sequence orfX gene (highly conserved open reading frame in *S. aureus*[10, 53]) are amplified during PCR reaction. The oligotargeter sequences are designed so that they detect conserved regions within the PCR product. In case of direct detection of unamplified MRSA DNA, the assay is performed in two reactions. The first reaction confirms that the causative organism is *S. aureus* (AuNP-based assay performed using two oligotargeters targeting conserved sequence of orfX gene) and the second determines the presence of MRSA (using two oligotargeters against conserved region within MexA gene).

Hepatitis B virus (HBV): Two primers are designed against regions previously reported to be conserved; namely 1450-1469 in pre-S2 region and 1657-1679 in the S region (numbering takes CTTTTTC of X ORF as start point). The oligotargeters are designed against the conserved region (1571-1592 in S region) within the PCR product. These oligotargeters are used in the AuNP assay for both the direct detection of HBV DNA as well as for the detection of HBV amplicons.

HBV genotyping, 8 pairs of genotype-specific oligotargeters are designed targeting HBV polymerase gene. For each sample, 8 reactions (using unmodified AuNPs) are performed; each reaction utilizing 1 pair of oligotargeters specific to a certain genotype.

With regards to antiviral resistance testing, 12 oligotargeter pairs are designed to detect mutations in reverse transcriptase enzyme at codons 80, 173, 180, and 204 (lamivudine resistance) and at codons 181 and 236 (adefovir resistance). Twelve reaction tubes (using unmodified AuNPs) will be performed per sample, each using a pair of oligotargeters specific either to a wild type or to a mutant at codons 80, 173, 180, 204, 181 or 236.

Regarding the determination of Core Promoter/Precore Mutations that are linked to antiviral resistance mutations, 6 oligotargeter pairs are designed to detect mutations in basal core promoter nucleotides (1762 and 1764) and precore codon 28. Six reaction tubes are performed per sample, each using a pair of oligotargeters specific either to a wild type or to a mutant at basal core promoter nucleotides (1762 and 1764) or precore codon 28.

Human immunodeficiency virus (HIV): One oligotargeter that specifically targets a conserved region in the HIV-1 polymerase gene is designed and tested in the AuNPs-based assay. In case of the PCR AuNP based assay, appropriate primers are designed to amplify the above mentioned region using RT-PCR approach and two oligotargeters that detect a conserved region within the amplified product will be used.

Influenza A Virus (H5N1): Concerning the direct detection of H5N1 RNA, two reactions will be performed; one using an oligotargeter against the matrix gene to confirm the specimen contains influenza A virus and the other using an oligotargeter against HA gene to detect the H5N1 virus. Concerning the PCR AuNP based detection, primers are designed to perform two RT-PCR reactions for each sample; one for the amplification of the matrix gene and the other to amplify the HA gene. Two oligotargeters that recognize a conserved region within each of the two amplified regions (matrix gene and HA gene) will be used.

Target region describes the portion of the *Acinetobacter*, mycobacteria, *staphylococcus*, HBV, HIV, Influenza or West Nile virus nucleic acids to which the oligotargeter binds. This target region may lie in a conserved or unique region of the nucleic acid of the pathogen or on a portion unique to a particular genus, species, strain or subtype. The target region is not limited to protein-encoding sequences, but may encompass other portions of a pathogen's genomic or cellular nucleic acids, including control or regulatory sequences or introns or non-transcribe or non-translated nucleic acids.

Nucleic acid generally refers to DNA or RNA or their chemical derivatives. It encompasses nucleic acids isolated from a pathogen as well as amplified nucleic acids or cDNA. It also encompasses modified or mutated nucleic acids, such as variants of a known nucleic acid sequence containing one or more single nucleotide polymorphisms, or more generally, those having a sequence containing 1, 2, 3, 4, 5 or more insertions, deletions, transpositions, or substitutions to a known sequence.

Reaction buffer is one that permits or facilitates interaction of an oligotargeter, a target nucleic acid sequence, and gold nanoparticles. Exemplary buffers include phosphate buffer saline, and other buffers used in PCR reaction mixtures.

Citrate buffer is one containing citrate that can be used to prepare or suspend the colloidal gold nanoparticles (AuNPs). Alternatively, a buffer containing hydrazine, L-tryptophan, an alcohol, especially a lower $C_1$-$C_6$ alcohol, an ether, or sodium diphenyl aminosulfonate may be used. A preferred salt is trisodium citrate salt at a concentration of 30-50 mM or 1-2 wt % (no specific pH). Suitable buffers and methods for making and using colloidal gold are incorporated by reference to John Turkevich. Colloidal gold. Part I. Gold Bull. 1985; 18(3): 86-92; John Turkevich. Colloidal gold. Part II. Gold Bull. 1985; 18(4):125-131; and Katherine C. Graber, R. Grissith Freeman, Micheal B. Hommer, Micheal J. Natan. Preparation and characterization of gold colloid monolayers. Analytical Chemistry 1995; 67(4): 735-743.

Fluorometric detection refers to a method in which a fluorescent dye, such as a fluorescein derivative like FAM (Fluorescein amidite) dye or other fluorophore, has been conjugated to the 5'end of the oligotargeter sequence as described above and used to develop a nanoparticle surface energy transfer (NSET)-based detection assay. For example, an FAM molecule is quenched in the absence of target nucleic acid by the gold nanoparticles, while in the presence of target nucleic acids, hybridization occurs between the oligotargeter and the target RNA and so, the polynucleotide sequence is detached from the gold nanoparticles and hybridizes to the target complementary sequence. FAM emission becomes detectable and indicates a positive sample.

Kit refers to a composition of matter containing one or more ingredients necessary to practice the method of detecting mycobacteria according to the invention. Preferably, the kit will contain gold nanoparticles and a polynucleotide that binds to target nucleic acids in separate containers. A kit may also contain at least one biological sample preservative or additive for a sample, such as an agent that prevents degradation of DNA or RNA, a DNA or an RNA extractant buffer for extracting, isolating or purifying target nucleic acid from a sample, a reaction buffer in which gold nanoparticles, the polynucleotide binding to target nucleic acids and the biological sample are mixed, a negative control sample, a positive control sample, one or more reaction containers, such as tubes or wells, a colorimetric chart, a packaging material, an instruction for use in detecting Acinetobacteria, mycobacteria or the other pathogens described herein.

A subject includes humans, other primates (e.g., a chimpanzee), mammals, birds, reptiles as well as other and other animals susceptible to microbial infection.

SNPs: Single Nucleotide Polymorphisms.

SPR: Surface Plasmon Resonance.

Designing and Verification of Primers and Oligotargeters

The selection and design of primers and oligotargeters were done according to the following approach.

Sequence Retrieval

The target organisms whole genome sequence of the representative strains were retrieved from the NCBI gene bank database as (genebankfull) file format.

The whole genome files were used for testing the designed primers and targeters in silico.

Target gene sequences representing different strain was retrieved from NCBI database in FASTA format.

Multiple Sequence alignment: AlignX Vector NTI Advance® v. 11.5

Target genes from different strain were aligned using alignX.

Multiple sequence alignment was examined for conserved region, GC % content and Tm Genomic regions showed high similarity and conservation among strains in addition to suitable GC content and melting temperature were chosen for oligotargeter design.

Primers and Oligotargeter Specificity

After selecting conserved regions and regions of difference, proper primers and oligotargeters were selected.

The specificity of primers and oligotargeters were evaluated by blasting them against Nucleotide collection Database (nr/nt) using NCBI blast.

Interference with Human RNA

For pathogens that to be tested in biological fluids such as blood or serum, interference with Homo sapiens genomic material is expected.

The oligotargeter sequence was also blasted against Human genome and transcript database and reference RNA database to evaluate the interference of the human chromosomal element DNA or RNA with the probe functionality.

In Silico PCR

Primers pairs were finally in silico tested for ability to amplify selected targets using NCBI primer blast and Vector NTI.

Selection of Primer Pairs and Oligotargeters for Detection of Microbial Pathogen after PCR-Based Amplification Different combinations of primer pairs and oligotargeters were tested experimentally by manipulation of reaction conditions and parameters to identify the sequence combinations that can detect the target microbial nucleic acids with highest sensitivity and specificity.

Combination Sets of Primers and Oligotargeters

Primer sets were selected to cover/flank the target gene while oligotargeters were selected to hybridize to the middle region of the target gene. Primers and oligotargeters were selected to have close GC content and annealing conditions and similar length, but minimal secondary structure and no complementary sequences to attempt to optimize amplification and detection strategies. For example, specific primer sets were selected for use in nested, semi-nested, or multiplex PCR reactions. However, after rigorous and systematic assessment of different combinations of sequences, it was surprising that only some combinations of primers and oligotargeters provided high sensitivity and specificity for detection of the particular target pathogens. While not being limited to any particular explanation of these surprising results, factors that may explain success of certain sets to achieve highest specificity and sensitivity include: length of the primer/oligotargeter, sequence conservation of target regions, presence of stable secondary structure of target sequence, number of mismatches in the primers/oligotargeters, number of copies and concentration of target gene, hybridization format (solid phase vs. liquid), stringency of hybridization conditions, and technical strategies implemented to eliminate/reduce cross-hybridization or background noise signals. The tables below describe combinations of primers and oligotargeters for the target pathogens described herein that provide excellent specificity and sensitivity.

Examples of Combinations of Primers and Oligotargeter Sets Conferring Excellent Sensitivity and/or Specificity

*Acinetobacter* Primers & Oligotargeters

| SEQ ID NO: | Type | Sequence | Target |
|---|---|---|---|
| 16S Region Set 1 | | | |
| 2 | Sense Primer | TTTGATCATGGCT CAGATTGAACGC | 16S Region |
| 14 | Antisense primer | GAACGTATTCACC GCGGCATTCTGA | 16S Region |
| 40 | Oligotargeter | CCAGGTGTAGCGG TGAAATGCGTAGA GATCTGGAGG | 16S Region |
| 16S Region Set 2 | | | |
| 3 | Sense Primer | GATGCTAATACCG CATACGTCCTACG | 16S Region |
| 16 | Antisense primer | TCTCACGACACGA GCTGACGACAGC | 16S Region |
| 24 | Oligotargeter | GCAGGGGATCTTC GGACCTTGCGCTA ATAG | 16S Region |
| ITS Region set 1 | | | |
| 67 | Sense Primer | GGCTGGATCACCT CCTTAACGAAAG | ITS Region |
| 69 | Antisense primer | TCACGTCTTTCAT CGCCTCTGACTG | ITS Region |

| SEQ ID NO: | Type | Sequence | Target |
|---|---|---|---|
| 78 | Oligotargeter | TGTTCACTCAAGA GTTTAGGTTAAGC AATTAATC | ITS Region |
| 23S Region set 1 | | | |
| 83 | Sense Primer | TATAGTCAAGTAA TTAAGTGCATGTG GTGG | 23S Region |
| 94 | Antisense primer | TTGGGTGTTGTAT AGTCAAGCCTCAC | 23S Region |
| 118 | Oligotargeter | CCCGTTCGCCGAA AGACCAAGGGTTC CAGTCCAACGT | 23S Region |
| 5S Region set 1 | | | |
| 128 | Sense Primer | GCAGTTGTATATA AAGCATCAATCG | 5S Region set 1 |
| 130 | Antisense primer | GAGCTGGCGATGA CTTACTCTCACAT | 5S Region set 1 |
| 131 | Oligotargeter | GTGAACCACCTGA TCCCTTCCCGAAC TCAG | 5S Region set 1 |
| Oxa-23 Region set 1 | | | |
| 133 | Sense Primer | CTCTGTACACGAC AAATTTCACAGA | Oxa-23 region |
| 142 | Antisense primer | TCAAGCTCTTAAA TAATATTCAGCTG | Oxa-23 region |
| 168 | Oligotargeter | TCCCAGTCTATCA GGAACTTGCGCGA CGTATCGGTC | Oxa-23 region |

Mycobacteria Primers & Oligotargeters

| SEQ ID NO: | Type | Sequence | Target |
|---|---|---|---|
| 16S Region set 1 | | | |
| 170 | Sense Primer | GGGAAACTGGGTCT AATACCGGATAGG | 16S |
| 179 | Antisense primer | TTTACGCCCAGTAA TTCCGGACAAC | 16S |
| 192 | Oligotargeter | CACCATCGACGAAG GTCCGGGTTCTCTC GGATTG | 16S |
| 16S Region Set 2 | | | |
| 171 | Sense Primer | AAACTGGGTCTAAT ACCGGATAGGACCA | 16S |
| 182 | Antisense primer | TTCCAGTCTCCCCT GCAGTACTCTAGTC | 16S |

| SEQ ID NO: | Type | Sequence | Target |
|---|---|---|---|
| 193 | Oligotargeter | TGTTCGTGAAATCT CACGGCTTAAC | 16S |
| ITS Region set 1 (Mycobacteria TB complex) | | | |
| 209 | Sense Primer | AGCACCACGAAAAC GCCCCAACTGG | ITS |
| 211 | Antisense primer | CCGGCAGCGTATCC ATTGATGCTCG | ITS |
| 215 | Oligotargeter | ACTTGTTCCAGGTG TTGTCCCACCGCCT TGG | ITS |
| ITS Region set 1 (Mycobacteria Genus) | | | |
| 209 | Sense Primer | AGCACCACGAAAAC GCCCCAACTGG | ITS |
| 211 | Antisense primer | CCGGCAGCGTATCC ATTGATGCTCG | ITS |
| 217 | Oligotargeter | AGGGGTTCTTGTCT GTAGTGGGCGAGAG CCGGGTGC | ITS |
| IS6110 Conserved Region | | | |
| 226 | Sense Primer | CTGGCGTTGAGCGT AGTAGGCAGCCTCG A | IS6110 |
| 228 | Antisense primer | TCGCTGATCCGGCC ACAGCCCGT | IS6110 |
| 230 | Oligotargeter | TGGATGCCTGCCTC GGCGAGCCGCTCGC TG | IS6110 |

Methicillin Resistant *Staphylococcus Aureus* Primers & Oligotargeters

| SEQ ID NO: | Type | Sequence | Target |
|---|---|---|---|
| 16S Region set 1 | | | |
| 238 | Sense Primer | AGAGTTTGATCCT GGCTCAGGATG | 16S |
| 245 | Antisense primer | AGGTGATCCAGCC GCACCTT | 16S |
| 256 | Oligotargeter | CTCATCGTTTACG GCGTGGACTACCA GGGT | 16S |
| 23S Region set 1 | | | |
| 260 | Sense Primer | TTAAGTTATTAAG GGCGCACG | 23S |
| 271 | Antisense primer | GATCTTATAACCG AAGTTGGGAA | 23S |

-continued

| SEQ ID NO: | Type | Sequence | Target |
|---|---|---|---|
| 287 | Oligotargeter | CGTAAGGTGATGT ATAGGGCTGACG CCTG | 23S |

ITS Region set 1

| SEQ ID NO: | Type | Sequence | Target |
|---|---|---|---|
| 292 | Sense Primer | AAGGATATATTCG GAACATCTTCTT | ITS |
| 294 | Antisense primer | AAACGCGTTATTA ATCTTGTGAG | ITS |
| 298 | Oligotargeter | TTTTAAATAAGCT TGAATTCATAAGA AATAATCGC | | mecA Region

| SEQ ID NO: | Type | Sequence | Target |
|---|---|---|---|
| 303 | Sense Primer | TGTTTTGTTATTC ATCTATATCGTAT TTT | mecA gene |
| 311 | Antisense primer | ATGAAAAAGATAA AAATTGTTCCACT | |
| 321 | Oligotargeter | TAACGGTTTTAAG TGGAACGAAGGTA TCAT | |

Hepatitis B Virus Primers & Targeter

| SEQ ID NO: | Type | Sequence | Target |
|---|---|---|---|
| 400 | Sense Primer | ATGGAGAGCACAA CATCAGGA | SURFACE HBsAg |
| 401 | Antisense primer | CCAACGTTTGGTT TTATTAGGG | SURFACE HBsAg |
| 422 | Oligotargeter | GCAGTCCCCAACC TCCAATCACTCAC CAAC | SURFACE HBsAg |

Influenza a Virus (H5N1) Primers & Oligotargeter

| SEQ ID NO: | Type | Sequence | Target |
|---|---|---|---|
| 455 | Sense Primer | ATTGGAATATGGT AACTGCAACACC | HA gene |
| 462 | Antisense primer | GTTATTAAATTCC CTTCCAACAGCC | HA gene |

-continued

| SEQ ID NO: | Type | Sequence | Target |
|---|---|---|---|
| 473 | Oligotargeter | GAGTGGGTACGCT GCAGACAAAGAAT CCAC | Surface HBsAg |

West Nile Virus Primers & Oligortargeter

| SEQ ID NO: | Type | Sequence | Target |
|---|---|---|---|
| 527 | Sense Primer | AGTAGTTCGCCTG TGTGAGCT | 5'UTR_1 |
| 528 | Antisense primer | GTTTTGAGCTCCG CCGATTG | 5'UTR_1 |
| 551 | Oligotargeter | GGCTCTCTTGGCG TTCTTCAGGTTCA CAGC | 5'UTR_1 Mat_Peptide 1 |

The Examples below are provided only for illustrative purposes and do not limit the scope of the present invention. Numerous embodiments within the scope of the claims will be apparent to those of ordinary skill in the art, thus the following non-limiting examples only describe particular embodiments of the invention.

Example 1

Rapid Detection of *Acinetobacter baumannii* Complex Using Unmodified Gold Nanoparticles Background

*Acinetobacter*

*Acinetobacter* spp. are aerobic Gram-negative bacilli commonly present in soil and water as free-living saprophytes. They are also isolated as commensals from skin, throat and various secretions of healthy people, as well as causing human infections (Bergogne-Berezin 2001).

Epidemiology

Strains of *Acinetobacter* are widely distributed in nature and are found in virtually all samples of soil and fresh water when appropriate culture techniques are used (Bergogne-Berezin and Towner 1996). A range of species have been identified from soil, sewage, plants and food products, although the species associated with human disease are not normally found in such sites.

Human Carriage

Human carriage of *Acinetobacter* has been demonstrated in normal individuals: it forms part of the bacterial flora of the skin and has been found in the axillae, groin and toe webs of normal individuals. *Acinetobacter* colonizes the oral cavity, the respiratory tract and the gastrointestinal tract and is found predominantly in moist skin areas (Bergogne-Berezin and Towner 1996)

Sources and Spread in Nosocomial Infections

Sporadic cases of *Acinetobacter* infections are seen in many hospitals and in a variety of patient settings. However, outbreaks of infection caused by endemic strains are being increasingly described, particularly in ICUs. The carriage rate of *Acinetobacter* on the skin of hospitalized patients is significantly higher than the community, and this site has been thought to be an important source (Seifert et al., 1997). This has been postulated to be due to reduced hygiene standards among hospitalized patients and the warm, humid atmosphere of hospital beds, which is supported by the observation that colonization is more frequent in summer months. However, two recent studies using DNA-based identification techniques have demonstrated that much of this colonization is due to species of Acinetobacter not commonly associated with clinical infection (Seifert et al., 1997; Berlau et al., 1999)

Laboratory Diagnosis

Isolation

All the frequently encountered species of Acinetobacter grow readily on common laboratory media. In investigating outbreaks, commonly used selective and/or differential media [e.g., MacConkey agar, cysteine lactose electrolyte-deficient (CLED) agar] have been made more selective for particular strains with specific antibiotic resistance patterns by the addition of antibiotics (Allen and Green 1987). Alternatively, a selective medium such as Leeds Acinetobacter medium may be used for the selective isolation of most Acinetobacter spp. (Jawad, Hawkey et al. 1994). When looking for small numbers in environmental specimens, liquid enrichment in minimal media with vigorous shaking has been useful (Bergogne-Berezin and Towner 1996). Although A. baumannii, genomospecies 3 and 3TU have growth optima of 37 degrees C., a lower temperature such as 30 degrees C. will ensure that all species are isolated.

Identification

The differentiation of the different genomospecies is not possible using phenotypic characteristics, although some level of discrimination is possible. Few clinical laboratories have the facilities for the molecular identification of genomospecies and rely on commercial phenotypic systems (e.g. API2ONE [BioMerieux]).

Several studies have shown a poor correlation with DNA-based methods (Bernards, van der Toorn et al. 1996; Jawad, Snelling et al. 1998) Ribotyping (Gerner-Smidt 1992) and rRNA sequencer fingerprinting (Janssen and Dijkshoorn 1996), AFLP (Ehrenstein, Bernards et al. 1996) and ARDRA should all accurately identify individual genomospecies, particularly differentiating 1, 2, 3 and 3TU.

Therapeutic Options for Treatment of Acinetobacter Infection

The therapeutic options for treating Acinetobacter nosocomial infection are restricted because of the high levels of antimicrobial resistance. Based on the results of animal models of Acinetobacter pneumonia (Joly-Guillou, Wolff et al. 1997), carbapenems or carboxypenicillins have been used, in most cases in combination with an aminoglycoside, as an empirical treatment for nosocomial pneumonia. Other strategies have used β-lactamase inhibitors, and among them, sulbactam has demonstrated therapeutic efficacy largely because of its intrinsic activity as a single drug against Acinetobacter (Wood, Hanes et al. 2002).

Materials and Methods for Example 1:

Acinetobacter Samples

A total of 25 clinical samples were obtained (10 pus, 10 sputum, 2 urine, 2 endotracheal tube swap, 1 wound).

Samples Processing and Isolates Identification

Clinical samples were processed and isolated on MacConkey agar media. Isolated colonies were identified by their colony morphology, microscopical examination including gram's and capsule stain, growth at 44° C., biochemical identification and PCR. Biochemical identification tests were Oxidase test, citrate utilization test and Glucose utilization test PCR Amplification Multiplex PCR ofb/aOXA-51-like, blaOXA-23-like and class I integrase of Acinetobacter baumannii:

Oxa-23, Oxa-51 and class I integrase gene were simultaneously amplified in a multiplex PCR reaction for the identification of Acinetobacter baumannii. PCR was carried out in 25 µl reaction volumes with 12.5 pmol of each primer, and 1.5 U of TaqDNA polymerase in 1×PCR buffer containing 1.5 mM $MgCl_2$ and 200 µM of each dNTPs. PCR reaction conditions were, 94° C. for 3 min, and then 35 cycles at (94° C. for 45 s, at 57° C. for 45 s, and at 72° C. for 1 min), followed by a final extension at 72° C. for 5 min. See FIG. 10 which describes the genes, PCR primers sequences and amplicon length (b).

Amplification of ITS Regions:

PCR of ITS region was performed on extracted DNA and directly isolated colonies (colony PCR). PCR was performed in a total reaction volume of 50 µl consisting of 75 mM Tris-HCl (pH 8.8), 20 mM ammonium sulfate, 1.5 mM $MgCl_2$, 0.8 mM deoxyribonucleoside triphosphates (0.2 mM each), 1 µM (each) primer, and 1 U of Taq DNA polymerase (Fermentas). The PCR performed in 35 cycles: initial denaturation 94° C. for 3 min at 94° C. for 1 min, annealing 55° C. for 1 min, and extension 72° C. for 1.5 min and a final extension step at 72° C. for 7 min. A negative control was included with each test run by replacing the template DNA with sterilized water in the PCR mixture. See FIG. 11 which describes the genes, PCR primers sequences and amplicon length (bp).

Nested PCR

Nested PCR was performed on purified ITS amplicons. PCR was performed in a total reaction volume of 50 µl consisting of 75 mMTris-HCl (pH 8.8), 20 mM ammonium sulfate, 1.5 mM $MgCl_2$, 0.8 mM deoxyribonucleoside triphosphates (0.2 mM each), 1 µM (each) primer, and 1 U of Taq DNA polymerase (Fermentas). The PCR performed in 35 cycles: initial denaturation 94° C. for 3 min, 94° C. for 1 min, annealing 48° C. for 1 min, and extension 72° C. for 1.0 min and a final extension step at 72° C. for 7 min. Negative control (No template control) was included with each test run.

Gold Nanoparticles Synthesis

Spherical gold colloid was prepared using citrate reduction method. Gold colloid absorption peak was scanned by spectrophotometer in the range of 400-700 nm with a concentration of 14 nM.

AuNPs Detection Probes and Optimization

Detection of PCR Product

Colony PCR was performed on isolated colonies as previously described followed by detection of the amplicon using specific oligotargeters. Detection of PCR product was done by preparing 10 ul reaction containing 52 mM NaCl, 1 µL 100 mM PB, 1.5 µM oligo-targeters and 2 µL PCR product followed by denaturation at 95° C. for 60 s and annealing at 48.9° C. for 60s. Then 30 µL gold colloid 15 nm±2 was added. See FIG. 12 which describes the oligo-targeter sequences, Blast hits, and Alignment Identity.

Figure 3:
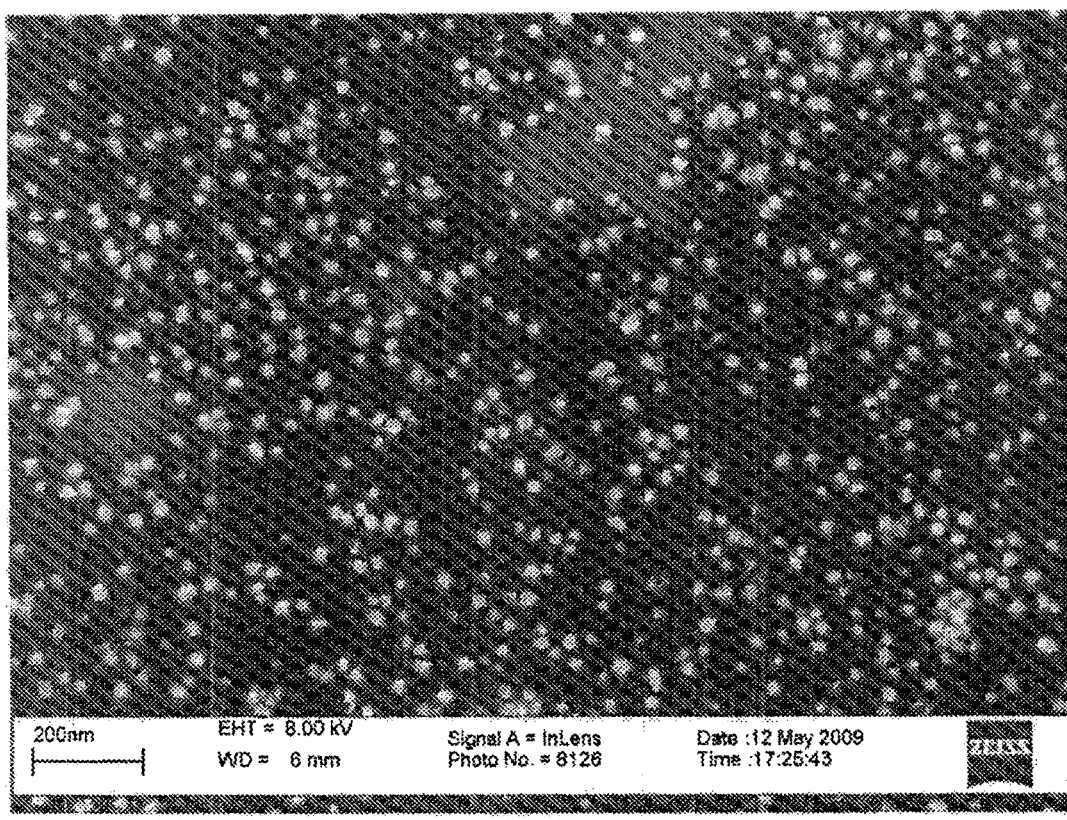
FIG. 3. Scanning electron monographs of the prepared AuNPs. One drop of AuNPs was placed on silicon slide and left to dry then examined using field emission scanning electron microscopy (Model: Leo Supra 55).
Figure 4:
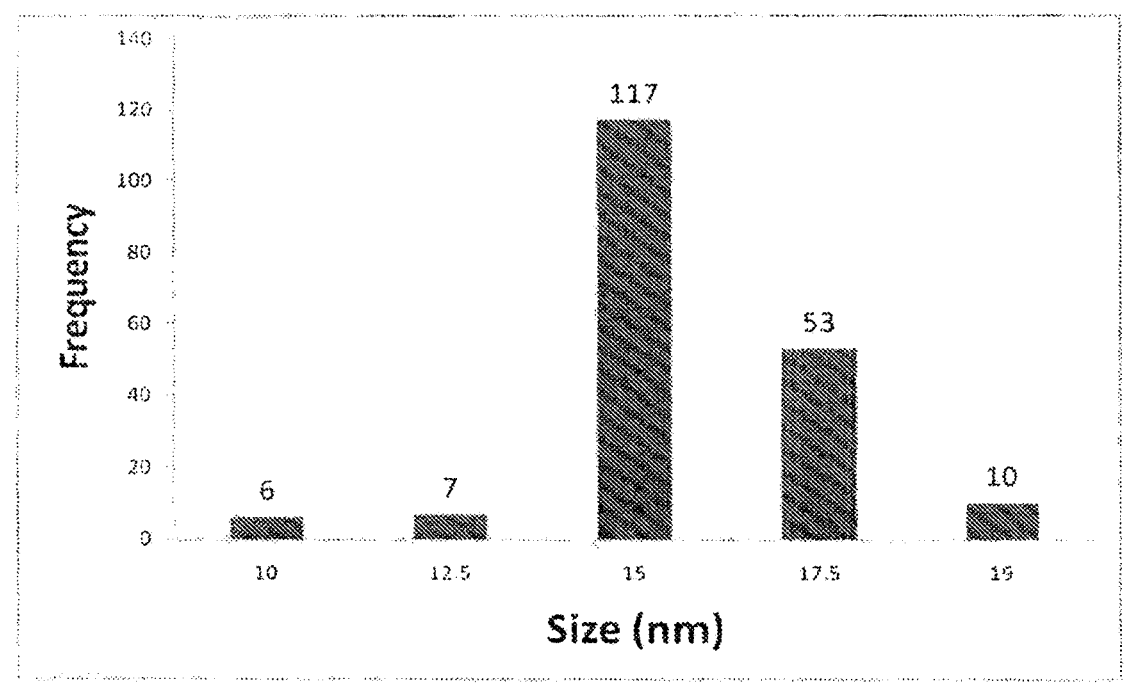
FIG. 4. Analysis of AuNPs size distribution. The scanning electron microscope image in FIG. 3 was analyzed by Image J 1.4 software Wayne Rasband, National Institutes of Health, USA. http://_rsb.info.nih.gov/ij/java 1.6.0_05.
Figure 5:
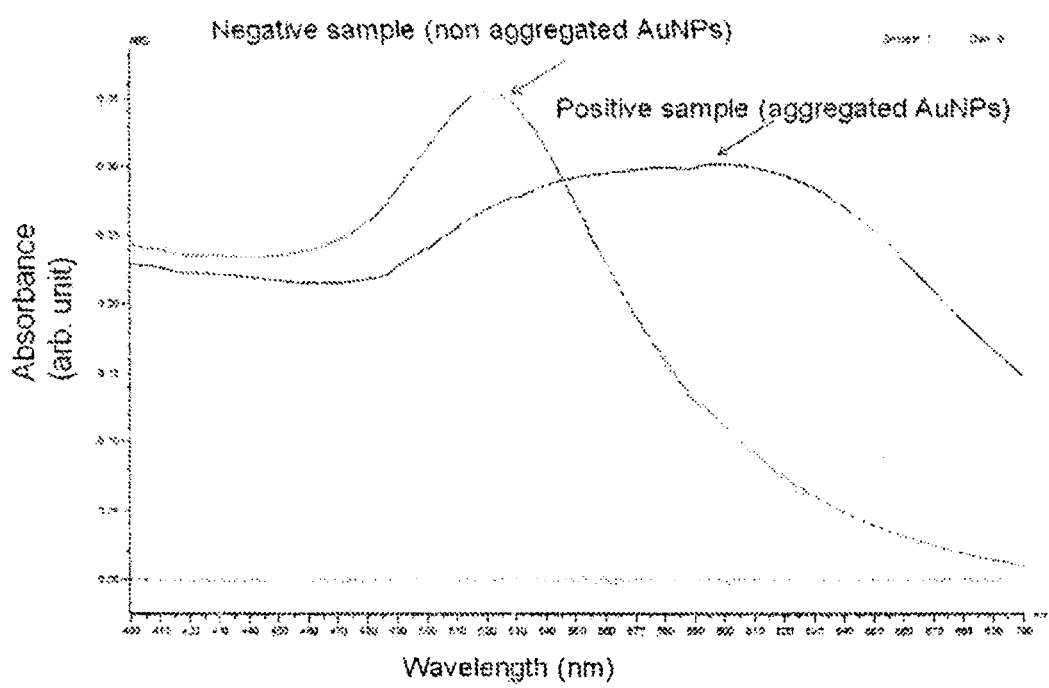
FIG. 5. Extinction spectra of positive and negative samples. The absorption spectra of positive sample (aggregated AuNPs, black) and negative sample (non-aggregated AuNPs, red). Note the red shift and broadening of the peak of the positive sample due to aggregation of AuNPs. For the negative sample, the λmax was around 518-520 nm.
Figure 7:
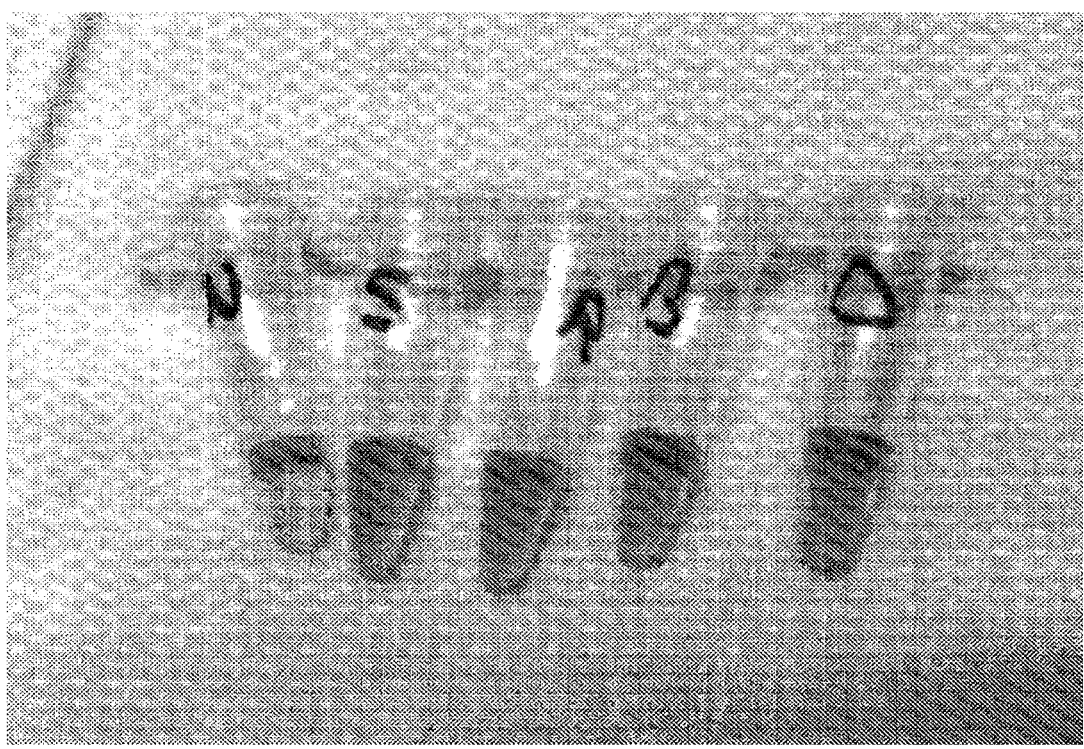
FIG. 7. Detection of TB DNA extracted from clinical specimens using AuNPs. Blue samples show presence of TB DNA. Red samples are negative for TB DNA. N=Negative Samples; S=*Smegmatis* (Non-*Mycobacterium* complex strain); R=H37Ra standard strain (*Mycobacterium* complex Sample); B,D=clinical isolates (*Mycobacterium* complex strain).
Figure 8:
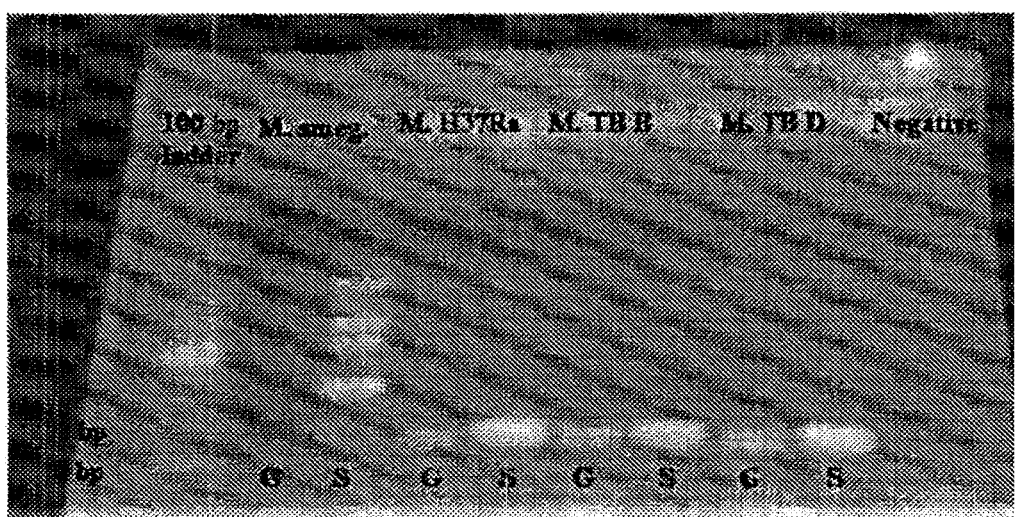
FIG. 8. Confirmation of the specificity of the probes by performing a second PCR using the first PCR as template (nested PCR). The PCR product was visualized by gel electrophoresis.

Results for Example 1:

Size & Distribution of the Prepared AuNPs:

Scanning electron microscope image was analysed and the mean particle diameter was found to be 15 nm, and the particles were monodispersed. FIG. 3 depicts a scanning electron micrograph of the prepared AuNPs and FIG. 4 shows AuNP size distribution.

Isolates Identifications are shown by the Table of FIG. 13.

Figure 14:
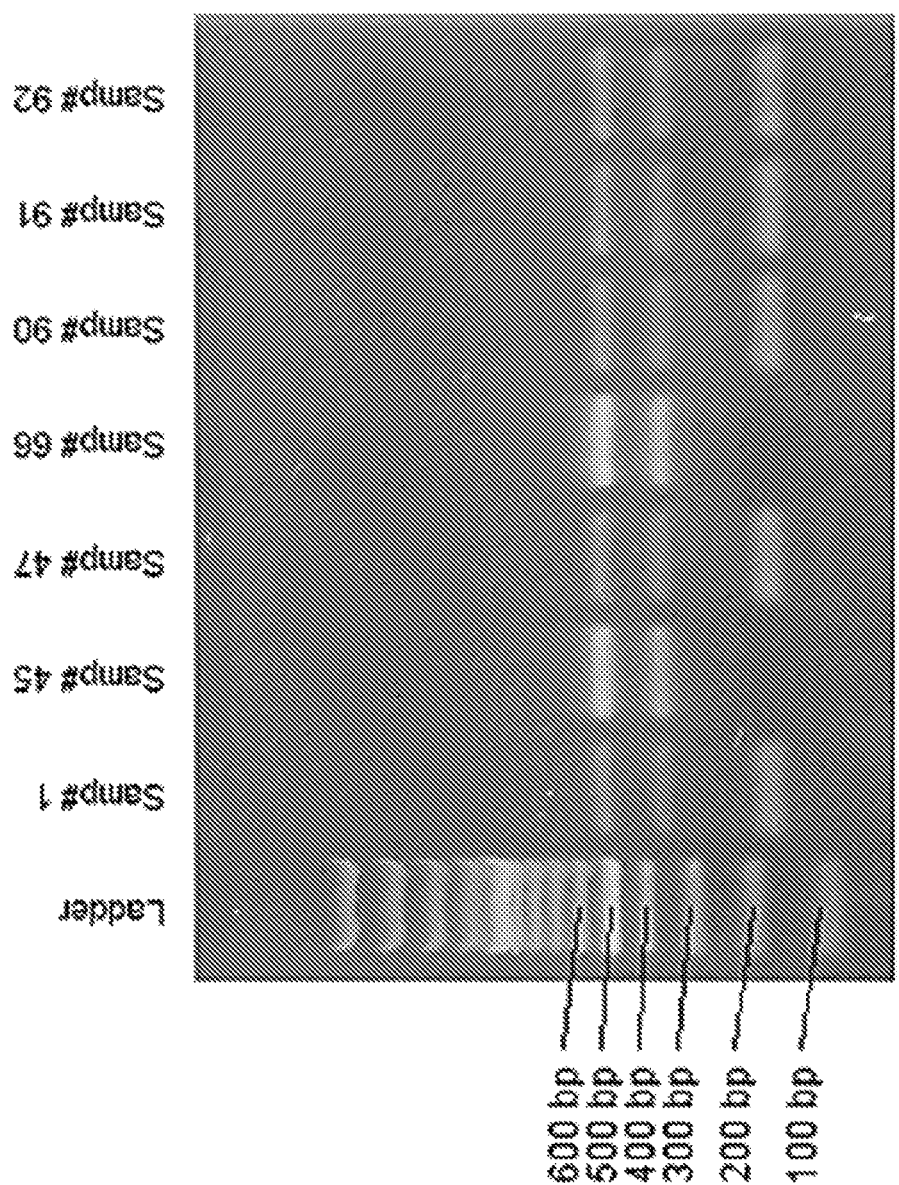
FIG. 14. Results of agarose gel electrophoresis of Multiplex PCR blaOXA-like genes.

The blaOXA-5 land blaOXA-23 like Multiplex PCR identification of *Acinetobacter baumannii*. FIG. 14 depicts results of agarose gel electrophoresis of Multiplex PCR blaOXA-like genes. Multiplex PCR Reaction 7/25 clinical isolates showing specific bands. Bands from top to bottom: oxa 23 (501 bp), oxa 51 (353 bp) and intl (167 bp).

Figure 15:
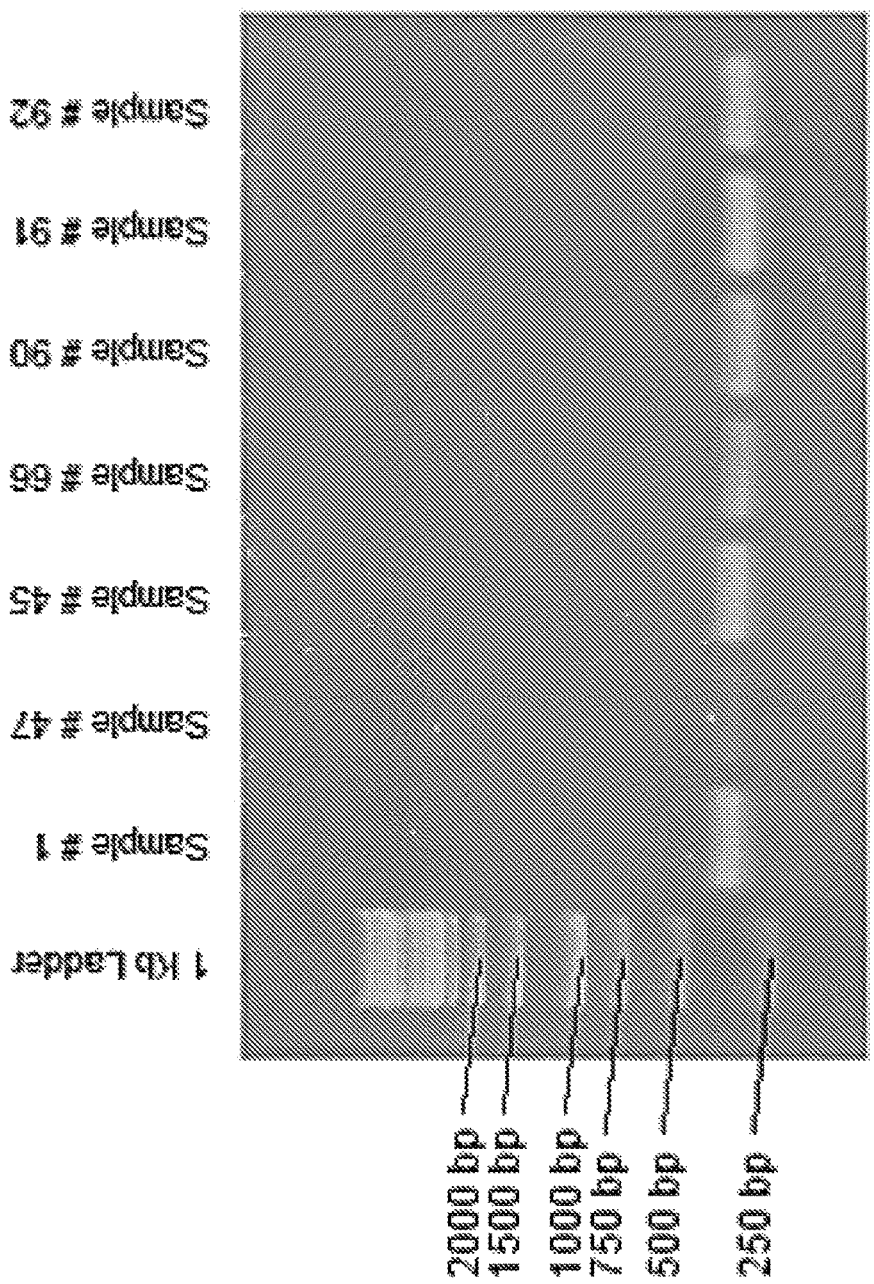
FIG. 15. Results of nested PCR by agarose gel electrophoresis.

Nested PCR. FIG. 15 depicts results of nested PCR by agarose gel electrophoresis of nested PCR reaction. The gel shows the expected bands (367 bp) confirming the specificity of the probes.

Figure 16:
FIG. 16. Assay Prototype showing detection of *Acinetobacter* in PCR Amplicons.

Assay Prototype: Detection of *Acinetobacter* in PCR Amplicons is depicted by FIG. 16.

AuNPs assay compared to Biochemical, PCR and Nested PCR tests. FIGS. 17A and 17B describes AuNP assay results.

Example 2

Direct Detection of *Mycobacterium tuberculosis* Complex Using Gold Nanoparticles Specimens Sputum samples could be cultured on either liquid (7H9 or 7H10 broth) or solid media (Lowenstein Jensen) and processed for DNA extraction. Other biological specimens such as sputum, bone marrow, whole blood, urine, or infected macrophages are treated first for inactivation in category 3 biosafety level and regarded as potential hazardous then processed for DNA extraction.

Clinical specimens are heated in a sealed tube for 80° C. for 1 hour for killing of bacterial cells. Subsequent steps of cell lysis, protein removal, DNA precipitation and recovery are done in class 2 or 3 laminar flow cabinet. All *Mycobacterium tuberculosis* molecular detection methods require culturing of samples followed by DNA extraction.

DNA Extraction

Briefly, cells were harvested and re-suspended in Tris-EDTA buffer (TE); pH 8.0 and cells were centrifuged and harvested. All cell pellets were stored at −20° C. for a minimum of 4 h. Cell pellets were thawed and suspended in TE buffer pH 8.0. An equal volume of chloroform/methanol (C/M) 2:1 were added and mixed. The suspension was centrifuged where the mycobacteria formed a firm band at the organic-aqueous interface. Tightly bacterial band was left in the tube and both the organic and aqueous layers were decanted. To remove the remaining of the organic solvent, the uncapped tube containing the depilated cells were put in water bath at 55° C. TE buffer pH 8.0 was added and the cells were suspended by vigorous vortex. Tris-HCl; pH 9.0 was added to increase the pH of the cell suspension. Lysozyme (Promega) was added to a final concentration of 100 µg/mL and incubated at 37° C. To remove cell proteins and contaminants, 10% SDS (Promega) and proteinase K (Promega) was added. The extract was mixed by inverting the tubes up and down several times and incubated at 55° C. for 3 h. Proteins were extracted from the resulting suspension by adding an equal volume of phenol/chloroform/isoamyl (P/C/I) 25:24:1 (Sigma Aldrich) and gentle shaking for 30 min followed by centrifugation. The aqueous layer was gently transferred to a sterile tube. To re-extract the aqueous layer, an equal volume of C/I 24:1 was added for 5 min with gentle rocking and repeat the step of centrifugation. To precipitate TB genomic DNA, 3 M sodium acetate (Sigma), pH 5.2, and isopropanol (Sigma) were added. The solution was centrifuged at room temperature to pellet the DNA. The supernatant was discarded and the pellet washed with cold 70% ethanol. The DNA pellet re-suspended in nuclease-free water. Other DNA extraction methods include: silica nanoparticles modified with TB DNA probes, silicon beads, sonication or chemical treatment using 2% SDS-10% Triton-X, guanidinium thiocyanate, NaOH with heating.

Restriction Digestion of DNA

Genomic DNA was digested with a restriction enzyme Bam HI (Promega) by incubation at 37° C. for 1 hour followed by deactivation at 65° C. for 15 min.

PCR Amplification

PCR primers are TBF: ACATGCAAGTCGAACG-GAAAGG (SEQ ID NO: 612) and TBR: CCTCCTGA-TATCTGCGCATTCCAC (SEQ ID NO: 613).

PCR was done using PCR master mix (Promega) and Bam HI digested DNA. BamHI restriction enzyme was selected based on the absence of a restriction site within the specified region. 5% Dimethyl sulfoxide (DMSO, Promega) was added in the master mix. DMSO was added to facilitate TB DNA strand separation. Unidentified *mycobacterium* specimens were detected first by semi-nested PCR before AuNPs detection. Semi-nested PCR was done on purified amplicons. Genus and species semi-nested PCR used PCR amplicons as a target DNA and employed genus and species oligo-targeters as reverse and forward primers, respectively. Another aim for semi-nested PCR was to prove the specificity of the selected oligo-targeters. To confirm that genus oligotargeter is specific for *mycobacterium* genus and species oligotargeter is specific for *M. tuberculosis* complex.

Gold Nanoparticles Concentration.

Spherical gold colloid was prepared using citrate reduction method. The resulted spherical gold nanoparticles were filtered using a 0.45 µm pore size acetate filter (Sigma), and transferred into a clean storage glass bottle. Gold colloid absorption peak was scanned by spectrophotometer in the range of 400-700 nm with a concentration of 8-20 nM.

Oligo-Targeters Selection

Using Two Oligo-Targeters

Genus and species specific hybridization oligo-targeters were selected from previous literature based on a conserved 16s rDNA gene part and synthesized by BIONEER.

Using Single Oligo-Targeter

As an optimization of the assay, species specific hybridization oligotargeter only was used to increase the assay specificity. Other genomic DNA targets can be used for TB diagnosis such as Internal Transcribed Spacer (ITS) and Insertion sequence IS6110 region.

Assay Hybridization Buffer

Detection of PCR product was done by adding NaCl, Tris-HCl buffer; pH 8.

Two Versions of the TB Nano-Gold Assay

Two versions of the nano-gold assay were developed. The first assay detected *mycobacterium* genus from other bacteria. The second nano-gold method differentiated *M. tuberculosis* complex from *mycobacterium* genus using species specific oligotargeter. Both nano-gold prototypes detected TB DNA as PCR amplicons and genomic DNA directly.

Materials and Methods for Example 2

*Mycobacterium* Samples: For reference strains, two *Mycobacterium* reference strains of *Mycobacterium* H37Ra and *Mycobacterium smegmatis* were cultivated and refreshed on Lowenstein Jensen solid media. A total of 25 clinical DNA samples were obtained, 11 samples are anonymous and 14 samples are identified as *Mycobacterium tuberculosis*.

Samples Processing

All Mycobacteria reference strains were processed for DNA extraction according to established methods after enzymatic cell lysis.

PCR Amplification

16S DNA PCR

16S DNA PCR was done using PCR master mix (Promega). 5% Dimethyl sulfoxide (DMSO, Sigma-Aldrich) was added in the master mix. PCR was done in 30 cycles: initial denaturation at 95° C. for 2 min, denaturation at 95° C. for 30 s, annealing temperature at 46° C. for 1 min, extension at 72° C. for 45 s, and final extension at 72° C. for 2 min in a thermal cycler (MyCycler, Bio-Rad, California, USA). Genes, PCR primers sequences, Tm and amplicon length is shown by FIG. 18.

Semi-Nested PCR

Semi-nested PCR was done on purified 16S rDNA amplicons.

Genus and species semi-nested PCR were done in two separate reactions for each sample. Semi-nested PCR was done in 25 cycles: initial denaturation at 95° C. for 2 min, denaturation at 95° C. for 30 s, annealing temperature at 50° C. for genus and 52° C. for species for 1 min, extension at 72° C. for 45 s, and final extension at 72° C. for 2 min in a thermal cycler (Bio-Rad).

Gold Nanoparticles Synthesis

Spherical gold colloid was prepared using citrate reduction method. Gold colloid absorption peak was scanned by spectrophotometer in the range of 400-700 nm with a concentration of 14 nM.

TB Nano-Gold Assay

Detection of PCR Products

Detection of PCR product was done by adding 44 mM NaCl, 2.5 µL 1M Tris-HCl, 0.02 µM oligo-targeters and 5 µL PCR product followed by denaturation at 95° C. for 30 s and annealing at 48° C. for 30 s. Then 30 µL gold colloid 15 nm±2 was added. Oligotargeter sequences, Blast hits and Alignment identity is shown by FIG. 19.

Detection of Genomic DNA

Detection of genomic DNA of 25 clinical strains was done by adding 2.5 µL TrisHCl, 44 mM NaCl (0.5 M), 1 µL species oligotargeter (1 µM), 4 µL genomic DNA, and 3.54 µL $H_2O$. The mixture was denatured at 95° C. for 3 min and annealed at 46° C. for 1 min, then 30 µL AuNPs was added. Positive and negative samples were scanned with a spectrophotometer in the range of 400-700 nm.

Detection Limit of TB Nano-Gold Assay

For PCR products, a two fold serial dilution was done of *Mycobacterium* H37Ra for a DNA range from 14.1 ng to 0.44 ng. For genomic DNA, a two fold serial dilution was done for genomic DNA of a clinical strain of *Mycobacterium tuberculosis* complex (range from 40 ng to 10 ng). Dilutions were tested with nano-gold assay with different DNA concentrations as described above.

Results for Example 2

Size & Distribution of the Prepared AuNPs:

Scanning electron microscope image was analyzed and the mean particle diameter was found to be 15 nm, and the particles were monodispersed as shown in FIGS. 3 and 4.

16S rDNA PCR Amplification

Figure 20:
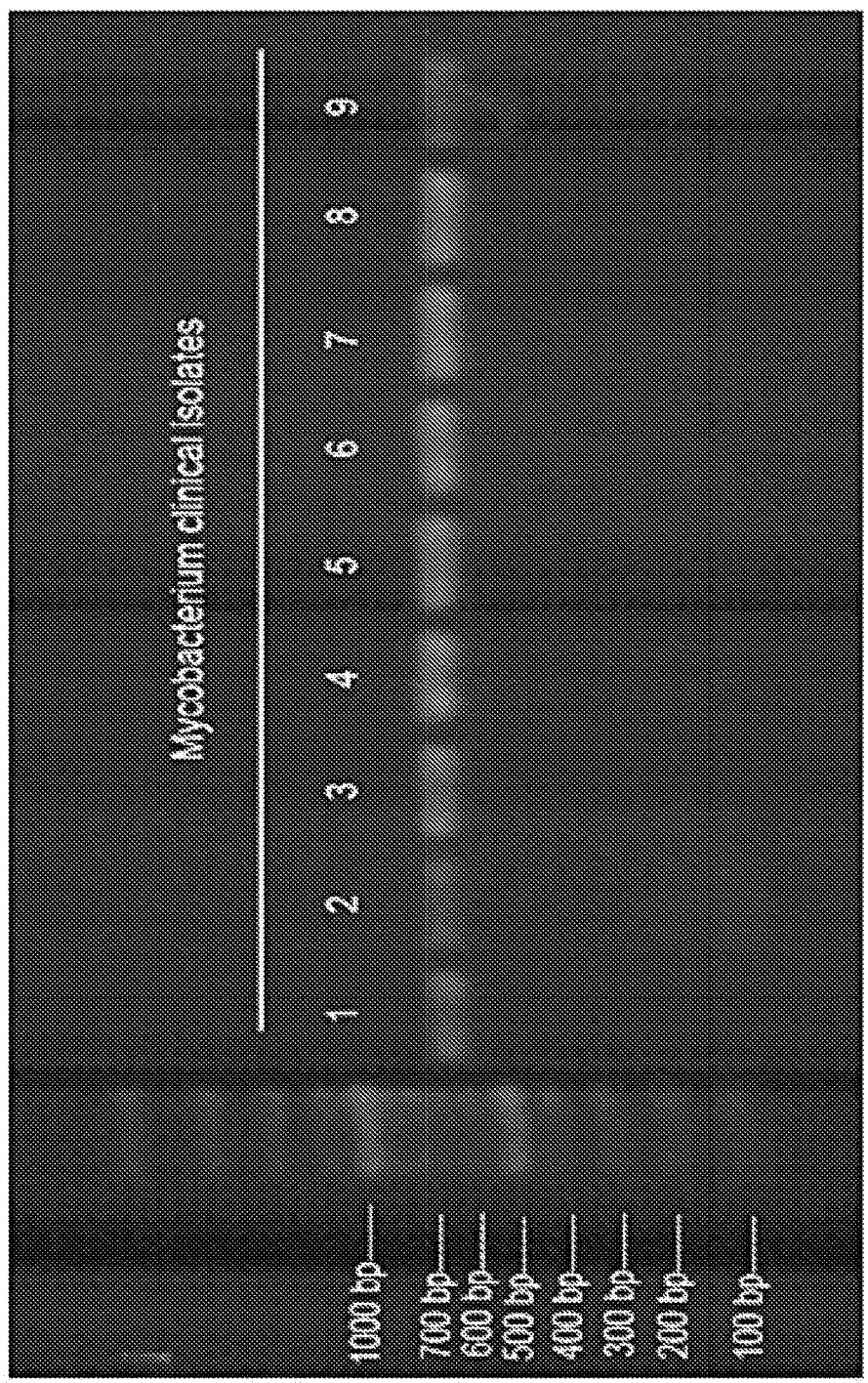
FIG. 20. Results of agarose gel electrophoresis of 16S rDNA amplified from unidentified *mycobacterium* clinical strains.

PCR for DNA of clinical strains resulted in 16S rDNA target amplification and clear bands of molecular weight about 700 bp were visualized on 0.7% agarose gel electrophoresis. FIG. 20 shows the results of agarose gel electrophoresis of 16S rDNA amplified from unidentified *mycobacterium* clinical strains. Mycobacteria 16S rDNA PCR amplicons for 9 unidentified clinical strains were separated on 0.7% agarose gel, stained with ethidium bromide. PCR resulted in about 700 bp specific amplicons.

Semi-Nested PCR Amplification

Figure 21:
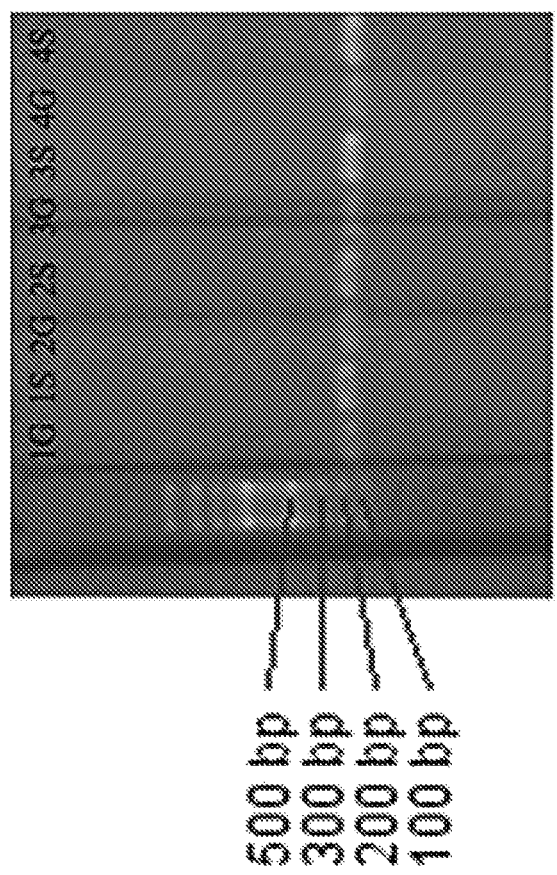
FIG. 21. Results of agarose gel electrophoresis of genus- and species-specific amplicons prepared by semi-nested PCR from unidentified mycobacteria clinical strains.

Semi-nested PCR was done to identify anonymous *mycobacterium* specimens before AuNPs detection and to prove the specificity of the selected oligotargeters. FIG. 21 shows the results of agarose gel electrophoresis of genus- and species-specific amplicons prepared by semi-nested PCR from unidentified mycobacteria clinical strains. Genus and species semi-nested PCR resulted in genus and species specific regions amplified confirming the isolates belong to *M. tuberculosis* complex.

Figure 22:
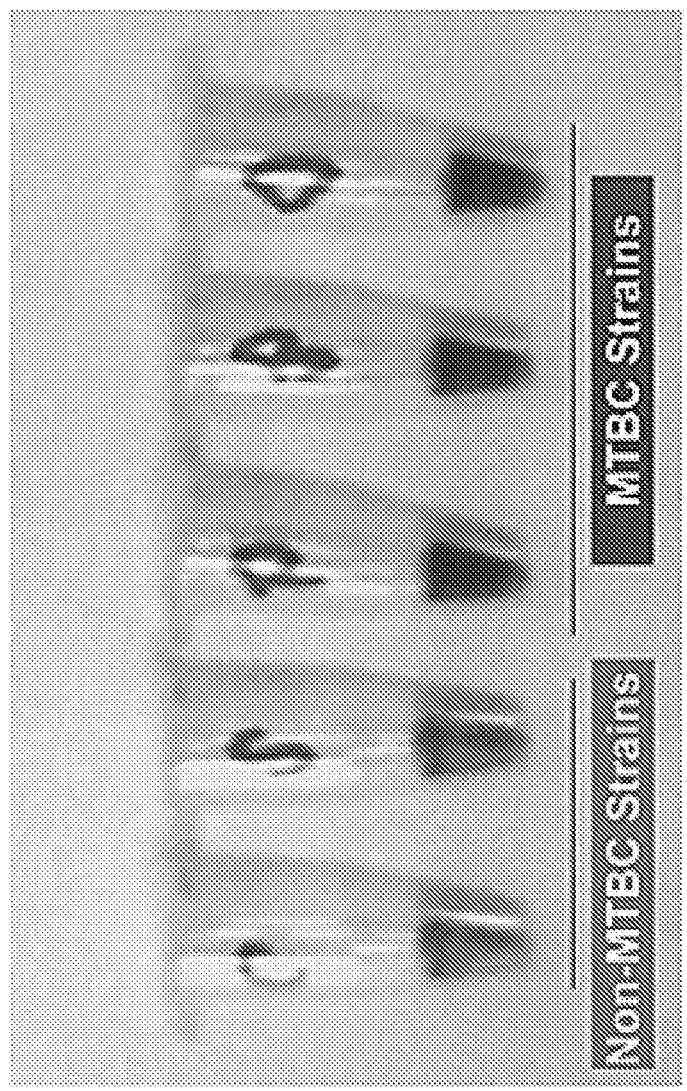
FIG. 22. Detection of MTBC in PCR Amplicons to differentiate MBTC from non-MBTC.

Assay Prototype 1: Detection Of MTBC in PCR Amplicons is shown by FIG. 22 illustrating the use of AuNPs for detection of PCR amplicons to differentiate MBTC from non-MBTC.

Figure 23:
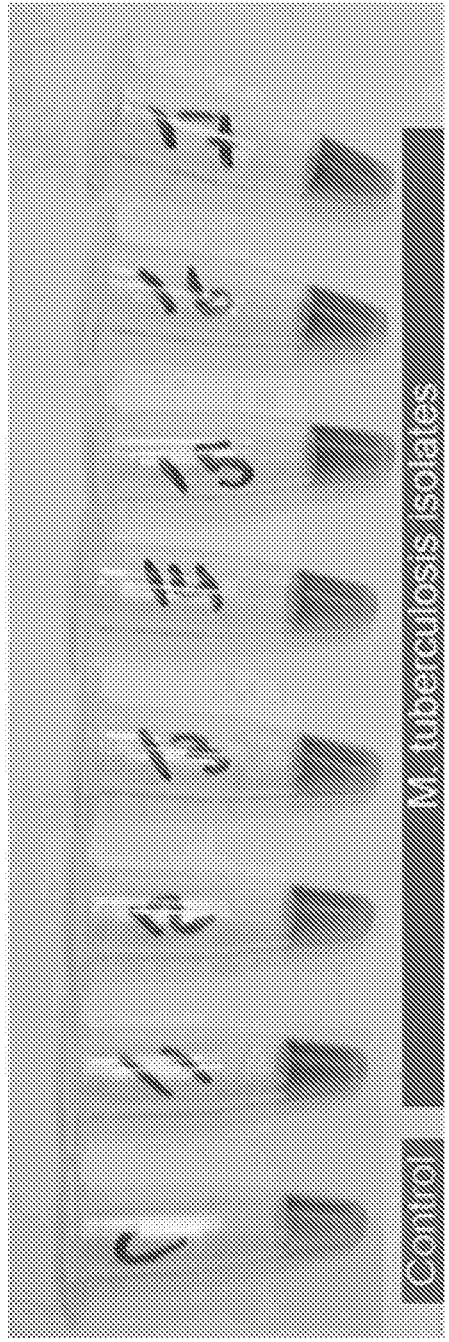
FIG. 23. Detection of MTBC in Genomic DNA.

Assay Prototype 2: Detection of MTBC in Genomic DNA is shown by FIG. 23 which depicts AuNPs detection of digested genomic DNA for 7/14 *M. tuberculosis* clinical isolates.

Assay Detection Limits are shown by FIG. 24.

Conclusions for Example 2

Unmodified spherical AuNPs were used for direct and quick detection of *Mycobacterium tuberculosis* complex DNA after PCR amplification. A second version of the assay detected TB DNA directly after restriction digestion of TB genomic DNA isolated from clinical specimens using a single oligotargeter that recognizes 16s rDNA gene segment. The assay detection limit was 1 ng for PCR product and 40 ng for digested genomic DNA. The assay showed 100% sensitivity and 100% specificity as compared with bacterial culture method (gold standard) and semi-nested PCR. The assay turnaround time is about 1 hour including sample digestion and detection of extracted DNA. The TB nano-gold assay is inexpensive and does not require sophisticated instruments or expensive reagents. It represents a promising front line test for diagnosing *Mycobacterium tuberculosis* complex. Pending further optimization, it can replace the Ziehl-Neelsen staining detection method in developing countries.

Example 2A

Colorimetric AuNPs Assay for Detecting Full Length Mycobacterial RNA in Clinical Specimens Targeting RNA sequences from mycobacteria presents several challenges due to the harsh assay conditions necessary required to lyse *Mycobacterium* cells and possible sample contamination with host RNA. Mycobacteria RNA sequences are detected under physical cell disruption condition or single step RNA extraction using guanidium thiocynate. This approach is applied to RNA obtained from isolates(colony) identification and to RNA obtained from clinical samples which contain a sufficient concentration of mycobacterial RNA and a sufficiently low concentration of host RNA. Oligotargeters and assay conditions are selected based on the quantity and quality of the RNA sample.

Example 2B

Detection of Mycobacterial DNA

Standard and Clinical Isolates used:
Standard strains:
*Mycobacterium smegmatis* (−ve M. tb complex)
*Mycobacterium* H37Ra (+ve M. tb complex)

Clinical Isolates:

Clinical isolates previously identified as mycobacteria tb were obtained from clinical Laboratory and were used to for testing

*Mycobacterium tuberculosis* strain B (+ve M.TB)

*Mycobacterium tuberculosis* strain D (+ve M.TB)

Strain Cultivation and DNA Extraction:

Strain cultivation and DNA extraction performed according to procedures previously described by Parish, et al. [16]. Purified DNA extract was then used as template for amplification of 16s rRNA gene target region.

PCR Amplification of Target Region

Genomic DNA extract was used to amplify the 16s rRNA gene target region using the primers TBF and TBR previously designed. The PCR product was visualized on agarose gel and analyzed the bands size confirmed by gel documentation using Lab Image software. PCR product was purified using Promega PCR clean up kit. M. Tb PCR Conditions are described by FIG. 25.

Nested PCR for detection of M. tb DNA. The specificity of the M. tb oligotargeters was confirmed by performing a second PCR using the first PCR as template (nested PCR) and the PCR product was visualized by gel electrophoresis as shown in FIG. 7 as further described by FIG. 26.

PCR Product Quantitation

PCR quantitation of amplicons was done through measuring spectroscopic absorbance for diluted samples (1/10) at 260 and 280 nm Example 2C Detection of TB DNA Extracted from Clinical Specimens Using AuNPs DNA was extracted from four different mycobacterial strains. Oligotargeters were added in hybridization buffer containing NaCl and the mixture was denatured, annealed, and allowed to cool to room temperature. AuNPs were then added and change in color was observed in tested specimens as shown in FIG. 6.

N=Negative Samples

S=*Smegmatis* (Non-*Mycobacterium* complex strain)

R=H37Ra standard strain (*Mycobacterium* complex Sample)

B, D=clinical isolates (*Mycobacterium* complex strain)

Detection Limit

Detection limit was determined by performing the assay on serial dilutions of PCR products. The detection limit was initially between 0.6-0.8 ng=0.0028-0.00373 pMol/ul respectively. Results for Example 2C are shown by FIG. 27.

Example 2D

Detection of Targets Directly from Mycobacterial Genomic DNA

After optimizing the assay on PCR template genomic DNA templates were evaluated using Mycobacteria DNA extract. Detection of the 16s rRNA gene target in genomic extract after novel treatment of the genomic extract was successful. Clear color change was observed between positive and negative samples.

Detection of *Mycobacterium Tuberculosis* DNA Using Gold Nanoparticles

Designing PCR Primers for the Required 16S rRNA Gene Part Using Vector NTI

Vector NTI v11 software was used to analyze the H37Ra sequence and to design PCR Primer to amplify the 16S rRNA gene target region. These primers were designated TBF (forward primer) and TBR (backward primer).

Confirming Specificity of 16SrRNA Gene Probes of Genus and Species Through Blasting on NCBI For proof of the inventors' concept, oligonucleotides described by Boddinghaus, B., T. Rogall, et al. (1990), *Detection and identification of mycobacteria by amplification of rRNA*. J. Clin. Microbiol. 28(8): 1751-1759 were used. These oligos were specific at the group, genus or species level and were used to develop a sensitive taxon-specific detection utilizing PCR. Two oligos were selected. The first one was specific to the mycobacteria genus and binds with all mycobacteria species thus differentiating mycobacteria from other strains. The second oligo was species specific differentiating pathogenic mycobacteria complex from non-*mycobacterium* complex strains. To confirm the specificity of the probes we performed blast against gene bank. These probes were designated TBG (genus probe) and TBS (species Probe). Both probes showed 100% specificity against their targets as shown by Blast results.

Example 2F

Identification of Highly-Specific Primers and Oligotargeters for *Mycobacterium* Genus Different primers and oligotargeters specific to different conserved regions in the genome Mycobacteria were designed; two overlapping regions in the 16S region, the ITS region, and the IS6110. The primers were designed using Vector NTI Advance® v. 11.5. The conserved regions were chosen based on the multiple alignment analysis performed against *Mycobacterium* genomes sequences published in NCBI Gene Bank. The determined conserved regions were used to design different specific primer pairs in addition to different oligotargeters. The alignment of the primers with the Mycobacteria genomes was performed using NCBI Nucleotide Blast, while that of the oligotargeters was performed using AlignX Vector NTI Advance® v. 11.5 and NCBI Nucleotide Blast. The oligotargeter sequences were run through a blast analysis against NCBI database to determine assess their specificity to different *mycobacterium* strains, and the respective degree of homology was determined.

The alignment of the primers with the Mycobacteria genomes was performed using NCBI Nucleotide Blast, while that of the oligotargeters was performed using AlignX Vector NTI Advance® v. 11.5 and NCBI Nucleotide Blast. The oligotargeter sequences were run through a blast analysis against NCBI database to determine assess their specificity to different *mycobacterium* strains, and the respective degree of homology was determined. selection criteria included:

a) Whole genome and selected region sequence alignments were done using sequences from GenBank.
b) Genomic regions such as 16s, 16s-23sITS region, and IS6110 known to contain conserved regions among mycobacteria genus and strains were targeted.
c) An untagged region that we have termed region-X was identified that was found to have high similarity in the mycobacterial complex strains.

d) Sequences that have very high similarity with mycobacteria were identified.
e) Sequences that contain SNPs and/or insertion-deletions were also identified that may allow specific targeting of certain mycobacterial strains.
f) BLAST analysis was then done to exclude any sequences that showed high similarity with other pathogens that may be present in the patient sample.
g) Sequences with low E-value (indicating that a particular sequence is actually present in mycobacteria and not by chance) were identified.
h) The specificity of the selected oligotargeters may be further improved by adjustment of hybridization conditions/stringency (including salt concentration and annealing temperature).

I. 16S Conserved Region

Different pairs of primers were designed targeting two conserved regions (region 1 and 2) in the 16S region of *Mycobacterium* genus using Vector NTI Advance® v. 11.5. The conserved regions were chosen based on the multiple alignment analysis performed against *Mycobacterium* genomes sequences published in NCBI Gene Bank. The determined conserved 16S regions were used to design the six primer pairs in addition to three different oligotargeters. The oligotargeters are specific for sequences within the amplicons produced by any of the primer pairs. Oligotargeters were found to have high degrees of homology only with pathogenic *mycobacterium* species.

ITS Conserved Region

Three different pairs of primers were designed targeting the conserved ITS region of *Mycobacterium* genus, in addition to five different oligotargeters. The oligotargeters are specific for sequences within the amplicons produced by any of the three primer pairs. One of the five oligotargeters (MycCompITS.1) is specific to *mycobacterium tuberculosis* complex, while the others are specific to the *mycobacterium* genus.

Example 3

Oligotargeter Design for West Nile Virus (WNV)

WNV Oligotargeter Design

The inventors have developed specific oligotargeter sequences for identifying WNV using the gold nanoparticle-based methods described herein. These oligotargeter sequences are shown by SEQ ID NOS: 539 (4603-5131 target), 550 (5'UTR), 551-553 (Mat_Peptide_2), 554-555 (Mat_Peptide_1), 556-557 (Mat_Peptide_3), 558-563 ((Mat_Peptide_5), 564-569 (Mat_Peptide_6), 570-571 (Mat_Peptide_7), 572-573 (Mat_Peptide_8), 574-581 (Mat_Peptide_9), 582-583 (Mat_Peptide_10), 584-587 (Mat_Peptide_12), 588-596 (Mat_Peptide_13) and 597-601 (3'UTR).

These sequences were developed using the multiple sequence alignment too AlignX Vector NTI Advance® v. 11.5. Sample results are shown in FIG. 9. The following West Nile virus complete genome were retrieved from NCBI Nucleotide database in FASTA format and used in multiple sequence alignment to identify conserved region suitable for Oligotargeter. GenBank Identifier (GI) numbers of the sequences used in alignment:
GI:315259427, GI:21929238, GI:21929234, GI:21929240, GI:21929236, GI:21929232, GI:21929232, GI:374670387, GI:374670383, GI:374670379, GI:374670375, GI:374670371, GI:374670367, GI:374670363, GI:374670359, GI:374670355, GI:374670351, GI:374670389, GI:374670381, GI:374670377. URL address: http://_www.ncbi.nlm.nih.gov/nuccore?term=west%20nile%20virus%20complete%20genome.

Blast analysis employed the NCBI blast engine http://_www.ncbi.nlm.nih.gov/Database: Human genome and Transcript and Nucleotide (nr/nt), RNA reference sequence.

The multiple sequence alignment was examined for conserved region, GC % content and Tm. Genomic regions showed high similarity and conservation among strains in addition to suitable GC content and melting temperature were chosen for oligotargeter design. Since detection of West Nile Virus will take place in serum samples interference with *Homo sapiens* genomic material is expected. Selected conserved regions were then blasted against Nucleotide collection Database (nr/nt) using NCBI blast to evaluate oligotargeter specificity. The oligotargeter sequence was also blasted against human genome and transcript database and reference RNA database to evaluate the interference of the human chromosomal element DNA or RNA with the probe functionality. PCR primers were evaluated by NCBI Primer blast.

An example of how WNV virus oligotargeter sequences were developed is shown in FIG. 9 which depicts the alignment of oligotargeter sequence WNV Targ 1 ACATAAGCGCGATAGTGCAGGGTGAAAGGATGG (SEQ ID NO: 549). Similar strategies were used to identify oligotargeter sequences of *Acinetobacter, Mycobacterium, Staphylococcus aureus* (MRSA), HBV, HIV and Influenza A virus.

Example 4

Synthesis of AuNPs

A colloidal solution of AuNPs with a diameter of 15 nm±2 was prepared by citrate reduction of hydrogen tetracloroaurate (III) (HAuCl$_4$. 3H$_2$O) as described elsewhere [16]. Briefly, the reflux system was cleaned by aqua regia and then rinsed with ultrapure water, and blown out with N$_2$. An aqueous solution of HAuCl$_4$.3H$_2$O (1 mM, 100 mL) was brought to reflux while stirring, then 10 mL of 1% trisodium citrate (38.8 mM) were added quickly. This resulted in consequent change in solution color from yellow to clear to black to purple to deep red. Afterwards, the solution was refluxed for an additional 15 minutes and then allowed to cool to room temperature. The colloidal solution was then filtered through 0.45 μm acetate filter, and transferred into a clean storage glass bottle.

The size and distribution of the prepared AuNPs were characterized using field emission scanning electron microscopy (Model: Leo Supra 55). One drop of the AuNPs solution was added onto a silicon slide that was allowed to air dry before examination. The $\lambda_{max}$ for AuNPs was measured using UV spectrophotometer (Jenway 6800). The concentration of the prepared AuNPs was calculated as described previously, which is incorporated by reference.

Example 5

Sample Collection and Processing

Sample Type & Nucleic Acid Extraction

*Acinetobacter*

Different types of samples will be collected from infected patients (*Acinetobacter* identified phenotypically on selective media and/or PCR-positive) and normal controls (non-infected healthy volunteers, *Acinetobacter* identified phenotypically on selective media and/or PCR negative) including urine, sputum, and whole blood. DNA extraction will be performed using either commercial DNA extraction kit or standard DNA extraction procedures. In both cases, DNA extraction procedures steps will include; cell lysis, protein removal, DNA precipitation and recovery, and finally DNA resuspension.

*Mycobacterium tuberculosis*

Various kinds of samples may be collected including sputum and other bacterial isolates. DNA extraction will be performed using either commercial DNA extraction kit or standard DNA extraction procedures. In both cases, DNA extraction procedures steps will include; cell lysis, protein removal, DNA precipitation and recovery, and finally DNA resuspension.

Methicillin-Resistant *Staphylococcus Aureus* (MRSA)

Different types of samples will be collected from infected patients/carriers (MRSA was identified phenotypically on selective media and antibiogram and/or PCR-positive) and normal controls (non-infected healthy volunteers, MRSA identified phenotypically on selective media and antibiogram and/or PCR negative) including swabs from anterior nares, throat, perineum, rectum and wounds and sputum of ventilated patients. Swabs will be taken using sterile cotton or Dacron swabs that will be placed in a liquid buffered medium for transportation to the laboratory. Samples should be refrigerated while transported and analyzed within 5 days. Bacterial cells from swabs will be lysed and genomic DNA extracted using QIAGEN Genomic DNA extraction kit according to manufacturer's instructions[38]. Overnight enrichment (culture) will be performed in samples prior to lysis if needed.

Hepatitis B Virus (HBV)

Serum samples from HBV PCR positive patients and healthy individuals (HBV PCR negative) will be collected, transported (refrigerated) and stored at −80° C. for a maximum of 5 days prior to DNA extraction. DNA extraction will be performed using QIAamp DNA Blood Mini Kit (Qiagen) according to manufacturer's protocol.

Human Immunodeficiency Virus (HIV)

Serum samples from HIV PCR positive patients and healthy individuals (HIV PCR negative) will be collected, transported (refrigerated) and stored at −80° C. for a maximum of 5 days prior to DNA extraction. Viral RNA will be extracted using Promega SV total RNA isolation system using a modified protocol.

Influenza A (H1N1 & H5N1)

The most appropriate sample for testing for influenza virus is from upper respiratory tract e.g. nasal or nasopharyngeal swabs. Swabs will be collected from infected birds/humans (H5N1, H1N1; PCR-positive) and normal controls (PCR negative). Samples can be stored for up to 72 hours at 4° C., and ideally, they should be tested within 24 hours of collection. For long term storage beyond 72 hours, samples should be stored −70° C.[31]. Viral RNA will be extracted using Promega SV total RNA isolation system using a modified protocol.

West Nile Virus (WNV)

Serum and cerebrospinal fluid can be used for the detection of WNV.

Example 6

Synthesis and Functionalization of Colloidal Silica Nanoparticles

Microbial nucleic acids were extracted using colloidal silica nanoparticles conjugated to an oligonucleotide specific to the target nucleic acid. First, 200 nm colloidal silica nanoparticles were synthesized with a modified Stober method. Briefly, absolute ethanol, deionized water, concentrated ammonia and tetraethyl ortho-silicate (TEOS) were mixed and stirred at room temperature for about 1 hour. Then, the formed colloidal solution was centrifuged at 4,000 rpm for 10 minutes, and the supernatant was discarded and the pellet was washed with absolute ethanol. This washing step was repeated for about 4 times or until no ammonia odor in the solution. The pellet was then dispersed in absolute ethanol and sonicated for about 5 minutes to remove any aggregates. The produced silica nanoparticles were examined using Scanning Electron Microscope (SEM), to get the morphology and the diameter of the prepared silica nanoparticles.

The prepared silica nanoparticles were functionalized with Amino Propyl Trimethoxy Silane (APMS) to introduce amino groups on the surface of the silica nanoparticles. Briefly, 1 ml of APMS was added to 20 ml of the prepared colloidal silica nanoparticles and stirred at room temperature for at least 2 hours, then the solution was centrifuged at 4,000 rpm for 10 minutes, and the supernatant was discarded and the pellet resuspended in phosphate buffer saline (PBS 1x). The number of silica nanoparticles per ml was calculated. Briefly, one mL of the prepared silica colloidal solution was taken centrifuged, and the supernatant was discarded, then the pellet was dried till complete dryness. The dried pellet was then weighted in milligrams and from the volume taken (1 ml) and the weight obtained, concentration of the colloidal solution has been calculated which is 12 mg/ml. The diameter of the silica nanoparticles was measured to be about 150 nm. The weight of one particle equals volume of the particle*specific gravity (2.3), the volume equals $4/3 \pi r3$, and the particles count equals concentration (12 mg/ml)/weight of one particle equals 2.95125E+12 silica nanoparticles/mL.

Synthesis of Silica Probes

To prepare silica probe, heterobifunctional cross linker (3-maleimidobenzoic acid N-hydroxyl succinimide, MBS) that has NHS ester at one end which reacts with primary amine groups to form stable amide bond, The other end has maleimide group which reacts with sulfhydryl groups, therefore the cross linker bound to the amine functionalized silica nanoparticles through the NHS ester and to thiolated probe through the maleimide group and HCV specific probe conjugated to silica nanoparticles was prepared. The thiol labeled probe was prepared as previously described. 10 mg of MBS dissolved in 1 ml dimethyl formamide plus 2.5 ml PBS and 2.5 ml of amino functionalized silica nanoparticles and mix at room temperature for at least 2 hours, and then purified by centrifugation, the thiol modified probe was added to the MBS conjugated silica nanoparticles and incubate at room temperature for at least 2 hours. The number of probes per one silica nanoparticle was calculated by first multiplying the number of moles of the probe by Avogadro's number, and then dividing the number of probes calculated by the silica nanoparticles count, and it was about 500 probes per one silica nanoparticle.

Extraction of Microbial Nucleic Acids from Clinical Samples Using the Prepared Silica Probes To 200 µL of clinical specimen, 200 µL of lysis buffer (Promega SV viral RNA) was added. After mixing by inversion, 50 µL Proteinase K (or other reagents according to the type of the clinical specimens) was added and left to incubate for 10 min. The mixture was heated to 95° C. in a heat block for 2 min then 50 µL silica-probes was added and the reaction mixed for 1 hr. The mixture was centrifuged at 3000 RPM for 3 min and the pellet was washed twice with nuclease-free water. The target nucleic acids were then eluted by heating at 95° C. for 5 min. The mixture was centrifuged and the supernatant contained the eluted nucleic acid was separated. The extracted nucleic acid was tested using both Real-time RT-PCR and the developed colorimetric AuNP-based assay.

Listing of Sense, Antisense and Oligotargeter Sequences
*Acinetobacter* Primers & Oligotargeters
16S Region: Primers & Oligotargeters

| SEQ ID Number | Type | sequence | target |
|---|---|---|---|
| 1. | Sense Primer | AGTCGAGCGGGGG AAGGTAGCTT | 16S Region |
| 2. | Sense Primer | TTTGATCATGGCT CAGATTGAACGC | 16S Region |
| 3. | Sense Primer | GATGCTAATACCG CATACGTCCTACG | 16S Region |
| 4. | Sense Primer | GACTGAGACACGG CCCAGACTCCTA | 16S Region |
| 5. | Sense Primer | CCTAGAGATAGTG GACGTTACTCGCA | 16S Region |
| 6. | Sense Primer | AACTTGGGAATTG CATTCGATACTG | 16S Region |
| 7. | Sense Primer | CGAAAGCATGGGG AGCAAACAGGAT | 16S Region |
| 8. | Sense Primer | AAATGAATTGACG GGGGCCCGCACAA GCG | 16S Region |
| 9. | Sense Primer | GTGTCGTGAGATG TTGGGTTAAGTCC | 16S Region |
| 10. | Sense Primer | ACACACGTGCTAC AATGGTCGGTAC | 16S Region |
| 11. | Sense Primer | ATACGTTCCCGGG CCTTGTACACAC | 16S Region |
| 12. | Antisense primer | TCACCCCAGTCAT CGGCCACA | 16S Region |
| 13. | Antisense primer | TCTAGGTGATCCA GCCGCAGGTTCCC CTAC | 16S Region |
| 14. | Antisense primer | GAACGTATTCACC GCGGCATTCTGA | 16S Region |
| 15. | Antisense primer | TTGTAGCACGTGT GTAGCCCTGGCC | 16S Region |
| 16. | Antisense primer | TCTCACGACACGA GCTGACGACAGC | 16S Region |
| 17. | Antisense primer | GTGCGGGCCCCCG TCAATTCATTTG | 16S Region |
| 18. | Antisense primer | GCTCCCCATGCTT TCGTACCTCAGC | 16S Region |
| 19. | Antisense primer | GCTCACCAGTATC GAATGCAATTCCC | 16S Region |
| 20. | Antisense primer | GCGAGTAACGTCC ACTATCTCTAGGT | 16S Region |
| 21. | Antisense primer | CTCAGTCCCAGTG TGGCGGATCATC | 16S Region |
| 22. | Antisense primer | GCGGTATTAGCAT CCCTTTCGAGATG | 16S Region |
| 23. | Oligotargeter | GCATACGTCCTAC GGGAGAAAGCAGG GGAT | 16S Region |
| 24. | Oligotargeter | GCAGGGGATCTTC GGACCTTGCGCTA ATAG | 16S Region |
| 25. | Oligotargeter | CCTACCAAGGCGA CGATCTGTAGCGG GTCTGAGAGGA | 16S Region |
| 26. | Oligotargeter | GACGATCTGTAGC GGGTCTGAGAGGA TGATCC | 16S Region |
| 27. | Oligotargeter | CGGGTCTGAGAGG ATGATCCGCCACA CTGGGACTGAGAC A | 16S Region |
| 28. | Oligotargeter | GGGTCTGAGAGGA TGATCCGCCACAC TGGGACTGAGA | 16S Region |
| 29. | Oligotargeter | GGTCTGAGAGGAT GATCCGCCACACT GGGACTGAGA | 16S Region |
| 30. | Oligotargeter | TGAGAGGATGATC CGCCACACTGGGA CTGAGACACG | 16S Region |
| 31. | Oligotargeter | CCAGACTCCTACG GGAGGCAGCAGTG GGGAATATTG | 16S Region |
| 32. | Oligotargeter | TCCTACGGGAGGC AGCAGTGGGGAAT ATTGGACAATGG | 16S Region |
| 33. | Oligotargeter | GGGAACCCTGATC CAGCCATGCCGCG TGTGTGAAGAA | 16S Region |
| 34. | Oligotargeter | CCCTGATCCAGCC ATGCCGCGTGTGT GAAGAAGGCCTTA | 16S Region |
| 35. | Oligotargeter | ATCCAGCCATGCC GCGTGTGTGAAGA AGGCCTTATG | 16S Region |
| 36. | Oligotargeter | GCCATGCCGCGTG TGTGAAGAAGGCC TTATGGTTGT | 16S Region |
| 37. | Oligotargeter | GTGGACGTTACTC GCAGAATAAGCAC CGGC | 16S Region |
| 38. | Oligotargeter | CTAACTCTGTGCC AGCAGCCGCGGTA ATAC | 16S Region |
| 39. | Oligotargeter | GGGAGAGGATGGT AGAATTCCAGGTG TAGCGG | 16S Region |
| 40. | Oligotargeter | CCAGGTGTAGCGG TGAAATGCGTAGA GATCTGGAGG | 16S Region |

-continued

| SEQ ID Number | Type | sequence | target |
|---|---|---|---|
| 41. | Oligotargeter | GCGGTGAAATGCGTAGAGATCTGGAGGAATACCGATGGCG | 16S Region |
| 42. | Oligotargeter | TGCGTAGAGATCTGGAGGAATACCGATGGCGAAGGC | 16S Region |
| 43. | Oligotargeter | GAGATCTGGAGGAATACCGATGGCGAAGGC | 16S Region |
| 44. | Oligotargeter | AGAGTTTGATCATGGCTCAGATTGAACGCT | 16S Region |
| 45. | Oligotargeter | GCAGCCATCTGGCCTAATACTGACGCTGAG | 16S Region |
| 46. | Oligotargeter | ACTGACGCTGAGGTACGAAAGCATGGGGAG | 16S Region |
| 47. | Oligotargeter | GGCCTTTGAGGCTTTAGTGGCGCAGCTAAC | 16S Region |
| 48. | Oligotargeter | GCCTGGGGAGTACGGTCGCAAGACTAAAAC | 16S Region |
| 49. | Oligotargeter | TGGTGCCTTCGGGAATCTAGATACAGGTGCTGCATGGC | 16S Region |
| 50. | Oligotargeter | GGTGCMCGGGAATCTAGATACAGGTGCTGCATGG | 16S Region |
| 51. | Oligotargeter | CCTTCGGGAATCTAGATACAGGTGCTGCATGGCTGTCG | 16S Region |
| 52. | Oligotargeter | CTGCATGGCTGTCGTCAGCTCGTGTCGTGAGATGTT | 16S Region |
| 53. | Oligotargeter | TGCATGGCTGTCGTCAGCTCGTGTCGTGAGATGTTG | 16S Region |
| 54. | Oligotargeter | CAGTGACAAACTGGAGGAAGGCGGGGACGACGTCAA | 16S Region |
| 55. | Oligotargeter | TGGAGGAAGGCGGGGACGACGTCAAGTCATCATGGCCCTT | 16S Region |
| 56. | Oligotargeter | GGGACGACGTCAAGTCATCATGGCCCTTAC | 16S Region |
| 57. | Oligotargeter | CCTTACGGCCAGGGCTACACACGTGCTACAATGGTC | 16S Region |
| 58. | Oligotargeter | TACGGCCAGGGCTACACACGTGCTACAATG | 16S Region |
| 59. | Oligotargeter | CGTAGTCCGGATTGGAGTCTGCAACTCGAC | 16S Region |
| 60. | Oligotargeter | GGTGAATACGTTCCCGGGCCTTGTACACAC | 16S Region |
| 61. | Oligotargeter | CCTAACTGCAAAGAGGGCGGTTACCACGGT | 16S Region |
| 62. | Oligotargeter | CTAACTGCAAAGAGGGCGGTTACCACGGTG | 16S Region |
| 63. | Oligotargeter | GGTGTGGCCGATGACTGGGGTGAAGTCGTAACAAGG | 16S Region |
| 64. | Oligotargeter | GTGTGGCCGATGACTGGGGTGAAGTCGTAACAAGGT | 16S Region |
| 65. | Oligotargeter | GTGGCCGATGACTGGGGTGAAGTCGTAACAAGGTAG | 16S Region |
| 66. | Oligotargeter | GCCGATGACTGGGTGAAGTCGTAACAAGG | 16S Region |

*Acinetobacter* ITS Region: Primers & Oligotargeters

| SEQ ID NO: Number | Type | sequence | target |
|---|---|---|---|
| 67. | Sense Primer | GGCTGGATCACCTCCTTAACGAAAG | ITS Region |
| 68. | Sense Primer | GGGGTGAAGTCGTAACAAGGTAGCC | ITS Region |
| 69. | Antisense primer | TCACGTCTTTCATCGCCTCTGACTG | ITS Region |
| 70. | Antisense primer | GAGATGTTTCACTTCCCCTCGTTCG | ITS Region |
| 71. | Oligotargeter | GGGACTTAGCTTAGTTGGTAGAGCGCCTGC | ITS Region |
| 72. | Oligotargeter | AACAAGTTGTTCTTCATAGATGTATCTGAGGGT | ITS Region |
| 73. | Oligotargeter | GGTATGTGAATTTAGATTGAAGCTGTACGGT | ITS Region |
| 74. | Oligotargeter | GCGTTTTGGTATGTGAATTTAGATTGAAGC | ITS Region |
| 75. | Oligotargeter | ACTGAATCAAGCGTTTTGGTATGTGAATTT | ITS Region |
| 76. | Oligotargeter | TAGCAAATTAACTGAATCAAGCGTTTTGGT | ITS Region |
| 77. | Oligotargeter | AATTGAGAACTAGCAAATTAACTGAATCAAGCG | ITS Region |
| 78. | Oligotargeter | TGTTCACTCAAGAGTTTAGGTTAAGCAATTAATC | ITS Region |

-continued

| SEQ ID NO: Number | Type | sequence | target |
|---|---|---|---|
| 79. | Oligotargeter | AAATAAATTGTTCACTCA AGAGTTTAGGTTAAGCA | ITS Region |
| 80. | Oligotargeter | TTGGCAAAATTGAGTCTG AAATAAATTGTTC | ITS Region |
| 81. | Oligotargeter | CTCATTAACAGATTGGCA AAATTGAGTCTG | ITS Region |
| 82. | Oligotargeter | TCACGGTAATTAGTGTGA TCTGACGAAGAC | ITS Region |

*Acinetobacter* 23S Region: Primers & Oligotargeters

| SEQ ID Number | Type | sequence | target |
|---|---|---|---|
| 83. | Sense Primer | TATAGTCAAGTAATTAAGTG CATGTGGTGG | 23S Region |
| 84. | Sense Primer | GGTAGCTATGTTCGGAAGGG ATAACC | 23S Region |
| 85. | Sense Primer | GCCATCGCTCAACGGATAAA AGGTACTC | 23S Region |
| 86. | Sense Primer | AGGTGGGAGGCTTTGAAGCT GGAAC | 23S Region |
| 87. | Sense Primer | GGACGTATAGGGTGTGATGC CTGCC | 23S Region |
| 88. | Sense Primer | GGGGTACTCTATGCTGAGAT CTGATAGC | 23S Region |
| 89. | Sense Primer | GTGTGTTGAGAAGCATGCTG GAGGTA | 23S Region |
| 90. | Sense Primer | CCAAACCGATGCAAACTCCG AATACC | 23S Region |
| 91. | Sense Primer | GTATAGGGGAGCCGTAGAGA AATCG | 23S Region |
| 92. | Sense Primer | GGAAGTGCGAACGTAGAGGG TGATA | 23S Region |
| 93. | Sense Primer | GTCAAGTAATTAAGTGCATG TGGTG | 23S Region |
| 94. | Antisense Primer | TTGGGTGTTGTATAGTCAAG CCTCAC | 23S Region |
| 95. | Antisense primer | TTGGGTGTTGTATAGTCAAG CCTCA | 23S Region |
| 96. | Antisense primer | CCCTCGTTCGCCTTGCAACA CTATGTAT | 23S Region |
| 97. | Antisense primer | TCACAGGGGTTCTTTTCGCC TTTCC | 23S Region |
| 98. | Antisense primer | GGCTTGATTAGCCTTTCACC CCTATC | 23S Region |
| 99. | Antisense primer | CCGACTCGACTAGTGAGCTA TTACGCTTTC | 23S Region |
| 100. | Antisense primer | ACACAGAAGTAATGGAATAT TAACCA | 23S Region |
| 101. | Antisense primer | CCCGAAGTTACGGTACCATT TTGCC | 23S Region |
| 102. | Antisense primer | TCACTGAGCCTCTGCTGGAG ACAGC | 23S Region |
| 103. | Antisense primer | ACGCTGAGCGCACCTTCGTA CTCCT | 23S Region |
| 104. | Antisense primer | TGTCTCACGACGTTCTAAAC CCAGC | 23S Region |
| 105. | Oligotargeter | GGTGTTGTATAGTCAAGCCT CACGAGCA | 23S Region |
| 106. | Oligotargeter | TTAGGTTAAGCAATTAATCT AGATGAA | 23S Region |
| 107. | Oligotargeter | GGATTACAGAAATTAGTAAA TAAAGATTGA | 23S Region |
| 108. | Oligotargeter | CAGTAGCGAGGTTAACCGTA TAGGGGAGCC | 23S Region |
| 109. | Oligotargeter | GATCCTGAAACCGCATGCAT ACAAGCAGTGGGAGCACC | 23S Region |
| 110. | Oligotargeter | CTGACCGATAGTGAACCAGT ACCGTGAGGG | 23S Region |
| 111. | Oligotargeter | GGGGACCATCCTCCAAGGCT AAATACTCCTGACTGACC | 23S Region |
| 112. | Oligotargeter | CACGAAAGGGCACACATAAT GATGACGAGTAGGGCGAGGC | 23S Region |
| 113. | Oligotargeter | GCTCTGGGAAGTGCGAACGT AGAGGGTGAT | 23S Region |
| 114. | Oligotargeter | GCAAGGCGAACGAGGGGAAG TGAAACATCTCAGTACCC | 23S Region |
| 115. | Oligotargeter | GGCGATGAAAGACGTGATAG CCTGCGAAAAGCTCCG | 23S Region |
| 116. | Oligotargeter | TACACAGGAATCGTACCCGA AACCGACACAGGTGGTCAGG | 23S Region |
| 117. | Oligotargeter | CCCCTAAGGCGAGGCCGAAA GGCGTAGTCGATGGGAAAA | 23S Region |
| 118. | Oligotargeter | CCCGTTCGCCGAAAGACCAA GGGTTCCAGTCCAACGT | 23S Region |
| 119. | Oligotargeter | GTATACGTGGTAGGGGAGCG TTCTGTAAGCCG | 23S Region |
| 120. | Oligotargeter | GCGTAATAGCTCACTAGTCG AGTCGGCCTG | 23S Region |
| 121. | Oligotargeter | CGATGTGGGAAGGCATAGAC AGCTAGGAGG | 23S Region |
| 122. | Oligotargeter | GTGTCTGGTGGGTAGTTTGA CTGGGGCGGTCTCCTCCTA | 23S Region |
| 123. | Oligotargeter | GTTCCAGTGGAGCCGTCCTT GAAATACCACCCTGGT | 23S Region |
| 124. | Oligotargeter | GTGTAGGATAGGTGGGAGGC TTTGAAGCTGGAACGC | 23S Region |
| 125. | Oligotargeter | CGCTGTCTCCAGCAGAGGCT CAGTGAAATC | 23S Region |

| SEQ ID Number | Type | sequence | target |
|---|---|---|---|
| 126. | Oligotargeter | TGGCATAATGATGGCGGCGC TGTCTCCAGCAGAGGCT | 23S Region |

5S rRNA region with intragenic region between 23S and 5S
Primers & Oligotargeters

| SEQ ID Number | Type | sequence | target |
|---|---|---|---|
| 127. | Sense Primer | CGTGAGGCTTGACTA TACAACACCC | 5S rRNA |
| 128. | Sense Primer | GCAGTTGTATATAAA GCATCAATCG | 5S rRNA |
| 129. | Antisense primer | TGAGCTGGCGATGAC TTACTCTCACA | 5S rRNA |
| 130. | Antisense primer | GAGCTGGCGATGACT TACTCTCACAT | 5S rRNA |
| 131. | Oligotargeter | GTGAACCACCTGATC CCTTCCCGAACTCAG | 5S rRNA |
| 132. | Oligotargeter | GCTGGCGACCATAGC AAGAGTGAACCACCT | 5S rRNA |

Insertion Sequence ISAba1, Complete Sequence; and OXA-23 Carbapenemase (Oxa-23) Gene
Primers & Oligotargeters

| SEQ ID Number | Type | sequence | target |
|---|---|---|---|
| 133. | Sense Primer | CTCTGTACACGACAAATTTC ACAGA | ISAba1-OXA-23 |
| 134. | Sense Primer | CTCTGTACACGACAAATTTC ACAGAA | ISAba1-OXA-23 |
| 135. | Sense Primer | CCATTTAGTGAAAAAGTGCA GGCTA | ISAba1-OXA-23 |
| 136. | Sense Primer | GATCGGATTGGAGAACCAGA AAACGG | ISAba1-OXA-23 |
| 137. | Sense Primer | AGAGCTCTTTTTTATTTTCT ATTGATC | ISAba1-OXA-23 |
| 138. | Sense Primer | CAACTGAGAAATTTGACGAT AATCA | ISAba1-OXA-23 |
| 139. | Sense Primer | AATGCAGAAGTTGATGTCTT GTTCA | ISAba1-OXA-23 |
| 140. | Sense Primer | AGGGTCTGTCAAGCGCGTAT TTCCA | ISAba1-OXA-23 |
| 141. | Sense Primer | ACAATGGTTCTCCAATATTC GCGGG | ISAba1-OXA-23 |
| 142. | Antisense primer | TCAAGCTCTTAAATAATATT CAGCTG | ISAba1-OXA-23 |
| 143. | Antisense primer | CAAGCTCTTAAATAATTCC AGCTGTTT | ISAba1-OXA-23 |
| 144. | Antisense primer | GCGGTGTTAGCTATAAGCTT CTGTT | ISAba1-OXA-23 |
| 145. | Antisense primer | TGTCACCAATCATTTAGGAA AGAAT | ISAba1-OXA-23 |
| 146. | Antisense primer | GACCAAGTGCAACTGACTTT AGATA | ISAba1-OXA-23 |
| 147. | Antisense primer | AATAGATAACTCATTGAAAT AATGTCATAA | ISAba1-OXA-23 |
| 148. | Antisense primer | TTAAATGTAGAGGCTGGCAC ATATT | ISAba1-OXA-23 |
| 149. | Antisense primer | GGAAACAAACTCTACCTCTT GAATA | ISAba1-OXA-23 |
| 150. | Antisense primer | TTTATAAAATTAGAGTTTCT GTCAAGCT | ISAba1-OXA-23 |
| 151. | Oligotargeter | CCAATTAAACGCTGAATCGC CATTTGAACA | ISAba1-OXA-23 |
| 152. | Oligotargeter | AAAACCAATTAAACGCTGAA TCGCCATTTG | ISAba1-OXA-23 |
| 153. | Oligotargeter | CCCTTATCCTATCAGGATTC TGCCTTCTTA | ISAba1-OXA-23 |
| 154. | Oligotargeter | CTCTGTACACGACAAATTTC ACAGAACCCT | ISAba1-OXA-23 |
| 155. | Oligotargeter | TTCCACGATAAACGATTGCG AGCATCAGGA | ISAba1-OXA-23 |
| 156. | Oligotargeter | CAATGTCCAAAGGATAGGTA TCGCTATTCC | ISAba1-OXA-23 |
| 157. | Oligotargeter | CTGAATTTCCACGTTTATTA AGCAATGTCC | ISAba1-OXA-23 |
| 158. | Oligotargeter | AAAATGGCTATAAAGCGTTG AATCAAAGCA | ISAba1-OXA-23 |
| 159. | Oligotargeter | CTGCGAACACATTCACAATA CGGTCMAC | ISAba1-OXA-23 |
| 160. | Oligotargeter | TCACCGATAAACTCTCTGTC TGCGAACACA | ISAba1-OXA-23 |
| 161. | Oligotargeter | ACACGAATGCAGAAGTTGAT GTCTTGTTCA | ISAba1-OXA-23 |
| 162. | Oligotargeter | CGCAAAGCACTTTAAATGTG ACTTGTTCCA | ISAba1-OXA-23 |
| 163. | Oligotargeter | GAGCGCAAAGCACTTTAAAT GTGACTTGTT | ISAba1-OXA-23 |
| 164. | Oligotargeter | GATGAGCGCAAAGCACTTTA AATGTGACTT | ISAba1-OXA-23 |
| 165. | Oligotargeter | ATGATGAGCGCAAAGCACTT TAAATGTGAC | ISAba1-OXA-23 |
| 166. | Oligotargeter | ATAATCACAAGCATGATGAG CGCAAAGCAC | ISAba1-OXA-23 |
| 167. | Oligotargeter | TTTAAAATAATCACAAGCAT GATGAGCGCA | ISAba1-OXA-23 |
| 168. | Oligotargeter | TCCCAGTCTATCAGGAACTT GCGCGACGTATCGGTC | ISAba1-OXA-23 |

| SEQ ID Number | Type | sequence | target |
|---|---|---|---|
| 169. | Oligotargeter | AGCTTTCTGCAGTCCCGTCT ATCAGGAACTTGCGCGACG | ISAba1-OXA-23 |

Mycobacteria Primer and Oligotargeter Sequences
16s rRNA Region: Primers & Probes

| SEQ ID Number | Type | Sequence | target |
|---|---|---|---|
| 170. | Sense Primer | GGGAAACTGGGTCTAATACC GGATAGG | 16S Region |
| 171. | Sense Primer | AAACTGGGTCTAATACCGGA TAGGACCA | 16S Region |
| 172. | Sense Primer | GCGTGGCCGTTTGTTTTGTC AGGAT | 16S Region |
| 173. | Sense Primer | CCCTTTTCCAAAGGGAGTGT TTGGG | 16S Region |
| 174. | Sense Primer | GACGACGGGTAGCCGGCCTG AGAGG | 16S Region |
| 175. | Sense Primer | TAGGTGGTTTGTCGCGTTGT TCGTG | 16S Region |
| 176. | Sense Primer | CTAACGCATTAAGTACCCCG CCTGG | 16S Region |
| 177. | Sense Primer | GGAAGGTGGGGATGACGTCA AGTCA | 16S Region |
| 178. | Sense Primer | GACGAAGTCGTAACAAGGTA GCCGT | 16S Region |
| 179. | Antisense primer | TTTACGCCCAGTAATTCCGG ACAAC | 16S Region |
| 180. | Antisense primer | AATTCCGGACAACGCTCGCA | 16S Region |
| 181. | Antisense primer | CCAGTAATTCCGGACAACGC TCG | 16S Region |
| 182. | Antisense primer | TTCCAGTCTCCCCTGCAGTA CTCTAGTC | 16S Region |
| 183. | Antisense primer | GAATTCCAGTCTCCCCTGCA GTACTCT | 16S Region |
| 184. | Antisense primer | TTCCAGTCTCCCCTGCAGTA CTCTAGTC | 16S Region |
| 185. | Antisense primer | CTTAGAAAGGAGGTGATCCA GCCGCAC | 16S Region |
| 186. | Antisense primer | TTGGGGCGTTTTCGTGGTGC TCCTT | 16S Region |
| 187. | Antisense primer | ATTCGCTTAACCTCGCGGCA TCGCAGC | 16S Region |
| 188. | Antisense primer | AGGTAAGGTTCTTCGCGTTG CATCG | 16S Region |
| 189. | Antisense primer | GTCTCCCCTGCAGTACTCTA GTCTG | 16S Region |
| 190. | Antisense primer | TATTCCCCACTGCTGCCTCC CGTAG | 16S Region |
| 191. | Antisense primer | TCGACTTGCATGTGTTAAGC ACGCC | 16S Region |
| 192. | oligotargeter | CACCATCGACGAAGGTCCGG GTTCTCTCGGATTG | 16S Region |
| 193. | oligotargeter | TGTTCGTGAAATCTCACGGC TTAAC | 16S Region |
| 194. | oligotargeter | GCGTGCGGGCGATACGGGCA GACTAGAGTACT | 16S Region |
| 195. | oligotargeter | CTAATACCGGATAGGACCAC GGGATG-CATGTCTTG | 16S Region |
| 196. | oligotargeter | GGCCACACTGGGACTGAGAT ACGGCCCAG | 16S Region |
| 197. | oligotargeter | CCATCGACGAAGGTCCGGGT TCTCTCGGA | 16S Region |
| 198. | oligotargeter | CGCGTCTAGAGATAGGCGTT CCCT | 16S Region |
| 199. | oligotargeter | GGGGGCCCGCACAAGCGGCG GAGCATGTGGA | 16S Region |
| 200. | oligotargeter | TGATCCTGGCTCAGGACGAA CGCTG | 16S Region |
| 201. | oligotargeter | GCTGGCGGCGTGCTTAACAC ATGCA | 16S Region |
| 202. | oligotargeter | GGACCACGGGATGCATGTCT TGTGG | 16S Region |
| 203. | oligotargeter | CCTGAGAGGGTGTCCGGCCA CACTG | 16S Region |
| 204. | oligotargeter | GGGGATGACGGCCTTCGGGT TGTAA | 16S Region |
| 205. | oligotargeter | AACTACGTGCCAGCAGCCGC GGTAA | 16S Region |
| 206. | oligotargeter | GGGTCTCTGGGCAGTAACTG ACGCTGAGGA | 16S Region |
| 207. | oligotargeter | GCGTGGGGAGCGAACAGGAT TAGATACCCT | 16S Region |
| 208. | oligotargeter | CTGGGGAGTACGGCCGCAAG GCTAAAACTC | 16S Region |

Mycobacteria ITS Region: Primers & Probes

| SEQ ID Number | Type | Sequence | Target |
|---|---|---|---|
| 209. | Sense Primer | AGCACCACGAAAACGCCCCA ACTGG | ITS Region |
| 210. | Sense Primer | AAGGAGCACCACGAAAACGC CCCAA | ITS Region |
| 211. | Antisense primer | CCGGCAGCGTATCCATTGAT GCTCG | ITS Region |
| 212. | Antisense primer | GCCGGCAGCGTATCCATTGA TGCTC | ITS Region |

| SEQ ID Number | Type | Sequence | Target |
|---|---|---|---|
| 213. | Antisense primer | AGCCGGCAGCGTATCCATTG ATGCT | ITS Region |
| 214. | Antisense primer | CCACCATGCGCCCTTAGACA CTTACAAACA | ITS Region |
| 215. | oligotargeter | ACTTGTTCCAGGTGTTGTCC CACCGCCTTGG | ITS Region |
| 216. | oligotargeter | ACACACTGTTGGGTCCTGAG GCAACANCTCG | ITS Region |
| 217. | oligotargeter | AGGGGTTCTTGTCTGTAGTG GGCGAGAGCCGGGTGC | ITS Region |
| 218. | oligotargeter | ACACACTGTTGGGTCCTGAG GCAACA | ITS Region |
| 219. | oligotargeter | GAACTGGATAGTGGTTGCGA GCATC | ITS Region |
| 220. | oligotargeter | GCGTAGGCCGTGAGGGGTTC TTGTCTGTAG | ITS Region |
| 221. | oligotargeter | TGGGGCGTAGGCCGTGAGGG GTTCTTGTCT | ITS Region |
| 222. | oligotargeter | CACTCGGACTTGTTCCAGGT GTTGTCCCAC | ITS Region |
| 223. | oligotargeter | CGAGCATCAATGGATACGCT GCCGGCTAGC | ITS Region |
| 224. | oligotargeter | GAGCCGGGTGCATGACAACA AAGTTG | ITS Region |
| 225. | oligotargeter | CACTCGGACTTGTTCCAGGT GTTGTCC | ITS Region |

ITS Region: Primers & Probes

| Seq. Number | Type | Sequence | Target |
|---|---|---|---|
| 226. | Sense Primer | CTGGCGTTGAGCGTAGTAGGCAG CCTCGA | IS6110 Region |
| 227. | Sense Primer | AGTCGACCCAGCGCGCGGTGGCC AA | |
| 228. | Antisense primer | TCGCTGATCCGGCCACAGCCCGT | IS6110 Region |
| 229. | Antisense primer | TTGCGGTGGGGTGTCGAGTCGAT CTGCAC | |
| 230. | oligotargeter | TGGATGCCTGCCTCGGCGAGCCG CTCGCTG | IS6110 Region |
| 231. | oligotargeter | TCGACATCCTCGATGGACCGCCA GGGCTTG | IS6110 Region |
| 232. | oligotargeter | CCGCCAGCCCAGGATCCTGCGAG CGTAGGC | IS6110 Region |
| 233. | oligotargeter | GAACCCTGCCCAGGTCGACACAT AGGTGAG | IS6110 Region |
| 234. | oligotargeter | AGTCGACCCAGCGCGCGGTGGCC AACTCGA | IS6110 Region |
| 235. | oligotargeter | CGCCAGGGCTTGCCGGGTTTGAT CAGCTCG | IS6110 Region |
| 236. | oligotargeter | GCTCGCTGAACCGGATCGATGTG TACTGAG | IS6110 Region |
| 237. | oligotargeter | AGGATCCTGCGAGCGTAGGCGTC GGTGACA | IS6110 Region |

Methicillin Resistant Staph *Aureus* (Mrsa) Primers & Oligotargeters

16S rRNA Region: Primers & Probes

| Seq. Number | Type | Sequence | Target |
|---|---|---|---|
| 238. | Sense Primer | AGAGTTTGATCCTGGCTCAG GATG | 16S rRNA |
| 239. | Sense Primer | TTAGTATTTATGAGCTAATC AAACATCAT | 16S rRNA |
| 240. | Sense Primer | GCTTACCAAGGCAACGATGC ATAGC | 16S rRNA |
| 241. | Sense Primer | GCAAGCGTTATCCGGAATTA TTGGGC | 16S rRNA |
| 242. | Sense Primer | CTAACGCATTAAGCACTCCG CCTGG | 16S rRNA |
| 243. | Sense Primer | CTAAGTTGACTGCCGGTGAC AAACC | 16S rRNA |
| 244. | Sense Primer | GGTGGGACAAATGATTGGGG TGAAG | 16S rRNA |
| 245. | Antisense primer | AGGTGATCCAGCCGCACCTT | 16S rRNA |
| 246. | Antisense primer | AAGAAGATGTTCCGAATATA TCCTT | 16S rRNA |
| 247. | Antisense primer | CTTTATGGGATTTGCTTGAC CTCGCG | 16S rRNA |
| 248. | Antisense primer | TGGTAAGGTTCTTCGCGTTG CTTCG | 16S rRNA |
| 249. | Antisense primer | TTCCTCTTCTGCACTCAAGT TTTCC | 16S rRNA |
| 250. | Antisense primer | AAGATTCCCTACTGCTGCCT CCCGT | 16S rRNA |
| 251. | Antisense primer | GTCCGTTCGCTCGACTTGCA TGTAT | 16S rRNA |
| 252. | Oligo-targeter | GTCCCACCTTCGACGGCTAG CTCCTAAAAG | 16S rRNA |
| 253. | Oligo-targeter | GTGTTACAAACTCTCGTGGT GTGACGGGCG | 16S rRNA |
| 254. | Oligo-targeter | ACCCAACATCTCACGACACG AGCTGACGAC | 16S rRNA |
| 255. | Oligo-targeter | GAGTTTCAACCTTGCGGTCG TACTCCCCAG | 16S rRNA |
| 256. | Oligo-targeter | CTCATCGTTTACGGCGTGGA CTACCAGGGT | 16S rRNA |
| 257. | Oligo-targeter | TATTACCGCGGCTGCTGGCA CGTAGTTAGC | 16S rRNA |
| 258. | Oligo-targeter | GATCACCCTCTCAGGTCGGC TATGCATCGT | 16S rRNA |
| 259. | Oligo-targeter | AGGTTATCCACGTGTTACTC ACCCGTCCGC | 16S rRNA |

MRSA 23S rRNA Region: Primers & Probes

| SEQ ID Number | Type | Sequence | target |
|---|---|---|---|
| 260. | Sense Primer | TTAAGTTATTAAGGGCGCACG | 23S rRNA |
| 261. | Sense Primer | CGAGAGGACCGGGATGGACAT ACCT | 23S rRNA |
| 262. | Sense Primer | GAGACCTACAAGTCGAGCAGG GTCG | 23S rRNA |
| 263. | Sense Primer | GGAAAGACCCCGTGGAGCTFT ACTG | 23S rRNA |
| 264. | Sense Primer | CAGTGAATAGGCCCAAGCGAC TGTT | 23S rRNA |
| 265. | Sense Primer | GATAGGCGAAGCGTGCGATTG GATT | 23S rRNA |
| 266. | Sense Primer | AGTGACACTGCGCCGAAAATG TACC | 23S rRNA |
| 267. | Sense Primer | GCTTTAGGGCTAGCCTCAAGT GATGA | 23S rRNA |
| 268. | Sense Primer | CGTGTGCTTACAAGTAGTCAG AGCCCGTTA | 23S rRNA |
| 269. | Sense Primer | GAGCCCAAACCAACAAGCTTG CTTGT | 23S rRNA |
| 270. | Sense Primer | AATAACGCGTTTCCTGTAGGA TGGA | 23S rRNA |
| 271. | Antisense primer | GATCTTATAACCGAAGTTGGG AA | 23S rRNA |
| 272. | Antisense primer | CTCGCCGCTACTAAGGGAATC GAATT | 23S rRNA |
| 273. | Antisense primer | AGGTTCTATTTCACTCCCCTT CCGG | 23S rRNA |
| 274. | Antisense primer | CCAGGTTCGATTGGAATTTCT CCGCT | 23S rRNA |
| 275. | Antisense primer | CTCGACTAGTGAGCTATTACG CACTC | 23S rRNA |
| 276. | Antisense primer | ATAGGTGGTACAGGAATATCA ACCT | 23S rRNA |
| 277. | Antisense primer | GAGCACCCCTTCTCCCGAAGT TACG | 23S rRNA |
| 278. | Antisense primer | TGATTTCACCGAGTCTCTCGT TGAG | 23S rRNA |
| 279. | Antisense primer | CACTCTATGAATGATTTCCAA CCAT | 23S rRNA |
| 280. | Antisense primer | GACGGATAGGGACCGAACTGT CTCA | 23S rRNA |
| 281. | Antisense primer | AAGTAAAAGTGATTTTGCTTC GCAA | 23S rRNA |
| 282. | Oligo-targeter | GTCTCTCTTGAGTGGATCCTG AGTACGACGGAGC | 23S rRNA |
| 283. | Oligo-targeter | GGAGCCGTAGCGAAAGCGAGT CTGAATAGG | 23S rRNA |
| 284. | Oligo-targeter | AGTGAGCGGATGAACTGAGGG TAGCGGAGA | 23S rRNA |
| 285. | Oligo-targeter | GGACAATGGTAGGAGAGCGTT CTAAGGGCG | 23S rRNA |
| 286. | Oligo-targeter | CGGGAGAAGGGGTGCTCTTTA GGGTTAACG | 23S rRNA |
| 287. | Oligo-targeter | CGTAAGGTGATGTATAGGGGC TGACGCCTG | 23S rRNA |
| 288. | Oligo-targeter | TCGGCACAGCTTGTACAGGAT AGGTAGGAGCC | 23S rRNA |
| 289. | Oligo-targeter | GGCATAAGGGAGCTTGACTGC GAGACCTAC | 23S rRNA |
| 290. | Oligo-targeter | GACTGCGAGACCTACAAGTCG AGCAGGGTC | 23S rRNA |
| 291. | Oligo-targeter | CTGGGTTCAGAACGTCGTGAG ACAGTTCGG | 23S rRNA |

MRSA ITS rRNA Region: Primers & Probes

| SEQ ID Number | Type | Sequence | target |
|---|---|---|---|
| 292. | Sense Primer | AAGGATATATTCGGAACATCTT CTT | ITS |
| 293. | Sense Primer | TTGTACATTGAAAACTAGATAA GTAAGT | ITS |
| 294. | Antisense primer | AAACGCGTTATTAATCTTGTGA G | ITS |
| 295. | Antisense primer | AACGCGTTATTAATCTTGTGAG | ITS |
| 296. | Oligo-targeter | TTGAATTCATAAGAAATAATCG CTAGTGTTCG | ITS |
| 297. | Oligo-targeter | TAAGCTTGAATTCATAAGAAAT AATCGCTAGTGTT | ITS |
| 298. | Oligo-targeter | TTTTAAATAAGCTTGAATTCAT AAGAAATAATCGC | ITS |
| 299. | Oligo-targeter | AAACCGAGTGAATAAAGAGTTT TAAATAAGCTTG | ITS |
| 300. | Oligo-targeter | TTTACCAAGCAAAACCGAGTGA ATAAAGAG | ITS |
| 301. | Oligo-targeter | AGGATATATTCGGAACATCTTC TTCAGAAG | ITS |
| 302. | Oligo-targeter | GAATAACGTGACATATTGTATT CAGTTT | ITS |

MRSA mecA gene: Primers & Probes

| SEQ ID Number | Type | sequence | target |
|---|---|---|---|
| 303. | Sense Primer | TGTTTTGTTATTCATCTATA TCGTATTTT | mecA gene |

| SEQ ID Number | Type | sequence | target |
|---|---|---|---|
| 304. | Sense Primer | CGTTACGGATTGCTTCACTGTTTTG | mecA gene |
| 305. | Sense Primer | TTGTTGCATACCATCAGTTAATAGA | mecA gene |
| 306. | Sense Primer | TTACTGCCTAATTCGAGTGCTACTC | mecA gene |
| 307. | Sense Primer | TCGTTACTCATGCCATACATAAATG | mecA gene |
| 308. | Sense Primer | ACTGCATCATCTTTATAGCCTTTATA | mecA gene |
| 309. | Sense Primer | TTTGGAACGATGCCTATCTCATATG | mecA gene |
| 310. | Sense Primer | TGTTTATATCTTTAACGCCTAAACTATTAT | mecA gene |
| 311. | Antisense primer | ATGAAAAGATAAAAATTGTTCCACT | mecA gene |
| 312. | Antisense primer | GTAGTCTTATATAAGGAGGATATTG | mecA gene |
| 313. | Antisense primer | AAAAACGAGTAGATGCTCAATATAAA | mecA gene |
| 314. | Antisense primer | TTTCTGAAGACTATATCAAACAACAAA | mecA gene |
| 315. | Antisense primer | GCTCCAACATGAAGATGGCTATCGTGTC | mecA gene |
| 316. | Antisense primer | GCTCAACAAGTTCCAGATTACAACT | mecA gene |
| 317. | Antisense primer | GATATACCAAGTGATTATCCATTTTATAA | mecA gene |
| 318. | Antisense primer | AATTGGCAAATCCGGTACTGCAGAA | mecA gene |
| 319. | Oligo-targeter | GTAGTCTTATATAAGGAGGATATTG | mecA gene |
| 320. | Oligo-targeter | TTGGAACGATGCCTATCTCATATGCTGTTC | mecA gene |
| 321. | Oligo-targeter | TAACGGTTTTAAGTGGAACGAAGGTATCAT | mecA gene |
| 322. | Oligo-targeter | TTCTTCAGAGTTAATGGGACCAACATAACC | mecA gene |
| 323. | Oligo-targeter | TTTTCGTGTCTTTTAATAAGTGAGGTGCGT | mecA gene |
| 324. | Oligo-targeter | CCGGATTTGCCAATTAAGTTTGCATAAGAT | mecA gene |
| 325. | Oligo-targeter | GCCATCATCATGTTTGGATTATCTTTATCA | mecA gene |
| 326. | Oligo-targeter | TCATCATACACTTTACCTGAGATTTTGGCA | mecA gene |
| 327. | Oligo-targeter | CCTGTTTGAGGGTGGATAGCAGTACCTGAGCC | mecA gene |
| 328. | Oligo-targeter | AATTGGCAAATCCGGTACTGCAGAA | mecA gene |
| 329. | Oligo-targeter | GATATACCAAGTGATTATCCATTTTATAA | mecA gene |
| 330. | Oligo-targeter | GCTCAACAAGTTCCAGATTACAACT | mecA gene |
| 331. | Oligo-targeter | TTTCTGAAGACTATATCAAACAACAAA | mecA gene |
| 332. | Oligo-targeter | AAAAACGAGTAGATGCTCAATATAAA | mecA gene |

MRSA femA gene: Primers & Probes

| SEQ ID Number | Type | sequence | target |
|---|---|---|---|
| 333. | Sense Primer | CGAGAGACAAATAGGAGTAATGATAATGAA | femA gene |
| 334. | Sense Primer | TGAATATGTTGGTGACTTTATTAAACC | femA gene |
| 335. | Sense Primer | TGAGCAAAAGATTGAAGAAGGTAAA | femA gene |
| 336. | Sense Primer | TGTTAAAGTAAGATATTTATCTGAAGAAGA | femA gene |
| 337. | Sense Primer | TCTTTAATGAATTATCAAAATATGTTAAAA | femA gene |
| 338. | Sense Primer | AACGAGAGACAAATAGGAGTAATGAT | femA gene |
| 339. | Antisense primer | TCCCTTCCTAAAAAATTCTGTCTTTAAC | femA gene |
| 340. | Antisense primer | GTGGCCAACAGTTTGCGTGAAATGAC | femA gene |
| 341. | Antisense primer | CAATCATTACCAGCATTACCTGTAA | femA gene |
| 342. | Antisense primer | AAGCGATTGTAATAAAACTTGTCAT | femA gene |
| 343. | Antisense primer | CGGAATGCATTTGATGTACCACCAGC | femA gene |
| 344. | Antisense primer | ATTTCATGTTTTGATAATTCCCTTC | femA gene |
| 345. | Oligo-targeter | TTGACCGTTATAATTTCTATGGTGTTAGTGGTAAAT | femA gene |
| 346. | Oligo-targeter | GATGCAAATGAGCAAAAGATTGAAGAAGGT | femA gene |
| 347. | Oligo-targeter | TTGACCGTTATAATTTCTATGGTGTTAGTGGTAAAT | femA gene |
| 348. | Oligo-targeter | CGTTGTCTATACCTACATATCGATCCATATTTACC | femA gene |
| 349. | Oligo-targeter | GCGGTCCAGTGATCGATTATGAAAATCAAG | femA gene |
| 350. | Oligo-targeter | CAGTCATTTCACGCAAACTGTTGGCCACTA | femA gene |

-continued

| SEQ ID Number | Type | sequence | target |
|---|---|---|---|
| 351. | Oligo-targeter | GAGTTTGGTGCCTTTACAGATAGCATGCCA | femA gene |
| 352. | Oligo-targeter | ACAAATTTAACAGCTAAAGAGTTTGGTGCC | femA gene |

MRSA gyrA gene: Primers & Probes

| SEQ ID Number | Type | sequence | target |
|---|---|---|---|
| 353. | Sense Primer | ATGGCTGAATTACCTCAATCAAGAA | gyrA gene |
| 354. | Sense Primer | CAGCACAAGGTGTTCGCTTAATTCGC | gyrA gene |
| 355. | Sense Primer | GGTATTACACTTCGTGAAGGTGACG | gyrA gene |
| 356. | Sense Primer | TTGAACTTGAAAATGATGAAATCAT | gyrA gene |
| 357. | Sense Primer | GGTGGATTTGAAGACTTAGAGGACGAGGAC | gyrA gene |
| 358. | Sense Primer | ATGAAATTATTTCAACGATTCGTGA | gyrA gene |
| 359. | Sense Primer | TGATGAAACAAGTTTACGTACTGGT | gyrA gene |
| 360. | Sense Primer | TCAATGGTGTACTTAGCTTAAGTAAGA | gyrA gene |
| 361. | Sense Primer | ATGGCTCAAGATTTCAGTTATCGTT | gyrA gene |
| 362. | Sense Primer | GCGCTGTGAACTGAACTTTTGAAGGAGG | gyrA gene |
| 363. | Antisense primer | CCCCCTACATATAGGGAAGTCTTATTT | gyrA gene |
| 364. | Antisense primer | CATACGTACCATTGCTTCATAGATA | gyrA gene |
| 365. | Antisense primer | CCATTGATCAATTCTGTTAAGTTATG | gyrA gene |
| 366. | Antisense primer | CACGTAAATCAGTAATACCGTCAAT | gyrA gene |
| 367. | Antisense primer | ATTTCATCGATATGATCTAACGCAA | gyrA gene |
| 368. | Antisense primer | CCTCGTCCTCTAAGTCTTCAAATCCACC | gyrA gene |
| 369. | Antisense primer | TTTTCAAGTTCAATAGCATTCACTA | gyrA gene |
| 370. | Antisense primer | AGTGTAATACCTTTCACACCCGTTG | gyrA gene |
| 371. | Antisense primer | TAAGCGAACACCTTGTGCTGCACGA | gyrA gene |
| 372. | Antisense primer | CCCTACATATAGGGAAGTCTTATTTT | gyrA gene |
| 373. | Oligo-targeter | TAGGGCTTGATGTAGCTCATGCAAACAGTG | gyrA gene |
| 374. | Oligo-targeter | GCAACGGGTGTGAAAGGTATTACACTTCGT | gyrA gene |
| 375. | Oligo-targeter | ATCAAGACAGTCTAAAGGTATTCCTGTAGTGAATG | gyrA gene |
| 376. | Oligo-targeter | CCAAGTGAATAAGGCTCGTATGATTGAAAA | gyrA gene |
| 377. | Oligo-targeter | TCCTGATATTTCAATTGCTGAGTTAATGGA | gyrA gene |
| 378. | Oligo-targeter | ACCCTCATGGTGACTTATCTATCTATGAAGCA | gyrA gene |
| 379. | Oligo-targeter | TGCCAGATGTTCGTGACGGTTTAAAACCAG | gyrA gene |
| 380. | Oligo-targeter | AAATGAACGAAATATTACCAGTGAAATGCG | gyrA gene |
| 381. | Oligo-targeter | AGAGAGCCGTCAGTCTTACCTGCTCGATTCCC | gyrA gene |

MRSA spagene: Primers & Probes

| SEQ ID Number | Type | sequence | target |
|---|---|---|---|
| 382. | Sense Primer | TTTTTATAGTTCGCGACGACGTC | spa gene |
| 383. | Sense Primer | GATATCTATCGTTGTGTATTGTTTGTT | spa gene |
| 384. | Sense Primer | CACCAGGTTTAACGACATGTACTCCG | spa gene |
| 385. | Sense Primer | CTTCCTCTTTTGGTGCTTGAGCATCG | spa gene |
| 386. | Sense Primer | AGAAAGCATTTTGTTGTTCTTTGTT | spa gene |
| 387. | Antisense primer | TATGATGACTTTACAAATACATACAGGGG | spa gene |
| 388. | Antisense primer | AGAACAACGTAACGGCTTCATCCAA | spa gene |
| 389. | Antisense primer | TGACCCAAGTCAAAGTGCTAACCTT | spa gene |
| 390. | Antisense primer | CAAGCTCCAAAAGCTGATGCGCAAC | spa gene |
| 391. | Antisense primer | ATGACTTTACAAATACATACAGGGG | spa gene |
| 392. | Oligo-targeter | TTACAGATGCAATACCTACACCTAGTTTAC | spa gene |
| 393. | Oligo-targeter | GATCAGCGTTTAAGTTAGGCATATTTAACA | spa gene |
| 394. | Oligo-targeter | AATGAAACCATTGCGTTGCTCTTCGTTTAA | spa gene |
| 395. | Oligo-targeter | GTTGCCGTCTTCTTTACCAGGTTTGTTGCC | spa gene |
| 396. | Oligo-targeter | ACGACATGTACTCCGTTGCCGTCTTCTTTACC | spa gene |

-continued

| SEQ ID Number | Type | sequence | target |
|---|---|---|---|
| 397. | Oligo-targeter | ATAGTTCGCGACGACGTCCAGCTAATAACG | spa gene |

Hepatitis B Virus Primers & Oligotargeters
Primers & Oligotargeters:

| SEQ ID Number | Type | Sequence | target |
|---|---|---|---|
| 398. | Sense Primer | GGGACGTCCTTTGTCTACGTCCCGT | 1411-1880 |
| 399. | Antisense primer | ACAGCTTGGAGGCTTGAACAGTAGGACA | 1411-1880 |
| 400. | Sense Primer | ATGGAGAGCACAACATCAGGA | SURFACE HBsAg |
| 401. | Antisense primer | CCAACGTTTGGTTTTATTAGGG | SURFACE HBsAg |
| 402. | Sense Primer | TGGGGTACTTTACCGCAGGA | RNA PRE alpha region |
| 403. | Antisense primer | GTTTCGCTCCAGACCGGCTG | RNA PRE alpha region |
| 404. | Sense Primer | TCCTTTGTCTACGTCCCGTC | RNA PRE beta region |
| 405. | Antisense primer | CATGGTGCTGGTGAACAGAC | RNA PRE beta region |
| 406. | Sense Primer | GGCCTCTACCGTCCCCTTCTTCAT | RNA Epsilon element |
| 407. | Antisense primer | CCATGCCCCAAAGCCACCCA | RNA Epsilon element |
| 408. | Sense Primer | ATGTCCTACTGTTCAAGCCTCC | CDS C0 PEPTIDE |
| 409. | Antisense primer | CTCAAGGACAGTTTCTCTTCCA | CDS C0 PEPTIDE |
| 410. | Sense Primer | ATGGACATTGACCCGTATAAAG | CORE HBcAg |
| 411. | Antisense primer | CTAACATTGAGATTCCCGAGATT | CORE HBcAg |
| 412. | Sense Primer | CTTATAGACCACCAAATGCCCCTATC | CDC Polymerase (P) |
| 413. | Antisense primer | TGTGTAAGACCTTGGGCAAGACCTG | CDC Polymerase (P) |
| 414. | Oligo-targeter | CGCACCTCTCTTTACGCGGACTCCCCGTCTGT | 1411-1880 |
| 415. | Oligo-targeter | ACTTTTTCCCCTCTGCCTAATCATCTCATGTTCATG | CDC Polymerase (P) |
| 416. | Oligo-targeter | TTCAAGCCTCCAAGCTGTGCCTTGGGTGGCTTTGG | CDC Polymerase (P) |
| 417. | Oligo-targeter | TATAAAGAATTTGGAGCTTCTGTGGA | CDC Polymerase (P) |
| 418. | Oligo-targeter | GGAGTGTGGATTCGCACTCCTCCCGCTTACAG | CDC Polymerase (P) |
| 419. | Oligo-targeter | CAAATGCCCCTATCTTATCAACACTTCCGGA | CDC Polymerase (P) |
| 420. | Oligo-targeter | CAGGTCCCCTAGAAGAAGAACTCCCTCGCCT | CDC Polymerase (P) |
| 421. | Oligo-targeter | GGATTCCTAGGACCCCTGCTCGTGTTACAG | SURFACE HBsAg |
| 422. | Oligo-targeter | GCAGTCCCCAACCTCCAATCACTCACCAAC | SURFACE HBsAg |
| 423. | Oligo-targeter | TCCTATGGGAGTGGGCCTCAGTCCGTTTCT | SURFACE HBsAg |
| 424. | Oligo-targeter | CGGTCAGGTCTCTGCCAAGTGTTTGCTGAC | RNA PRE alpha region |
| 425. | Oligo-targeter | CTTTGCTGCCCCTTTTACACAATGTGGCTA | RNA PRE alpha region |
| 426. | Oligo-targeter | GCCTTTATATGCATGTATACAATCTAAGCAGGC | RNA PRE alpha region |
| 427. | Oligo-targeter | CTGTGCCTTCTCATCTGCCGGACCGTGTGCACTT | RNA PRE beta region |
| 428. | Oligo-targeter | CTTCGCTTCACCTCTGCACGTAGCATGGAG | RNA PRE beta region |
| 429. | Oligo-targeter | GAGGACTCTTGGACTCTCAGCAATGTCAAC | DNA Enhancer 2 |
| 430. | Oligo-targeter | AAAGACTGTTTGTTTAAAGACTGGGAGGAGT | DNA Enhancer 2 |
| 431. | Oligo-targeter | GAGATCTCCTCGACACCGCCTCTGCTCTGT | CDS C0 PEPTIDE |
| 432. | Oligo-targeter | GCCTCTGCTCTGTATCGGGAGGCCTTAGAG | CDS C0 PEPTIDE |

Human Immunodeficiency Virus 1: Primers and Oligotargeters

| SEQ ID Number | Type | sequence | target |
|---|---|---|---|
| 433. | Sense Primer | ATGGGTGCGAGAGCGTCAGT | Gag gene |
| 434. | Antisense primer | TTATTGTGACGAGGGGTCGTTG | Gag gene |
| 435. | Sense Primer | CCCTTCAGACAGGATCAGAAGAAC | Gag gene |

| SEQ ID Number | Type | sequence | target |
|---|---|---|---|
| 436. | Antisense primer | GTGCCCTTCTTTGCCACAATTG | Gag gene |
| 437. | Oligo-targeter | CTGACACAGGACACAGCAATCAGGTCAGCC | Gag gene |
| 438. | Oligo-targeter | TAGTGCAGAACATCCAGGGGCAAATGGTAC | Gag gene |
| 439. | Oligo-targeter | GTAGAAGAGAAGGCTTTCAGCCCAGAAGTG | Gag gene |
| 440. | Oligo-targeter | AAACTCTAAGAGCCGAGCAAGCTTCACAGG | Gag gene |
| 441. | Oligo-targeter | AGCATTGGGACCAGCGGCTACACTAGAAGA | Gag gene |
| 442. | Oligo-targeter | AATGATGACAGCATGTCAGGGAGTAGGAGG | Gag gene |

Human Immunodeficiency Virus 2: Primers and Oligotargeters

| SEQ ID Number | Type | sequence | Target |
|---|---|---|---|
| 443. | Sense Primer | TTGTGTGGGCAGCGAATGAA | gag-pol |
| 444. | Antisense primer | ACCTCTTTGTATGGTCTCTCCCTCTG | gag-pol |
| 445. | Sense Primer | GCTTGCACGCAGAAGAGAAAGT | gag-pol |
| 446. | Antisense primer | AGTGTCCCTCCTTTCCACAGTTC | gag-pol |
| 447. | Oligo-targeter | ATGAATCCCACCCTAGAAGAGATGCTAACCGC | gag-pol |
| 448. | Oligo-targeter | TGAGGGCAGAACAAACAGACCCAGCAGTAA | gag-pol |
| 449. | Oligo-targeter | GGATGTATAGGCCACAAAATCCCGTACCGG | gag-pol |
| 450. | Oligo-targeter | CTTACCAGCAGGACAGCTCAGAGACCCAAG | gag-pol |
| 451. | Oligo-targeter | CAGGATTTCAGGCACTCTCAGAAGGCTGCA | gag-pol |
| 452. | Oligo-targeter | AGTGGAGGAAAAGAAGTTCGGGGCAGAAGT | gag-pol |
| 453. | Oligo-targeter | ACAGCACCACCTAGTGGGAAAAGAGGAAAC | gag-pol |
| 454. | Oligo-targeter | TACAAGTAGACCAACGCACCACCTAGTGG | gag-pol |

Influenza A Virus (H5N1) Primers & Oligotargeters

Hemagglutinin Gene: Primers & Oligotargeters

| SEQ ID Number | Type | Sequence | target |
|---|---|---|---|
| 455. | Sense Primer | ATTGGAATATGGTAACTGCAACACC | HA gene |
| 456. | Sense Primer | GCTTCTTCTTGCAATAGTCAGTCTT | HA gene |
| 457. | Sense Primer | GCCAATGACCTCTGTTACCCAGGGAATT | HA gene |
| 458. | Sense Primer | GAGCAGACAAGGCTCTATCAAAACCC | HA gene |
| 459. | Sense Primer | ATTCCACAACATCCACCCTCTCACC | HA gene |
| 460. | Sense Primer | ACTCAGTTTGAGGCTGTTGGAAGGG | HA gene |
| 461. | Sense Primer | GACTACCCGCAGTATTCAGAAGAAGC | HA gene |
| 462. | Antisense primer | GTTATTAAATTCCCTTCCAACAGCC | HA gene |
| 463. | Antisense primer | TGTAACGATCCATTGGAGCACATCC | HA gene |
| 464. | Antisense primer | TGAGTCATGAAAGTCTAGAGTTCTCTC | HA gene |
| 465. | Antisense primer | CCTGCCATCCTCCCTCTATAAAACCTGCTA | HA gene |
| 466. | Antisense primer | CAAAGTTTATTGCATCATTCGATTT | HA gene |
| 467. | Antisense primer | GGGTCCTCCCTGGTATGGACATGCT | HA gene |
| 468. | Antisense primer | GCAGAGTTTCCCGTTGTGTGTCTTTTCC | HA gene |
| 469. | Oligo-targeter | GCAACACCAAGTGTCAAACTCCAATAGGGG | HA gene |
| 470. | Oligo-targeter | GGCTGTTGGAAGGGAATTTAATAAC | HA gene |
| 471. | Oligo-targeter | TAGGGGCGATAAACTCCAGTATGCCATTCC | HA gene |
| 472. | Oligo-targeter | GCTATAGCAGGTTTTATAGAGGGAGGATGGCAGG | HA gene |
| 473. | Oligo-targeter | GAGTGGGTACGCTGCAGACAAAGAATCCAC | HA gene |
| 474. | Oligo-targeter | AGTTCCCTAGCACTGGCAATCATGGTGGCT | HA gene |
| 475. | Oligo-targeter | GCGACTACAGCTTAGGGATAATGCAAAGGAGC | HA gene |
| 476. | Oligo-targeter | CTTTACGACAAGGTGCGACTACAGCTTAGG | HA gene |
| 477. | Oligo-targeter | GGAATGCCCCAAATATGAAATCAAACAG | HA gene |
| 478. | Oligo-targeter | GCTCAGAAATAGCCCTCAAGGAGAGAGAAG | HA gene |
| 479. | Oligo-targeter | GCAAAGTGGAAGGGTGGAGTCTTTTTGGAC | HA gene |

-continued

| SEQ ID Number | Type | Sequence | target |
|---|---|---|---|
| 480. | Oligo-targeter | GATCTAAGGTAAACGGGCAAAGTGGAAGGG | HA gene |
| 481. | Oligo-targeter | CTATGAAGAACTGAAACACCTATTGAGCAG | HA gene |
| 482. | Oligo-targeter | CTGTTACCCAGGGAATTTCAACAACTATGA | HA gene |

Influenza Neuraminidase Gene: Primers & Oligotargeters

| Seq. Number | Type | Sequence | target |
|---|---|---|---|
| 483. | Sense Primer | GTCAAAGACAGAAGCCCTCACAGA | NA |
| 484. | Sense Primer | TTGGAATAGTTAGCTTAATGTTACAG | NA |
| 485. | Sense Primer | AGCCTTGCTGAATGACAAGCAC | NA |
| 486. | Sense Primer | TTGCTTTACTGTAATGACTGATGGACC | NA |
| 487. | Sense Primer | GGTGTCCCCTAACGGGGCATAT | NA |
| 488. | Antisense primer | GGATGCTGGACAAAACTCCCAC | NA |
| 489. | Antisense primer | CCCTGAGTCAAAAAGAAAGTTCT | NA |
| 490. | Antisense primer | GAGCCATTTACACATGCACATTCA | NA |
| 491. | Antisense primer | GGACCACAACTACCTGTTCCATCA | NA |
| 492. | Antisense primer | CAAATTGTGCTCTCTTTAGGCCGC | NA |
| 493. | Oligo-targeter | AGACAGGGAATCAATGCCAAGCTGAACCGA | NA |
| 494. | Oligo-targeter | TAGCGGATGGGCGGTATACAGTAAGGACAA | NA |
| 495. | Oligo-targeter | GGGGCTGTGGCTGTATTGAAATACAATGGC | NA |
| 496. | Oligo-targeter | GGAATTTCTGGTCCAGACAATGGGGCTGTG | NA |
| 497. | Oligo-targeter | TGTTGCTTGGTCAGCTAGTGCTTGCCATGA | NA |
| 498. | Oligo-targeter | GCTGAATGACAAGCACTCCAATGGGACTGT | NA |
| 499. | Oligo-targeter | ATGCAGTGGAGTTTTCGGAGACAATCCACG | NA |
| 500. | Oligo-targeter | ATCAAAATCTGGAGTATCAAATAGGATATA | NA |
| 501. | Oligo-targeter | AAATCACATGTGTGTGTAGGGATAATTGGC | NA |
| 502. | Oligo-targeter | CCGGCGAAATCACATGTGTGTGTAGGGATA | NA |
| 503. | Oligo-targeter | CCTGTTATCCTGATGCCGGCGAAATCACAT | NA |
| 504. | Oligo-targeter | CTGTAATGACTGATGGACCAAGTAGTGGGC | NA |
| 505. | Oligo-targeter | GAGTTTTGTCCAGCATCCAGAACTGACAGG | NA |
| 506. | Oligo-targeter | CCTAACGGGGCATATGGGGTAAAAGGGTTT | NA |

Influenza Matrix protein (M1) gene: Primers & Oligotargeters

| Seq. Number | Type | Sequence | target |
|---|---|---|---|
| 507. | Sense Primer | ACGTTCTCTCTATCATCCCGTCAG | M1 |
| 508. | Sense Primer | TAAGCTATATAAGAAGCTGAAAAGAGAA | M1 |
| 509. | Sense Primer | GCAGGCAGCGGAAGCCATGGAGGTCG | M1 |
| 510. | Antisense primer | ACTGCCCTATCCATATTATTTGGATCT | M1 |
| 511. | Antisense primer | TCACTTGATCCCGCCATCTG | M1 |
| 512. | Antisense primer | TCACTTGAATCGCTGCATCTGCACTCCCA | M1 |
| 513. | Oligo-targeter | CGCTTTGTCCAGAATGCCCTAAATGGAAAT | M1 |
| 514. | Oligo-targeter | GCGTAGACGCTTTGTCCAGAATGCCCTAAA | M1 |
| 515. | Oligo-targeter | GGGATGTTGGGATTTGTATTCACGCTCACC | M1 |
| 516. | Oligo-targeter | GACCAATCCTGTCACCTCTGACTAAAGGGA | M1 |
| 517. | Oligo-targeter | CCGATCTCGAGGCTCTCATGGAGTGGCTAA | M1 |
| 518. | Oligo-targeter | AAGCCGAGATCGCGCAGAAACTTGAAGATG | M1 |
| 519. | Oligo-targeter | TGGCAACTATCACCAACCCACTAATCAGGC | M1 |
| 520. | Oligo-targeter | ACAACAGAATGGGCACAGTGACCACGGAAG | M1 |
| 521. | Oligo-targeter | AATAACATTCCATGGGCTAAGGAGGTCGC | M1 |
| 522. | Oligo-targeter | TTGAAAATTTGCAGGCCTACCAGAAACGAA | M1 |
| 523. | Oligo-targeter | ACTCATCCCAACTCTAGTGCTGGTCTGAGA | M1 |
| 524. | Oligo-targeter | CCATGGAGGTCGCTAATCAGGCTAGGCAGA | M1 |

West Nile Virus Primers & Oligotargeters

| SEQ ID Number | Type | sequence | target |
|---|---|---|---|
| 525. | Sense Primer | GGCAATCTTGCCCTCAGTAG TTGGA | 4603-5131 |
| 526. | Antisense primer | CTCTCAGTGCTTCAGCCATC TCAGC | 4603-5131 |
| 527. | Sense Primer | AGTAGTTCGCCTGTGTGAGC T | 5'UTR_1 |
| 528. | Antisense primer | GTTTTGAGCTCCGCCGATTG | 5'UTR_1 |
| 529. | Sense Primer | AATTAACACAGTGCGAGCTG | Mat_Peptide |
| 530. | Antisense primer | CTGGCGATCAGGCCAATCAT | Mat_Peptide |
| 531. | Sense Primer | ACATCGACTGTTGGTGCACA | Mat_Peptide |
| 532. | Antisense primer | CAGCTGTCGCCTTCGAGAAC | Mat_Peptide |
| 533. | Sense Primer | TTCAACTGCCTTGGAATGAG | Mat_Peptide |
| 534. | Antisense primer | AGCGTGCACGTTCACGGAGA | Mat_Peptide |
| 535. | Sense Primer | GACACTGGGTGTGCCATAGA | Mat_Peptide |
| 536. | Antisense primer | AGCATTCACTTGTGACTGCA C | Mat_Peptide |
| 537. | Sense Primer | TATAATGCTGATATGATTGA CCCTTTTCAGTTGG | Mat_Peptide |
| 538. | Antisense primer | GCGTTTACGGTTGGGATCAC ATGCA | Mat_Peptide |
| 539. | Sense Primer | GCGGATGGCCCGCAACTGAA GTGAT | Mat_Peptide |
| 540. | Antisense primer | CCTCCTCTCTTTGTGTATTG GA | Mat_Peptide _8 |
| 541. | Sense Primer | AGGAGGCGTGTTGTGGGACA | Mat_Peptide _9 |
| 542. | Antisense primer | ACGTTTTCCCGAGGCGAAGT | Mat_Peptide _9 |
| 543. | Sense Primer | CGCCTCGGGAAAACGTTCTC | Mat_Peptide _10 |
| 544. | Antisense primer | CTGCGAACGTTGCTTCTCTG | Mat_Peptide _10 |
| 545. | Sense Primer | AACGAGATGGGTTGGCTAGA TAAGACCAA | Mat_Peptide _12 |
| 546. | Antisense primer | CTCTTTTTAGTCCTGGTTTT TCCATGTTCTT | Mat_Peptide _12 |
| 547. | Sense Primer | ATATTTAATCAATTGTAAAT AGACAATATAAGTA | 3'UTR_1 |
| 548. | Antisense primer | AGATCCTGTGTTCTCGCACC | 3'UTR_1 |

-continued

| SEQ ID Number | Type | sequence | target |
|---|---|---|---|
| 549. | Oligo-targeter | ACATAAGCGCGATAGTGCAG GGTGAAAGGATGG | 4603-5131 |
| 550. | Oligo-targeter | TCGCCTGTGTGAGCTGACAA ACTTAGTAGT | 5'UTR_1 Mat_Peptide |
| 551. | Oligo-targeter | GGCTCTCTTGGCGTTCTTCA GGTTCACAGC | _2 |
| 552. | Oligo-targeter | GCAGTGCTGGATCGATGGAG AGGTGTGAAC | |
| 553. | Oligo-targeter | AGGATTAACAACAATTAACA CAGTGCGAGC | |
| 554. | Oligo-targeter | GGCTCTCTTGGCGTTCTTCA GGTTCACAGC | Mat_Peptide 1 |
| 555. | Oligo-targeter | GCAAGAGCCGGGCTGTCAAT ATGCTAAAAC | Mat_Peptide _1 |
| 556. | Oligo-targeter | GGATCTTGAGGAACCCTGGA TATGCCCTGG | Mat_Peptide _3 |
| 557. | Oligo-targeter | CCACTCAAGACGCAGTCGGA GGTCACTGAC | Mat_Peptide _3 |
| 558. | Oligo-targeter | GTTCATGGACCTCAACCTCC CTTGGAGCAG | Mat_Peptide _5 |
| 559. | Oligo-targeter | GACTGTGAACCACGGTCAGG GATTGACACC | Mat_Peptide _5 |
| 560. | Oligo-targeter | GTCGCACGGAAACTACTCCA CACAGGTTGG | Mat_Peptide _5 |
| 561. | Oligo-targeter | GGACCAACTACTGTGGAGTC GCACGGAAAC | Mat_Peptide _5 |
| 562. | Oligo-targeter | GCTACCGTCAGCGATCTCTC CACCAAAGCT | Mat_Peptide _5 |
| 563. | Oligo-targeter | GGTTCTCGAAGGCGACAGCT GCGTGACTAT | Mat_Peptide _5 |
| 564. | Oligo-targeter | GACACTGGGTGTGCCATAGA CATCAGCCGG | Mat_Peptide _6 |
| 565. | Oligo-targeter | GGAACTACGGTCACCCTGAG TGAGAGCTGC | Mat_Peptide _6 |
| 566. | Oligo-targeter | GATAATACCAGTCACACTGG CGGGACCACG | Mat_Peptide _6 |
| 567. | Oligo-targeter | GGTCTCACCAGCACTCGGAT GTTCCTGAAG | Mat_Peptide _6 |
| 568. | Oligo-targeter | GGGAAGCAGTGAAGGACGAG CTGAACACTC | Mat_Peptide _6 |
| 569. | Oligo-targeter | CCGGCAAGAGCTGAGATGTG GAAGTGGAGT | Mat_Peptide _6 |
| 570. | Oligo-targeter | AGGCAGCTTGATCAGGGAGA AGAGGAGTGC | Mat_Peptide _7 |
| 571. | Oligo-targeter | CACTGGCGGTAGCTTGGATG ATACTGAGAGCC | Mat_Peptide _7 |
| 572. | Oligo-targeter | ATTTCTGGGAAATCAACAGA TATGTGGATT | Mat_Peptide _8 |
| 573. | Oligo-targeter | GCTCATGTTTGCTGCTTTCG TGATTTCTGG | Mat_Peptide _8 |
| 574. | Oligo-targeter | CGTCTACAGGATCATGACTC GTGGGCTGCT | Mat_Peptide _9 |

| SEQ ID Number | Type | sequence | target |
|---|---|---|---|
| 575. | Oligo-targeter | CATACTGGGGCAGTGTCAAGGAGGATCGAC | Mat_Peptide_9 |
| 576. | Oligo-targeter | ACAGAAGACTGAGAACAGCCGTGCTAGCGC | Mat_Peptide_9 |
| 577. | Oligo-targeter | CTACCCTCACCCACAGGCTGATGTCTCCTC | Mat_Peptide_9 |
| 578. | Oligo-targeter | CAGACTGAGATCCCGGATCGAGCTTGGAAC | Mat_Peptide_9 |
| 579. | Oligo-targeter | GAGCAGGGTGATTGACAGCCGGAAGAGTGT | Mat_Peptide_9 |
| 580. | Oligo-targeter | AGGGAGAGTGATCCTGGGAGAACCATCTGC | Mat_Peptide_9 |
| 581. | Oligo-targeter | GGATGGGGAATACCGGCTCAGAGGAGAAGA | Mat_Peptide_9 |
| 582. | Oligo-targeter | AGATAGGTTTGGGAGGCGCTGTCTTGGGAG | Mat_Peptide_10 |
| 583. | Oligo-targeter | GACACCATGTACGTTGTGGCCACTGCAGAG | Mat_Peptide_10 |
| 584. | Oligo-targeter | CCGTCTGTGAAGACAGTACGAGAAGCCGGA | Mat_Peptide_12 |
| 585. | Oligo-targeter | GTCCCAGAATTAGAGCGCACCACACCCATC | Mat_Peptide_12 |
| 586. | Oligo-targeter | GGACAAGTCACCCTCACCGTTACGGTAACAGC | Mat_Peptide_12 |
| 587. | Oligo-targeter | GTGACAACAGCGGTCCTCACTCCACTGCTA | Mat_Peptide_12 |
| 588. | Oligo-targeter | CTGGTGAGGATGATGGAAGGGGAAGGAGTG | Mat_Peptide_13 |
| 589. | Oligo-targeter | AGAAAGAACTCAGGAGGAGGTGTCGAGGGC | Mat_Peptide_13 |
| 590. | Oligo-targeter | GAGGAGCGCCAGAGAAGCAGTTGAAGATCC | Mat_Peptide_13 |
| 591. | Oligo-targeter | GAGTGGTCAGGCTCCTCTCAAAACCATGGG | Mat_Peptide_13 |
| 592. | Oligo-targeter | ACGACTCAGGCGTGAGTACAGTTCGACGTG | Mat_Peptide_13 |
| 593. | Oligo-targeter | GGGTGAGTCGAGCTTCAGGCAATGTGGTAC | Mat_Peptide_13 |
| 594. | Oligo-targeter | GTGACATCGGAGAGTCCTCGTCAAGTGCTG | Mat_Peptide_13 |
| 595. | Oligo-targeter | CCAAGAAGTCAGAGGGTACACAAAGGGCGG | Mat_Peptide_13 |
| 596. | Oligo-targeter | GGCATCCAGTCTCTAGGGGCACAGCAAAAC | Mat_Peptide_13 |
| 597. | Oligo-targeter | GAAGTTGAGTAGACGGTGCTGCCTGCGACT | 3'UTR_1 |
| 598. | Oligo-targeter | CATGTAAGCCCTCAGAACCGTCTCGGAAGG | 3'UTR_1 |
| 599. | Oligo-targeter | ACCAGGGCGAAAGGACTAGAGGTTAGAGGAGACC | 3'UTR_1 |
| 600. | Oligo-targeter | GGTCAGGGGAAGGACTAGAGGTTAGTGGAG | 3'UTR_1 |
| 601. | Oligo-targeter | GGAGATCTTCTGCTCTGCACAACCAGCCAC | 3'UTR_1 |

REFERENCES

Gold Nanoparticles:

Shawky S M, Bald D, Azzazy H M. Direct detection of unamplified hepatitis C virus RNA using unmodified gold nanoparticles. Clin Biochem 2010; 43:1163-8.

Storhoff J J, Lucas A D, Garimella V, Bao Y P, Muller U R. Homogeneous detection of unamplified genomic DNA sequences based on colorimetric scatter of gold nanoparticle probes. Nat Biotechnol 2004; 22:883-7.

*Mycobacterium Tuberculosis* (TB):

Falkinham J O, 3rd. Surrounded by mycobacteria: nontuberculous mycobacteria in the human environment. J Appl Microbiol 2009; 107:356-67.

Fukushima M, Kakinuma K, Hayashi H, Nagai H, Ito K, Kawaguchi R. Detection and identification of *Mycobacterium* species isolates by DNA microarray. Journal of clinical microbiology 2003; 41:2605.

Gazouli, M., E. Liandris, et al. (2010). "Specific Detection of Unamplified Mycobacterial DNA by Use of Fluorescent Semiconductor Quantum Dots and Magnetic Beads." J. Clin. Microbiol. 48(8): 2830-2835.

Gordon S V, Bottai D, Simeone R, Stinear T P, Brosch R. Pathogenicity in the tubercle *bacillus*: molecular and evolutionary determinants. Bioessays 2009; 31:378-88.

Kashino S S, Pollock N, Napolitano D R, Rodrigues V, Jr., Campos-Neto A. Identification and characterization of *Mycobacterium tuberculosis* antigens in urine of patients with active pulmonary tuberculosis: an innovative and alternative approach of antigen discovery of useful microbial molecules. Clin Exp Immunol 2008; 153:56-62.

Kolk A, Schuitema A, Kuijper S, et al. Detection of *Mycobacterium tuberculosis* in clinical samples by using polymerase chain reaction and a nonradioactive detection system. Journal of Clinical Microbiology 1992; 30:2567.

Parish T, Stoker N G. *Mycobacterium tuberculosis* protocols. Totowa, N.J.: Humana Press; 2001.

Ritacco P L. Tuberculosis 2007 From basic science to patient care. In: Ritacco JCPSCLV, ed.; 2007.

Smith I. *Mycobacterium tuberculosis* pathogenesis and molecular determinants of virulence. Clin Microbiol Rev 2003; 16:463-96.

Somoskovi A, Mester J, Hale Y M, Parsons L M, Salfinger M. Laboratory diagnosis of nontuberculous mycobacteria. Clin Chest Med 2002; 23:585-597.

Steingart K R, Henry M, Laal S, et al. Commercial serological antibody detection tests for the diagnosis of pulmonary tuberculosis: a systematic review. PLoS Med 2007; 4:e202.

T. J. Brown L H-L, R. M. Anthony, F. A. Drobniewski. The use of macroarrays for the identification of MDR *Mycobacterium tuberculosis*. Journal of Microbiological Methods 2006; 65:294-300.

World Health Organization., Stop TB Partnership. Task Force on Retooling. New laboratory diagnostic tools for tuberculosis control. Geneva: World Health Organization; 2008.

World Health Organization. Global tuberculosis control: epidemiology, planning, financing: WHO report 2009. Geneva: World Health Organization; 2009.

World Health Organization. Global tuberculosis control: a short update to the 2009 report. Geneva: World Health Organization; 2009.

Acintobacter:

Allen, K. D. and H. T. Green (1987). "Hospital outbreak of multi-resistant *Acinetobacter* anitratus: an airborne mode of spread?" J Hosp Infect 9(2): 110-9.

Bergogne-Berezin, E. (2001). "The Increasing Role of *Acinetobacter* Species As Nosocomial Pathogens." Curr Infect Dis Rep 3(5): 440-444.

Bergogne-Berezin E, Towner K J. *Acinetobacter* spp. as nosocomial pathogens: microbiological, clinical, and epidemiological features. Clin Microbiol Rev 1996; 9:148-65.

Bernards, A. T., J. van der Toorn, et al. (1996). "Evaluation of the ability of a commercial system to identify *Acinetobacter* genomic species." Eur J ClinMicrobiol Infect Dis 15(4): 303-8.

Davis K A, Moran K A, McAllister C K, Gray P J. Multidrug-resistant *Acinetobacter* extremity infections in soldiers. Emerg Infect Dis 2005; 11:1218-24.

Ehrenstein, B., A. T. Bernards, et al. (1996). "*Acinetobacter* species identification by using tRNA spacer fingerprinting." J ClinMicrobiol 34(10): 2414-20.

Garnacho-Montero J, Amaya-Villar R. Multiresistant *Acinetobacter baumannii* infections: epidemiology and management. Curr Opin Infect Dis 2010; 23:332-9.

Gerner-Smidt, P. (1992). "Ribotyping of the *Acinetobacter calcoaceticus-Acinetobacter baumannii* complex." J ClinMicrobiol 30(10): 2680-5.

Gurtler, V. and V. A. Stanisich (1996). "New approaches to typing and identification of bacteria using the 16S-23S rDNA spacer region." Microbiology 142 (Pt 1): 3-16.

Jawad, A., P. M. Hawkey, et al. (1994). "Description of Leeds *Acinetobacter* Medium, a new selective and differential medium for isolation of clinically important *Acinetobacter* spp., and comparison with Herellea agar and Holton's agar." J ClinMicrobiol 32(10): 2353-8.

Jawad, A., A. M. Snelling, et al. (1998). "Comparison of ARDRA and recA-RFLP analysis for genomic species identification of *Acinetobacter* spp." FEMS Microbiol-Lett 165(2): 357-62.

Janssen, P. and L. Dijkshoorn (1996). "High resolution DNA fingerprinting of *Acinetobacter* outbreak strains." FEMS MicrobiolLett 142(2-3): 191-4.

Hsueh P R, Teng L J, Chen C Y, et al. Pandrug-resistant *Acinetobacter baumannii* causing nosocomial infections in a university hospital, Taiwan. Emerg Infect Dis 2002; 8:827-32.

Ko, W. C., N. Y. Lee, et al. (2008). "Oligonucleotide array-based identification of species in the *Acinetobacter calcoaceticus-A. baumannii* complex in isolates from blood cultures and antimicrobial susceptibility testing of the isolates." J ClinMicrobiol 46(6): 2052-9.

Seifert, H., L. Dijkshoorn, et al. (1997). "Distribution of *Acinetobacter* species on human skin: comparison of phenotypic and genotypic identification methods." J Clin-Microbiol 35(11): 2819-25.

Sunenshine R H, Wright M O, Maragakis L L, et al. Multidrug-resistant *Acinetobacter* infection mortality rate and length of hospitalization. Emerg Infect Dis 2007; 13:97-103.

Talbot G H, Bradley J, Edwards J E, Jr., Gilbert D, Scheld M, Bartlett J G. Bad bugs need drugs: an update on the development pipeline from the Antimicrobial Availability Task Force of the Infectious Diseases Society of America. Clin Infect Dis 2006; 42:657-68.

Wood, G. C., S. D. Hanes, et al. (2002). "Comparison of ampicillin-sulbactam and imipenem-cilastatin for the treatment of *Acinetobacter* ventilator-associated pneumonia." Clin Infect Dis 34(11): 1425-30.

Mecithillin-Resitant Staph *Aureus* (MRSA):

Adebayo O. shittu, Udo E E, Lin J. Insights on Virulence and Antibiotic Resistance: A Review of the Accessory Genome of *Staphylococcus aureus*. Wounds 2007; 19:237-44.

Borg M A, de Kraker M, Scicluna E, et al. Prevalence of methicillin-resistant *Staphylococcus aureus* (MRSA) in invasive isolates from southern and eastern Mediterranean countries. J Antimicrob Chemother 2007; 60:1310-5.

Cataldo M A, Taglietti F, Petrosillo N. Methicillin-resistant *Staphylococcus aureus*: a community health threat. Postgrad Med 2010; 122:16-23.

Holfelder M, Eigner U, Turnwald A M, Witte W, Weizenegger M, Fahr A. Direct detection of methicillin-resistant *Staphylococcus aureus* in clinical specimens by a nucleic acid-based hybridisation assay. Clin Microbiol Infect 2006; 12:1163-7.

Kobayashi S D, DeLeo F R. An update on community-associated MRSA virulence. Curr Opin Pharmacol 2009; 9:545-51.

Malhotra-Kumar S, Haccuria K, Michiels M, et al. Current trends in rapid diagnostics for methicillin-resistant *Staphylococcus aureus* and glycopeptide-resistant *enterococcus* species. J Clin Microbiol 2008; 46:1577-87.

Methicillin-Resistant *Staphylococcus aureus* (MRSA) PCR. Quest Diagnostics 2006.

Ramakrishnan R, Buckingham W, Domanus M, et al. Sensitive assay for identification of methicillin-resistant *Staphylococcus aureus*, based on direct detection of genomic DNA by use of gold nanoparticle probes. Clin Chem 2004; 50:1949-52.

Struelens M J, Hawkey P M, French G L, Witte W, Tacconelli E. Laboratory tools and strategies for methicillin-resistant *Staphylococcus aureus* screening, surveillance and typing: state of the art and unmet needs. Clin Microbiol Infect 2009; 15:112-9.

Warren D K, Liao R S, Merz L R, Eveland M, Dunne W M, Jr. Detection of methicillin-resistant *Staphylococcus aureus* directly from nasal swab specimens by a real-time PCR assay. J Clin Microbiol 2004; 42:5578-81.

Yuen K. CA-MRSA as an Emerging Public Health Threat. Medical Bulletin 2007; 12.

Hepatitis B Virus (HBV):

Bowden D S, Thompson A J. New developments in HBV molecular diagnostics and quantitative serology. Hepatol Int 2008; 2:3-11.

Guirgis B S, Abbas R O, Azzazy H M. Hepatitis B virus genotyping: current methods and clinical implications. Int J Infect Dis 2010; 14:e941-53.

Ismail A M, Ziada H N, Sheashaa H A, Shehab El-Din A B. Decline of viral hepatitis prevalence among asymptomatic Egyptian blood donors: a glimmer of hope. Eur J Intern Med 2009; 20:490-3.

Perrillo R, Mimms L, Schechtman K, Robbins D, Campbell C. Monitoring of antiviral therapy with quantitative evaluation of HBeAg: a comparison with HBV DNA testing. Hepatology 1993; 18:1306-12.

Sablon E, Shapiro F. Advances in Molecular Diagnosis of HBV Infection and Drug Resistance. Int J Med Sci 2005; 2:8-16.

Shen G, Zhang Y. Highly sensitive electrochemical stripping detection of hepatitis B surface antigen based on copper-enhanced gold nanoparticle tags and magnetic nanoparticles. Anal Chim Acta 2010; 674:27-31.

Tang D, Yuan R, Chai Y, Dai J, Zhong X, Liu Y. A novel immunosensor based on immobilization of hepatitis B surface antibody on platinum electrode modified colloidal gold and polyvinyl butyral as matrices via electrochemical impedance spectroscopy. Bioelectrochemistry 2004; 65:15-22.

Tang D, Yuan R, Chai Y, et al. New amperometric and potentiometric immunosensors based on gold nanoparticles/tris(2,2'-bipyridyl)cobalt(III) multilayer films for hepatitis B surface antigen determinations. Biosens Bioelectron 2005; 21:539-48.

Valsamakis A. Molecular testing in the diagnosis and management of chronic hepatitis B. Clin Microbiol Rev 2007; 20:426-39, table of contents.

Wang Y F, Pang D W, Zhang Z L, Zheng H Z, Cao J P, Shen J T. Visual gene diagnosis of HBV and HCV based on nanoparticle probe amplification and silver staining enhancement. J Med Virol 2003; 70:205-11.

Zhang Q, Wu G, Richards E, Jia S, Zeng C. Universal primers for HBV genome DNA amplification across subtypes: a case study for designing more effective viral primers. Virol J 2007; 4:92.

Human Immunodeficiceny Virus (HIV):

Butto S, Raimondo M, Fanales-Belasio E, Suligoi B. Suggested strategies for the laboratory diagnosis of HIV infection in Italy. Ann Ist Super Sanita 2010; 46:34-41.

Centers for Disease Control and Prevention. (Accessed 15 Mar. 2011, at http://_www.cdc.gov/hiv/resources/qa/transmission.htm.)

Douek D C, Roederer M, Koup R A. Emerging concepts in the immunopathogenesis of AIDS. Annu Rev Med 2009; 60:471-84.

Fearon M. The laboratory diagnosis of HIV infections. Can J Infect Dis Med Microbiol 2005; 16:26-30.

Girardi E, Sabin C A, Monforte A D. Late diagnosis of HIV infection: epidemiological features, consequences and strategies to encourage earlier testing. J Acquir Immune Defic Syndr 2007; 46 Suppl 1:S3-8.

Guidelines for using HIV testing technologies in surveillance: selection, evaluation and implementation-2009 Update. (Accessed 14 Mar. 2011, at http://www.who.int/hiv/pub/surveillance/hiv_testing_technologies/en/index.html.)

Holmes C B, Losina E, Walensky R P, Yazdanpanah Y, Freedberg K A. Review of human immunodeficiency virus type 1-related opportunistic infections in sub-Saharan Africa. Clin Infect Dis 2003; 36:652-62.

Katsoulidou A, Rokka C, Issaris C, et al. Comparative evaluation of the performance of the Abbott RealTime HIV-1 assay for measurement of HIV-1 plasma viral load on genetically diverse samples from Greece. Virol J 2011; 8:10.

Krogstad P. Molecular biology of the human immunodeficiency virus: current and future targets for intervention. Semin Pediatr Infect Dis 2003; 14:258-68.

Robb M L. Failure of the Merck HIV vaccine: an uncertain step forward. Lancet 2008; 372:1857-8.

Sickinger E, Jonas G, Yem A W, et al. Performance evaluation of the new fully automated human immunodeficiency virus antigen-antibody combination assay designed for blood screening. Transfusion 2008; 48:584-93.

Sierra S, Kupfer B, Kaiser R. Basics of the virology of HIV-1 and its replication. J Clin Virol 2005; 34:233-44.

Silva Mde O, Bastos M, Netto E M, et al. Acute HIV infection with rapid progression to AIDS. Braz J Infect Dis 2010; 14:291-3.

Troppan K T, Stelzl E, Violan D, Winkler M, Kessler H H. Evaluation of the new VERSANT HIV-1 RNA 1.0 Assay (kPCR) for quantitative detection of human immunodeficiency virus type 1 RNA. J Clin Virol 2009; 46:69-74.

Avian Infleunza Virus (AIV):

Bautista E, Chotpitayasunondh T, Gao Z, et al. Clinical aspects of pandemic 2009 influenza A (H1N1) virus infection. N Engl J Med 2010; 362:1708-19.

Boggild A K, McGeer A J. Laboratory diagnosis of 2009 H1N1 influenza A virus. Crit Care Med 2010; 38:e38-42.

Broor S, Chahar H, Kaushik S. Diagnosis of influenza viruses with special reference to novel H1N1 2009 influenza virus. Indian Journal of Microbiology 2009; 49:301-7.

Girard M P, Tam J S, Assossou O M, Kieny M P. The 2009 A (H1N1) influenza virus pandemic: A review. Vaccine 2010; 28:4895-902.

Graham M, Liang B, Van Domselaar G, et al. Nationwide molecular surveillance of pandemic H1N1 influenza A virus genomes: Canada, 2009. PLoS One 2011; 6:e16087.

Greninger A L, Chen E C, Sittler T, et al. A metagenomic analysis of pandemic influenza A (2009 H1N1) infection in patients from North America. PLoS One 2010; 5:e13381.

Sullivan S J, Jacobson R M, Dowdle W R, Poland G A. 2009 H1N1 influenza. Mayo Clin Proc 2010; 85:64-76.

Takahashi H, Otsuka Y, Patterson B K. Diagnostic tests for influenza and other respiratory viruses: determining performance specifications based on clinical setting. J Infect Chemother 2010; 16:155-61.

Wang R, Taubenberger J K. Methods for molecular surveillance of influenza. Expert Rev Anti Infect Ther 2010; 8:517-27.

Woo T M. 2009 H1N1 Influenza Pandemic. Journal of Pediatric Health Care 2010; 24:258-66.

West Nile Virus (WNV)

CDC: West Nile Virus Diagnostic Testing. (Accessed 30 Mar. 2012, at http://_www.cdc.gov/ncidod/dvbid/westnile/wnv_DiagnosticTesting.html.)

Dauphin G, Zientara S. West Nile virus: recent trends in diagnosis and vaccine development. Vaccine 2007; 25:5563-76.

De Filette M, Ulbert S, Diamond M, Sanders N N. Recent progress in West Nile virus diagnosis and vaccination. Vet Res 2012; 43:16.

Rossi S L, Ross T M, Evans J D. West Nile virus. Clinics in laboratory medicine 2010; 30:47.

WHO West Nile Virus Factsheet. (Accessed 29 Mar. 2012, at http://_www.who.int/mediacentre/factsheets/fs354/en/index.html.)

Zhang W, Wu J, Li Y, Li F, Njoo H. Rapid and accurate in vitro assays for detection of West Nile virus in blood and tissues. Transfus Med Rev 2009; 23:146-54.

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

The invention claimed is:
1. A method for detecting mycobacteria comprising:
contacting unamplified genomic DNA extracted from a sample suspected of containing said mycobacteria with a single-stranded DNA oligotargeter that ranges in length from 15 to 40 contiguous bases and that binds to mycobacteria genomic DNA for a time and under conditions sufficient for the oligotargeter to hybridize to the mycobacteria genomic DNA,
contacting a mixture of oligotargeter DNA and the unamplified genomic DNA with non-functionalized gold nanoparticles, and detecting the mycobacteria in the sample when the gold nanoparticles aggregate,
wherein aggregated gold nanoparticles exhibit a blue color and non-aggregated gold nanoparticles exhibit a red color.
2. The method of claim 1, wherein the unamplified genomic DNA is extracted from plasma or serum.

* * * * *